US010221197B2

(12) United States Patent
Du et al.

(10) Patent No.: US 10,221,197 B2
(45) Date of Patent: Mar. 5, 2019

(54) PHOSPHATIDYLINOSITOL 3-KINASE INHIBITORS

(71) Applicant: Gilead Sciences, Inc., Foster City, CA (US)

(72) Inventors: Zhimin Du, Belmont, CA (US); Jerry Evarts, Seattle, WA (US); Joshua Kaplan, Foster City, CA (US); Musong Kim, Bothell, WA (US); Devan Naduthambi, San Bruno, CA (US); Leena Patel, Mercer Island, WA (US); Stephane Perreault, Brier, WA (US); Barton W. Phillips, San Mateo, CA (US); Gary Phillips, Issaquah, WA (US); Kirk L. Stevens, Bothell, WA (US); Jennifer A. Treiberg, Redmond, WA (US); Joshua Van Veldhuizen, Seattle, WA (US); William J. Watkins, Saratoga, CA (US); Suet Chung Yeung, Redmond, WA (US)

(73) Assignee: Gilead Sciences, Inc., Foster City, CA (US)

( * ) Notice: Subject to any disclaimer, the term of this patent is extended or adjusted under 35 U.S.C. 154(b) by 40 days.

(21) Appl. No.: 14/735,939

(22) Filed: Jun. 10, 2015

(65) Prior Publication Data

US 2015/0361095 A1 Dec. 17, 2015

Related U.S. Application Data

(60) Provisional application No. 62/011,977, filed on Jun. 13, 2014.

(51) Int. Cl.
| | |
|---|---|
| *C07D 513/04* | (2006.01) |
| *C07D 403/12* | (2006.01) |
| *C07D 413/14* | (2006.01) |
| *C07D 403/14* | (2006.01) |
| *C07D 239/91* | (2006.01) |
| *C07D 487/04* | (2006.01) |
| *C07D 401/14* | (2006.01) |
| *C07D 473/34* | (2006.01) |

(52) U.S. Cl.
CPC ......... *C07D 513/04* (2013.01); *C07D 239/91* (2013.01); *C07D 401/14* (2013.01); *C07D 403/12* (2013.01); *C07D 403/14* (2013.01); *C07D 413/14* (2013.01); *C07D 473/34* (2013.01); *C07D 487/04* (2013.01)

(58) Field of Classification Search
USPC ...................................................... 514/243
See application file for complete search history.

(56) References Cited

U.S. PATENT DOCUMENTS

| | | |
|---|---|---|
| 6,518,277 B1 | 2/2003 | Sadhu et al. |
| 6,667,300 B2 | 12/2003 | Sadhu et al. |
| 6,800,620 B2 | 10/2004 | Sadhu et al. |
| 6,949,535 B2 | 9/2005 | Sadhu et al. |
| 7,932,260 B2 | 4/2011 | Fowler et al. |
| 8,138,195 B2 | 3/2012 | Sadhu et al. |
| 8,207,153 B2 | 6/2012 | Fowler et al. |
| 8,435,988 B2 | 5/2013 | Qu et al. |
| 8,492,389 B2 | 7/2013 | Sadhu et al. |
| RE44,599 E | 11/2013 | Fowler et al. |
| 8,586,597 B2 | 11/2013 | Fowler et al. |

(Continued)

FOREIGN PATENT DOCUMENTS

| | | |
|---|---|---|
| CA | 2 895 782 C | 8/2017 |
| CN | 1440408 A | 9/2003 |

(Continued)

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802 (Year: 1995).*
Intl. Search Report—Written Opinion dated Oct. 28, 2015 for PCT/US2015/035147.
Office Action dated Apr. 24, 2017, for New Zealand Patent Application No. 726052, 7 pages.
Office Action dated Dec. 12, 2017 for New Zealand Patent Application No. 7266052, 3 pages.

(Continued)

*Primary Examiner* — Marcos L Sznaidman
(74) *Attorney, Agent, or Firm* — Morrison & Foerster LLP

(57) ABSTRACT

The present application provides the compounds of formula (J), or pharmaceutically acceptable salts, isomers, or a mixture thereof, wherein n, m, q, A', $W^1$, $W^2$, $W^3$, $R^1$, $R^2$, and $R^3$ are described herein. The compounds are inhibitors to the activities of phosphatidylinositol 3-kinase (PI3K) and are useful for treating conditions mediated by one or more PI3K isoforms. The present application further provides pharmaceutical compositions that include a compound of formula (J), or pharmaceutically acceptable salts, isomers, tautomer, or mixture thereof, and methods of using these compounds and compositions for treating conditions mediated by one or more PI3K isoforms.

13 Claims, No Drawings

(56) References Cited

U.S. PATENT DOCUMENTS

| | | | |
|---|---|---|---|
| RE44,638 E | 12/2013 | Fowler et al. | |
| 8,623,881 B2 | 1/2014 | Sadhu et al. | |
| 8,637,533 B2 | 1/2014 | Sadhu et al. | |
| 8,653,077 B2 | 2/2014 | Sadhu et al. | |
| 8,673,906 B2 | 3/2014 | Barlaam et al. | |
| 8,779,131 B2 | 7/2014 | Kesicki et al. | |
| 8,980,901 B2 | 3/2015 | Fowler et al. | |
| 8,993,583 B2 | 3/2015 | Fowler et al. | |
| 9,029,384 B2 | 5/2015 | Evarts et al. | |
| 9,149,477 B2 | 10/2015 | Kesicki et al. | |
| 9,221,795 B2 | 12/2015 | Evarts et al. | |
| 9,266,878 B2 | 2/2016 | Everts et al. | |
| 9,487,772 B2 | 11/2016 | Sadhu et al. | |
| 9,499,523 B2 | 11/2016 | Kim et al. | |
| 9,676,759 B2 | 6/2017 | Aronov et al. | |
| 9,765,060 B2 | 9/2017 | Evarts et al. | |
| 2002/0161014 A1 | 10/2002 | Sadhu et al. | |
| 2004/0266780 A1 | 12/2004 | Sadhu et al. | |
| 2008/0287469 A1 | 11/2008 | Diacovo et al. | |
| 2009/0312319 A1 | 12/2009 | Ren et al. | |
| 2010/0256167 A1 | 10/2010 | Fowler et al. | |
| 2012/0015964 A1 | 1/2012 | Fowler et al. | |
| 2013/0053362 A1 | 2/2013 | Castro et al. | |
| 2013/0274253 A1 | 10/2013 | Brollo et al. | |
| 2014/0179673 A1 | 6/2014 | Evarts et al. | |
| 2015/0087663 A1 | 3/2015 | Xi et al. | |
| 2015/0361054 A1 | 12/2015 | Shaopei et al. | |
| 2015/0361068 A1 | 12/2015 | Shaopei et al. | |
| 2015/0361070 A1 | 12/2015 | Evarts et al. | |
| 2016/0075705 A1 | 3/2016 | Kesicki et al. | |
| 2017/0049772 A1 | 2/2017 | Sadhu et al. | |
| 2017/0340633 A1 | 11/2017 | Sadhu et al. | |
| 2018/0065953 A1 | 3/2018 | Evarts et al. | |

FOREIGN PATENT DOCUMENTS

| | | | |
|---|---|---|---|
| CN | 101031569 A | | 9/2007 |
| JP | 2003-512461 A | | 4/2003 |
| JP | 2005-509635 A | | 4/2005 |
| JP | 2007-537291 A | | 12/2007 |
| JP | 2013-515074 A | | 5/2013 |
| JP | 2013-526586 A | | 6/2013 |
| JP | 2013-540746 A | | 11/2013 |
| JP | 2016-503805 A | | 2/2016 |
| JP | 2016-527238 A | | 9/2016 |
| JP | 6125663 B2 | | 5/2017 |
| JP | 2017-517527 A | | 6/2017 |
| JP | 6207100 B2 | | 10/2017 |
| WO | WO-2001/30768 A1 | | 5/2001 |
| WO | WO-2001/081346 A2 | | 11/2001 |
| WO | WO-2003/035075 A1 | | 5/2003 |
| WO | WO2005/113556 | * | 12/2005 |
| WO | WO-2005/113556 A1 | | 12/2005 |
| WO | WO-2006/089106 A2 | | 8/2006 |
| WO | WO-2006/089106 A3 | | 8/2006 |
| WO | WO-2009/088986 A1 | | 7/2009 |
| WO | WO-2011/146882 A1 | | 11/2011 |
| WO | WO-2012/037204 A1 | | 3/2012 |
| WO | WO-2013/032591 A1 | | 3/2013 |
| WO | WO-2014/023083 A1 | | 2/2014 |
| WO | WO2014/100765 | * | 6/2014 |
| WO | WO-2014/100765 A1 | | 6/2014 |
| WO | WO-2014/100767 A1 | | 6/2014 |
| WO | WO-2014/128612 A1 | | 8/2014 |
| WO | WO-2015/010641 A1 | | 1/2015 |
| WO | WO-2015/051241 A1 | | 4/2015 |
| WO | WO-2015/081127 A1 | | 6/2015 |
| WO | WO-2015/168079 A1 | | 11/2015 |
| WO | WO-2015/191726 A1 | | 12/2015 |
| WO | WO-2015/191743 A1 | | 12/2015 |
| WO | WO-2015/191745 A1 | | 12/2015 |
| WO | WO-2015/191752 A1 | | 12/2015 |
| WO | WO-2015/191754 A1 | | 12/2015 |

OTHER PUBLICATIONS

Office Action dated Sep. 27, 2017 for European Patent Application No. 15734488.8, filed Dec. 29, 2016, 8 pages.
Office Action dated Dec. 4, 2017, for Eurasian Patent Application No. 201692267, 10 pages (including English translation).
Office Action dated Nov. 14, 2017 for Japanese Patent Application No. 2016-570274, 21 pages (including English translation).
Office Action dated Dec. 15, 2017 for Canadian Patent Application No. 2952025, 5 pages.
U.S. Appl. No. 15/680,045, filed Aug. 17, 2017, by Evarts et al.
Office Action dated Sep. 27, 2017 for European Patent Application No. 1573448.8, 8 pages.
Cannon, J.G. (1995). "Analog Design," Chapter 19 in Burger's Medicinal Chemistry and Drug Discovery, Fifth Edition, Wolff, M.E. ed., John Wiley & Sons Inc., NY, USA, vol. 1, pp. 783-802, 22 pages.
Chemical Encyclopedia (1988), publisher "Soviet encyclopedia", Moscow, 2:365-370.
Engelman, J.A. et al. (Aug. 2009). "Targeting PI3K Signaling in Cancer: Opportunities, Challenges and Limitations", Nat. Rev. Cancer 9:550-562.
Foster, A.B. (Dec. 1984). "Deuterium Isotope Effects in Studies of Drug Metabolism", Trends Pharmacol. Sci. 5(12):524-527.
Hiles, I.D. et al. (Aug. 7, 1992). "Phosphatidylinositol 3-kinase: Structure and Expression of the 110 kd Catalytic Subunit," Cell 70(3):419-429.
McMahon, G. (2000). "VEGF Receptor Signaling in the Tumor Angiogenesis," The Oncologist 5(Suppl. 1):3-10.
Otsu, M. et al. (Apr. 5, 1991). "Characterization of Two 85 kd Proteins that Associate with Receptor Tyrosine Kinases, Middle-T/pp60$^{c-src}$ Complexes, and P13-Kinase," Cell 65:91-104.
Panayotou, G. et al. (Dec. 1992). "Phosphatidyl-Inositol 3-Kinase: A Key Enzyme in Diverse Signalling Processes," Trends in Cell Biol. 2:358-360.
Pinedo, H.M. et al. (2000). "Translational Research: The Role of VEGF in Tumor Angiogenesis," The Oncologist 5(Suppl. 1):1-2.
Rameh, L.E. et al. (Mar. 26, 1999). "The Role of Phosphoinositide 3-Kinase Lipid Products in Cell Function," J. Biol. Chem. 274(13):8347-8350, 5 pages.
Notice of Allowance dated Mar. 6, 2018, for Australian Patent Application No. 2015274628, filed Jun. 10, 2016, 3 pages.
Office Action dated Feb. 28, 2018, for Korean Patent Application No. 1020177000710, filed Jun. 10, 2015, 18 pages. (including English translation).
Office Action dated Mar. 20, 2018, for New Zealand Patent Application No. 726052, filed Jun. 10, 2015, 3 pages.
Office Action dated Mar. 21, 2018, for European Patent Application No. 15734488.8, filed Jun. 10, 2015, 5 pages.
Notice of Allowance dated Apr. 17, 2018 for New Zealand Patent Application No. 726052, filed Jun. 10, 2015, 1 page.
Korean Office Action dated Jul. 10, 2018, for Patent Application No. 10-2017-7000710, filed Jan. 10, 2017, 9 pages. (including English translation).
Office Action dated Jan. 25, 2017 for European Appl. No. 15734488.8 (Previously cited in an IDS filed May 12, 2017).
Office Action dated Mar. 10, 2017 for Australian Appl. No. 2015274628 (Previously cited in an IDS filed May 12, 2017).
IPRP dated Dec. 15, 2016 for PCT Appl. No. PCT/US2015/035147 (Previously cited in an IDS filed May 12, 2017).
Office Action dated Jan. 25, 2017 for European Appl. No. 15734488.8.
Office Action dated Mar. 10, 2017 for Australian Appl. No. 2015274628.
IPRP dated Dec. 15, 2016 for PCT Appl. No. PCT/US2015/035147.

* cited by examiner

PHOSPHATIDYLINOSITOL 3-KINASE INHIBITORS

CROSS REFERENCE TO RELATED APPLICATIONS

This application claims priority to and the benefit under 35 U.S.C. 119(e) of U.S. Provisional Patent Application Ser. No. 62/011,977, filed Jun. 13, 2014, the disclosure of which is hereby incorporated by reference in its entirety.

FIELD

The present application relates to novel compounds that selectively inhibit the activities of PI3K isoforms and their uses in therapeutic treatments.

BACKGROUND

Cell signaling via 3'-phosphorylated phosphoinositides has been implicated in a variety of cellular processes, e.g., malignant transformation, growth factor signaling, inflammation, and immunity (Rameh et al., *J. Biol. Chem.*, 274: 8347-8350, 1999). Phosphatidylinositol 3-kinase (PI 3-kinase or PI3K) is responsible for generating these phosphorylated signaling products. PI3K was initially identified as a protein associated with viral oncoproteins and growth factor receptor tyrosine kinases that phosphorylate phosphatidylinositol (PI) and its phosphorylated derivatives at the 3'-hydroxyl of the inositol ring (Panayotou et al., *Trends Cell Biol.*, 2:358-60, 1992).

Three classes of the PI3-kinase (PI3K) are proposed based on the substrate specificities. Class I PI3Ks phosphorylate phosphatidylinositol (PI), phosphatidylinositol-4-phosphate, and phosphatidylinositol-4,5-biphosphate ($PIP_2$) to produce phosphatidylinositol-3-phosphate (PIP), phosphatidylinositol-3,4-biphosphate, and phosphatidylinositol-3,4,5-triphosphate, respectively. Also, Class II PI3Ks phosphorylate PI and phosphatidylinositol-4-phosphate, and Class III PI3Ks phosphorylate PI.

The initial purification and molecular cloning of PI3-kinase revealed that it was a heterodimer consisting of p85 and p110 subunits (Otsu et al., *Cell*, 65:91-104, 1991; Hiles et al., *Cell*, 70:419-29, 1992). Later, four distinct Class I PI3Ks were identified and designated as PI3K α, β, δ, and γ isoforms. Each isoform consists of a distinct 110 kDa catalytic subunit and a regulatory subunit. The catalytic subunits of PI3K α, β, and δ (i.e., p110α, p110β, and p110δ, respectively) interacts, individually, with the same regulatory subunit p85, whereas the catalytic subunit of PI3Kγ (p110γ) interacts with a distinct regulatory subunit p101.

Studies have also shown that each PI3K isoform has distinct expression pattern. For example, PIK3CA which encodes PI3Kα is frequently mutated in human cancers (Engelman, *Nat. Rev. Cancer*, 9: 550-562, 2009). Also, PI3Kδ is generally expressed in hematopoietic cells. Moreover, PI3K isoforms are shown to be associated with proliferation or survival signaling in cancers, inflammatory, or autoimmune diseases. As each PI3K isoform has different biological function, PI3K isoforms are potential targets to treat cancer or disorders (U.S. Pat. Nos. 6,800,620; 8,435,988; 8,673,906; US Patent Application Publication No. US2013/0274253).

Therefore, there is a need for developing therapeutic agents that inhibit PI3K isoforms to treat diseases, disorders, or conditions that are mediated by PI3K.

SUMMARY

The present application provides novel compounds that are inhibitors of PI3K isoforms. The application also provides compositions, including pharmaceutical compositions, kits that include the compounds, and methods of using and making the compounds. The compounds provided herein are useful in treating diseases, disorders, or conditions that are mediated by PI3K isoforms. The application also provides compounds for use in therapy. The application further provides compounds for use in a method of treating a disease, disorder, or condition that is mediated by PI3K isoforms. Moreover, the application provides uses of the compounds in the manufacture of a medicament for the treatment of a disease, disorder or condition that is mediated by PI3K isoforms.

The application provides compounds having the structure of formula J:

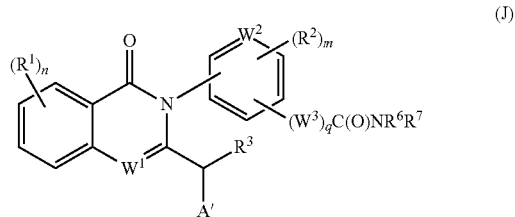

(J)

wherein:
n is 0, 1, 2, 3, or 4;
m is 0, 1, 2, 3, or 4;
q is 0 or 1;
$W^1$ and $W^2$ are independently $C(R^w)$ or N;
$W^3$ is $CH_2$ or NH;
$R^w$ is hydrogen, halo, or optionally substituted alkyl;
A' is $NR^5R^4$, $OR^4$, or $NR^5C(O)R^4$;
each $R^1$ is independently halo, cyano, optionally substituted alkyl, optionally substituted haloalkyl, optionally substituted alkoxy, hydroxy, optionally substituted sulfonyl, optionally substituted aryl, optionally substituted alkenyl optionally substituted heteroaryl, optionally substituted cycloalkyl, or optionally substituted heterocycloalkyl,
each $R^2$ is independently halo, cyano, optionally substituted alkyl, optionally substituted haloalkyl, optionally substituted alkoxy, or optionally substituted sulfonyl;
$R^3$ is hydrogen, optionally substituted alkyl, optionally substituted haloalkyl, optionally substituted cycloalkyl, or optionally substituted aryl;
$R^4$ is heteroaryl optionally substituted with one, two, or three members independently selected from halo, nitro, carboxy, cyano, optionally substituted alkyl, —$NH_2$, or optionally substituted alkynyl;
$R^5$ is hydrogen or optionally substituted alkyl, wherein $R^5$ and $R^3$ together with the atoms to which they are attached optionally form an optionally substituted heterocyclic ring,
$R^6$ is hydrogen, optionally substituted alkyl, optionally substituted heteroalkyl, optionally substituted alkoxy, optionally substituted haloalkyl, optionally substituted sulfonyl, optionally substituted cycloalkyl, optionally substituted heterocycloalkyl, optionally substituted aryl, or optionally substituted heteroaryl, and
$R^7$ is hydrogen;
or a pharmaceutically acceptable salt, isomer, or a mixture thereof.

Also provided are compounds having the structure of formula (I):

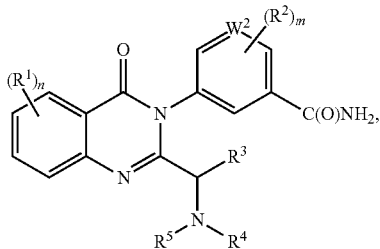

wherein:
n is 0, 1, 2, 3, or 4;
m is 0, 1, 2, 3, or 4;
$W^2$ is $C(R^w)$ or N;
$R^w$ is hydrogen, halo, or alkyl;
each $R^1$ is independently halo, cyano, optionally substituted alkyl, optionally substituted haloalkyl, optionally substituted alkoxy, optionally substituted sulfonyl, optionally substituted aryl, optionally substituted heteroaryl, optionally substituted cycloalkyl, or optionally substituted heterocycloalkyl;
each $R^2$ is independently halo, cyano, optionally substituted alkyl, optionally substituted haloalkyl, or optionally substituted alkoxy;
$R^3$ is hydrogen, optionally substituted alkyl, optionally substituted cycloalkyl, or optionally substituted aryl;
$R^4$ is heteroaryl optionally substituted with one, two, or three members independently selected from halo, cyano, optionally substituted alkyl, optionally substituted alkynyl, haloalkyl, and —$NH_2$; and
$R^5$ is hydrogen or optionally substituted alkyl; or $R^5$ and $R^3$ together with the atoms to which they are attached optionally form a heterocyclic ring;
or a pharmaceutically acceptable salt, isomer, or a mixture thereof.

Also provided are compounds having the structure of formula (II)

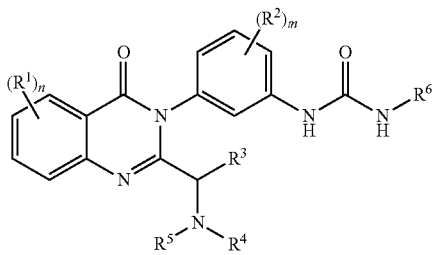

wherein:
n is 0, 1, 2, 3, or 4;
m is 0, 1, 2, 3, or 4;
each $R^1$ is independently halo, cyano, optionally substituted alkyl, optionally substituted alkenyl, optionally substituted haloalkyl, optionally substituted alkoxy, optionally substituted sulfonyl, optionally substituted aryl, optionally substituted heteroaryl, optionally substituted cycloalkyl, or optionally substituted heterocycloalkyl;
each $R^2$ is independently halo, cyano, optionally substituted alkyl, optionally substituted haloalkyl, or optionally substituted alkoxy;
$R^3$ is hydrogen, optionally substituted alkyl, optionally substituted cycloalkyl, or optionally substituted aryl;
$R^4$ is heteroaryl optionally substituted with one, two, or three members which are independently halo, nitro, carboxy, cyano, optionally substituted alkyl, —$NH_2$, optionally substituted haloalkyl, or optionally substituted alkynyl; $R^5$ is hydrogen or optionally substituted alkyl; or $R^5$ and $R^3$ together with the atoms to which they are attached optionally form an optionally substituted heterocyclic ring; and
$R^6$ is hydrogen, optionally substituted alkyl, optionally substituted alkoxy, optionally substituted haloalkyl, optionally substituted sulfonyl, optionally substituted cycloalkyl, optionally substituted aryl, or optionally substituted heteroaryl; or a pharmaceutically acceptable salt, isomer, or a mixture thereof.

Also provided are compounds having the structure of formula (III):

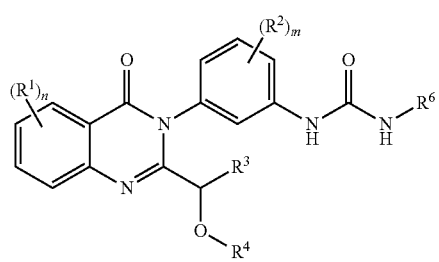

wherein:
n is 0, 1, 2, 3, or 4;
m is 0, 1, 2, 3, or 4;
each $R^1$ is independently halo, cyano, optionally substituted alkyl, optionally substituted haloalkyl, optionally substituted alkoxy, optionally substituted sulfonyl, optionally substituted aryl, optionally substituted heteroaryl, optionally substituted cycloalkyl, or optionally substituted heterocycloalkyl;
each $R^2$ is independently halo, cyano, optionally substituted alkyl, optionally substituted haloalkyl, or optionally substituted alkoxy;
$R^3$ is hydrogen, optionally substituted alkyl, optionally substituted cycloalkyl, or optionally substituted aryl; and
$R^4$ is heteroaryl optionally substituted with one, two, or three groups which are independently halo, cyano, optionally substituted alkyl, or —$NH_2$; and
$R^6$ is hydrogen, optionally substituted alkyl, optionally substituted alkoxy, optionally substituted haloalkyl, optionally substituted sulfonyl, optionally substituted cycloalkyl, optionally substituted aryl, or optionally substituted heteroaryl; or a pharmaceutically acceptable salt, isomer, or a mixture thereof.

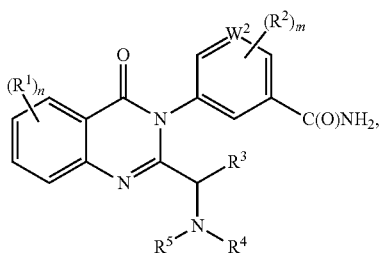

(I)

wherein:
n is 0, 1, 2, 3, or 4;
m is 0, 1, 2, 3, or 4;
$W^2$ is $C(R^w)$ or N;
$R^w$ is hydrogen, halo, or alkyl;
each $R^1$ is independently selected from halo, cyano, optionally substituted alkyl, optionally substituted haloalkyl, optionally substituted alkoxy, optionally substituted sulfonyl, optionally substituted aryl, optionally substituted heteroaryl, optionally substituted cycloalkyl, and optionally substituted heterocycloalkyl;
each $R^2$ is independently selected from halo, cyano, optionally substituted alkyl, optionally substituted haloalkyl, and optionally substituted alkoxy;
$R^3$ is hydrogen, optionally substituted alkyl, optionally substituted cycloalkyl, or optionally substituted aryl;
$R^4$ is heteroaryl optionally substituted with one, two, or three members independently selected from halo, cyano, optionally substituted alkyl, and —$NH_2$; and
$R^5$ is hydrogen or optionally substituted alkyl, wherein $R^5$ and $R^3$ together with the atoms to which they are attached optionally form a heterocyclic ring;
or a pharmaceutically acceptable salt, isomer, or a mixture thereof.

In some embodiments, the compounds have the structure of formula (I), wherein:
n is 1, 2, or 3;
m is 0, 1, or 2;
$W^2$ is $C(R^w)$ or N;
$R^w$ is hydrogen, halo, or $C_{1-6}$ alkyl;
each $R^1$ is independently selected from halo, cyano, optionally substituted $C_{1-6}$ alkyl, and $C_{1-6}$ alkylsulfonyl;
each $R^2$ is independently selected from halo, optionally substituted $C_{1-6}$ alkyl, optionally substituted $C_{1-6}$ alkoxy, and optionally substituted $C_{3-8}$ cycloalkyl;
$R^3$ is hydrogen, optionally substituted $C_{1-6}$ alkyl, optionally substituted $C_{3-8}$ cycloalkyl, or optionally substituted $C_{3-8}$ aryl;
$R^4$ is a six- to twelve-membered heteroaryl having at least one aromatic ring and at least two heteroatoms selected from N, O, S, and the heteroaryl is optionally substituted with one, two, or three members independently selected from halo, cyano, —$NH_2$, and optionally substituted $C_{1-6}$ alkyl; and
$R^5$ is hydrogen or optionally substituted $C_{1-6}$ alkyl; $R^5$ and $R^3$ together with the atoms to which they are attached optionally form a four- to eight-membered heterocyclic ring;
or a pharmaceutically acceptable salt, isomer, or a mixture thereof.

In other embodiments of the compounds of formula (I), each $R^1$ is selected from chloro, bromo, fluoro, methyl, ethyl, propyl, and cyano. In some embodiments, the compound of formula (I) wherein each $R^2$ is selected from chloro, bromo, fluoro, methyl, ethyl, propyl, cyclopropyl, methoxyproroyl, methoxyethyl, ethoxypropyl, and ethoxy-ethyl. In certain other embodiments, the compound of formula (I) wherein $R^3$ is selected from hydrogen, methyl, ethyl, propyl, butyl, cyclopropyl, cyclobutyl, and phenyl. In further embodiment, $R^5$ is hydrogen, methyl, ethyl, or propyl. In some further embodiments, $R^5$ and $R^3$ together with the atoms to which they are attached optionally form pyrrolidinyl. In additional embodiments, $R^4$ is a monocyclic heteroaryl having at least two nitrogen atoms, wherein $R^4$ is optionally substituted with two or three members independently selected from bromo, chloro, fluoro, cyano, methyl, ethyl, propyl, and —$NH_2$. In some additional embodiments, $R^4$ is pyrimidinyl substituted with two or three members selected from the group consisting of bromo, chloro, fluoro, cyano, methyl, ethyl, propyl, and —$NH_2$.

In certain embodiments, the PI3K inhibitors are the compounds selected from Table 1, a pharmaceutically acceptable salt, isomer, or a mixture thereof. In certain embodiments, the compounds are selected from Compounds 1 to 164, a pharmaceutically acceptable salt, isomer, or a mixture thereof. In additional embodiments, the compound is an (S)-enantiomer. In other embodiments, the compound is an (R)-enantiomer. In other additional embodiments, the compound is an atropisomer.

The application also provides a pharmaceutical composition that comprises a compound of the present application, a pharmaceutically acceptable salt, isomer, or a mixture thereof, together with at least one pharmaceutically acceptable vehicle. Examples of a pharmaceutically acceptable vehicle may be selected from carriers, adjuvants, and excipients.

The application also provides a pharmaceutical composition that comprises a compound of formula (I), a pharmaceutically acceptable salt, isomer, or a mixture thereof, together with at least one pharmaceutically acceptable vehicle. Examples of a pharmaceutically acceptable vehicle may be selected from carriers, adjuvants, and excipients.

Further provided herein is a method of treating a disease, disorder, or condition in a human in need thereof by administering to the human a therapeutically effective amount of a compound of the present application or a pharmaceutically acceptable salt, isomer, or a mixture thereof. Further provided is a compound of the present application for use in a method of treating a disease, disorder or condition that is mediated by PI3K isoforms. The application also provides the use of a compound of the present application in the manufacture of a medicament for the treatment of a disease, disorder or condition that is mediated by PI3K isoforms. In certain embodiments, the disease, disorder, or condition is associated or mediated by PI3K. In some embodiments, the disease, disorder, or condition is an inflammatory disorder. In other embodiments, the disease, disorder, or condition is a cancer.

Further provided herein is a method of treating a disease, disorder, or condition in a human in need thereof by administering to the human a therapeutically effective amount of a compound of formula (I) or a pharmaceutically acceptable salt, isomer, or a mixture thereof. Further provided is a compound of formula (I) for use in a method of treating a disease, disorder or condition that is mediated by PI3K isoforms. The application also provides the use of a compound of formula (I) in the manufacture of a medicament for the treatment of a disease, disorder or condition that is mediated by PI3K isoforms. In certain embodiments, the disease, disorder, or condition is associated or mediated by PI3K. In some embodiments, the disease, disorder, or condition is an inflammatory disorder. In other embodiments, the disease, disorder, or condition is a cancer.

Also provided herein is a method of inhibiting the activity of a phosphatidylinositol 3-kinase polypeptide by contacting the polypeptide with a compound of the present application or a pharmaceutically acceptable salt, isomer, or a mixture thereof.

Also provided herein is a method of inhibiting the activity of a phosphatidylinositol 3-kinase polypeptide by contacting the polypeptide with a compound of formula (I) or a pharmaceutically acceptable salt, isomer, or a mixture thereof.

Further provided is a method of inhibiting excessive or destructive immune reactions, comprising administering an effective amount of a compound of the present application or a pharmaceutically acceptable salt, isomer, or a mixture thereof.

Further provided is a method of inhibiting excessive or destructive immune reactions, comprising administering an effective amount of a compound of formula (I) or a pharmaceutically acceptable salt, isomer, or a mixture thereof.

Also provided is a method of inhibiting growth or proliferation of cancer cells comprising contacting the cancer cells with an effective amount of a compound of the present application or a pharmaceutically acceptable salt, isomer, or a mixture thereof.

Also provided is a method of inhibiting growth or proliferation of cancer cells comprising contacting the cancer cells with an effective amount of a compound of formula (I) or a pharmaceutically acceptable salt, isomer, or a mixture thereof.

Also provided is a kit that includes a compound of the present application or a pharmaceutically acceptable salt, isomer, or a mixture thereof. The kit may further comprise a label and/or instructions for use of the compound in treating a disease, disorder, or condition in a human in need thereof. In some embodiments, the disease, disorder, or condition may be associated or mediated by PI3K activity Also provided is a kit that includes a compound of formula (I) or a pharmaceutically acceptable salt, isomer, or a mixture thereof. The kit may further comprise a label and/or instructions for use of the compound in treating a disease, disorder, or condition in a human in need thereof. In some embodiments, the disease, disorder, or condition may be associated or mediated by PI3K activity.

Also provided are articles of manufacture that include a compound of the present application or a pharmaceutically acceptable salt, isomer, or a mixture thereof, and a container. In one embodiment, the container may be a vial, jar, ampoule, preloaded syringe, or an intravenous bag.

Also provided are articles of manufacture that include a compound of formula (I) or a pharmaceutically acceptable salt, isomer, or a mixture thereof, and a container. In one embodiment, the container may be a vial, jar, ampoule, preloaded syringe, or an intravenous bag.

DETAILED DESCRIPTION

The following description sets forth exemplary methods, parameters and the like. Such description is not intended as a limitation on the scope of the present application but is instead provided as exemplary embodiments.

As used herein, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms.

For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, isobutyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" includes n-butyl, sec-butyl, isobutyl and t-butyl; "propyl" includes n-propyl and isopropyl.

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Acyl" refers to a group "—C(=O)R" wherein R is hydrogen, alkyl, cycloalkyl, heterocycloalkyl, aryl, heteroalkyl, or heteroaryl; each of which may be optionally substituted, as defined herein. Examples of acyl include formyl, acetyl, cyclohexylcarbonyl, cyclohexylmethyl-carbonyl, and benzoyl.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Carbamoyl" refers to the group —OC(O)NR$^y$R$^z$ where R$^y$ and R$^z$ are defined as in "amino" above.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the group —C(O)OR, wherein R is hydrogen, alkyl, aryl, arylalkyl, heteroalkyl, or heteroaryl, each of which may be optionally substituted. In certain embodiments R is alkyl, aryl, arylalkyl, heteroalkyl, or heteroaryl, each of which may be optionally substituted.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cycloalkyl group having at least one alkenyl). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$), trifluoromethyl (—CF$_3$), difluoroethyl (—CH$_2$CHF$_2$), and trifluoroethyl (—CH$_2$CF$_3$).

"Heteroalkyl" refers to an alkyl group in which one or more of the carbon atoms (and any associated hydrogen atoms) are each independently replaced with the same or different heteroatomic group. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocycloalkyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl include 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocycloalkyl" refers to a saturated or unsaturated cyclic alkyl group, with one or more ring heteroatoms independently selected from nitrogen, oxygen and sulfur. The term "heterocycloalkyl" includes heterocycloalkenyl groups (i.e. the heterocycloalkyl group having at least one alkenyl). A heterocycloalkyl may be a single ring or multiple rings wherein the multiple rings may be fused, bridged, or spiro. As used herein, heterocycloalkyl has 2 to 20 ring carbon atoms (i.e., C$_{2-20}$ heterocycloalkyl), 2 to 12 ring carbon atoms (i.e., C$_{2-12}$ heterocycloalkyl), 2 to 10 ring carbon atoms (i.e., C$_{2-10}$ heterocycloalkyl), 2 to 8 ring carbon atoms (i.e., C$_{2-8}$ heterocycloalkyl), 3 to 12 ring carbon atoms (i.e., C$_{3-12}$ heterocycloalkyl), 3 to 8 ring carbon atoms (i.e., C$_{3-8}$ heterocycloalkyl), or 3 to 6 ring carbon atoms (i.e., C$_{3-6}$ heterocycloalkyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocycloalkyl groups include pyrrolidinyl, piperidinyl, piperazinyl, oxetanyl, dioxolanyl, azetidinyl, and morpholinyl. The above definition also encompasses "heterocyclic ring."

"Hydroxy" or "hydroxyl" refers to the group —OH.

"Nitro" refers to the group —NO$_2$.

"Oxo" refers to the group (=O) or (O).

"Sulfonyl" refers to the group —S(O)$_2$R, where R is alkyl, haloalkyl, cycloalkyl, heterocycloalkyl, heteroaryl, or aryl. Examples for sulfonyl are methylsulfonyl, ethylsulfonyl, cyclopropylsulfonyl, cyclobutylsulfonyl, cyclopentylsulfonyl, phenylsulfonyl, and toluenesulfonyl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to (substituted aryl (substituted aryl)) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted. One or more substituents may include, for example, 1, 2, 3, 4, 5, or 6 substitutents, 1, 2, 3, 4, or 5 substitutents, 1, 2, 3, or 4 substitutents, 1, 2, or 3 substituents, 1 or 2 substituents, or 1 substituent.

In some embodiments, the term "substituted alkyl" refers to an alkyl group having one or more substituents including hydroxyl, alkoxy, arylalkoxy, and carboxyl; the term "substituted alkoxy" refers to an alkoxy group having one or more substituents including aryl, carboxyl, and hydroxyl; the term "substituted alkynyl" refers to an alkynyl group having one or more substituents including heterocycloalkyl and heteroaryl; the term "substituted heterocycloalkyl" refers to a heterocycloalkyl group having one or more substituents including alkyl, haloalkyl, alkoxy, cyano, halo; "substituted aryl" refers to an aryl group having one or more substituents including halo, alkyl, haloalkyl, alkoxy, cyano, and carboxyl, sulfonyl, and heterocycloalkyl; the term "substituted heteroaryl" refers to a heteroaryl group having one or more substituents including alkyl, haloalkyl, and halo; and "substituted sulfonyl" refers to the group —SO$_2$R where R is substituted with one or more halogen molecules. In other embodiments, the one or more substituents may be further substituted with halo, alkyl, haloalkyl, alkoxy, cycloalkyl, heterocycloalkyl, aryl, or heteroaryl, each of which is substituted. In other embodiments, the one or more substituents may be further substituted with halo, alkyl, haloalkyl, alkoxy, cycloalkyl, heterocycloalkyl, aryl, or heteroaryl, each of which is unsubstituted.

PI3K Inhibitor Compounds

The present application provides the compounds that function as inhibitors of PI3K isoforms. In one aspect, the PI3K inhibitors are the compounds having the structure of formula (J):

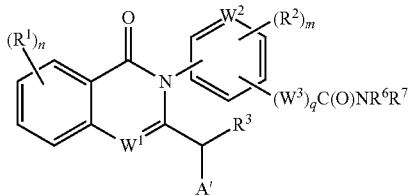

wherein:
n is 0, 1, 2, 3, or 4;
m is 0, 1, 2, 3, or 4;
q is 0 or 1;
$W^1$ and $W^2$ are independently $C(R^w)$ or N;
$W^3$ is $CH_2$ or NH;
$R^w$ is hydrogen, halo, or optionally substituted alkyl;
A' is $NR^5R^4$, $OR^4$, or $NR^5C(O)R^4$;
each $R^1$ is independently selected from halo, cyano, optionally substituted alkyl, optionally substituted haloalkyl, optionally substituted alkoxy, hydroxy, optionally substituted sulfonyl, optionally substituted aryl, optionally substituted alkenyl; optionally substituted heteroaryl, optionally substituted cycloalkyl, and optionally substituted heterocycloalkyl,
$R^2$ is independently selected from halo, cyano, optionally substituted alkyl, optionally substituted haloalkyl, optionally substituted alkoxy, and optionally substituted sulfonyl;
$R^3$ is hydrogen, optionally substituted alkyl, optionally substituted haloalkyl, optionally substituted cycloalkyl, or optionally substituted aryl;
$R^4$ is heteroaryl optionally substituted with one, two, or three members independently selected from halo, cyano, optionally substituted alkyl, —NH$_2$, and optionally substituted alkynyl;
$R^5$ is hydrogen or optionally substituted alkyl, wherein $R^5$ and $R^3$ together with the atoms to which they are attached optionally form a heterocyclic ring, wherein the heterocyclic ring is optionally substituted;
$R^6$ is hydrogen, optionally substituted alkyl, optionally substituted heteroalkyl, optionally substituted alkoxy, optionally substituted haloalkyl, optionally substituted sulfonyl, optionally substituted cycloalkyl, optionally substituted heterocycloalkyl, optionally substituted aryl, or optionally substituted heteroaryl; and
$R^7$ is hydrogen;
or a pharmaceutically acceptable salt, isomer, or a mixture thereof.

In one aspect, the PI3K inhibitors are the compounds having the structure of formula (J):

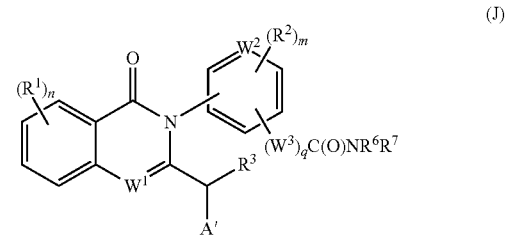

wherein:
n is 0, 1, 2, 3, or 4;
m is 0, 1, 2, 3, or 4;

q is 0 or 1;

$W^1$ and $W^2$ are independently $C(R^w)$ or N;

$W^3$ is $CH_2$ or NH;

$R^w$ is hydrogen, halo, or optionally substituted alkyl;

A' is $NR^5R^4$, $OR^4$, or $NR^5C(O)R^4$;

each $R^1$ is independently halo, cyano, optionally substituted alkyl, optionally substituted haloalkyl, optionally substituted alkoxy, hydroxy, optionally substituted sulfonyl, optionally substituted aryl, optionally substituted alkenyl optionally substituted heteroaryl, optionally substituted cycloalkyl, or optionally substituted heterocycloalkyl, each $R^2$ is independently halo, cyano, optionally substituted alkyl, optionally substituted haloalkyl, optionally substituted alkoxy, or optionally substituted sulfonyl;

$R^3$ is hydrogen, optionally substituted alkyl, optionally substituted haloalkyl, optionally substituted cycloalkyl, or optionally substituted aryl;

$R^4$ is heteroaryl optionally substituted with one, two, or three members independently selected from halo, nitro, carboxy, cyano, optionally substituted alkyl, $-NH_2$, or optionally substituted alkynyl;

$R^5$ is hydrogen or optionally substituted alkyl, wherein $R^5$ and $R^3$ together with the atoms to which they are attached optionally form an optionally substituted heterocyclic ring, $R^6$ is hydrogen, optionally substituted alkyl, optionally substituted heteroalkyl, optionally substituted alkoxy, optionally substituted haloalkyl, optionally substituted sulfonyl, optionally substituted cycloalkyl, optionally substituted heterocycloalkyl, optionally substituted aryl, or optionally substituted heteroaryl, and $R^7$ is hydrogen; or a pharmaceutically acceptable salt, isomer, or a mixture thereof.

In certain embodiments, the PI3K inhibitors are compounds of formula (J) having the structure of formula (Ja):

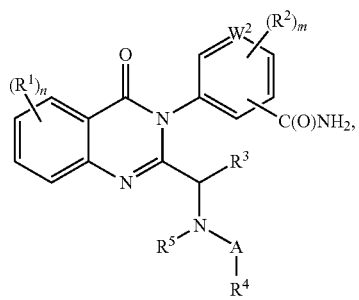

(Ja)

wherein n, m, $W^2$, $R^1$, $R^2$, $R^3$, $R^4$, and $R^5$ are described herein, A is a single bond or C(O);

or a pharmaceutically acceptable salt, isomer, or a mixture thereof.

In certain embodiments, the PI3K inhibitors are compounds of formula (J) having the structure of formula (Jb):

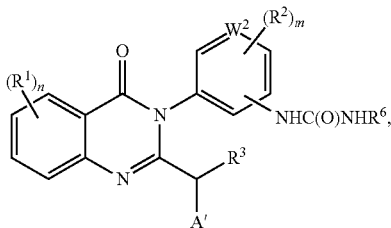

(Jb)

wherein n, m, $W^2$, $R^1$, $R^2$, $R^3$, $R^4$, $R^5$, and $R^6$ are described herein, A' is $NR^5R^4$ or $OR^4$;

or a pharmaceutically acceptable salt, isomer, or a mixture thereof.

The application also provides the compounds having the structure of formula (I) that function as inhibitors of PI3K isoforms. In one embodiment, the PI3K inhibitors are the compound of the formula (I) having the structure of:

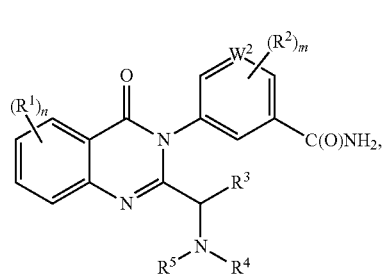

(I)

wherein:

n is 0, 1, 2, 3, or 4;

m is 0, 1, 2, 3, or 4;

$W^2$ is $C(R^w)$ or N;

$R^w$ is hydrogen, halo, or alkyl;

each $R^1$ is independently halo, cyano, optionally substituted alkyl, optionally substituted haloalkyl, optionally substituted alkoxy, optionally substituted sulfonyl, optionally substituted aryl, optionally substituted heteroaryl, optionally substituted cycloalkyl, or optionally substituted heterocycloalkyl;

each $R^2$ is independently halo, cyano, optionally substituted alkyl, optionally substituted haloalkyl, or optionally substituted alkoxy;

$R^3$ is hydrogen, optionally substituted alkyl, optionally substituted cycloalkyl, or optionally substituted aryl;

$R^4$ is heteroaryl optionally substituted with one, two, or three members independently selected from halo, cyano, optionally substituted alkyl, optionally substituted alkynyl, haloalkyl, and $-NH_2$; and $R^5$ is hydrogen or optionally substituted alkyl; or $R^5$ and $R^3$ together with the atoms to which they are attached optionally form a heterocyclic ring;

or a pharmaceutically acceptable salt, isomer, or a mixture thereof.

In some embodiments, the compounds have the structure of formula (I) wherein n is 0, 1, 2, or 3;

m is 0, 1, or 2;

$W^2$ is $C(R^w)$ or N;

$R^w$ is hydrogen, halo, or $C_{1-6}$ alkyl;

each $R^1$ is independently halo, cyano, optionally substituted $C_{1-6}$ alkyl, $C_{1-6}$ haloalkyl, or $C_{1-6}$ alkylsulfonyl;

each $R^2$ is independently halo, optionally substituted $C_{1-6}$ alkyl, optionally substituted $C_{1-6}$ alkoxy, or optionally substituted $C_{3-8}$ cycloalkyl;

$R^3$ is hydrogen, optionally substituted $C_{1-6}$ alkyl, optionally substituted $C_{3-8}$ cycloalkyl, or optionally substituted $C_{3-8}$ aryl;

$R^4$ is a six- to twelve-membered heteroaryl having at least one aromatic ring and at least two heteroatoms selected from N, O, and S, and the heteroaryl is optionally substituted with one, two, or three members which are independently halo, cyano, —$NH_2$, $C_{1-6}$ haloalkyl, $C_{2-4}$ alkynyl which is substituted with heteroaryl, or optionally substituted $C_{1-6}$ alkyl; and $R^5$ is hydrogen or optionally substituted $C_{1-6}$ alkyl; or $R^5$ and $R^3$ together with the atoms to which they are attached optionally form a four- to eight-membered heterocyclic ring; or a pharmaceutically acceptable salt, isomer, or a mixture thereof.

In some embodiments, the compounds have the structure of formula (I) wherein
n is 0, 1, or 2;
m is 0 or 1;
$W^2$ is $C(R^w)$ or N;
$R^w$ is hydrogen, fluoro, chloro, methyl, ethyl, or propyl;
each $R^1$ is independently chloro, bromo, fluoro, methyl, difluoromethyl, trifluoromethyl, ethyl, propyl, or cyano;
each $R^2$ is independently $C_{1-4}$ alkyl;
$R^3$ is hydrogen, $C_{1-6}$ alkyl, or cyclopropyl;
$R^4$ is a pyrimidinyl which is optionally substituted with two or three groups which are independently bromo, chloro, fluoro, cyano, methyl, ethyl, propyl, difluoromethyl, trifluoromethyl, —$NH_2$, or alkynyl substituted with a six-membered heteroaryl having 1 or 2 nitrogen atoms; and
$R^5$ is hydrogen, methyl, ethyl, or propyl; or $R^5$ and $R^3$ together with the atoms to which they are attached optionally form a pyrolidinyl ring;
or a pharmaceutically acceptable salt, isomer, or a mixture thereof.

The application also provides the compounds having the structure of formula (I) that function as inhibitors of PI3K isoforms. In one embodiment, the PI3K inhibitors are the compound of the formula (T) having the structure of:

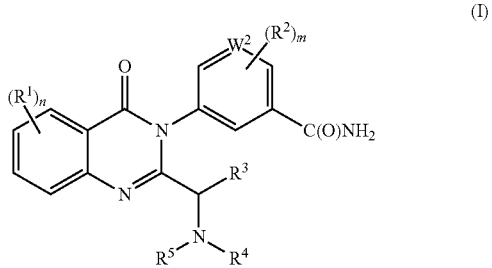

(I)

wherein:
n is 0, 1, 2, 3, or 4;
m is 0, 1, 2, 3, or 4;
$W^2$ is $C(R^w)$ or N;
$R^w$ is hydrogen, halo, or alkyl;
each $R^1$ is independently selected from halo, cyano, optionally substituted alkyl, optionally substituted haloalkyl, optionally substituted alkoxy, optionally substituted sulfonyl, optionally substituted aryl, optionally substituted heteroaryl, optionally substituted cycloalkyl, and optionally substituted heterocycloalkyl;

each $R^2$ is independently selected from halo, cyano, optionally substituted alkyl, optionally substituted haloalkyl, and optionally substituted alkoxy;

$R^3$ is hydrogen, optionally substituted alkyl, optionally substituted cycloalkyl, or optionally substituted aryl;

$R^4$ is heteroaryl optionally substituted with one, two, or three members independently selected from halo, cyano, optionally substituted alkyl, and —$NH_2$; and $R^5$ is hydrogen or optionally substituted alkyl, wherein $R^5$ and $R^3$ together with the atoms to which they are attached optionally form a heterocyclic ring;

or a pharmaceutically acceptable salt, isomer, or a mixture thereof.

In some embodiments, the compounds have the structure of formula (I) wherein
n is 1, 2, or 3;
m is 0, 1, or 2;
$W^2$ is $C(R^w)$ or N;
$R^w$ is hydrogen, halo, or $C_{1-6}$ alkyl;
each $R^1$ is independently selected from halo, cyano, optionally substituted $C_{1-6}$ alkyl, and $C_{1-6}$ alkylsulfonyl;
each $R^2$ is independently selected from halo, optionally substituted $C_{1-6}$ alkyl, optionally substituted $C_{1-6}$ alkoxy, and optionally substituted $C_{1-6}$ cycloalkyl;
$R^3$ is hydrogen, optionally substituted $C_{1-6}$ alkyl, optionally substituted $C_{3-8}$ cycloalkyl, or optionally substituted $C_{3-8}$ aryl;
$R^4$ is a six- to twelve-membered heteroaryl having at least one aromatic ring and at least two heteroatoms selected from N, O, S, and the heteroaryl is optionally substituted with one, two, or three members independently selected from halo, cyano, —$NH_2$, and optionally substituted $C_{1-6}$ alkyl; and
$R^5$ is hydrogen or optionally substituted $C_{1-6}$ alkyl; $R^5$ and $R^3$ together with the atoms to which they are attached optionally form a four- to eight-membered heterocyclic ring;
or a pharmaceutically acceptable salt, isomer, or a mixture thereof.

In some embodiment, the compound having the structure of the formula (I) wherein:
n is 0, 1, or 2;
m is 0 or 1;
$W^2$ is $C(R^w)$ or N;
$R^w$ is hydrogen, fluoro, chloro, methyl, ethyl, or propyl;
each $R^1$ is independently selected from chloro, bromo, fluoro, methyl, ethyl, propyl, and cyano;
each $R^2$ is independently selected from chloro, bromo, fluoro, methyl, ethyl, propyl, cyclopropyl, methoxyproproyl, methoxyethyl, ethoxypropyl, and ethoxyethyl;
$R^3$ is hydrogen, methyl, ethyl, propyl, butyl, cyclopropyl, cyclobutyl, or phenyl;
$R^5$ is hydrogen, methyl, ethyl, or propyl; $R^5$ and $R^3$ together with the atoms to which they are attached optionally form a five-membered heterocyclic ring; and
$R^4$ is a six- to twelve-membered monocyclic or bicyclic heteroaryl having at least two heteroatoms selected from N, O, or S, wherein the heteroaryl is substituted with two or three members independently selected from bromo, chloro, fluoro, cyano, methyl, ethyl, propyl, and —$NH_2$;
or a pharmaceutically acceptable salt, isomer, or a mixture thereof.

In one embodiment, the compound having the structure of the formula (I), wherein:
n is 1 or 2;
m is 0 or 1;
$W^2$ is CH;

each $R^1$ is independently selected from chloro, bromo, fluoro, methyl, ethyl, and propyl;

each $R^2$ is independently selected from chloro, bromo, fluoro, methyl, ethyl, and propyl;

$R^3$ is hydrogen, methyl, ethyl, propyl, butyl, cyclopropyl, or cyclobutyl;

$R^5$ is hydrogen, methyl, ethyl, or propyl; $R^5$ and $R^3$ together with the atoms to which they are attached optionally form pyrrolidinyl; and $R^4$ is a pyrimidinyl substituted with two or three members independently selected from bromo, chloro, fluoro, cyano, methyl, ethyl, and —$NH_2$;

or a pharmaceutically acceptable salt, isomer, or a mixture thereof.

In some embodiments, the compounds of formulae (I) and (J) have the structure of formula (Ia):

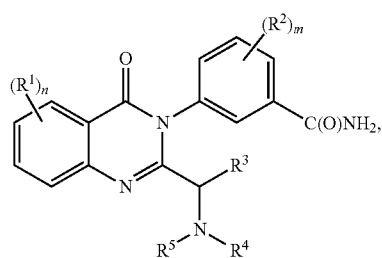

(Ia)

wherein n, m, $R^1$, $R^2$, $R^3$, $R^4$, and $R^5$ are defined herein, or a pharmaceutically acceptable salt, isomer, or a mixture thereof.

In other embodiments, the compounds of formulae (I) and (J) have the structure of formula (Ib):

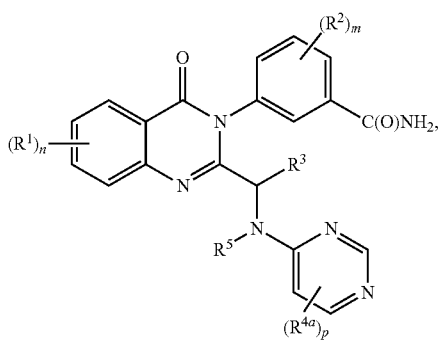

(Ib)

wherein n, m, $R^1$, $R^2$, $R^3$, and $R^5$ are defined herein, p is 2 or 3;

$R^{4a}$ is independently selected from halo, cyano, $C_{1-6}$ alkyl, and —$NH_2$;

or a pharmaceutically acceptable salt, isomer, or a mixture thereof.

In the embodiments where the compounds having the structure of formulae (Ib), each $R^{4a}$ is independently selected from halo, cyano, $C_{1-6}$ alkyl, and —$NH_2$. In some embodiments, $R^{4a}$ is independently selected from bromo, chloro, fluoro, cyano, methyl, ethyl, propyl, and —$NH_2$.

In certain embodiments, the compound of Formula (J) or (Ja) have the structure of Formula (II):

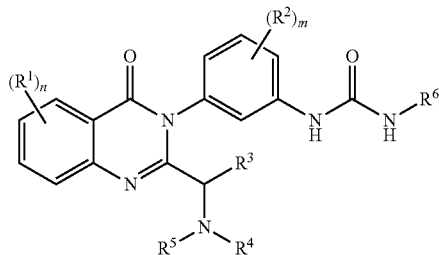

(II)

wherein:
n is 0, 1, 2, 3, or 4;
m is 0, 1, 2, 3, or 4;

each $R^1$ is independently halo, cyano, optionally substituted alkyl, optionally substituted alkenyl, optionally substituted haloalkyl, optionally substituted alkoxy, optionally substituted sulfonyl, optionally substituted aryl, optionally substituted heteroaryl, optionally substituted cycloalkyl, or optionally substituted heterocycloalkyl;

each $R^2$ is independently halo, cyano, optionally substituted alkyl, optionally substituted haloalkyl, or optionally substituted alkoxy;

$R^3$ is hydrogen, optionally substituted alkyl, optionally substituted cycloalkyl, or optionally substituted aryl;

$R^4$ is heteroaryl optionally substituted with one, two, or three members which are independently halo, nitro, carboxy, cyano, optionally substituted alkyl, —$NH_2$, optionally substituted haloalkyl, or optionally substituted alkynyl;

$R^5$ is hydrogen or optionally substituted alkyl; or $R^5$ and $R^3$ together with the atoms to which they are attached optionally form an optionally substituted heterocyclic ring; and $R^6$ is hydrogen, optionally substituted alkyl, optionally substituted alkoxy, optionally substituted haloalkyl, optionally substituted sulfonyl, optionally substituted cycloalkyl, optionally substituted aryl, or optionally substituted heteroaryl; or a pharmaceutically acceptable salt, isomer, or a mixture thereof.

In certain embodiments, the compounds have the structure of formula (II), wherein
n is 0, 1, 2, or 3;
m is 0, 1, or 2;

each $R^1$ is independently halo, cyano, optionally substituted $C_{1-6}$ alkyl, optionally substituted $C_{1-6}$ alkenyl, or optionally substituted $C_{1-6}$ alkoxy;

each $R^2$ is independently halo, optionally substituted $C_{1-6}$ alkyl, or optionally substituted $C_{1-6}$ alkoxy;

$R^3$ is hydrogen, optionally substituted $C_{1-6}$ alkyl, or optionally substituted $C_{3-8}$ cycloalkyl;

$R^4$ is a six- to twelve-membered monocyclic or bicyclic heteroaryl having 1, 2, 3, or 4 heteroatoms selected from N, O, and S, wherein the heteroaryl is optionally substituted with 1, 2, or 3 members which are independently halo, nitro, carboxy, cyano, $C_{1-6}$ alkyl, $C_{1-6}$haloalkyl, —$NH_2$, or $C_{2-4}$ alkynyl which is substituted with heteroaryl;

$R^5$ is hydrogen or optionally substituted $C_{1-6}$ alkyl; $R^5$ and $R^3$ together with the atoms to which they are attached optionally form a four- to eight-membered heterocyclic ring optionally substituted with 1, 2, or 3 groups which are each independently halo, hydroxyl, sulfonyl, or $C_{1-4}$ alkoxy which is optionally substituted with 1, 2, or 3 halo; and $R^6$ is hydrogen, optionally substituted $C_{1-6}$ alkyl, optionally substituted $C_{1-6}$ alkoxy, optionally substituted $C_{1-6}$ haloalkyl, optionally substituted $C_{1-6}$ alkyl sulfonyl, optionally substituted $C_{3-8}$ cycloalkyl sulfonyl, optionally substituted $C_{6-10}$ aryl sulfonyl, optionally substituted $C_{3-8}$ cycloalkyl, optionally substituted $C_{6-10}$ aryl, or optionally substituted $C_{5-8}$ heteroaryl; or a pharmaceutically acceptable salt, isomer, or a mixture thereof.

In certain embodiments, the compounds have the structure of formula (II), wherein n is 0, 1, or 2;
m is 0, 1, or 2;
each $R^1$ is independently halo, cyano, $C_{1-4}$ alkoxy, $C_{1-4}$ haloalkyl, $C_{1-4}$ alkyl, or $C_{1-4}$ alkenyl;
each $R^2$ is independently halo or $C_{1-4}$ alkyl.

$R^3$ is methyl, ethyl, propyl, butyl, cyclopropyl, cyclobutyl, or methyl substituted with phenylmethoxy or methoxy;

$R^4$ is purinyl, pyrimidinyl, thiazolopyrimidinyl, triazinyl, or imidazotriazinyl, wherein the pyrimidinyl and triazinyl are each optionally substituted with 1, 2, or 3 groups which are independently nitro, carboxy, fluoro, chloro, bromo, iodo, cyano, methyl, ethyl, propyl, fluoromethyl, difluoromethyl, trifluoromethyl, fluoroethyl, difluoroethyl, —NH$_2$, or —C≡C optionally substituted with

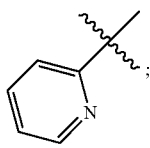 [SMILES: *c1ccccn1]

$R^5$ is hydrogen; or $R^5$ and $R^3$ together with the atoms to which they are attached form a 5 membered heterocyclic ring optionally having one additional heteroatom selected from N, O, and S wherein the 5 membered heterocyclic ring is optionally substituted with methoxy, difluoromethoxy, trifluoromethoxy, hydroxy, halo, or methylsulfonylamino; and $R^6$ is hydrogen; $C_{1-6}$ alkyl optionally substituted with 1, 2, or 3 groups which are independently hydroxy, $C_{1-6}$ alkoxy, carboxy, amino, or $C_{3-6}$ heterocycloalkyl; $C_{1-6}$ alkoxy, $C_{1-6}$ haloalkyl; $C_{1-6}$ alkyl sulfonyl; cyclopropyl sulfonyl; cyclobutyl sulfonyl; cyclopentyl sulfonyl; cyclohexyl sulfonyl; phenyl sulfonyl wherein the phenyl is optionally substituted with 1, 2, or 3 groups which are independently halo, $C_{1-6}$alkyl, amino, or cyano; cyclopropyl optionally substituted with 1, 2, or 3 groups which are independently halo, $C_{1-6}$ haloalkyl, carboxy, or hydroxyl; cyclobutyl optionally substituted with 1, 2, or 3 groups which are independently halo, $C_{1-6}$ haloalkyl, carboxy, or hydroxyl; cyclopentyl optionally substituted with 1, 2, or 3 groups which are independently halo, $C_{1-6}$ haloalkyl, carboxy, or hydroxyl; cyclohexyl optionally substituted with 1, 2, or 3 groups which are independently halo, $C_{1-6}$ haloalkyl, carboxy, or hydroxyl; phenyl optionally substituted with 1, 2, or 3 groups which are independently carboxy, halo, $C_{1-3}$ haloalkyl, $C_{1-3}$ alkyl, cyano, —S(O)$_2$OH, —S(O)$_2$CH$_3$, or $C_{1-3}$ alkoxy optionally substituted with 1, 2, or 3 groups which are independently hydroxy, carboxy, halo, or cyano; pyridinyl optionally substituted with 1, 2, or 3 groups which are independently halo, $C_{1-3}$ haloalkyl, $C_{1-3}$ alkyl, or cyano; isoxazolyl optionally substituted 1, 2, or 3 groups which are independently halo, $C_{1-3}$ haloalkyl, $C_{1-3}$ alkyl, or cyano; or tetrazolyl; or a pharmaceutically acceptable salt, isomer, or a mixture thereof.

In certain embodiments, the compounds of Formula (J) or (Jb) have the structure of Formula (III):

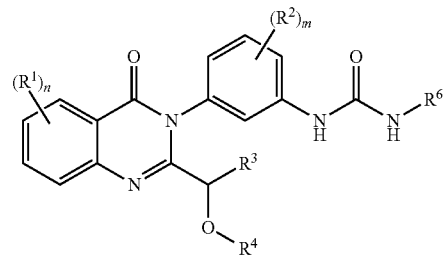

wherein:

n is 0, 1, 2, 3, or 4;
m is 0, 1, 2, 3, or 4;
each $R^1$ is independently halo, cyano, optionally substituted alkyl, optionally substituted haloalkyl, optionally substituted alkoxy, optionally substituted sulfonyl, optionally substituted aryl, optionally substituted heteroaryl, optionally substituted cycloalkyl, or optionally substituted heterocycloalkyl;

each $R^2$ is independently halo, cyano, optionally substituted alkyl, optionally substituted haloalkyl, or optionally substituted alkoxy;

$R^3$ is hydrogen, optionally substituted alkyl, optionally substituted cycloalkyl, or optionally substituted aryl; and $R^4$ is heteroaryl optionally substituted with one, two, or three groups which are independently halo, cyano, optionally substituted alkyl, or —NH$_2$; or a pharmaceutically acceptable salt, isomer, or a mixture thereof.

In certain embodiments, the compounds have the structure of formula (III), wherein n is 0, 1, 2, or 3; m is 0, 1, or 2;
each $R^2$ is independently halo, cyano, optionally substituted $C_{1-6}$ alkyl, optionally substituted $C_{1-6}$ alkenyl, or optionally substituted $C_{1-6}$ alkoxy;

each $R^2$ is independently halo, optionally substituted $C_{1-6}$ alkyl, or optionally substituted $C_{1-6}$ alkoxy;

$R^3$ is hydrogen, optionally substituted $C_{1-6}$ alkyl, or optionally substituted $C_{3-8}$ cycloalkyl;

$R^4$ is a six- to twelve-membered monocyclic or bicyclic heteroaryl having 1, 2, 3, or 4 heteroatoms selected from N, O, and S, wherein the heteroaryl is optionally substituted with 1, 2, or 3 groups which are independently halo, nitro, carboxy, cyano, $C_{1-6}$ alkyl, $C_{1-6}$haloalkyl, —NH$_2$, or $C_{2-4}$ alkynyl which is substituted with heteroaryl; and $R^6$ is hydrogen, optionally substituted $C_{1-6}$ alkyl, optionally substituted $C_{1-6}$ alkoxy, optionally substituted $C_{1-6}$ haloalkyl, optionally substituted $C_{1-6}$ alkyl sulfonyl, optionally substituted $C_{3-8}$ cycloalkyl sulfonyl, optionally substituted $C_{6-10}$ aryl sulfonyl, optionally substituted $C_{3-8}$ cycloalkyl, optionally substituted $C_{6-10}$ aryl, or optionally substituted $C_{5-8}$ heteroaryl; or a pharmaceutically acceptable salt, isomer, or a mixture thereof.

In certain embodiments, the compounds have the structure of formula (III), wherein n is 0, 1, or 2;
m is 0, 1, or 2;
each $R^1$ is independently halo, cyano, $C_{1-4}$alkoxy, $C_{1-4}$ haloalkyl, $C_{1-4}$alkyl, or $C_{1-4}$ alkenyl;
each $R^2$ is independently halo, $C_{1-4}$alkoxy or $C_{1-4}$alkyl;

$R^3$ is methyl, ethyl, propyl, butyl, cyclopropyl, cyclobutyl, or methyl substituted with phenylmethoxy or methoxy;

$R^4$ is purinyl, pyrimidinyl, thiazolopyrimidinyl, triazinyl, or imidazotriazinyl, wherein the pyrimidinyl and triazinyl are each optionally substituted with 1, 2, or 3 members which are independently nitro, carboxy, fluoro, chloro, bromo, iodo, cyano, methyl, ethyl, propyl, fluoromethyl, difluoromethyl, trifluoromethyl, fluoroethyl, difluoroethyl, or —$NH_2$; and $R^6$ is $C_{1-6}$ alkyl optionally substituted with 1, 2, or 3 groups which are independently hydroxy, $C_{1-6}$ alkoxy, carboxy, amino, or $C_{3-6}$ heterocycloalkyl; $C_{1-6}$ alkoxy; $C_{1-6}$ haloalkyl; $C_{1-6}$ alkyl sulfonyl; cyclopropyl sulfonyl; cyclobutyl sulfonyl; cyclopentyl sulfonyl; cyclohexyl sulfonyl; phenyl sulfonyl wherein the phenyl is optionally substituted with 1, 2, or 3 groups which are independently halo, $C_{1-6}$alkyl, amino, or cyano; cyclopropyl optionally substituted with 1, 2, or 3 groups which are independently halo, $C_{1-6}$ haloalkyl, carboxy, or hydroxyl; cyclobutyl optionally substituted with 1, 2, or 3 groups which are independently halo, $C_{1-6}$ haloalkyl, carboxy, or hydroxyl; cyclopentyl optionally substituted with 1, 2, or 3 groups which are independently halo, $C_{1-6}$ haloalkyl, carboxy, or hydroxyl; cyclohexyl optionally substituted with 1, 2, or 3 groups which are independently halo, $C_{1-6}$ haloalkyl, carboxy, or hydroxyl; phenyl optionally substituted with 1, 2, or 3 groups which are independently carboxy, halo, $C_{1-3}$ haloalkyl, $C_{1-3}$ alkyl, cyano, —$S(O)_2OH$, —$S(O)_2CH_3$, or $C_{1-3}$ alkoxy optionally substituted with 1, 2, or 3 groups which are independently hydroxy, carboxy, halo, or cyano; pyridinyl optionally substituted with 1, 2, or 3 groups which are independently halo, $C_{1-3}$ haloalkyl, $C_{1-3}$ alkyl, or cyano; isoxazolyl optionally substituted with halo, $C_{1-3}$ haloalkyl, $C_{1-3}$ alkyl, or cyano; or tetrazolyl; or a pharmaceutically acceptable salt, isomer, or a mixture thereof.

In certain embodiments, $R^6$ is $C_{1-6}$ alkyl optionally substituted with 1, 2, or 3 groups independently selected from hydroxy, $C_{1-6}$ alkoxy, and $C_{3-6}$ heterocycloalkyl, $C_{1-6}$ alkoxy, $C_{1-6}$ haloalkyl, cyclopropyl optionally substituted with 1, 2, or 3 groups independently selected from halo, $C_{1-6}$ haloalkyl, carboxy, and hydroxy, cyclobutyl optionally substituted with 1, 2, or 3 groups independently selected from halo, $C_{1-6}$ haloalkyl, carboxy, and hydroxy, cyclopentyl optionally substituted with 1, 2, or 3 groups independently selected from halo, $C_{1-6}$ haloalkyl, carboxy, and hydroxy, cyclohexyl optionally substituted with 1, 2, or 3 groups independently selected from halo, $C_{1-6}$ haloalkyl, carboxy, and hydroxy, phenyl optionally substituted with 1, 2, or 3 groups independently selected from carboxy, halo, $C_{1-3}$ haloalkyl, $C_{1-3}$ alkyl, cyano, —$S(O)_2OH$, —$S(O)_2CH_3$, and $C_{1-3}$ alkoxy optionally substituted with 1, 2, or 3 groups independently selected from hydroxy, carboxy, halo, and cyano, or isoxazolyl optionally substituted with halo, $C_{1-3}$ haloalkyl, $C_{1-3}$ alkyl, and cyano.

In one embodiment, n is 0. In some embodiments, n is 1, 2, 3, or 4. In some embodiments, n is 1, 2, or 3. In other embodiments, n is 1 or 2. In certain embodiments, n is 1 and the $R^1$ moiety may be located at any position of the phenyl of the quinazolinone ring. In another embodiment, n is 2. Both $R^1$ substituents or moieties may be the same or different. Two $R^1$ moieties may be located at any two positions of the phenyl of the quinazolinone ring. By way of example, the first $R^1$ may be ortho, meta, or para to the second $R^1$. In yet another embodiment, n is 3. All $R^1$ substituents or moieties may be the same or different, or two $R^1$ may be the same and different from the third $R^1$. Three $R^1$ moieties may be located on any three positions of the phenyl of the quinazolinone ring. For example, the first $R^1$ may be ortho to the second $R^1$, and the first $R^1$ may be para to the third $R^1$. In yet another embodiment, n is 4. All $R^1$ substituents may be the same or different, three $R^1$ may be the same and different from the fourth $R^1$, two $R^1$ may be the same and different from the third and the fourth $R^1$.

In some other embodiments, each $R^1$ is independently halo, cyano, optionally substituted $C_{1-6}$ alkyl, optionally substituted $C_{1-6}$ haloalkyl, optionally substituted $C_{1-6}$ alkoxy, hydroxy, optionally substituted amino, optionally substituted $C_{3-6}$ cycloalkyl, optionally substituted $C_{6-10}$ aryl, or optionally substituted $C_{1-6}$ alkylsulfonyl. In certain embodiments, each $R^1$ is independently halo, cyano, optionally substituted $C_{1-4}$ alkyl, optionally substituted $C_{1-4}$ haloalkyl, optionally substituted $C_{1-4}$ alkoxy, optionally substituted $C_{6-10}$ aryl, or amino optionally substituted with $C_{1-4}$ alkyl. In some other embodiments, each $R^1$ is halo, cyano, $C_{1-4}$ haloalkyl, $C_{1-4}$ alkyl, $C_{1-4}$ alkylsulfonyl, —$N(C_{1-4}$ alkyl$)_2$, or $C_{6-10}$ aryl wherein $C_{6-10}$ aryl is optionally substituted with $C_{2-8}$ heterocycloalkyl optionally substituted with $C_{2-4}$ alkyl. In certain embodiments, each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methoxy, ethoxy, propoxy, —$N(CH_3)_2$, or phenyl where phenyl is optionally substituted with pyrrolidinyl, morpholinyl or piperazinyl, each of which is optionally substituted with methyl, ethyl, or propyl. In some embodiments, each $R^1$ is independently fluoro, chloro, bromo, iodo, cyano, methyl, ethyl, difluoromethyl (—$CHF_2$), trifluoromethyl (—$CF_3$), methoxy, —$N(CH_3)_2$, phenyl, or phenyl substituted with pyrrolidinylmethyl, morpholinylmethyl or piperazinyl. In additional embodiments, each $R^1$ is independently halo. In one additional embodiment, each $R^1$ is independently fluoro, chloro, bromo, or iodo. In certain embodiments, each $R^1$ is independently halo, cyano, $C_{1-4}$alkoxy, $C_{1-4}$haloalkyl, $C_{1-4}$alkyl, or $C_{1-4}$ alkenyl. In certain embodiments, each $R^1$ is independently chloro, bromo, fluoro, methyl, difluoromethyl, trifluoromethyl, ethyl, propyl, or cyano. In certain embodiments, each $R^1$ is independently halo, cyano, $C_{1-4}$alkoxy, $C_{1-4}$haloalkyl, $C_{1-4}$alkyl, or $C_{2-4}$ alkenyl.

In one embodiment, m is 0. In some embodiments, m is 1, 2, 3, or 4. In certain embodiment, m is 1, 2 or 3. In certain other embodiment, m is 1 or 2. In the embodiment where m is 1, the $R^2$ substituent or moiety may be located on any position of the ring having the —$(W^3)_qC(O)NH_2$ moiety. For example, the $R^2$ moiety may be in the para-, meta- or ortho-positions relative to the —$(W^3)_qC(O)NH_2$ moiety. In the embodiment where m is 2, both $R^2$ substituents may be the same or different. Two $R^2$ moieties may be located on any two positions of the ring having the —$(W^3)_qC(O)NH_2$ moiety. For example, the first $R^1$ may be ortho to the second $R^1$, and the first $R^1$ may be para to the second $R^1$. In embodiments where m is 3, all three $R^2$ may be the same or different, or two $R^2$ may be the same and different from the third $R^2$. Three $R^2$ moieties may be located on any three positions of the ring having the —$(W^3)_qC(O)NH_2$ moiety. In embodiments where m is 4, all $R^2$ may be the same or different, three $R^2$ may be the same and different from the fourth $R^2$, two $R^2$ may be the same and different from the third and the fourth $R^2$.

In certain embodiments, each $R^2$ is independently halo, cyano, optionally substituted $C_{1-6}$ alkyl, optionally substituted $C_{1-6}$ haloalkyl, optionally substituted $C_{1-6}$ alkoxy, optionally substituted $C_{3-8}$ cycloalkyl, optionally substituted $C_{2-8}$ heterocycloalkyl, optionally substituted $C_{6-10}$ aryl, or optionally substituted $C_{2-8}$ heteroaryl. In some embodiments, each $R^2$ is independently halo, cyano, $C_{1-4}$ alkyl, $C_{1-4}$ haloalkyl, $C_{6-10}$ aryl, or $C_{3-6}$ cycloalkyl. In some other embodiments, each $R^2$ is independently fluoro, chloro, bromo, iodo, methoxy, ethoxy, propoxy, butoxy, —CH$_2$F, —CHF$_2$, —CF$_3$, fluoroethyl, difluoroethyl, methyl, ethyl, propyl, butyl, cyclopropyl, cyclobutyl, cyclopentyl, or cyclohexyl. In one embodiment, each R$^2$ is independently fluoro, chloro, methyl, ethyl, propyl, —CHF$_2$, —CF$_3$, or cyclopropyl. In other embodiments, each R$^2$ is independently halo and C$_{1-4}$ alkyl. In additional embodiments, each R$^2$ is independently fluoro, chloro, bromo, iodo, methyl, ethyl, and propyl. In some other embodiments, each R$^2$ is independently C$_{1-4}$ alkyl. In some additional embodiments, each R$^2$ is independently methyl, ethyl, and propyl. In some other embodiments, each R$^2$ is independently halo. In yet some other embodiments, each R$^2$ is independently fluoro, chloro, bromo, and iodo. In certain embodiments, each R$^2$ is independently chloro, bromo, fluoro, methyl, ethyl, propyl, cyclopropyl, methoxypropyl, methoxyethyl, ethoxypropyl, or ethoxyethyl. In certain embodiments, each R$^2$ is independently halo or C$_{1-4}$alkyl. In certain embodiments, each R$^2$ is independently halo, C$_{1-4}$alkoxy, or C$_{1-4}$alkyl.

C(O)NR6R7

In a further embodiment, q is 0. In some embodiments, q is 1. When q is 1, W$^3$ is CH$_2$ or NH. In certain embodiment, W$^3$ is CH$_2$. In other embodiments, W$^3$ is NH. In the embodiment where q is 0, the —C(O)NR$^6$R$^7$ (e.g. where R$^6$ and R$^7$ are hydrogen, —C(O)NH$_2$ or its equivalent —C(=O)NH$_2$ or —CONH$_2$) moiety may be located on any position of the ring attached to the quinazolinone ring as exemplified below:

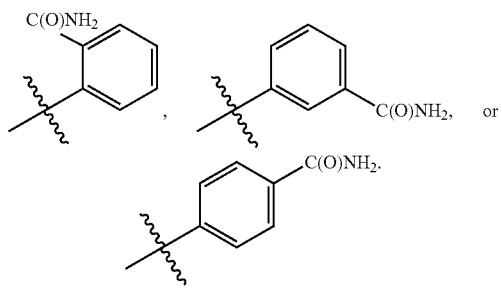

Also, in the embodiment where q is 1 and W$^3$ is NH, the —(NH)C(O)NR$^6$R$^7$ (e.g. where R$^6$ and R$^7$ are hydrogen, —(NH)C(O)NH$_2$ or its equivalent —(NH)C(=O)NH$_2$ or —(NH)CONH$_2$) moiety may be located on any position of the ring attached to the quinazolinone ring as depicted below:

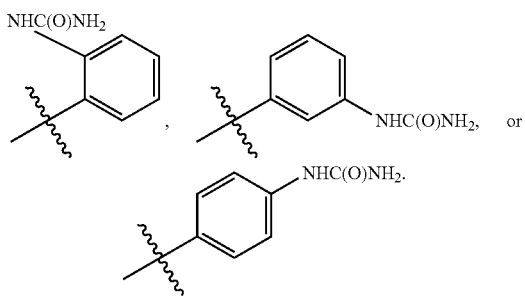

Moreover, in the embodiment where q is 1 and W$^3$ is CH$_2$, the —CH$_2$C(O)NR$^6$R$^7$ (e.g. where R$^6$ and R$^7$ are hydrogen, —CH$_2$C(O)NH$_2$ (or its equivalent —(CH$_2$)C(=O)NH$_2$ or —(CH$_2$)CONH$_2$) moiety may be located on any position of the ring attached to the quinazolinone ring as depicted below:

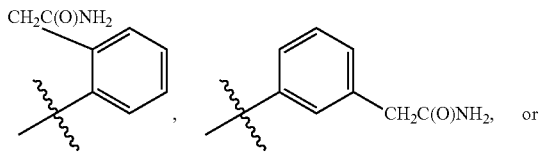

In one embodiment, the —C(O)NR$^6$R$^7$ moiety (e.g. where R$^6$ and R$^7$ are hydrogen, —C(O)NH$_2$) may be located on the ring attached to the quinazolinone ring as exemplified below:

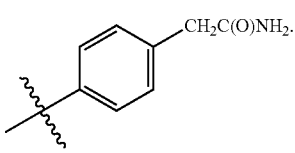

In one embodiment, the —(NH)C(O)NR$^6$R$^7$ moiety (e.g. where R$^6$ and R$^7$ are hydrogen, —NHC(O)NH$_2$) may be located on the ring attached to the quinazolinone ring as exemplified:

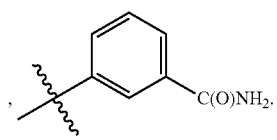

In one embodiment, the —C(O)NR$^6$R$^7$ moiety (e.g. where R$^6$ and R$^7$ are hydrogen, —C(O)NH$_2$) may be located on the ring attached to the quinazolinone ring as exemplified below:

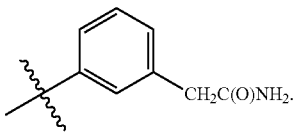

In a further embodiment, q is 0. In some embodiments, q is 1. When q is 1, W$^3$ is CH$_2$ or NH. In certain embodiment, W$^3$ is CH$_2$. In other embodiments, W$^3$ is NH. In the embodiment where q is 0, the —C(O)NH$_2$ (or its equivalent —C(=O)NH$_2$ or —CONH$_2$) moiety may be located on any position of the ring attached to the quinazolinone ring as depicted below:

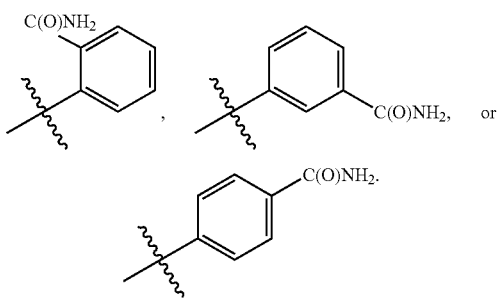

Also, in the embodiment where q is 1 and $W^3$ is NH, the —(NH)C(O)NH$_2$ (or its equivalent —(NH)C(=O)NH$_2$ or —(NH)CONH$_2$) moiety may be located on any position of the ring attached to the quinazolinone ring as depicted below:

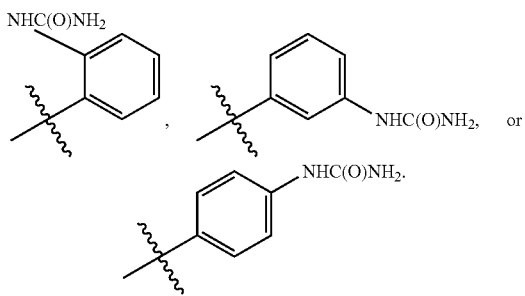

Moreover, in the embodiment where q is 1 and $W^3$ is CH$_2$, the —CH$_2$C(O)NH$_2$ (or its equivalent —(CH$_2$)C(=O)NH$_2$ or —(CH$_2$)CONH$_2$) moiety may be located on any position of the ring attached to the quinazolinone ring as depicted below:

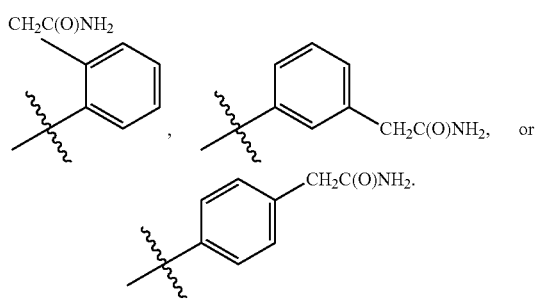

In one embodiment, the —C(O)NH$_2$ moiety may be located on the ring attached to the quinazolinone ring as:

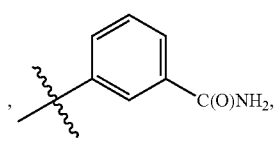

In one embodiment, the —NHC(O)NH$_2$ moiety may be located on the ring attached to the quinazolinone ring as:

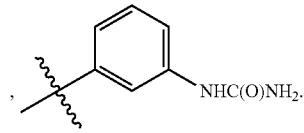

In one embodiment, the —CH$_2$C(O)NH$_2$ moiety may be located on the ring attached to the quinazolinone ring as:

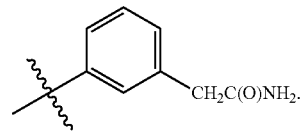

In certain embodiments, $R^3$ is hydrogen, optionally substituted $C_{1-6}$ alkyl, optionally substituted $C_{1-6}$ haloalkyl, optionally substituted $C_{3-8}$ cycloalkyl, or optionally substituted $C_{6-10}$ aryl. In one embodiment, $R^3$ is hydrogen, $C_{3-6}$ cycloalkyl, $C_{1-4}$ alkyl optionally substituted with hydroxy, $C_{6-10}$ aryl$C_{1-4}$ alkoxy, or $C_{3-6}$ cycloalkyl. In some embodiments, $R^3$ is hydrogen, methyl, ethyl, propyl, butyl, cyclopropylmethyl, cyclopentyl, cyclohexyl, —CH$_2$OH, —C$_2$H$_4$OH, —C$_3$H$_6$OH, benzyloxymethyl (i.e. 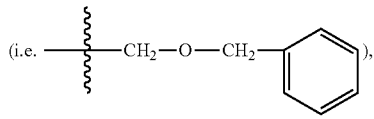), or phenyl (i.e. 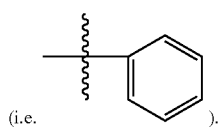).

In other embodiments, $R^3$ is methyl, ethyl, propyl, butyl, cyclopropyl, cyclobutyl, or methyl substituted with phenylmethoxy or methoxy. In one embodiment, $R^3$ is $C_{3-6}$ cycloalkyl or $C_{1-4}$ alkyl. In other embodiments, $R^3$ is methyl, ethyl, propyl, butyl, cyclopropyl, or cyclobutyl. In one embodiment, $R^3$ is $C_{1-4}$ alkyl optionally substituted with $C_{6-10}$ aryl$C_{1-4}$ alkoxy. In other embodiments, $R^3$ is methyl, ethyl, propyl, butyl, cyclopropyl, cyclobutyl, benzyloxymethyl, or phenyl. In certain embodiments, $R^3$ is hydrogen, methyl, ethyl, propyl, butyl, cyclopropyl, cyclobutyl, or phenyl.

In additional embodiments, $R^5$ is hydrogen or optionally substituted $C_{1-6}$ alkyl. In some embodiments, $R^5$ is hydrogen or $C_{1-4}$ alkyl. In certain embodiments, $R^5$ is hydrogen, methyl, ethyl, propyl or butyl. In certain embodiments, $R^5$ is hydrogen, methyl, ethyl, or propyl. In certain other embodiments, $R^5$ is hydrogen.

In further embodiments, $R^3$ and $R^5$ together with the atoms to which they are attached (e.g. carbon and nitrogen, respectively) optionally form a heterocyclic ring which is optionally substituted. In other embodiments, the $R^3$-$R^5$ heterocyclic ring is a three- to eight-membered heterocycloalkyl (i.e. heterocycloalkyl having three to eight ring members and at least one ring member is a heteroatom). In one embodiment, the $R^3$-$R^5$ heterocyclic ring is a five-membered heterocycloalkyl. In one embodiment, the $R^3$-$R^5$ heterocyclic ring is a five-membered heterocycloalkyl optionally having one additional heteroatom selected from N, O, and S. In certain other embodiments, the $R^3$-$R^5$ heterocyclic ring is $C_{2-8}$ heterocycloalkyl. In certain embodiments, $R^5$ and $R^3$ together with the atoms to which they are attached form a 5 membered heterocyclic ring optionally having one additional heteroatom selected from N, O, and S wherein the 5 membered heterocyclic ring is optionally substituted with methoxy, difluoromethoxy, trifluoromethoxy, hydroxy, halo, or methylsulfonylamino. In some other embodiments, the $R^3$-$R^5$ heterocyclic ring is pyrrolidinyl. In some other embodiments, the $R^3$-$R^5$ heterocyclic ring is pyrrolidinyl which is optionally substituted with methoxy, difluoromethoxy, trifluoromethoxy, hydroxy, halo, or methylsulfonylamino. In one other embodiment, the $R^3$-$R^5$ heterocyclic ring is a five-membered heterocycloalkyl substituted with halo. In other additional embodiments, the $R^3$-$R^5$ heterocyclic ring is pyrrolidinyl substituted with fluoro, chloro, bromo, or iodo.

In one embodiment, $R^4$ is heteroaryl optionally substituted with one, two, or three members independently selected from halo, cyano, optionally substituted $C_{1-6}$ alkyl, and —$NH_2$. In one embodiment, $R^4$ heteroaryl having at least two heteroatoms selected from N, O, and S and at least one aromatic ring. In certain embodiments, $R^4$ heteroaryl is a six- to twelve-membered heteroaryl (i.e. heteroaryl having six to twelve ring members). $R^4$ heteroaryl may be a monocyclic or bicyclic heteroaryl. In some embodiments, $R^4$ heteroaryl is a monocyclic heteroaryl having at least two nitrogen atoms. In certain embodiments, $R^4$ heteroaryl is a bicyclic heteroaryl having at least one aromatic ring, at least two nitrogen atoms, and at least one additional heteroatom selected from N, O, or S. In certain other embodiments, $R^4$ heteroaryl is selected from purinyl, pyrimidinyl, thiazolopyrimidinyl, pyridopyrimidinyl, thienopyrimidinyl, pyrrolopyrimidinyl, furopyrimidinyl, or imidazotriazinyl. In some other embodiments, $R^4$ is purinyl or pyrimidinyl. In certain other embodiments, $R^4$ heteroaryl is purinyl, pyrimidinyl, thiazolopyrimidinyl, triazinyl, or imidazotriazinyl.

In some embodiments, $R^4$ is heteroaryl optionally substituted with one, two, or three members independently selected from halo, cyano, —$NH_2$, $C_{1-6}$ alkyl, and $C_{1-6}$ haloalkyl, wherein the $R^4$ heteroaryl is selected from the group consisting of

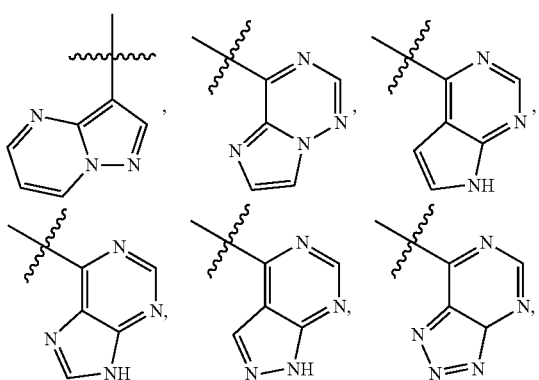

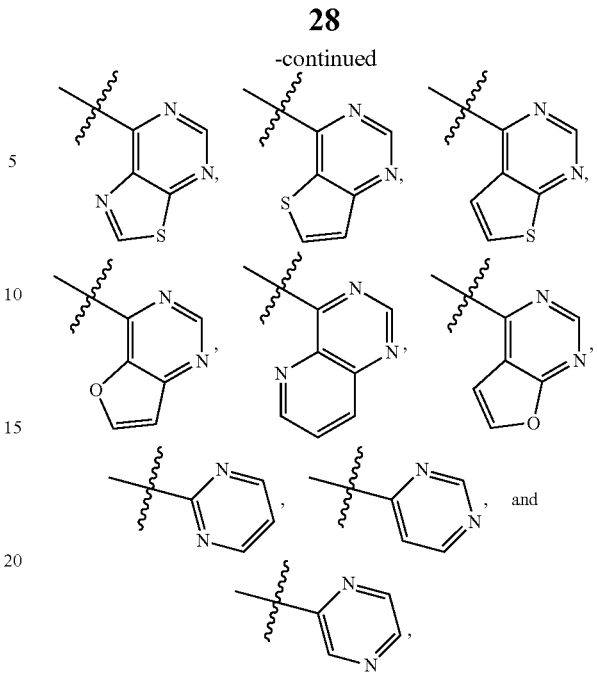

In some other embodiments, $R^4$ is optionally substituted with one to three members independently selected from fluoro, chloro, bromo, iodo, cyano, methyl, ethyl, propyl, fluoromethyl, difluoromethyl, trifluoromethyl, fluoroethyl, difluoroethyl, and —$NH_2$. In one embodiment, $R^4$ is optionally substituted with one member of $C_{2-6}$ alkynyl, wherein $C_{2-6}$ alkynyl is optionally substituted with $C_{4-8}$ heteroaryl optionally substituted with halo. In such embodiment, $R^4$ is optionally substituted with one member of —C≡C— optionally substituted with

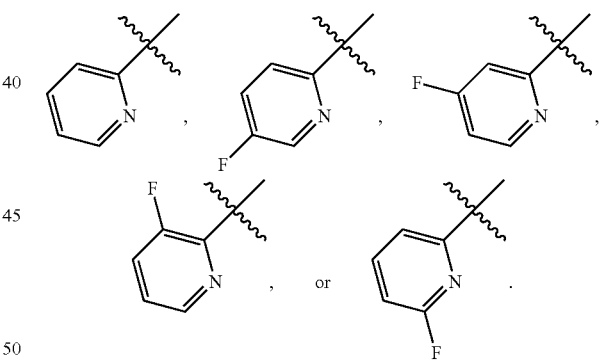

In any of the foregoing formulae, $R^4$ heteroaryl is optionally substituted with $C_{2-6}$ alkynyl optionally substituted with $C_{6-10}$ aryl or $C_{4-8}$ heteroaryl, each of which is optionally substituted with halo or $C_{1-6}$ haloalkyl. In some embodiment, $R^4$ is heteroaryl optionally substituted with one member of $C_{2-6}$ alkynyl substituted with $C_{6-10}$ aryl or $C_{4-8}$ heteroaryl, wherein each of the $C_{6-10}$ aryl or $C_{3-8}$ heteroaryl moieties is optionally substituted with fluoro, chloro, bromo, iodo, fluoromethyl, difluoromethyl, trifluoromethyl, fluoroethyl, difluoroethyl, or trifluoroethyl.

In some other embodiments, $R^4$ heteroaryl is optionally substituted with one to three members independently selected from fluoro, chloro, bromo, iodo, cyano, methyl, ethyl, propyl, fluoromethyl, difluoromethyl, trifluoromethyl, fluoroethyl, difluoroethyl, —N—$H_2$, and —C≡C— optionally substituted with

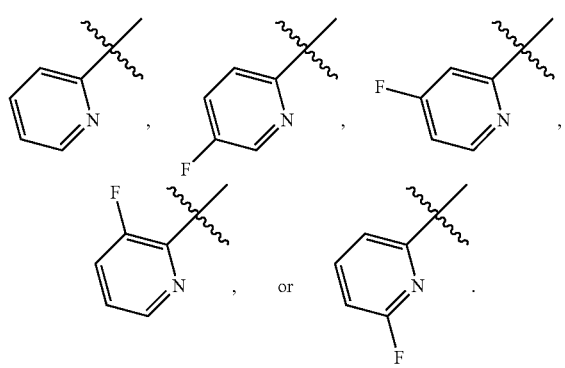

In certain other embodiments, R⁴ is selected from purinyl, pyrimidinyl, thiazolopyrimidinyl, pyridopyrimidinyl, thienopyrimidinyl, pyrrolopyrimidinyl, furopyrimidinyl, and imidazotriazinyl, each of which is optionally substituted with one, two, or three members independently selected from chloro, fluoro, bromo, iodo, methyl, ethyl, propyl, cyano, and —NH₂. In certain other embodiments, R⁴ is selected from thiazolopyrimidinyl, pyridopyrimidinyl, thienopyrimidinyl, pyrrolopyrimidinyl, furopyrimidinyl, and imidazotriazinyl, each of which is optionally substituted with one or two members independently selected from chloro, fluoro, bromo, iodo, methyl, ethyl, propyl, cyano, and —NH₂. In other embodiments, R⁴ is selected from thiazolopyrimidinyl, pyridopyrimidinyl, thienopyrimidinyl, pyrrolopyrimidinyl, furopyrimidinyl, and imidazotriazinyl, each of which is optionally substituted with one member selected from chloro, fluoro, bromo, iodo, methyl, ethyl, propyl, cyano, and —NH₂. In other embodiments, R⁴ is selected from thiazolopyrimidinyl, pyridopyrimidinyl, thienopyrimidinyl, pyrrolopyrimidinyl, furopyrimidinyl, and imidazotriazinyl, each of which is optionally substituted with two members independently selected from chloro, fluoro, bromo, iodo, methyl, ethyl, propyl, cyano, and —NH₂.

In some other embodiments, R⁴ is pyrimidinyl or pyrazinyl and R⁴ is optionally substituted with at least one —NH₂. In certain other embodiments, R⁴ is pyrimidinyl or pyrazinyl, each substituted with two or three members independently selected from chloro, fluoro, bromo, iodo, methyl, ethyl, propyl, cyano, and —NH₂, and at least one of the two or three members is —NH₂.

In certain embodiments, R⁴ is a monocyclic heteroaryl having at least two nitrogen atoms, wherein R⁴ is optionally substituted with two or three members independently selected from bromo, chloro, fluoro, cyano, methyl, ethyl, propyl, difluoromethyl, trifluoromethyl, —NH₂, and alkynyl substituted with a six-membered heteroaryl having 1 or 2 nitrogen atoms, and —NH₂. In certain embodiments, R¹ is pyrimidinyl substituted with two or three members selected from the group consisting of bromo, chloro, fluoro, cyano, methyl, ethyl, propyl, difluoromethyl, pyridin-2-ylethynyl, pyrazin-2-ylethynyl, and —NH₂.

In certain embodiments, R⁴ is a monocyclic heteroaryl having at least two nitrogen atoms, wherein R⁴ is optionally substituted with two or three groups which are independently bromo, chloro, fluoro, cyano, methyl, ethyl, propyl, difluoromethyl, trifluoromethyl, alkynyl substituted with a six-membered heteroaryl having 1 or 2 nitrogen atoms, or —NH₂. In certain embodiments, R⁴ is pyrimidinyl substituted with two or three groups independently selected from bromo, chloro, fluoro, cyano, methyl, ethyl, propyl, difluoromethyl, pyridin-2-ylethynyl, pyrazin-2-ylethynyl, or —NH₂.

In certain embodiments, R⁴ is purinyl, pyrimidinyl, thiazolopyrimidinyl, triazinyl, or imidazotriazinyl, wherein the pyrimidinyl and triazinyl are each optionally substituted with 1, 2, or 3 groups which are independently nitro, carboxy, fluoro, chloro, bromo, iodo, cyano, methyl, ethyl, propyl, fluoromethyl, difluoromethyl, trifluoromethyl, fluoroethyl, difluoroethyl, —NH₂, or —C≡C optionally substituted with a

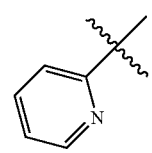

In certain embodiments, R⁴ is

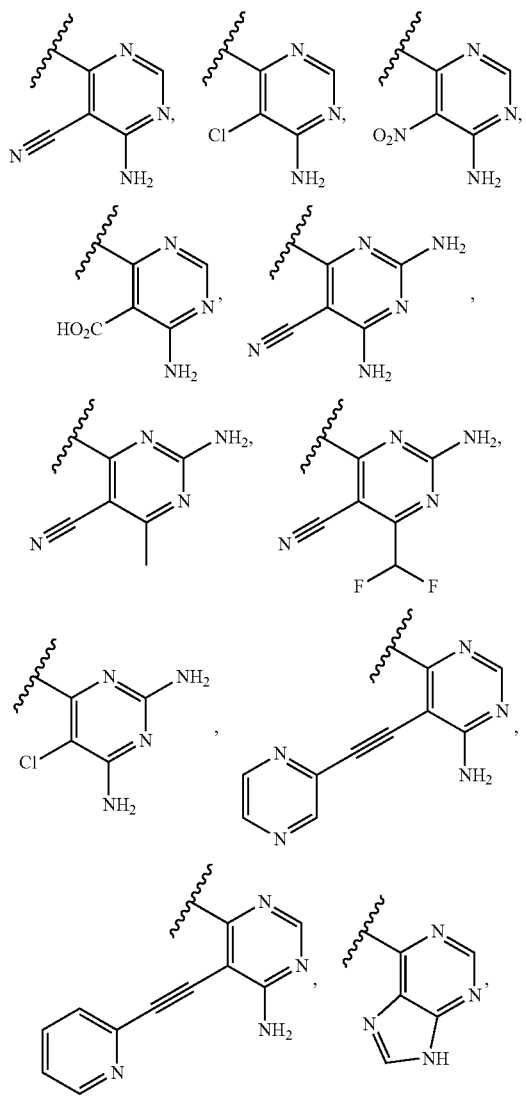

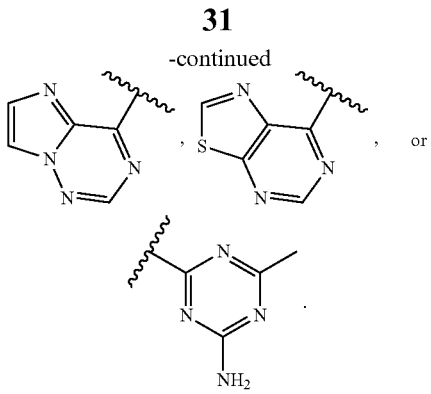

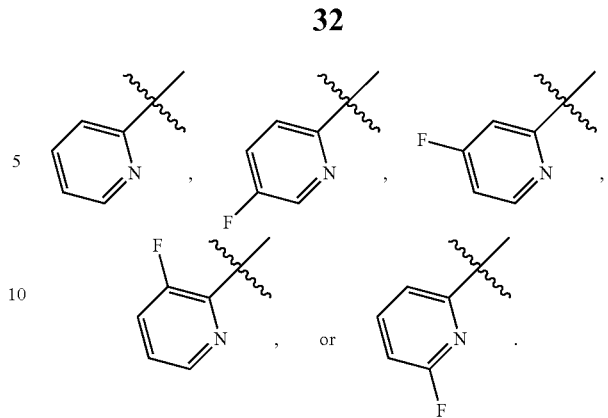

In certain embodiments, $R^4$ is purinyl, pyrimidinyl, thiazolopyrimidinyl, triazinyl, or imidazotriazinyl, wherein the pyrimidinyl and triazinyl are each optionally substituted with 1, 2, or 3 members selected from nitro, carboxy, fluoro, chloro, bromo, iodo, cyano, methyl, ethyl, propyl, fluoromethyl, difluoromethyl, trifluoromethyl, fluoroethyl, difluoroethyl, or —NH$_2$.

In certain embodiments, $R^4$ is

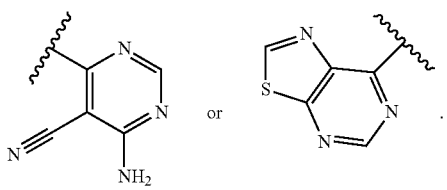 [SMILES: *c1ncnc(N)c1C#N ; *c1ncnc2scnc12]

In some embodiments, $R^w$ is hydrogen, halo, or optionally substituted $C_{1-6}$ alkyl. In some embodiments, $R^w$ is hydrogen, fluoro, chloro, methyl, ethyl, or propyl. In certain embodiments, $R^w$ is hydrogen. In other embodiments, $R^w$ is fluoro or chloro. In certain other embodiments, $W^1$ is C(R$^w$) wherein $R^w$ is hydrogen. In yet other embodiments, $W^1$ is N. In some other embodiments, $W^2$ is C(R wherein $R^w$ is hydrogen. In additional embodiments, $W^2$ is N. In some additional embodiments, $W^1$ is N and $W^2$ is CH. In yet additional embodiments, $W^1$ is N and $W^2$ is N. In additional embodiments, $W^1$ is CH and $W^2$ is CH. In yet additional embodiments, $W^1$ is CH and $W^2$ is N. Each and every variation of $W^1$ may be combined with each and every variation of n, m, q, $W^2$, $W^3$, $R^w$, A, A', $R^1$, $R^2$, $R^3$, $R^4$, $R^5$, $R^6$, and $R^7$ as described above.

In one embodiment, p is 0. In some embodiments, p is 1 or 2. In some other embodiments, p is 1, 2, or 3. In certain embodiments, p is 0, 1, 2, or 3. In some embodiments where p is 1, $R^{4a}$ moiety may be located of any position of the ring. In other embodiments where p is 2, both $R^{4a}$ substituents or moieties may be the same or different. In another embodiment where p is 3, all three $R^{4a}$ substituents or moieties may be the same or different. In some another embodiment where p is 3, two $R^{4a}$ substituents or moieties may be the same or differ from the third $R^4$ substituent.

In the present application, $R^{4a}$ is independently selected from halo, cyano, optionally substituted $C_{1-6}$ alkyl, —NH$_2$, and optionally substituted $C_{1-6}$ alkynyl. In some embodiments, $R^{4a}$ is independently selected from bromo, chloro, fluoro, cyano, methyl, ethyl, propyl, —NH$_2$, and —C≡C optionally substituted with In some embodiments where the compounds having the structure of formulae (Ib), p is 2 or 3, and each $R^{4a}$ is independently selected from halo, cyano, $C_{1-6}$ alkyl, and —NH$_2$. In some embodiments, $R^{4a}$ is independently selected from bromo, chloro, fluoro, cyano, methyl, ethyl, propyl, and —NH$_2$. Each and every variation of p and $R^{4a}$ may be combined with each and every variation of n, m, $R^1$, $R^2$, $R^3$, and $R^5$ as described above.

In certain embodiments, $R^7$ is hydrogen.

In certain embodiments, $R^6$ is hydrogen, optionally substituted $C_{1-6}$ alkyl, optionally substituted $C_{1-6}$ heteroalkyl, optionally substituted $C_{1-6}$ alkoxy, optionally substituted $C_{1-6}$ haloalkyl, optionally substituted $C_{1-6}$ alkylsulfonyl, optionally substituted $C_{3-10}$ cycloalkyl, optionally substituted $C_{2-8}$ heterocycloalkyl, optionally substituted $C_{6-10}$ aryl, optionally substituted $C_{5-8}$ heteroaryl. In some embodiments, $R^6$ is hydrogen, $C_{1-6}$ alkyl, $C_{1-6}$ heteroalkyl, $C_{1-6}$ alkoxy which is optionally substituted with —OH or —COOH, $C_{1-6}$ haloalkyl, $C_{1-6}$ alkylsulfonyl which is optionally substituted with halo, $C_{3-8}$ cycloalkyl, $C_{2-8}$ heterocycloalkyl, $C_{6-10}$ aryl which is optionally substituted with halo, $C_{1-6}$ haloalkyl, $C_{1-6}$ alkyl, $C_{1-6}$ alkoxy, —COOH, cyano, —SO$_2$R where R is hydroxyl or $C_{1-6}$ alkyl, $C_{1-6}$ alkoxy where $C_{1-6}$ alkoxy is optionally substituted with $C_{1-6}$ alkoxy, or $C_{5-8}$ heteroaryl optionally substituted with $C_{1-6}$ alkyl. In other embodiments, $R^6$ is hydrogen, —(CH$_2$)$_2$NHCH$_3$, —(CH$_2$)$_2$NHCH$_2$CH$_3$, —CH$_2$NHCH$_3$, —(CH$_2$)$_3$NHCH$_3$, methoxy, —OCH$_2$COOH, —O(CH$_2$)$_2$H, fluoromethyl, difluoromethyl, trifluoromethyl, fluoroethyl, difluoroethyl, trifluoroethyl, methoxyethyl, fluoroethyl, —SO$_2$CH$_3$, cyclopentanylsulfonyl, cyclopropylsulfonyl, cyclohexyl, cyclopentyl, cyclobutyl, cyclopropyl, dioxolanyl, phenyl, phenyl which is substituted with fluoro, chloro, bromo, iodo, fluoromethyl, difluoromethyl, trifluoromethyl, fluoroethyl, difluoroethyl, trifluoroethyl, methyl, ethyl, propyl, methoxy, ethoxy, COOH, cyano, —SO$_2$CH$_3$, —OCH$_2$OCH$_3$, —OCH$_2$OCH$_2$CH$_3$, —OCH$_2$CH$_2$OCH$_3$, or —OCH$_2$CH$_2$OCH$_2$CH$_3$, pyridinyl, tetrazolyl, or isoxazolyl w/ butyl. In some other embodiments, $R^6$ is hydrogen, —(CH$_2$)$_2$NHCH$_3$, methoxy, —OCH$_3$COOH, —O(CH$_2$)$_2$OH, trifluoromethyl, difluoroethyl, trifluoroethyl, methoxyethyl, fluoroethyl, cyclopentyl, cyclopropyl, —SO$_2$CH$_3$, cyclopentyl, cyclohexyl, cyclobutyl, cyclopropyl, dioxolanyl, phenyl, phenyl w/ chloro, phenyl, phenyl substituted with fluoro, chloro, trifluoromethyl, methyl, methoxy, COOH, cyano, —O(CH$_2$)$_2$OH, —OCH$_2$OCH$_2$CH$_2$CH$_3$, pyridinyl, tetrazolyl, or isoxazolyl w/ butyl.

In certain embodiments, $R^6$ is hydrogen, optionally substituted alkyl, optionally substituted alkoxy, optionally substituted haloalkyl, optionally substituted sulfonyl, optionally substituted cycloalkyl, optionally substituted aryl, or optionally substituted heteroaryl. In certain embodiments, $R^6$ is optionally substituted $C_{1-6}$ alkyl, optionally substituted $C_{1-6}$ alkoxy, optionally substituted $C_{1-6}$ haloalkyl, optionally substituted $C_{1-6}$ alkyl sulfonyl, optionally substituted $C_{3-8}$ cycloalkyl sulfonyl, optionally substituted $C_{6-10}$ aryl sulfonyl, optionally substituted $C_{3-8}$ cycloalkyl, optionally substituted $C_{6-10}$ aryl, or optionally substituted $C_{5-8}$ heteroaryl. In certain embodiments, $R^6$ is optionally substituted $C_{1-6}$ alkyl, $C_{1-6}$ alkoxy, optionally substituted $C_{1-6}$ haloalkyl, $C_{1-6}$ alkyl sulfonyl, cyclopropyl sulfonyl, cyclobutyl sulfonyl, cyclopentyl sulfonyl, cyclohexyl sulfonyl, optionally substituted phenyl sulfonyl, optionally substituted cyclopropyl, optionally substituted cyclobutyl, optionally substituted cyclopentyl, optionally substituted cyclohexyl, optionally substituted phenyl, optionally substituted pyridinyl, optionally substituted isoxazolyl, or optionally substituted tetrazolyl.

In certain embodiments, $R^6$ is hydrogen; $C_{1-6}$ alkyl optionally substituted with 1, 2, or 3 groups which are independently hydroxy, $C_{1-6}$ alkoxy, carboxy, amino, or $C_{3-6}$ heterocycloalkyl; $C_{1-6}$ alkoxy; $C_{1-6}$ haloalkyl; $C_{1-6}$ alkyl sulfonyl; cyclopropyl sulfonyl; cyclobutyl sulfonyl; cyclopentyl sulfonyl; cyclohexyl sulfonyl; phenyl sulfonyl wherein the phenyl is optionally substituted with 1, 2, or 3 groups which are independently halo, $C_{1-6}$alkyl, amino, or cyano; cyclopropyl optionally substituted with 1, 2, or 3 groups which are independently halo, $C_{1-6}$ haloalkyl, carboxy, or hydroxyl; cyclobutyl optionally substituted with 1, 2, or 3 groups which are independently halo, $C_{1-6}$ haloalkyl, carboxy, or hydroxyl; cyclopentyl optionally substituted with 1, 2, or 3 groups which are independently halo, $C_{1-6}$ haloalkyl, carboxy, or hydroxyl; cyclohexyl optionally substituted with 1, 2, or 3 groups which are independently halo, $C_{1-6}$ haloalkyl, carboxy, or hydroxyl; phenyl optionally substituted with 1, 2, or 3 groups which are independently carboxy, halo, $C_{1-3}$ haloalkyl, $C_{1-3}$ alkyl, cyano, $-S(O)_2OH$, $-S(O)_2CH_3$, or $C_{1-3}$ alkoxy optionally substituted with 1, 2, or 3 groups which are independently hydroxy, carboxy, halo, or cyano; pyridinyl optionally substituted with 1, 2, or 3 groups which are independently halo, $C_{1-3}$ haloalkyl, $C_{1-3}$ alkyl, or cyano; isoxazolyl optionally substituted 1, 2, or 3 groups which are independently halo, $C_{1-3}$ haloalkyl, $C_{1-3}$ alkyl, or cyano; or tetrazolyl.

In other embodiments, $R^1$ is hydrogen, methyl, ethyl, propyl, butyl, (1,3-dioxolanyl)methyl, (dimethylamino)ethyl, hydroxyethyl, carboxyethyl, fluoroethyl, difluoroethyl, methoxyethyl, trifluoroethyl, hydroxymethylpropanyl, carboxypropanyl, hydroxypropyl, methoxy propyl, pentafluoropropyl, hydroxydimethylpropyl, hydroxymethylbutyl, hydroxy-methylbutanyl, methoxy, $SO_2CH_3$, cyclopentanylsulfonyl, cyclopropylsulfonyl, fluorophenylsulfonyl, cyclohexyl, cyclopentyl, cyclobutyl, cyclopropyl, (trifluoromethyl)cyclopropyl, pyridinyl, trifluoromethylpyridinyl, tetrazolyl, (trifluoromethyl)isoxazolyl, (trifluoromethyl)isoxazolyl, phenyl, carboxyphenyl, sulfinophenyl, (carboxyethoxy)phenyl, chloro(trifluoromethyl)phenyl, trifluoromethylphenyl, dichlorophenyl, difluorophenyl, cyanophenyl, (hydroxyethoxy)phenyl, (methylsulfonyl)phenyl, methylphenyl, chlorophenyl, or methoxyphenyl.

In other embodiments, $R^6$ is hydrogen, methyl, ethyl, propyl, butyl, (1,3-dioxolan-2-yl)methyl, 2-(dimethylamino)ethyl, 2-hydroxyethyl, 2-carboxyethyl, 2-fluoroethyl, 2,2-difluoroethyl, 2-methoxyethyl, 2,2,2-trifluoroethyl, 1-hydroxy-2-methylpropan-2-yl, 2-carboxypropan-2-yl, 2-hydroxypropyl, 3-hydroxypropyl, 3-methoxy propyl, 2,2,3,3,3-pentafluoropropyl, 3-hydroxy-2,2-dimethylpropyl, 3-hydroxy-3-methylbutyl, 4-hydroxy-2-methylbutan-2-yl, methoxy, $SO_2CH_3$, cyclopentanylsulfonyl, cyclopropylsulfonyl, 4-fluorophenylsulfonyl, cyclohexyl, cyclopentyl, cyclobutyl, cyclopropyl, 1-(trifluoromethyl)cyclopropyl, pyridin-3-yl, 2-trifluoromethylpyridin-3-yl, tetrazolyl, 3-(trifluoromethyl)isoxazol-5-yl, 5-(trifluoromethyl)isoxazol-3-yl, phenyl, 2-carboxyphenyl, 2-sulfinophenyl, 2-(2-carboxyethoxy)phenyl, 4-chloro-3-(trifluoromethyl)phenyl, 2-trifluoromethylphenyl, 2,6-dichlorophenyl, 2,4-difluorophenyl, 2-cyanophenyl, 2-(2-hydroxyethoxy)phenyl, 2-(methylsulfonyl)phenyl, 2-methylphenyl, 2-chlorophenyl, or 2-methoxyphenyl. In certain embodiments, $R^6$ is $C_{1-6}$ alkyl optionally substituted with 1, 2, or 3 groups which are independently hydroxy, $C_{1-6}$ alkoxy, or $C_{3-6}$ heterocycloalkyl; $C_{1-6}$ alkoxy, $C_{1-6}$ haloalkyl, cyclopropyl optionally substituted with 1, 2, or 3 groups which are independently halo, $C_{1-6}$ haloalkyl, carboxy, or hydroxy; cyclobutyl optionally substituted with 1, 2, or 3 groups which are independently halo, $C_{1-6}$ haloalkyl, carboxy, or hydroxy; cyclopentyl optionally substituted with 1, 2, or 3 groups which are independently halo, $C_{1-6}$ haloalkyl, carboxy, or hydroxy cyclohexyl optionally substituted with 1, 2, or 3 groups which are independently halo, $C_{1-6}$ haloalkyl, carboxy, or hydroxy; phenyl optionally substituted with 1, 2, or 3 groups which are independently carboxy, halo, $C_{1-3}$ haloalkyl, $C_{1-3}$ alkyl, cyano, $-S(O)_2OH$, $-S(O)_2CH_3$, or $C_{1-3}$ alkoxy optionally substituted with 1, 2, or 3 groups which are independently hydroxy, carboxy, halo, or cyano; or isoxazolyl optionally substituted with halo, $C_{1-3}$ haloalkyl, $C_{1-3}$ alkyl, or cyano.

It is understood that for each formula described herein (e.g. formulae (J), (Ja), (Jb), (I), (Ia), (Ib), (II), and (III)) the variables described herein may be combined with any other variable described herein.

The compounds of the present application may bear one or more chiral centers. The compounds 3-(5-chloro-2-(1-((2,6-diamino-5-cyanopyrimidin-4-yl)amino)ethyl)-4-oxoquinazolin-3(4H)-yl)benzamide bearing the chiral center have the same molecular formula and the same chemical name with different stereoisomer designations. For example, the below bearing one chiral center can be resolved into the (S) and (R) enantiomers: (S)-3-(5-chloro-2-(1-((2,6-diamino-5-cyanopyrimidin-4-yl)amino)ethyl)-4-oxoquinazolin-3(4H)-yl)benzamide and (R)-3-(5-chloro-2-(1-((2,6-diamino-5-cyanopyrimidin-4-yl)amino)ethyl)-4-oxoquinazolin-3(4H)-yl)benzamide.

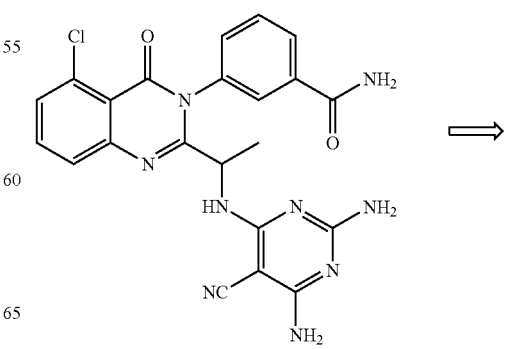

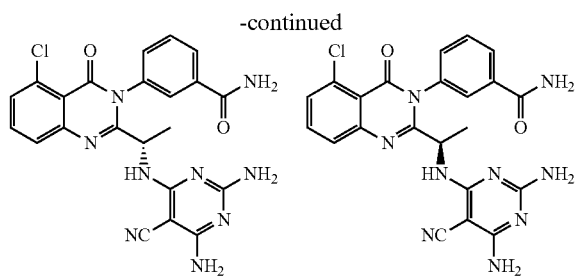

Representative compounds of the present application are listed in Table 1 below. Representative compounds also include any of Compounds 1-164. The compounds may be named using the nomenclature systems and symbols that are commonly recognized in the art of chemistry including, for example, ChemBioDraw Ultra 12.0, Chemical Abstract Service (CAS), and International Union of Pure and Applied Chemistry (IUPAC). For example, compound 1 in table 1 may be named as 3-[5-chloro-2-[(1S)-1-[(2,6-diamino-5-chloropyrimidin-4-yl)amino]ethyl]-4-oxo-quinazolin-3-yl] benzamide or (S)-3-(5-chloro-2-(1-((2,6-diamino-5-chloro-pyrimidin-4-yl)amino)ethyl)-4-oxoquinazolin-3(4H)-yl) benzamide, using IUPAC or ChemBioDraw Ultra 12.0, respectively.

TABLE 1

Representative Compounds

| compound | Structure | Name |
|---|---|---|
| 1 | 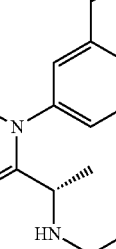 | (S)-3-(5-chloro-2-(1-((2,6-diamino-5-chloropyrimidin-4-yl)amino)ethyl)-4-oxoquinazolin-3(4H)-yl)benzamide |
| 2 | 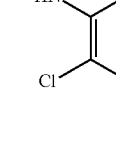 | (S)-3-(5-chloro-2-(1-((2,6-diamino-5-cyanopyrimidin-4-yl)amino)ethyl)-4-oxoquinazolin-3(4H)-yl)benzamide |
| 3 | 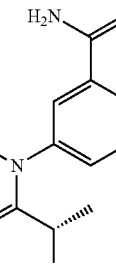 | (S)-3-(5,8-dichloro-2-(1-((2,6-diamino-5-cyanopyrimidin-4-yl)amino)ethyl)-4-oxoquinazolin-3(4H)-yl)benzamide |

TABLE 1-continued

Representative Compounds

| compound | Structure | Name |
|---|---|---|
| 4 | 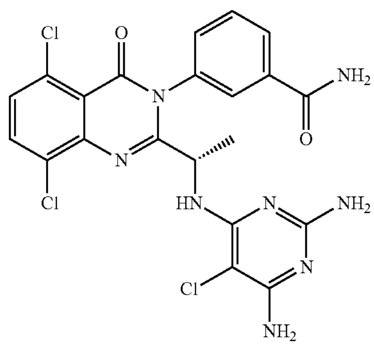 [SMILES: C[C@H](Nc1nc(N)nc(N)c1Cl)c1nc2c(Cl)ccc(Cl)c2c(=O)n1-c1cccc(C(N)=O)c1] | (S)-3-(5,8-dichloro-2-(1-((2,6-diamino-5-chloropyrimidin-4-yl)amino)ethyl)-4-oxoquinazolin-3(4H)-yl)benzamide |
| 5 | 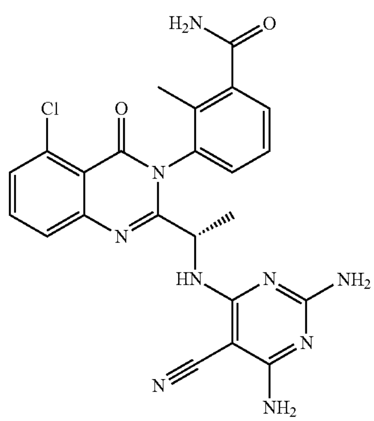 [SMILES: Cc1c(C(N)=O)cccc1-n1c([C@H](C)Nc2nc(N)nc(N)c2C#N)nc2cccc(Cl)c2c1=O] | (S)-3-(5-chloro-2-(1-((2,6-diamino-5-cyanopyrimidin-4-yl)amino)ethyl)-4-oxoquinazolin-3(4H)-yl)-2-methylbenzamide |
| 6 | 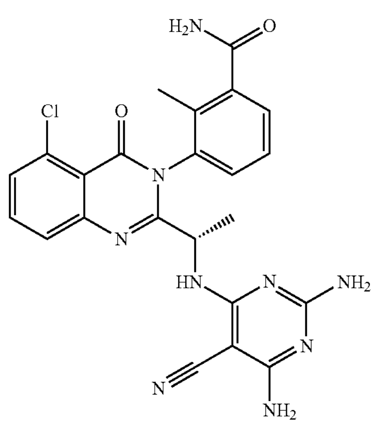 [SMILES: Cc1c(C(N)=O)cccc1-n1c([C@H](C)Nc2nc(N)nc(N)c2C#N)nc2cccc(Cl)c2c1=O] | (S)-3-(5-chloro-2-(1-((2,6-diamino-5-cyanopyrimidin-4-yl)amino)ethyl)-4-oxoquinazolin-3(4H)-yl)-2-methylbenzamide |

TABLE 1-continued
Representative Compounds
| compound | Structure | Name |
|---|---|---|
| 7 | 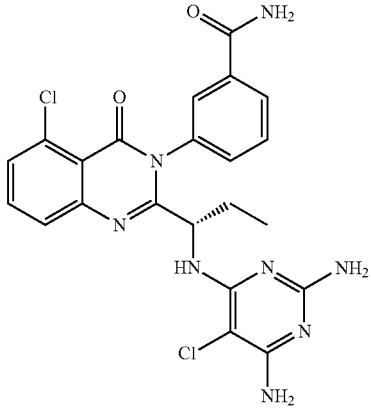 [SMILES: CC[C@H](Nc1nc(N)nc(N)c1Cl)c1nc2cccc(Cl)c2c(=O)n1-c1cccc(C(N)=O)c1] | (S)-3-(5-chloro-2-(1-((2,6-diamino-5-chloropyrimidin-4-yl)amino)propyl)-4-oxoquinazolin-3(4H)-yl)benzamide |
| 8 | 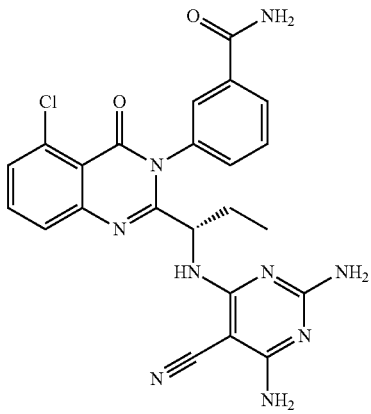 [SMILES: CC[C@H](Nc1nc(N)nc(N)c1C#N)c1nc2cccc(Cl)c2c(=O)n1-c1cccc(C(N)=O)c1] | (S)-3-(5-chloro)-2-(1-((2,6-diamino-5-cyanopyrimidin-4-yl)amino)propyl)-4-oxoquinazolin-3(4H)-yl)benzamide |
| 9 | 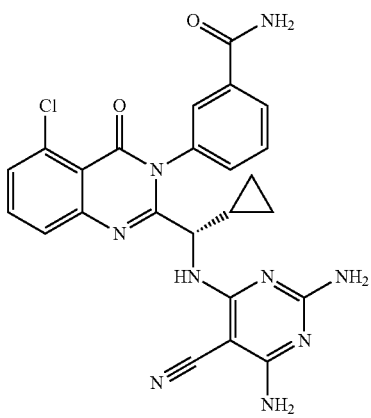 [SMILES: N#Cc1c(N)nc(N)nc1N[C@H](c1nc2cccc(Cl)c2c(=O)n1-c1cccc(C(N)=O)c1)C1CC1] | (S)-3-(5-chloro-2-(cyclopropyl((2,6-diamino-5-cyanopyrimidin-4-yl)amino)methyl)-4-oxoquinazolin-3(4H)-yl)benzamide |

TABLE 1-continued
Representative Compounds
| compound | Structure | Name |
|---|---|---|
| 10 | 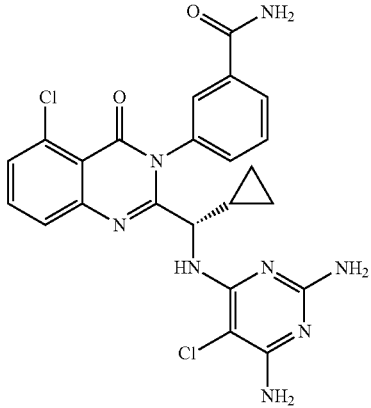 [SMILES: NC(=O)c1cccc(-n2c([C@@H](Nc3nc(N)nc(N)c3Cl)C3CC3)nc3cccc(Cl)c3c2=O)c1] | (S)-3-(5-chloro-2-(cyclopropyl((2,6-diamino-5-chloropyrimidin-4-yl)amino)methyl)-4-oxoquinazolin-3(4H)-yl)benzamide |
| 11 | 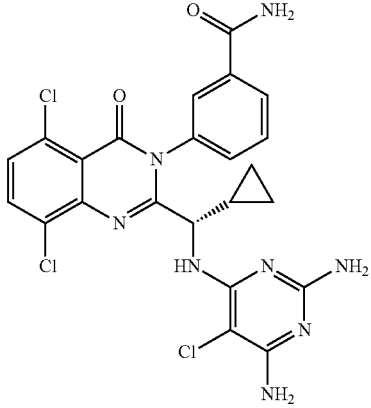 [SMILES: NC(=O)c1cccc(-n2c([C@@H](Nc3nc(N)nc(N)c3Cl)C3CC3)nc3c(Cl)ccc(Cl)c3c2=O)c1] | (S)-3-(5,8-dichloro-2-(cyclopropyl((2,6-diamino-5-chloropyrimidin-4-yl)amino)methyl)-4-oxoquinazolin-3(4H)-yl)benzamide |
| 12 | 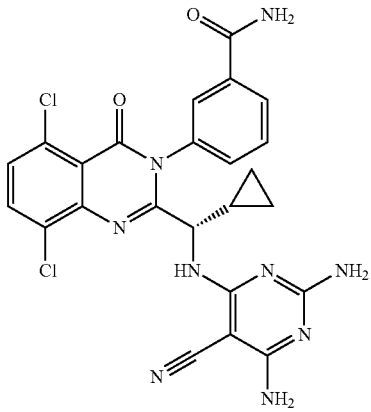 [SMILES: N#Cc1c(N)nc(N)nc1N[C@H](c1nc2c(Cl)ccc(Cl)c2c(=O)n1-c1cccc(C(N)=O)c1)C1CC1] | (S)-3-(5,8-dichloro-2-(cyclopropyl((2,6-diamino-5-cyanopyrimidin-4-yl)amino)methyl)-4-oxoquinazolin-3(4H)-yl)benzamide |

TABLE 1-continued

Representative Compounds

| compound | Structure | Name |
|---|---|---|
| 13 | 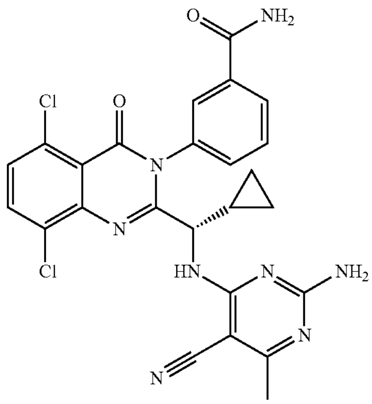 [SMILES: Cc1nc(N)nc(N[C@H](c2nc3c(Cl)ccc(Cl)c3c(=O)n2-c2cccc(C(N)=O)c2)C2CC2)c1C#N] | (S)-3-(2-(((2-amino-5-cyano-6-methylpyrimidin-4-yl)amino)(cyclopropyl)methyl)-5,8-dichloro-4-oxoquinazolin-3(4H)-yl)benzamide |
| 14 | 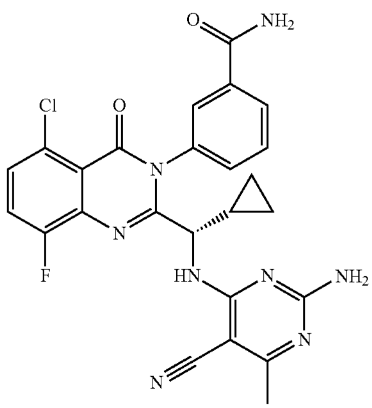 [SMILES: Cc1nc(N)nc(N[C@H](c2nc3c(F)ccc(Cl)c3c(=O)n2-c2cccc(C(N)=O)c2)C2CC2)c1C#N] | (S)-3-(2-(((2-amino-5-cyano-6-methypyrimidin-4-yl)amino)(cyclopropyl)methyl)-5-chloro-8-fluoro-4-oxoquinazolin-3(4H)-yl)benzamide |
| 15 | 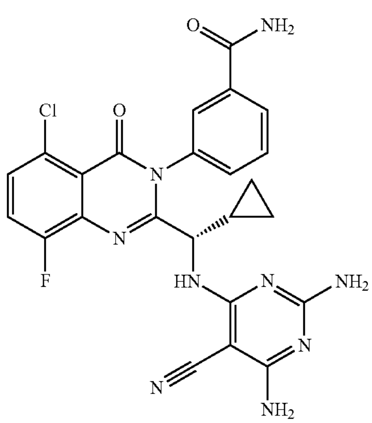 [SMILES: N#Cc1c(N)nc(N)nc1N[C@H](c1nc2c(F)ccc(Cl)c2c(=O)n1-c1cccc(C(N)=O)c1)C1CC1] | (S)-3-(5-chloro-2-(cyclopropyl((2,6-diamino-5-cyanopyrimidin-4-yl)amino)methyl)-8-fluoro-4-oxoquinazolin-3(4H)-yl)benzamide |

TABLE 1-continued

Representative Compounds

| compound | Structure | Name |
|---|---|---|
| 16 | 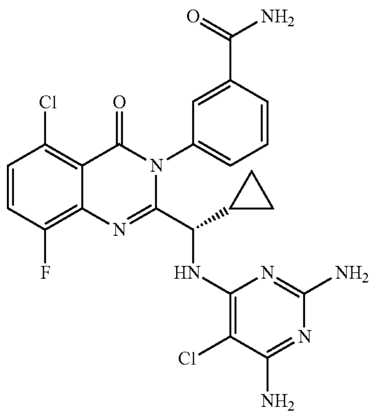 [SMILES: NC(=O)c1cccc(-n2c([C@@H](Nc3nc(N)nc(N)c3Cl)C3CC3)nc3c(F)ccc(Cl)c3c2=O)c1] | (S)-3-(5-chloro-2-(cyclopropyl((2,6-diamino-5-chloropyrimidin-4-yl)amino)methyl)-8-fluoro-4-oxoquinazolin-3(4H)-yl)benzamide |
| 17 | 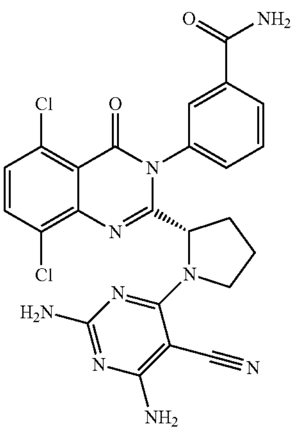 | (S)-3-(5,8-dichloro-2-(1-(2,6-diamino-5-cyanopyrimidin-4-yl)pyrrolidin-2-yl)-4-oxoquinazolin-3(4H)-yl)benzamide |
| 18 | 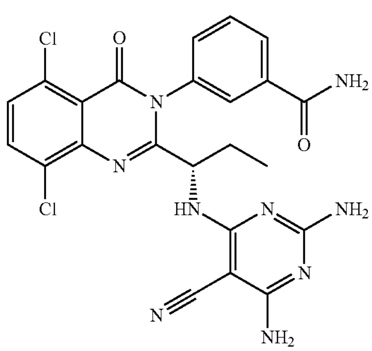 [SMILES: CC[C@H](Nc1nc(N)nc(N)c1C#N)c1nc2c(Cl)ccc(Cl)c2c(=O)n1-c1cccc(C(N)=O)c1] | (S)-3-(5,8-dichloro-2-(1-((2,6-diamino-5-cyanopyrimidin-4-yl)amino)propyl)-4-oxoquinazolin-3(4H)-yl)benzamide |
| 19 | 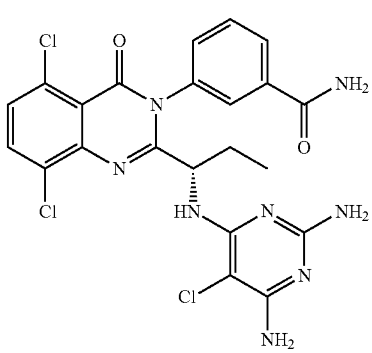 [SMILES: CC[C@H](Nc1nc(N)nc(N)c1Cl)c1nc2c(Cl)ccc(Cl)c2c(=O)n1-c1cccc(C(N)=O)c1] | (S)-3-(5,8-dichloro-2-(1-((2,6-diamino-5-chloropyrimidin-4-yl)amino)propyl)-4-oxoquinazolin-3(4H)-yl)benzamide |

TABLE 1-continued

Representative Compounds

| compound | Structure | Name |
|---|---|---|
| 20 | 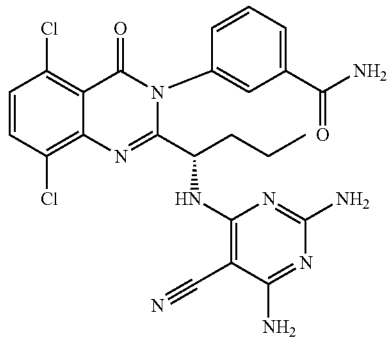 [SMILES: CCC[C@H](Nc1nc(N)nc(N)c1C#N)c1nc2c(Cl)ccc(Cl)c2c(=O)n1-c1cccc(C(N)=O)c1] | (S)-3-(5,8-dichloro-2-(1-((2,6-diamino-5-cyanopyrimidin-4-yl)amino)butyl)-4-oxoquinazolin-3(4H)-yl)benzamide |
| 21 | 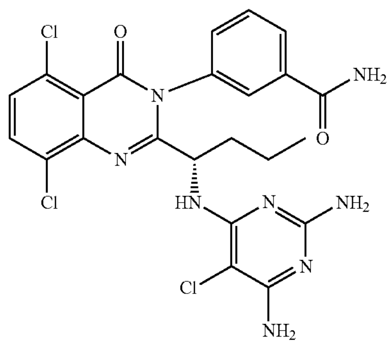 [SMILES: CCC[C@H](Nc1nc(N)nc(N)c1Cl)c1nc2c(Cl)ccc(Cl)c2c(=O)n1-c1cccc(C(N)=O)c1] | (S)-3-(5,8-dichloro-2-(1-((2,6-diamino-5-chloropyrimidin-4-yl)amino)butyl)-4-oxoquinazolin-3(4H)-yl)benzamide |
| 22 | 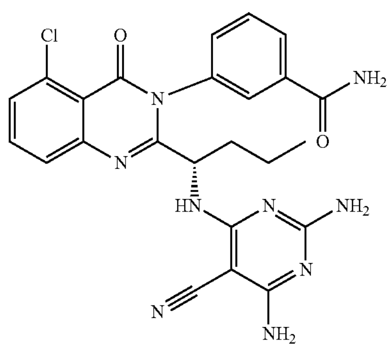 [SMILES: CCC[C@H](Nc1nc(N)nc(N)c1C#N)c1nc2cccc(Cl)c2c(=O)n1-c1cccc(C(N)=O)c1] | (S)-3-(5-chloro-2-(1-((2,6-diamino-5-cyanopyrimidin-4-yl)amino)butyl)-4-oxoquinazolin-3(4H)-yl)benzamide |
| 23 | 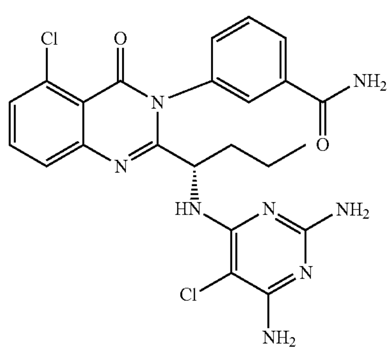 [SMILES: CCC[C@H](Nc1nc(N)nc(N)c1Cl)c1nc2cccc(Cl)c2c(=O)n1-c1cccc(C(N)=O)c1] | (S)-3-(5-chloro-2-(1-((2,6-diamino-5-chloropyrimidin-4-yl)amino)butyl)-4-oxoquinazolin-3(4H)-yl)benzamide |

Compounds of the present application also include any one of Compounds 1-164 or a pharmaceutically acceptable salt thereof, as described herein.

The present application provides pharmaceutically acceptable salts, hydrates, solvates, isomers, tautomers, stereoisomers, enantiomers, racemates, atropisomers, polymorphs, prodrugs, or a mixture thereof, of the compounds described herein. In addition, the present application provides the compounds in which from 1 to n hydrogen atoms attached to a carbon atom may be replaced by a deuterium atom or D, in which n is the number of hydrogen atoms in the molecule. It is known that the deuterium atom is a non-radioactive isotope of the hydrogen atom. Such compounds may increase resistance to metabolism, and thus may be useful for increasing the half-life of the compounds of any of the formulae described herein or pharmaceutically acceptable salts, isomers, prodrugs, or solvates thereof, when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

The terms "a compound of the present application," "a compound described herein," "a compound of any of the formulae described herein," or variant thereof refer to a compound having the structure of any of the foregoing formulae (J), (Ja), (I), (II), (III), (Ia), and (Ib), including at least any one of Compounds 1-164 as described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" refer to salts of pharmaceutical compounds that retain the biological effectiveness and properties of the underlying compound, and which are not biologically or otherwise undesirable. There are acid addition salts and base addition salts. Pharmaceutically acceptable acid addition salts may be prepared from inorganic and organic acids. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources. If the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

"Isomers" refers to compounds that have the same molecular formula. As used herein, the term isomers include double bond isomers, racemates, stereoisomers, enantiomers, diastereomers, and atropisomers. Single isomers, such as enantiomers or diastereomers, can be obtained by asymmetric synthesis or by resolution of a mixture of isomers. Resolution of a mixture of isomers (e.g. racemates) maybe accomplished, for example, by conventional methods such as crystallization in the presence of a resolving agent, or chromatography, using, for example a chiral high pressure liquid chromatography (HPLC) column. "Double bond isomers" refer to Z- and E-forms (or cis- and trans-forms) of the compounds with carbon-carbon double bonds.

"Atropisomers" refer to conformational stereoisomers which occur when rotation about a single bond in the molecule is prevented, or greatly hindered, as a result of steric interactions with other parts of the molecule and the substituents at both ends of the single bond are asymmetrical, i.e., they do not require a stereocenter. Where the rotational barrier about the single bond is high enough, and interconversion between conformations is slow enough, separation and isolation of the isomeric species may be permitted. Atropisomers may be separated by the methods well known in the art. Unless otherwise indicated, the description is intended to include individual atropisomers as well as mixtures. Also, as understood by those skilled in the art, the atropisomers may be represented by the same chemical name with different atropisomer designations. By way of example, the below structures are atropisomers (compounds 5 and 6), (S)-3-(5-chloro-2-(1-((2,6-diamino-5-cyanopyrimidin-4-yl)amino)ethyl)-4-oxoquinazolin-3 (4H)-yl)-2-methylbenzamide.

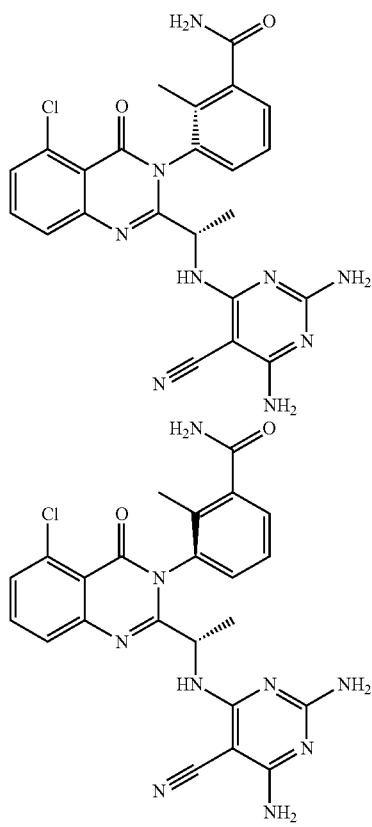

"Racemates" refers to a mixture of enantiomers.

"Stereoisomers" or "stereoisomeric forms" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomers" or "tautomeric formers" refer to alternate forms of a compound that differ in the position of a proton, such as enol-keto and imine-enamine tautomers, or heteroaryls such as pyrazoles, imidazoles, benzimidazoles, triazoles, and tetrazoles.

A "solvate" is formed by the interaction of a solvent and a compound. Solvates of salts of the compounds of any of the formulae described herein are also provided. Hydrates of the compounds of any of the formulae are also provided.

A "prodrug" is defined in the pharmaceutical field as a biologically inactive derivative of a drug that upon administration to the human body is converted to the biologically active parent drug according to some chemical or enzymatic pathway.

In any one of the foregoing embodiments, the compound described herein or a pharmaceutically acceptable salt thereof is a (S)-enantiomer. In any one of the foregoing embodiments, the compound described herein or a pharmaceutically acceptable salt thereof is a (R)-enantiomer. In any one of the foregoing embodiments, the compound described herein or a pharmaceutically acceptable salt thereof is an atropisomer.

The application also provides a composition containing a mixture of enantiomers of the compound or a pharmaceutically acceptable salt thereof. In one embodiment, the mixture is a racemic mixture. In other embodiments, the composition comprises the (S)-enantiomer of a compound in excess over the corresponding (R)-enantiomer of the compound. In some embodiments, the composition contains the (S)-enantiomer of the compound and is substantially free of its corresponding (R)-enantiomer. In certain embodiments, a composition substantially free of the (R)-enantiomer has less than or about 40%, 35%, 30%, 25%, 20%, 15%, 10%, 5%, 1%, 0.05%, or 0.01% of the (R)-enantiomer. In other embodiments, the composition containing the (S)-enantiomer of a compound or a pharmaceutically acceptable salt thereof, predominates over its corresponding (R)-enantiomer by a molar ratio of at least or about 9:1, at least or about 19:1, at least or about 40:1, at least or about 80:1, at least or about 160:1, or at least or about 320:1.

The composition containing a compound according to any of the formulae described herein or a pharmaceutically acceptable salt thereof, may also contain the compound in enantiomeric excess (e.e.). By way of example, a compound with 95% (S)-isomer and 5% (R)-isomer will have an e.e. of 90%. In some embodiments, the compound has an e.e. of at least or about 60%, 75%, 80%, 85%, 90%, 95%, 98% or 99%.

In any one of the foregoing embodiments, the compound or a pharmaceutically acceptable salt thereof, is an atropisomer. Another embodiment provides the composition containing a mixture of atropisomers of the compound or a pharmaceutically acceptable salt thereof. By way of example, a compound with 95% of one atropisomer and 5% of the other atropisomers. In some embodiments, a compound with about 90, 80, 70, 60, 50, 40, 30, 20, or 10% of one atropisomer and 10, 20, 30, 40, 50, 60, 70, 80, or 90%, respectively, of the other atropisomers.

The application also provides the free base forms of the compounds described herein. In certain embodiments, provided herein are the enantiomers, (R) or (S), of the compounds of the formulae described herein. In other embodiments, provided herein are the atropisomers of the compounds of the formulae described herein.

The application further provides compositions comprising the compounds described herein or a pharmaceutically acceptable salt, isomer, prodrug, or solvate thereof. The composition may include racemic mixtures, mixtures containing an enantiomeric excess of one enantiomer or single diastereomers or diastereomeric mixtures. All such isomeric forms of these compounds are expressly included herein, the same as if each and every isomeric form were specifically and individually listed.

In certain embodiments, provided herein are also polymorphs, such as crystalline and amorphous forms, of the compounds described herein. In some embodiments, provided are also chelates, non-covalent complexes, and mixtures thereof, of the compounds of the formula described herein or pharmaceutically acceptable salts, prodrugs, or solvates thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The compounds of the formulae described herein or a pharmaceutically acceptable salt, isomer, prodrug, or solvate thereof may be used for the treatment of diseases and/or conditions mediated by PI3K isoforms. In addition, the application provides the compounds for use in therapy. Also, provided herein are methods for inhibiting one or more PI3K isoforms. In one embodiment, provided are methods for inhibiting PI3Kδ activity using the compound described herein or a pharmaceutically acceptable salt, isomer, prodrug, or solvate thereof. In other embodiment, provided are methods for inhibiting PI3Kδ and/or PI3Kβ activities using the compound or a pharmaceutically acceptable salt, isomer, prodrug, or solvate thereof. The application further provides methods for use in such methods. The PI3K isoforms may be selectively or specifically inhibited. Additionally, the compounds may be used to inhibit PI3K activity therapeutically or prophylactically, such as PI3Kδ and/or PI3Kβ.

The compounds according to the present application may be used in combination with one or more additional therapeutic agents. The therapeutic agents may be in the forms of compounds, antibodies, polypeptides, or polynucleotides. The therapeutic agent includes, but is not limited to, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In one embodiment, the application provides a product comprising a compound described herein and an additional therapeutic agent as a combined preparation for simultaneous, separate or sequential use in therapy, e.g. a method of treating a disease, disorder, or condition that is mediated by PI3K isoforms.

Also, the therapeutic agents may be those that inhibit or modulate the activities of Bruton's tyrosine kinase, spleen tyrosine kinase, apoptosis signal-regulating kinase, Janus kinase, lysyl oxidase, lysyl oxidase-like proteins, matrix metallopeptidase, bromodomain-containing protein, adenosine A2B receptor, isocitrate dehydrogenase, serine/threonine kinase TPL2, discoidin domain receptor, serine/threonine-protein kinases, IKK, MEK, EGFR, histone deacetylase, protein kinase C, or any combination thereof.

In certain embodiments, the therapeutic agent may be selected from a PI3K (including PI3Kγ, PI3Kδ, PI3Kβ, PI3Kα, and/or pan-PI3K) inhibitor, a JAK (Janus kinase, including JAK1, JAK2, and/or JAK3) inhibitor, a SYK (spleen tyrosine kinase) inhibitor, a BTK (Bruton's tyrosine kinase) inhibitor, an A2B (adenosine A2B receptor) inhibitor, an ACK (activated CDC kinase, including ACK1) inhibitor, an ASK (apoptosis signal-regulating kinase, including ASK1) inhibitor, Auroa kinase, a BRD (bromodomain-containing protein, including BRD4) inhibitor, a Bcl (B-cell CLL/lymphoma, including Bcl-1 and/or Bcl-2) inhibitor, a CAK (CDK-activating kinase) inhibitor, a CaMK (calmodulin-dependent protein kinases) inhibitor, a CDK (cyclin-dependent kinases, including CDK1, 2, 3, 4, and/or 6) inhibitor, a CK (casein kinase, including CK1 and/or CK2) inhibitor, a DDR (discoidin domain receptor, including DDR1 and/or DDR2) inhibitor, a EGFR inhibitor, a FXR (farnesoid×receptor) inhibitor, a FAK (focal adhesion kinase) inhibitor, a GSK (glycogen synthase kinase) inhibitor, a HDAC (histone deacetylase) inhibitor, an IDO (indoleamine 2,3-dioxygenase) inhibitor, an IDH (isocitrate dehydrogenase, including IDH1) inhibitor, an IKK (I-Kappa-B kinase) inhibitor, a KDM5 (lysine demethylase) inhibitor, a LCK (lymphocyte-specific protein tyrosine kinase) inhibitor, a LOX (lysyl oxidase) inhibitor, a LOXL (lysyl oxidase like protein, including LOXL1, LOXL2, LOXL3, LOXL4, and/or LOXL5) inhibitor, a MTH (mut T homolog) inhibitor, a MEK (mitogen-activated protein kinase kinase) inhibitor, a matrix metalloprotease (MMP, including MMP2 and/or MMP9) inhibitor, a mitogen-activated protein kinases (MAPK) inhibitor, a PD-1 (programmed cell death protein 1) inhibitor, a PD-L1 (programmed death-ligand 1) inhibitor, a PDGF (platelet-derived growth factor) inhibitor, a phosphorylase kinase (PK) inhibitor, a PLK (polo-like kinase, including PLK1, 2, 3) inhibitor, a protein kinase (PK, including protein kinase A, B, C) inhibitor, a STK (serine/threonine kinase) inhibitor, a STAT (signal transduction and transcription) inhibitor, a serine/threonine-protein kinase inhibitor, a TBK (tank-binding kinase) inhibitor, a TLR (toll-like receptor modulators, including TLR-1, TLR-2. TLR-3, TLR-4, TLR-5, TLR-6, TLR-7, TLR-8, TLR-9, TLR-10, TLR-11, TLR-12, and/or TLR-13) inhibitor, a TK (tyrosine kinase) inhibitor, a TPL2 (serine/threonine kinase) inhibitor, a NEK9 inhibitor, an Abl inhibitor, a p38 kinase inhibitor, a PYK inhibitor, a PYK inhibitor, a c-Kit inhibitor, a NPM-ALK inhibitor, a Flt-3 inhibitor, a c-Met inhibitor, a KDR inhibitor, a TIE-2 inhibitor, a VEGFR inhibitor, a SRC inhibitor, a HCK inhibitor, a LYN inhibitor, a FYN inhibitor, a YES inhibitor, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In some embodiments, the JAK inhibitor is N-(cyanomethyl)-4-[2-(4-morpholinoanilino)pyrimidin-4-yl]benzamide as named by ChemDraw (may also be referred to as CYT0387 or momelotinib) and may be synthesized by the methods described in U.S. Pat. No. 8,486,941. In certain embodiment, the SyK inhibitor is 6-(1H-indazol-6-yl)-N-(4-morpholinophenyl)imidazo[1,2-a]pyrazin-8-amine as named by ChemDraw (may also be referred to as 6-(1H-indazol-6-yl)-N-[4-(morpholin-4-yl)phenyl]imidazo[1,2-a]pyrazin-8-amine) and may be synthesized by the methods described in U.S. Pat. No. 8,450,321. In other embodiments, the BTK inhibitor is (S)-6-amino-9-(1-(but-2-ynoyl)pyrrolidin-3-yl)-7-(4-phenoxyphenyl)-7H-purin-8(9H)-one as named by ChemDraw (may also be 6-amino-9-[(3R)-1-(2-butynoyl)-3-pyrrolidinyl]-7-(4-phenoxyphenyl)-7,9-dihydro-8H-purin-8-one) and may be synthesized by the methods in U.S. Pat. No. 8,557,803.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors, antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiopspsphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothesin), corticosteroids (cortisone, dexamethasone, hydrocortisone, methylpednisolone, prednisone, and prenisolone); growth factor signal transduction kinase inhibitors; dysfunction inducers, toxins such as Cholera toxin, ricin, *Pseudomonas* exotoxin, *Bordetella pertussis* adenylate cyclase toxin, or diphtheria toxin, and caspase activators; and chromatin.

As used herein the term "chemotherapeutic agent" or "chemotherapeutic" (or "chemotherapy," in the case of treatment with a chemotherapeutic agent) is meant to encompass any non-proteinaceous (i.e, non-peptidic) chemical compound useful in the treatment of cancer. Examples of chemotherapeutic agents include alkylating agents such as thiotepa and cyclophosphamide (CYTOXAN); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trotosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK(r); razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL(r) and docetaxel (TAXOTERE(r)); chlorambucil; gemcitabine (Gemzar(r)); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine(r)); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; FOLFIR1 (fluorouracil, leucovorin, and irinotecan) and pharmaceutically acceptable salts, acids or derivatives of any of the above. One or more chemotherapeutic agent are used or included in the present application.

Also included in the definition of"chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston(r)); inhibitors of the enzyme aromatase, which regulates estrogen production in the adrenal glands, such as, for example, 4(5)-imidazoles, aminoglutethimide, megestrol acetate (Megace(r)), exemeestane, formestane, fadrozole, vorozole (Rivisor(r)), letrozole (Femara(r)), and anastrozole (Arimidex(r)); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN(r), ENDOSTATIN(r), suramin, squalamine, tissue inhibitor of metalloproteinase-1, tissue inhibitor of metalloproternase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline, .alpha.-dipyridyl, beta-aminopropionitrile fumarate, 4-propyl-5-(4-pyridinyl)-2 (3h)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-2-carboxyphenyl-4-chloroanthronilic acid disodium or "CCA", thalidomide; angiostatic steroid, carboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N. and Alitalo, K. "Clinical application of angiogenic growth factors and their inhibitors" (1999) Nature Medicine 5:1359-1364.

The anti-fibrotic agents include, but are not limited to, the compounds such as beta-aminoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. No. 5,021,456; U.S. Pat. No. 5,059,714; U.S. Pat. No. 5,120,764; U.S. Pat. No. 5,182,297; U.S. Pat. No. 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotnumab, tigatuzumab, tositumomab, trastuzumab, tucotuzumab, ublituximab, veltuzumab, vorsetuzumab, votumumab, zalutumumab, obinutuzumab, CC49 and 3F8. The exemplified therapeutic antibodies may be further labeled or combined with a radioisotope particle, such as indium In 111, yttrium Y 90, iodine I-131.

The application also provides method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" Hematology 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

Examples of immunotherapeutic agents include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SON-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, ABT-199, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CCI-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (R-MCP).

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxart® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

In some embodiments, the methods include administering a compound of the formula described herein or a pharmaceutically acceptable salt, isomer, prodrug, or solvate thereof, in a therapeutically effective amount to a human in need thereof. The method can be employed to treat a patient who has or is believed to have a disease or condition whose symptoms or pathology is mediated by expression or activity of PI3Kδ and/or PI3Kβ. The patient may be a mammal or a human. In certain embodiments, the patient is a human.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing the effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" or "patient" refer to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human. "Human in need thereof" refers to a human who may have or is suspect to have diseases, or disorders, or conditions that would benefit from certain treatment; for example, being treated with the PI3K inhibitor of the compounds according to the present application. In certain embodiments, the subject may be a human who (i) has not received any treatment including chemotherapy treatment, (ii) is substantially refractory to at least one chemotherapy treatment, (iii) is in relapse after treatment with chemotherapy, or both (i) and (ii). In some of embodiments, the subject is refractory to at least one, at least two, at least three, or at least four chemotherapy treatments (including standard or experimental chemotherapies).

The terms "therapeutically effective amount" or "effective amount" of a compound of the present application or a pharmaceutically acceptable salt, isomers, prodrug, or solvate thereof, mean an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of PI3Kδ and PI3Kβ activity. The therapeutically effective amount may vary depending on the subject, and disease or condition being treated, the weight and age of the subject, the severity of the disease or condition, and the manner of administering, which can readily be determined by one or ordinary skill in the art.

In addition to the therapeutic uses, the compounds described herein have the selectivity or selective inhibition to certain PI3K isoforms. In one embodiment, the compounds have selectivity to PI3Kβ. In some embodiments, the compounds have selectivity to PI3Kδ. In yet other embodiments, the compounds have selectivity to PI3Kβ and PI3Kδ. The selectivity to PI3K isoforms may be determined by measuring the compound's activity in inhibiting certain PI3K isoforms using the assay described in the example below or the methods commonly used. It is understood that the conditions (e.g. the reagent concentration or the incubation temperature) may be varied and the results of the assay may vary. In some instances, the value may vary within a range of one to three-folds.

The term "inhibition" indicates a decrease in the baseline activity of a biological activity or process. The term "inhibition of activity of PI3K isoforms" or variants thereof refer to a decrease in activity in any PI3K isoform (e.g., alpha, beta, gamma, or delta) as a direct or indirect response to the presence of a compound of any of the formula described herein relative to the activity of PI3K isoform in the absence of such compound. "Inhibition of PI3Kδ and/or PI3Kβ activities" or variants thereof refer to a decrease in PI3Kδ and/or PI3Kβ activities as a direct or indirect response to the presence of the compounds described herein, relative to the activities of PI3Kδ and/or PI3Kβ in the absence of such compound. In some embodiments, the inhibition of PI3K isoform activities may be compared in the same subject prior to treatment, or other subjects not receiving the treatment.

Without being bound to any theory, the decrease in the activity of PI3K may be due to the direct interaction of the compound with PI3K, or due to the interaction of the compounds described herein with one or more other factors that affect PI3K activity. For example, the presence of the compounds may decrease the activities of PI3Kδ and/or PI3Kβ by directly binding to PI3Kδ and/or PI3Kβ, by causing (directly or indirectly) another factor to decrease PI3Kδ and/or PI3Kβ activities, or by (directly or indirectly) decreasing the amount of PI3Kδ and/or PI3Kβ present in the cell or organism.

The term "PI3K inhibitor" or variant thereof refers to a compound that inhibits the activity of PI3K. The term "PI3K isoform selective inhibitor" or variant thereof refers to a compound that inhibits the activity of one or more PI3K isoforms more effectively than the other remaining PI3K isoforms. By way of example, the term "PI3Kβ selective inhibitor" generally refers to a compound that inhibits the activity of the PI3Kβ isoform more effectively than other isoforms of the PI3K family, and the term "PI3Kδ selective inhibitor" generally refers to a compound that inhibits the activity of the PI3Kδ isoform more effectively than other isoforms of the PI3K family. The term "dual PI3Kδ/β selective inhibitor" generally refers to a compound that inhibits the activity of both PI3Kδ and PI3Kβ isoforms more effectively than other isoforms of the PI3K family (e.g., PI3Kα or γ).

The relative efficacies of compounds as inhibitors of an enzyme activity (or other biological activity) can be established by determining the concentrations at which each compound inhibits the activity to a predefined extent and then comparing the results. In one embodiment, the efficacy of a compound as an inhibitor of one or more PI3K isoforms can be measured by the compound concentration that inhibits 50% of the activity in a biochemical assay, i.e., the 50% inhibitory concentration or "$IC_{50}$". The determination of $IC_{50}$ values can be accomplished using conventional techniques known in the art, including the techniques described in the Examples below. In general, an $IC_{50}$ can be determined by measuring the activity of a given enzyme in the presence of a range of concentrations of the compound under the study. The experimentally obtained values of enzyme activity may then be plotted against the compound concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it may be desirable to establish a 90% inhibitory concentration, i.e., $IC_{90}$.

According to the present application, a PI3Kβ selective inhibitor is a compound that exhibits a 50% inhibitory concentration ($IC_{50}$) with respect to PI3Kβ that is at least 10-fold, at least 20-fold, at least 30-fold, at least 50-fold, at least 100-fold, at least 200-fold, or at least 500-fold lower than the $IC_{50}$ with respect to either PI3Kα or PI3Kγ or both PI3Kα and PI3Kγ. In addition, a PI3Kδ/β selective inhibitor is a compound that exhibits a 50% inhibitory concentration ($IC_{50}$) with respect to PI3Kβ and PI3Kδ that is at least 10-fold, at least 20-fold, at least 30-fold, at least 50-fold, at least 75-fold, at least 100-fold, at least 200-fold, and at least 500-fold lower than the $IC_{50}$ with respect to either PI3Kα or PI3Kγ. The dual PI3Kδ/β selective inhibitor may have the same or similar $IC_{50}$ to both PI3Kδ and PI3Kβ or may have different $IC_{50}$ to either PI3Kδ or PI3Kβ. As used herein, the term "potency," "potent," or variants thereof refer to the compound exhibiting an $IC_{50}$ value that is less than 100 nM. When comparing two compounds, the compound that exhibits a lower $IC_{50}$ value is referred to as a more potent inhibitor.

The compounds of the present application exhibit unexpected selectivity to PI3Kβ. As shown in the example, certain compounds disclosed herein (e.g. in Table 1) exhibit low $IC_{50}$ values (e.g. 1 to 100 nM) to both PI3Kβ and PI3Kδ. Additionally, certain compounds selected from Compounds 1-164 exhibit low $IC_{50}$ values (e.g. 1 to 100 nM) to both PI3Kβ and PI3Kδ. Also, certain compounds of formula (I) exhibited at least between 10-fold to 400-fold lower $IC_{50}$ values for PI3Kβ than PI3Kγ, suggesting the compounds exhibit more selectivity to PI3Kβ compared to PI3Kγ (i.e., inhibits the activity of the PI3Kβ isoform more effectively than the PI3Kγ isoform as shown by the PI3Kγ/PI3Kβ ratio). Also, certain compounds of the present application exhibited at least between 10-fold to 400-fold lower $IC_{50}$ values for PI3Kβ than PI3Kγ, suggesting the compounds exhibit more selectivity to PI3Kβ compared to PI3Kγ (i.e., inhibits the activity of the PI3Kβ isoform more effectively than the PI3Kγ isoform as shown by the PI3Kγ/PI3Kβ ratio). Moreover, the compounds described herein exhibit selectivity to both PI3Kβ and PI3Kδ. The compound of (S)-2,4-diamino-6-((1-(5-chloro-4-oxo-3-phenyl-3,4-dihydroquinazolin-2-yl)ethyl)amino)pyrimidine-5-carbonitrile, described in U.S. Provisional Application No. 61/745,437, exhibited less selectivity to PI3Kγ (e.g. the PI3Kγ/PI3Kβ ratio is less than 1-fold). The results of the present application suggest that certain compounds described herein are dual selective inhibitors of PI3Kδ and PI3Kβ and exhibit more selectivity to PI3Kβ compared to PI3Kγ.

Each of the patents and the patent applications provided in the present application is hereby incorporated by reference in the entirety.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds may be used for a variety of purposes, including therapeutic and experimental purposes. For example, it may be used ex vivo to determine the optimal schedule and/or dosing of administration of a PI3K selective inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The compounds of the formula described herein or a pharmaceutically acceptable salt, prodrug, or solvate thereof, may be further characterized to examine the safety or tolerance dosage in human or non-human subjects. Such properties may be examined using commonly known methods to those skilled in the art.

Compared to other PI3K isoforms, PI3Kδ is generally expressed in hematopoietic cells. Also, PI3Kβ is generally expressed in cancer cells. Aberrant proliferation of cells often interferes with normal tissue function, which may result in abnormal cellular response such as immunity, inflammation, and/or apoptosis. The selective inhibitors to PI3Kδ and/or PI3Kβ are useful in treating, inhibiting, or preventing aberrant proliferation of cancerous and/or hematopoietic cells and ameliorating the symptoms and secondary conditions.

The compounds described herein may be used to treat subjects having various disease states, disorders, and conditions (also collectively referred to as "indications") associated with PI3K isoforms or their activities. As used herein, the terms "diseases," "disorders," "conditions" are used interchangeably. Such indications may include, for example, cancer, including hematologic malignancies (e.g. leukemias and lymphomas, myeloproliferative disorders, myelodysplastic syndromes, plasma cell neoplasms) and solid tumors, inflammation, fibrosis, allergic conditions (including hypersensitivity), cardiovascular diseases, neurodegenerative diseases, renal disorders, viral infections, obesity, and autoimmune diseases.

In other embodiments, the compounds described herein may be used to treat cancers that are mediated by, dependent on, or associated with PI3K activity. In certain embodiments, the disease or condition is an autoimmune disease, an inflammatory disease, or a cancer. In some embodiments, the disease or condition is chosen from rheumatoid arthritis, osteoarthritis, atherosclerosis, psoriasis, systemic lupus erythematosus, multiple sclerosis, inflammatory bowel disease, asthma, chronic obstructive airways disease, pneumonitis, dermatitis, alopecia, nephritis, vasculitis, atherosclerosis, Alzheimer's disease, hepatitis, primary biliary cirrhosis, sclerosing cholangitis, diabetes (including type I diabetes), acute rejection of transplanted organs, lymphomas, multiple myelomas, leukemias, neoplasms and solid tumors.

In other embodiments, the disease is a solid tumor. By way of examples, the solid tumor includes but is not limited to pancreatic cancer, bladder cancer, colorectal cancer, breast cancer, prostate cancer, renal cancer, hepatocellular cancer, lung cancer, ovarian cancer, cervical cancer, rectum cancer, liver cancer, kidney cancer, stomach cancer, skin cancer, gastric cancer, esophageal cancer, head and neck cancer, melanoma, neuroendocrine cancers, CNS cancers (e.g., neuroblastoma), brain tumors (e.g., glioma, anaplastic oligodendroglioma, adult glioblastoma multiforme, and adult anaplastic astrocytoma), bone cancer, or soft tissue sarcoma. In some embodiments, the solid tumor is non-small cell lung cancer, small-cell lung cancer, colon cancer, CNS cancer, melanoma, ovarian cancer, renal cancer, pancreatic cancer, prostate cancer, or breast cancer.

The present application also provides a method for treating a human in need thereof, who has or is suspected of having a disease or condition responsive or believed to be responsive to the inhibition of PI3Kδ and/or PI3Kβ activity by administering to the subject a compound of the formulae described herein or a pharmaceutically acceptable salt, enantiomer, atropisomer, tautomer, prodrug, or solvate thereof.

Additionally, the application provides a method of inhibiting kinase activity of a PI3Kδ and/or PI3Kβ polypeptides by contacting the polypeptides with a compound of the formulae described herein or a pharmaceutically acceptable salt, isomer, prodrug, solvate, or a mixture thereof.

Moreover, the application provides a method of decreasing cell viability, increasing cell death or apoptosis, increasing interference with PI3K signaling pathways (including AKT, S6RP, ERK phosphorylation), and/or reduction in chemokine production with an effective amount of a compound of any of the formulae described herein or a pharmaceutically acceptable salt, isomer, prodrug, solvate, or a mixture thereof.

The application further provides a method of disrupting leukocyte function comprising contacting the leukocytes with an effective amount of a compound of any of the formulae described herein or a pharmaceutically acceptable salt, isomer, prodrug, solvate, or a mixture thereof, in a human in need thereof.

Provided is also a method of inhibiting growth or proliferation of cancer cells comprising contacting the cancer cells with an effective amount of a compound of the formulae described herein or a pharmaceutically acceptable salt, isomer, prodrug, solvate, or a mixture thereof.

Kits

Provided herein are also kits that include a compound of the formulae of the present application or a pharmaceutically acceptable salt, isomer, prodrug, or solvate thereof, and suitable packaging. In one embodiment, a kit further includes instructions for use. In one aspect, a kit includes a compound of the formulae described herein or a pharmaceutically acceptable salt, isomer, prodrug, or solvate thereof, and a label and/or instructions for use of the compounds in the treatment of the indications, including the diseases or conditions, described herein.

Provided herein are also articles of manufacture that include a compound of any of the formulae described herein or a pharmaceutically acceptable salt, isomer, prodrug, or solvate thereof, in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provides herein are also pharmaceutical compositions that contain one or more of the compounds of any of the formulae disclosed herein or a pharmaceutically acceptable salt, isomers, prodrug, or solvate thereof, and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizes and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal, and transdermal routes. In certain embodiments, the pharmaceutical composition may be administered by intra-arterial injection, intravenously, intraperitoneally, parenterally, intramuscularly, subcutaneously, orally, topically, or as an inhalant. In some embodiments, the pharmaceutical composition is administered orally.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound of any of the formulae described herein or a pharmaceutically acceptable salt, prodrug, or solvate thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders. In certain embodiments, the pharmaceutical composition is in the form of tablets.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of any of the formulae described herein or a pharmaceutically acceptable salt, isomer, prodrug, or solvate thereof, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound of any of the above formulae or a pharmaceutically acceptable salt, prodrug, or solvate thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the formulae described herein for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound of the formula per kilogram of the subject's body weight (mg/kg). Dosages of between about 0.01 and 200 mg/kg may be appropriate. In some embodiments, about 0.01 and 150 mg/kg may be appropriate. In other embodiments a dosage of between 0.05 and 100 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound of the formulae administered per dose or per day. Daily dosage of a compound may be between about 1 mg and 2,000 mg, between about 1,000 to 2,000 mg/day, between about 1 to 1,000 mg/day, between about 1 to 500 mg/day, between about 100 to 150 mg/day, between about 1 to 100 mg/day, between about between about 1 to 50 mg/day, between about 50 to 100 mg/day, between about 100 to 125 mg/day, between about 100 to 150 mg/day, between about 100 to 175 mg/day, between about 100 to 200 mg/day, between about 100 to 225 mg/day, between about 100 to 250 mg/day, between about 100 to 350 mg/day, between about 100 to 400 mg/day, between about 100 to 450 mg/day, or between about 100 to 500 mg/day.

When administered orally, the total daily dosage for a human subject may be between 1 mg and 1,000 mg/day, between about 1 to 100 mg/day, between about 1 to 50 mg/day, between about 50 to 100 mg/day, between 100 to 200 mg/day, between about 200 to 300 mg/day, between about 300 to 400 mg/day, between about 400 to 500 mg/day, between about 100 to 150 mg/day, between about 150 to 200 mg/day, between about 200 to 250 mg/day, between about 75 to 150 mg/day, or between about 150 to 300 mg/day.

The compounds of the present application or the compositions thereof may be administered once, twice, three, or four times daily, using any suitable mode described above. Also, administration or treatment with the compounds according to any of the formulae described herein may be continued for a number of days; for example, commonly treatment would continue for at least 7 days, 14 days, or 28 days, for one cycle of treatment. In some treatment, the compound or the composition thereof is administered continuously, i.e. every day. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 500 mg of a compound of the above formula and increasing the dose by increments until clinical efficacy is achieved. Increments of about 1, 5, 10, 25, 50, 75, or 100 mg can be used to increase the dose. The dosage can be increased daily, every other day, twice per week, or once per week.

Synthesis of the Compounds

The compounds of the present application may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure.

General Synthesis

Typical embodiments of compounds described herein may be synthesized using the general reaction schemes described below. It will be apparent given the description Synthetic Reaction Parameters The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like. Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Certain compounds of formula (I) may be prepared using the method shown in Reaction Scheme I. Certain compounds of formula (J) and (Ja) may be prepared using the method shown in Reaction Scheme I.

herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein.

Reaction Scheme I

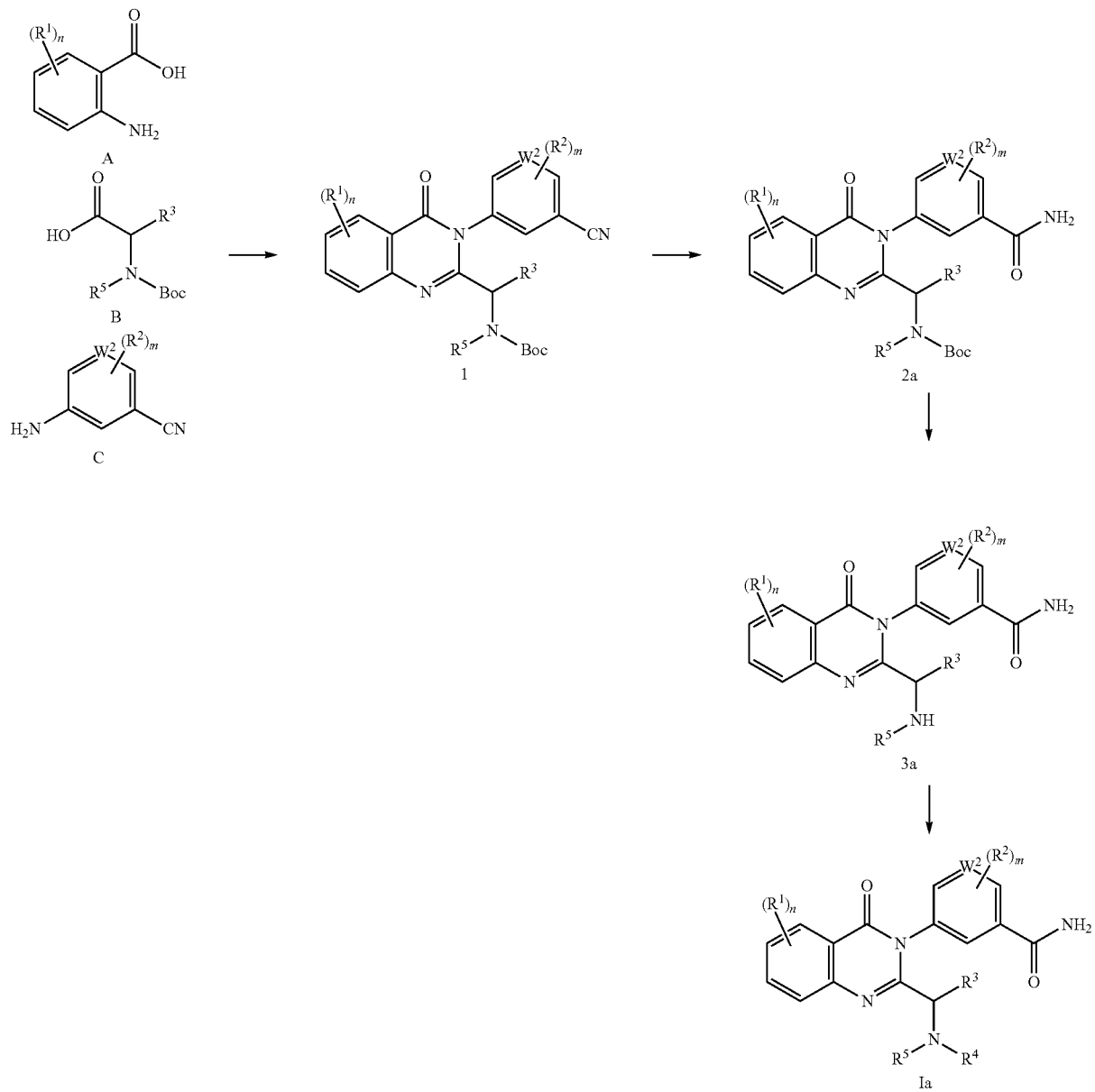

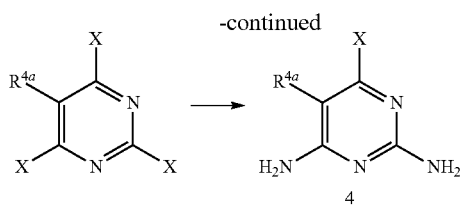

Step 1—Preparation of a Compound of Formula (1)

The compound of formula (1) may be made by combining compounds (A), (B) and (C) in the presence of a dehydrating agent. Compounds (A), (B), and (C) may be obtained commercially or made by the methods known in the art. In this synthetic scheme, $W^2$, $R^1$, $R^2$, $R^3$, $R^4$, and $R^5$ are defined as above. Compound (A) can be mixed with Compound (B) in the presence of a coupling agent, such as diphenyl phosphite, and a solvent, such as pyridine. After stirring at a temperature between ambient (e.g., room temperature) and 100° C. for between 1 and 5 hours, compound (C) is added. After further stirring at a temperature between ambient and 100° C. for between 5 and 24 hours, the reaction mixture is cooled to room temperature. To extract the compound of formula (1), an organic solvent such as ethyl acetate (EtOAc) is added, followed by washing with mild acid, water, and brine. The organic phase may be concentrated to obtain the compound of formula (1). The compound of formula (1) may be purified by any suitable methods known in the art, such as chromatography on silica gel. Alternatively the compound of formula (1) may be purified without an aqueous work-up. Alternatively, the compound of formula (1) may be used in the next step without purification. In some cases, a compound containing a carboxamide ($CONH_2$) instead of a nitrile as in compound (C) may be used to go directly to a compound of formula (2a).

Step 2—Preparation of a Compound of Formula (2a)

The compound of formula (1) is dissolved in a suitable solvent and treated with hydrido(dimethylphosphinous acid-kP)[hydrogen bis(dimethylphosphinito-kP)]platinum(II). Suitable solvents may include, for example, ethanol, dioxane, THF, and water. The reaction is conducted at temperatures between ambient and 100° C. between 1 and 48 hours. The solvent may be removed under reduced pressure and the product may be purified by methods known in the art.

In some cases, a compound containing a carboxamide ($CONH_2$) instead of a nitrile as in compound (C) may be used to directly prepare a compound of formula (2a) through the steps described in Step 1.

Step 3—Preparation of a Compound of Formula (3a)

The compound of formula (2a) is dissolved in a suitable solvent and treated with a suitable acid. Suitable solvents may include, for example, dichloromethane, dioxane, or the like. Suitable acids may include, for example, trifluoroacetic acid, hydrochloric acid, or boron tribromide ($BBr_3$). The reaction may be conducted at temperatures between −78° C. to ambient temperature. Subsequently, solvent is removed to obtain the compound of formula (3). When $BBr_3$ is used, the reaction may be treated with MeOH before an aqueous work-up to obtain a compound of formula (3).

Step 4—Preparation of a Compound of Formula (4)

The compound of formula (4) can be made by treating 5-substituted-2,4,6-trihalopyrimidine with ammonium hydroxide in a suitable solvent such as dioxane, where X is chloro or fluoro. The reaction is conducted at an elevated temperature between 30° C. and 80° C. for about 2 and 8 hours. When the reaction is complete, water is added to the cooled solution, and the precipitate is collected by filtration. The nitrile can be converted to the carboxamide under standard conditions.

Step 5—Preparation of a Compound of Formula (I)

The compound of formula (I) where $R^4$ is a 2,6-diaminopyrimidine may be prepared by coupling a compound of formula (3) and a compound of formula (4) in the presence of diisopropylethylamine in N-methylpyrrolidone (NMP). The reaction may be performed at a temperature between 50° C. to 150° C. for about 30 minutes to 24 hours. Alternatively, the reaction may be conducted in a microwave at a temperature between 100° C. to 150° C. for about 30 minutes to 24 hours. Water may be added to quench the reaction upon completion, and the precipitate may be filtered and then dissolved in an organic solvent such as dichloromethane (DCM). The product may be isolated by removal of solvent under reduced pressure and purified using chromatography of the residue on a silica column. Additional compounds of formula (I) with an alternate $R^4$ may be prepared in a similar fashion starting with a compound of formula (3) and $R^4$—X, where X is a halo and $R^4$ is defined herein. The reagents, the steps, and the conditions described herein exemplify the general synthesis scheme for the compounds of the present application; other suitable or equivalent reagents, steps, and/or conditions may be used.

Certain compounds of formula (J), (Jb) or (II) may be prepared according to Reaction Scheme II.

Reaction Scheme II

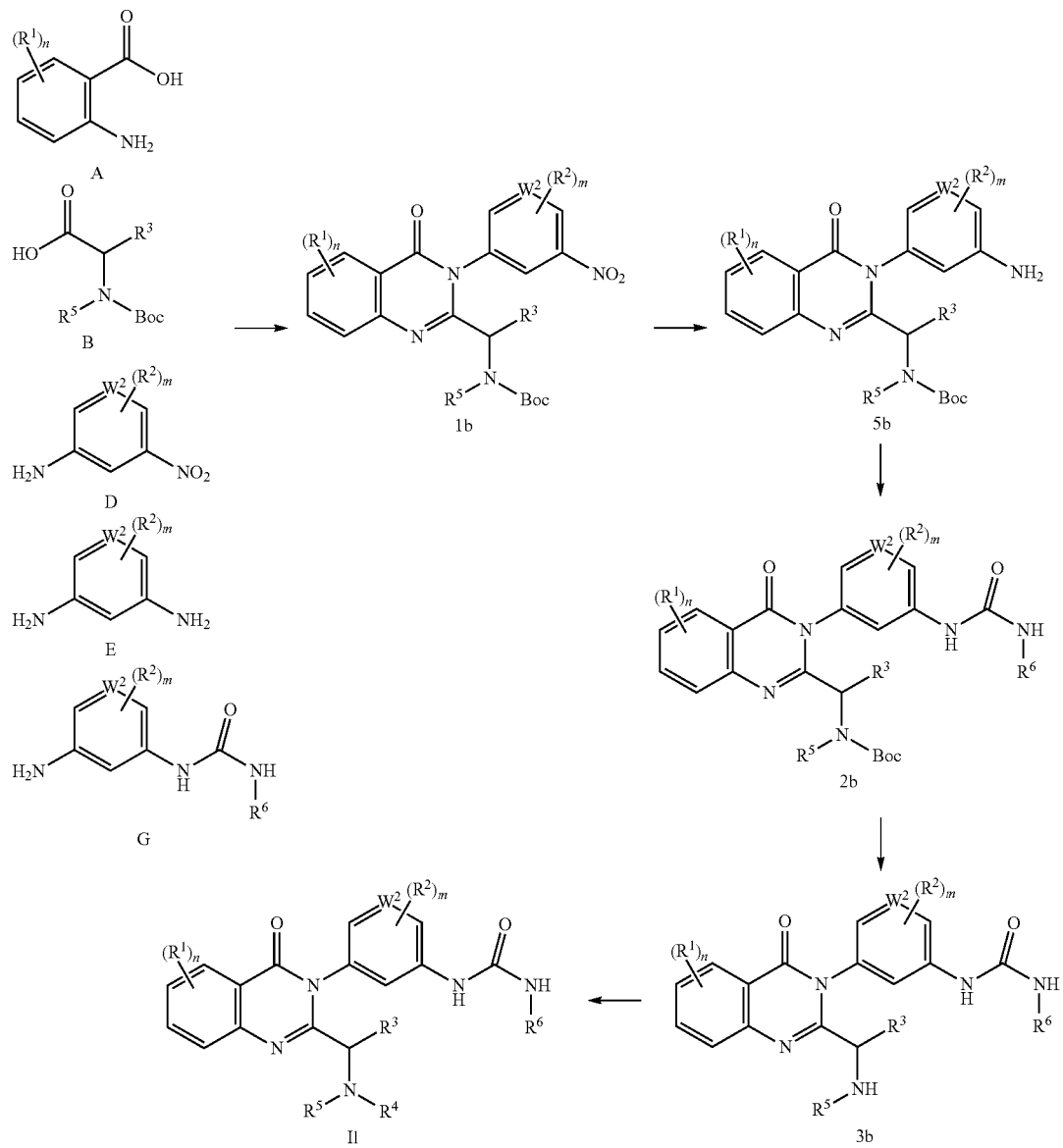

Preparation of a Compound of Formula (5b)

The compounds of formula (1b) can be prepared in a manner similar to those of formula (1a), but using the starting material (D) instead of the starting material (C). A compound of formula (5b) may be prepared by reducing a compound of formula (1b) under standard conditions, such as dissolving the material in a solvent such as ethanol, ethyl acetate, THF, or some mixture, adding an agent such as $SnCl_2$, or iron filings and allowing to react at a temperature between room temperature and 100° C. The compounds of formula (5b) can be prepared by using the starting material (E) instead of the starting material (C). Standard work-up and purification if necessary gives the product (5b).

Preparation of a Compound of Formula (2b)

The compound of formula (5b) is dissolved in a suitable solvent and treated with the appropriate isocyanate or a chloroformate. Suitable solvents may include, for example, dioxane, THF, dichloromethane, and DMF. The reaction is conducted at temperatures between ambient and 100° C. between 1 and 48 hours. The solvent may be removed under reduced pressure and the product may be purified by methods known in the art. Alternatively, the compound of formula (5b) may be reacted with phenyl chloroformate, nitrophenyl chloroformate, or pentafluorophenyl chloroformate as described above, and subsequently reacted with the appropriate amine. The solvent may be removed under reduced pressure and the product may be purified by methods known in the art. Alternatively, the compound of formula (5b) may be reacted with carbonyl diimidazole followed by the appropriate amine in an appropriate solvent such as DMSO or DMF at temperatures between ambient and 100° C. between 1 and 48 hours. The compound (2b) may be worked-up and purified by methods known in the art. For isocyanates that are not commercially available, the isocyanate can be preformed by reacting the desired amine or aniline with triphosgene, diphosgene, or phosgene in an appropriate solvent such as benzene or toluene at temperatures between ambient and 120° C. between 1 and 48 hours. The desired aniline is than added to the solution and reacted at a temperature between ambient and 100° C. between 1 and 24 hours. The desired compound (2b) may be worked-up and purified by methods known in the art. Alternatively, a compound of formula (2b) may be formed by reaction of starting materials of the formula (A), (B), and (G) under conditions as described for step 1. The compounds of formula (3b) and (II) may be prepared based on the corresponding steps described in Reaction Scheme I.

Certain compounds of formula (J), (Jb), or (III) may be prepared according to Reaction Scheme III.

Preparation of a Compound of Formula (5c)

The compounds of formula (1c) can be prepared in a manner similar to those of formula (1b), but using the starting material (F) instead of the starting material (B). PG represents a suitable protecting group such as triisopropylsilyl, t-butyldimethylsilyl or t-butyldiphenylsilyl. The compounds of formula (5c) can be prepared by using the starting material (E) instead of the starting material (D). Alternatively a compound of formula (5c) may be prepared by reducing a compound of formula (1c) under standard conditions, such as dissolving the material in a solvent such as ethanol, ethyl acetate, THF, or some mixture, adding an agent such as $SnCl_2$ or iron filings and allowing to react at

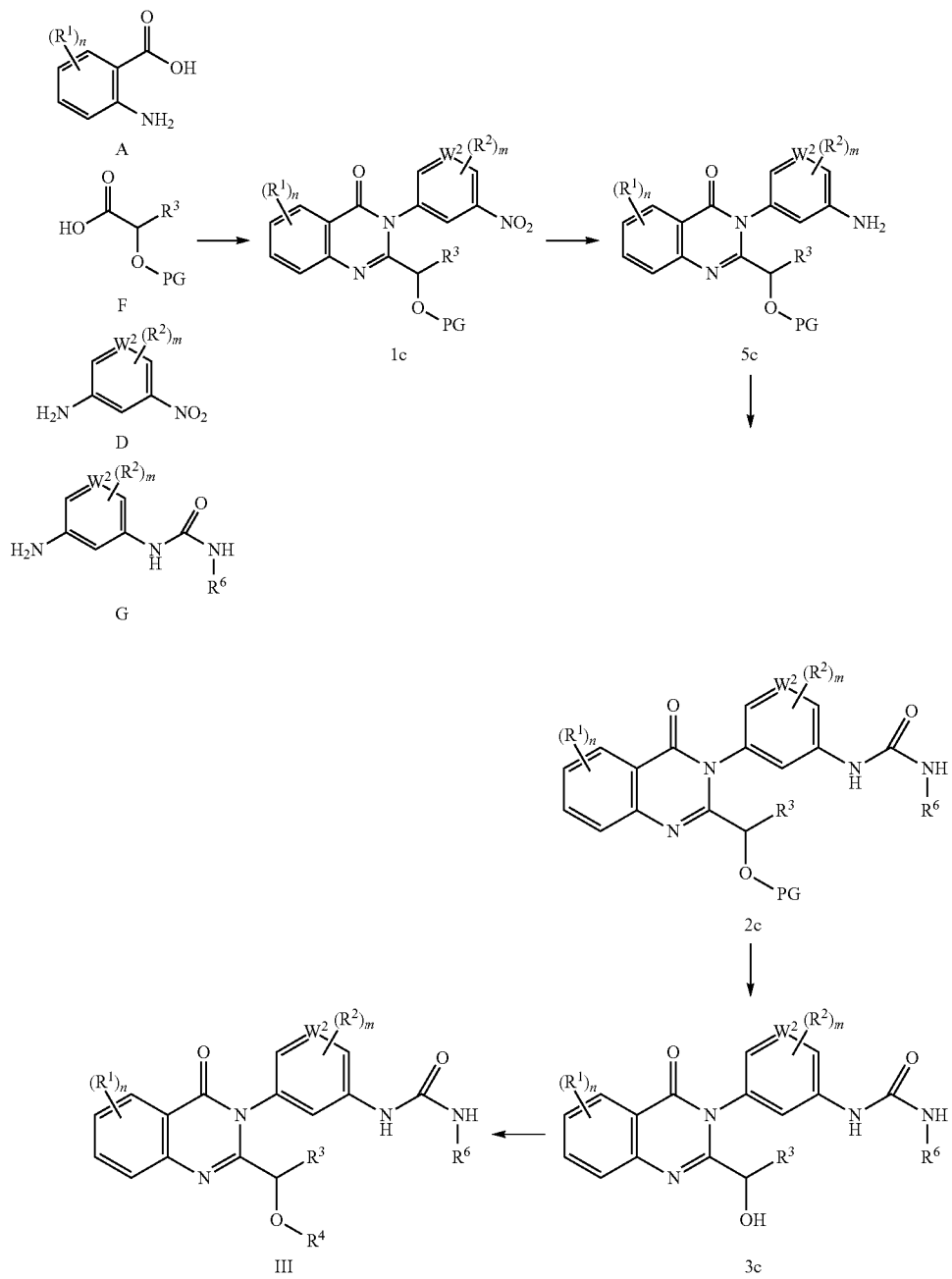

Reaction Scheme III a temperature between room temperature and 100° C. Standard work-up and purification if necessary gives the product (5c).

Preparation of a Compound of Formula (2c)

The compound of formula (5c) is dissolved in a suitable solvent and treated with the appropriate isocyanate or a chloroformate. Suitable solvents may include, for example, dioxane, THF, dichloromethane, and DMF. The reaction is conducted at temperatures between ambient and 100° C. between 1 and 48 hours. The solvent may be removed under reduced pressure and the product may be purified by methods known in the art. Alternatively, the compound of formula (5c) may be reacted with phenyl chloroformate, nitrophenyl chloroformate, or pentafluorophenyl chloroformate as described above, and subsequently reacted with the appropriate amine. The solvent may be removed under reduced pressure and the product may be purified by methods known in the art. Alternatively, the compound of formula (5c) may be reacted with carbonyl diimidazole and the appropriate amine in an appropriate solvent such as DMSO or DMF at temperatures between ambient and 100° C. between 1 and 48 hours. The desired compound (2c) may be worked-up and purified by methods known in the art. For isocyanates that are not commercially available, the isocyanate can be preformed by reacting the desired amine or aniline with triphosgene, diphosgene, or phosgene in an appropriate solvent such as benzene or toluene at temperatures between ambient and 120° C. between 1 and 48 hours. The desired aniline is than added to the solution and reacted at a temperature between ambient and 100° C. between 1 and 24 hours. The compound (2c) may be worked-up and purified by methods known in the art. Alternatively, a compound of formula (2c) may be formed by reaction of starting materials of the formula (A), (F), and (G) under conditions as described for step 1.

Preparation of a Compound of Formula (3c)

The compound of formula (2c) may be deprotected if the protecting group is a silyl, by dissolving in a suitable solvent and treating with the appropriate agent such as HF pyridine or tetrabutylammonium fluoride. Suitable solvents may include, for example, dioxane and THF. The reaction is conducted at temperatures between 0° C. and 100° C. between 15 minutes and 24 hours. The reaction may be worked up using standard methods and purified by methods known in the art.

Preparation of a Compound of Formula (III)

The compounds of formula (III) can be prepared by reacting an alcohol of formula (3c) with some base such as NaHMDS, NaH, or LiHMDS, in a suitable solvent such as ether or THF, followed by addition of a suitably substituted Cl—$R^4$ at a temperature between ambient and 80° C. The reaction may be worked up using standard methods and purified by methods known in the art.

After synthesis, the compounds may be isolated in the form of a free base or a trifluoroacetic acid salt and further characterized by NMR. The resulting compounds and their NMR characterizations may represent either the free base or salt form. The ratio of parent compound and corresponding salt is not determined.

Example 1. Preparation of a Compound of Formula (1, 2, 3, or 5)

A. Preparation of a compound of formula (1) where $W^2$ is CH, n is 1, $R^1$ is chloro, m is 0, $R^5$ is hydrogen, and $R^3$ is methyl

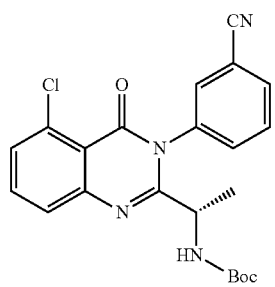 [SMILES: C[C@H](NC(=O)OC(C)(C)C)c1nc2cccc(Cl)c2c(=O)n1-c1cccc(C#N)c1]

A mixture of 6-chloroanthranilic acid (0.34 g, 2.0 mmol) and Boc-L-alanine (0.49 g, 2.6 mmol) in pyridine (2 mL) was warmed to 45° C. until homogeneous then cooled to room temperature, at which time diphenyl phosphite (1.3 mL, 8.8 mmol) was added. The mixture was stirred for one hour at 45° C., then treated with 3-aminobenzonitrile (0.28 g, 2.4 mmol) in a single portion. The mixture was stirred overnight at 55° C. After cooling to room temperature, the mixture was diluted with toluene (20 mL), washed three times with 10% aqueous hydrochloric acid solution, and concentrated under reduced pressure. The residue was chromatographed, using a 25 g SilicaSep flash column, eluting hexanes to 65% ethyl acetate. The combined fractions were concentrated under reduced pressure to give (S)-tert-butyl (1-(5-chloro-3-(3-cyanophenyl)-4-oxo-3,4-dihydroquinazolin-2-yl)ethyl)carbamate. ES/MS 425.2 (M+H+).

B. Preparation of the below compounds of formula (1) using the procedures described in Example 1A and Reaction Scheme I, II or III:

(S)-tert-butyl(1-(5,8-dichloro-3-(3(3-cyanophenyl)-4-oxo-3,4-dihydroquinazolin-2-yl)ethyl)carbamate;

(S)-tert-butyl(1-(5-chloro-3-(3-cyano-2-methylphenyl)-4-oxo-3,4-dihydroquinazolin-2-yl)ethyl)carbamate;

(S)-tert-butyl(1-(5-chloro-3-(3-cyanophenyl)-4-oxo-3,4-dihydroquinazolin-2-yl)propyl)carbamate;

(S)-tert-butyl((5-chloro-3-(3-cyanophenyl)-4-oxo-3,4-dihydroquinazolin-2-yl)(cyclopropyl)methyl)carbamate;

(S)-tert-butyl(cyclopropyl(5,8-dichloro-3-(3-cyanophenyl)-4-oxo-3,4-dihydroquinazolin-2-yl)methyl)carbamate;

(S)-tert-butyl((5-chloro-3-(3-cyanophenyl)-8-fluoro-4-oxo-3,4-dihydroquinazolin-2-yl)cyclopropyl)methyl)carbamate;

(S)-tert-butyl 2-(5,8-dichloro-3-(3-cyanophenyl)-4-oxo-3,4-dihydroquinazolin-2-yl)pyrrolidine-1-carboxylate;

(S)-tert-butyl(1-(5,8-dichloro-3-(3-cyanophenyl)-4-oxo-3,4-dihydroquinazolin-2-yl)propyl)carbamate;

(S)-tert-butyl(1-(5,8-dichloro-3-(3-cyanophenyl)-4-oxo-3,4-dihydroquinazolin-2-yl)butyl)carbamate;

(S)-tert-butyl(1-(5-chloro-3-(3-cyanophenyl)-4-oxo-3,4-dihydroquinazolin-2-yl)butyl)carbamate;

(S)-tert-butyl((3-(3-cyanophenyl)-5-(difluoromethyl)-4-oxo-3,4-dihydroquinazolin-2-yl)(cyclopropyl)methyl)carbamate;

(S)-tert-butyl((8-chloro-3-(3-cyanophenyl)-6-fluoro-4-oxo-3,4-dihydroquinazolin-2-yl)(cyclopropyl)methyl)carbamate;

(S)-tert-butyl((8-cyano-3-(3-cyanophenyl)-6-fluoro-4-oxo-3,4-dihydroquinazolin-2-yl)(cyclopropyl)methyl)carbamate;

(S)-tert-butyl(1-(3-(3-cyanophenyl)-5-(difluoromethyl)-4-oxo-3,4-dihydroquinazolin-2-yl)propyl)carbamate;

(S)-tert-butyl(1-(8-chloro-3-(3-cyanophenyl)-6-fluoro-4-oxo-3,4-dihydroquinazolin-2-yl)ethyl)carbamate;

(S)-tert-butyl(1-(8-cyano-3-(3-cyanophenyl)-6-fluoro-4-oxo-3,4-dihydroquinazolin-2-yl)ethyl)carbamate;
(S)-tert-butyl(1-(5,8-dichloro-3-(3-cyanophenyl)-4-oxo-3,4-dihydroquinazolin-2-yl)butyl)carbamate;
(S)-tert-butyl(1-(5,8-dichloro-3-(3-cyanophenyl)-4-oxo-3,4-dihydroquinazolin-2-yl)propyl)carbamate;
(R)-tert-butyl(1-(5-chloro-3-(3-(3-ethylureido)phenyl)-4-oxo-3,4-dihydroquinazolin-2-yl)ethyl)carbamate;
tert-butyl((1S,2S)-1-(5-chloro-3-(3-(3-ethylureido)phenyl)-4-oxo-3,4-dihydroquinazolin-2-yl)-2-methylbutyl)carbamate;
(S)-tert-butyl(1-(3-(3-aminophenyl)-8-chloro-4-oxo-3,4-dihydroquinazolin-2-yl)ethyl)carbamate;
(S)-1-(3-(2-(1-(((tert-butyldiphenylsilyl)oxy)ethyl)-5-chloro-4-oxoquinazolin-3(4H)-yl)phenyl)-3-ethylurea;
(2S,4S)-tert-butyl 2-(3-(3-aminophenyl)-5-chloro-4-oxo-3,4-dihydroquinazolin-2-yl)-4-fluoropyrrolidine-1-carboxylate;
(S)-tert-butyl(1-(3-(3-aminophenyl)-5-chloro-4-oxo-3,4-dihydroquinazolin-2-yl)ethyl)carbamate;
(S)-tert-butyl(1-(3-(3-amino-4-fluorophenyl)-5-chloro-4-oxo-3,4-dihydroquinazolin-2-yl)ethyl)carbamate;
(S)-tert-butyl 2-(3-(3-aminophenyl)-5-chloro-4-oxo-3,4-dihydroquinazolin-2-yl)pyrrolidine-1-carboxylate;
(S)-tert-butyl(1-(3-(3-(3-ethylureido)phenyl)-5-fluoro-4-oxo-3,4-dihydroquinazolin-2-yl)ethyl)carbamate;
(S)-tert-butyl(1-(5,8-dichloro-3-(3-(3-ethylureido)phenyl)-4-oxo-3,4-dihydroquinazolin-2-yl)ethyl)carbamate;
(S)-tert-butyl(1-(5-bromo-3-(3-(3-ethylureido)phenyl)-4-oxo-3,4-dihydroquinazolin-2-yl)ethyl)carbamate;
(S)-tert-butyl(1-(3-(3-(3-ethylureido)phenyl)-4-oxo-3,4-dihydroquinazolin-2-yl)ethyl)carbamate;
(S)-tert-butyl(1-(3-(3-(3-ethylureido)phenyl)-4-oxo-5-(trifluoromethyl)-3,4-dihydroquinazolin-2-yl)ethyl)carbamate;
(S)-tert-butyl(1-(3-(3-(3-ethylureido)phenyl)-5,8-difluoro-4-oxo-3,4-dihydroquinazolin-2-yl)ethyl)carbamate;
(S)-tert-butyl(1-(3-(3-(3-ethylureido)phenyl)-8-fluoro-4-oxo-3,4-dihydroquinazolin-2-yl)ethyl)carbamate;
(S)-tert-butyl(1-(3-(3-(3-ethylureido)phenyl)-5-methoxy-4-oxo-3,4-dihydroquinazolin-2-yl)ethyl)carbamate;
(S)-tert-butyl(1-(3-(3-(3-ethylureido)phenyl)-5-methyl-4-oxo-3,4-dihydroquinazolin-2-yl)ethyl)carbamate;
(S)-tert-butyl(1-(3-(3-(3-ethylureido)phenyl)-6-fluoro-4-oxo-3,4-dihydroquinazolin-2-yl)ethyl)carbamate;
(S)-tert-butyl(1-(3-(3-(3-ethylureido)phenyl)-7-fluoro-4-oxo-3,4-dihydroquinazolin-2-yl)ethyl)carbamate;
(S)-tert-butyl(1-(5-chloro-3-(2-chloro-5-(3-ethylureido)phenyl)-4-oxo-3,4-dihydroquinazolin-2-yl)ethyl)carbamate;
(S)-tert-butyl(1-(5-chloro-3-(3-(3-ethylureido)phenyl)-4-oxo-3,4-dihydroquinazolin-2-yl)ethyl)(methyl)carbamate;
(S)-tert-butyl(1-(5-chloro-3-(5-(3-ethylureido)-2-methylphenyl)-4-oxo-3,4-dihydroquinazolin-2-yl)ethyl)carbamate.
(S)-tert-butyl(1-(5-chloro-3-(3-(3-ethylureido)phenyl)-8-fluoro-4-oxo-3,4-dihydroquinazolin-2-yl)ethyl)carbamate;
(2S,4S)-tert-butyl 2-(5-chloro-3-(3-(3-ethylureido)phenyl)-4-oxo-3,4-dihydroquinazolin-2-yl)-4-fluoropyrrolidine-1-carboxylate;
(S)-tert-butyl((3-(3-carbamoyl-5-fluorophenyl)-5-chloro-4-oxo-3,4-dihydroquinazolin-2-yl)(cyclopropyl)methyl)carbamate;
(S)-tert-butyl((3-(5-carbamoylpyridin-3-yl)-5-chloro-4-oxo-3,4-dihydroquinazolin-2-yl)cyclopropyl)methyl)carbamate; and
(S)-2-(1-(((triisopropylsilyl)oxy)ethyl)-5-chloro-3-(3-nitrophenyl)quinazolin-4(3H)-one.

Example 2. Preparation of a Compound of Formula (2a)

A. Preparation of a compound of formula (2a) where $W^2$ is CH, n is 1, $R^1$ is chloro, m is 0, $R^5$ is hydrogen, and $R^3$ is methyl

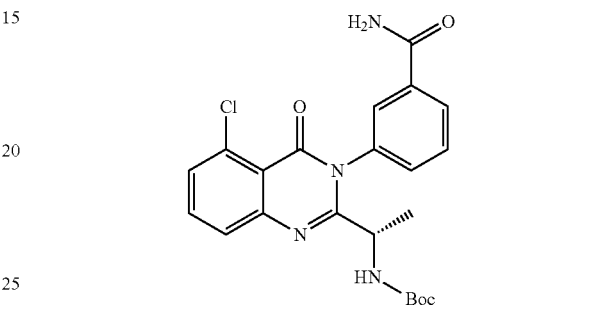

A mixture of (S)-tert-butyl(1-(5-chloro-3-(3-cyanophenyl)-4-oxo-3,4-dihydroquinazolin-2-yl)ethyl)carbamate (0.68 g, 2.0 mmol) in EtOH/water/tetrahydrofuran (18 mL, 10:5:3) was treated with hydrido(dimethylphosphinous acid-kP)[hydrogen bis(dimethylphosphinito-kP)]platinum(II) (1 mol %, 0.02 mmol, 0.85 mg). The mixture was stirred and heated overnight at 80° C. Concentration of the reaction mixture under reduced pressure afforded (S)-tert-butyl(1-(3-(3-carbamoylphenyl)-5-chloro-4-oxo-3,4-dihydroquinazolin-2-yl)ethyl)carbamate. ES/MS 443.2 (M+H$^+$)

B. Preparation of the below compounds of formula (2a) using the procedures described in Example 2A and Reaction Scheme I:
(S)-tert-butyl(1-(3-(3-carbamoylphenyl)-5,8-dichloro-4-oxo-3,4-dihydroquinazolin-2-yl)ethyl)carbamate;
(S)-tert-butyl(1-(3-(3-carbamoyl-2-methylphenyl)-5-chloro-4-oxo-3,4-dihydroquinazolin-2-yl)ethyl)carbamate;
(S)-tert-butyl(1-(3-(3-carbamoylphenyl)-5-chloro-4-oxo-3,4-dihydroquinazolin-2-yl)propyl)carbamate;
(S)-tert-butyl((3-(3-carbamoylphenyl)-5-chloro-4-oxo-3,4-dihydroquinazolin-2-yl)(cyclopropyl)methyl)carbamate;
(S)-tert-butyl((3-(3-carbamoylphenyl)-5,8-dichloro-4-oxo-3,4-dihydroquinazolin-2-yl)cyclopropyl)methyl)carbamate;
(S)-tert-butyl((3-(3-carbamoylphenyl)-5-chloro-8-fluoro-4-oxo-3,4-dihydroquinazolin-2-yl)(cyclopropyl)methyl)carbamate;
(S)-tert-butyl 2-(3-(3-carbamoylphenyl)-5,8-dichloro-4-oxo-3,4-dihydroquinazolin-2-yl)pyrrolidine-1-carboxylate;
(S)-tert-butyl(1-(3-(3-carbamoylphenyl)-5,8-dichloro-4-oxo-3,4-dihydroquinazolin-2-yl)propyl)carbamate;
(S)-tert-butyl(1-(3-(3-carbamoylphenyl)-5,8-dichloro-4-oxo-3,4-dihydroquinazolin-2-yl)butyl)carbamate;
(S)-tert-butyl(1-(3-(3-carbamoylphenyl)-5-chloro-4-oxo-3,4-dihydroquinazolin-2-yl)butyl)carbamate;
(S)-tert-butyl((3-(3-carbamoylphenyl)-5-(difluoromethyl)-4-oxo-3,4-dihydroquinazolin-2-yl)(cyclopropyl)methyl)carbamate;

(S)-tert-butyl((3-(3-carbamoylphenyl)-8-chloro-6-fluoro-4-oxo-3,4-dihydroquinazolin-2-yl)cyclopropyl)methyl)carbamate;

(S)-tert-butyl((3-(3-carbamoylphenyl)-8-cyano-6-fluoro-4-oxo-3,4-dihydroquinazolin-2-yl)(cyclopropyl)methyl)carbamate;

(S)-tert-butyl(1-(3-(3-carbamoylphenyl)-5-(difluoromethyl)-4-oxo-3,4-dihydroquinazolin-2-yl)propyl)carbamate;

(S)-tert-butyl(1-(3-(3-carbamoylphenyl)-8-chloro-6-fluoro-4-oxo-3,4-dihydroquinazolin-2-yl)ethyl)carbamate;

(S)-tert-butyl(1-(3-(3-carbamoylphenyl)-8-cyano-6-fluoro-4-oxo-3,4-dihydroquinazolin-2-yl)ethyl)carbamate;

(S)-tert-butyl(1-(3-(3-carbamoylphenyl)-5,8-dichloro-4-oxo-3,4-dihydroquinazolin-2-yl)butyl)carbamate;

(S)-tert-butyl(1-(3-(3-carbamoylphenyl)-5,8-dichloro-4-oxo-3,4-dihydroquinazolin-2-yl)propyl)carbamate;

(S)-tert-butyl(1-(5-chloro-3-(3-(3-methylureido)phenyl)-4-oxo-3,4-dihydroquinazolin-2-yl)ethyl)carbamate;

(S)-tert-butyl(1-(5-chloro-4-oxo-3-(3-ureidophenyl)-3,4-dihydroquinazolin-2-yl)ethyl)carbamate;

(S)-tert-butyl 2-(3-(3-(2-(1-((tert-butoxycarbonyl)amino)ethyl)-5-chloro-4-oxoquinazolin-3(4H)-yl)phenyl)ureido)benzoate;

(S)-tert-butyl(1-(5-chloro-3-(2-chloro-3-(3-ethylureido)phenyl)-4-oxo-3,4-dihydroquinazolin-2-yl)ethyl)carbamate;

(S)-tert-butyl(1-(5-chloro-3-(3-(3-ethylureido)phenyl)-4-oxo-3,4-dihydroquinazolin-2-yl)ethyl)carbamate;

(S)-tert-butyl 2-(2-(3-(3-(2-(1-((tert-butoxycarbonyl)amino)ethyl)-5-chloro-4-oxoquinazolin-3(4H)-yl)phenyl)ureido)phenoxy)acetate; and (S)-2-(3-(3-(2-(1-((tert-butoxycarbonyl)amino)ethyl)-5-chloro-4-oxoquinazolin-3(4H)-yl)phenyl)ureido)benzenesulfonate.

C. Preparation of a compound of formula (2a) where $W^2$ is CH, n is 1, $R^1$ is iodo, m is 0, $R^5$ is hydrogen, and $R^3$ is methyl

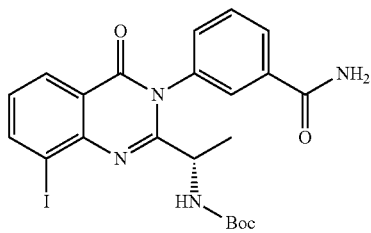 [SMILES: C[C@H](NC(=O)OC(C)(C)C)c1nc2c(I)cccc2c(=O)n1-c1cccc(C(N)=O)c1]

DPP (1.3 mL, 7 mmol) was added to a mixture of 2-amino-3-iodobenzoic acid (500 mg, 1.9 mmol), Boc-alanine (432 mg, 2.3 mmol), and pyridine (1.4 mL, 17 mmol) and the resulting solution was heated to 40° C. After stirring for 4 hours, 3-aminobenzamide (311 mg, 2.3 mmol) was added. The mixture was allowed to continue stirring at 40° C. for 3 days.

The reaction mixture was purified directly on silica (80 g column, 0-100% EtOAc/hexane) to provide (S)-tert-butyl (1-(3-(3-carbamoylphenyl)-8-iodo-4-oxo-3,4-dihydroquinazolin-2-yl)ethyl)carbamate. ES/MS 535.1 (M+H+).

D. Preparation of a Compound of Formula (2a) where $W^2$ is CH, n is 1, $R^1$ is Cyano, m is 0, $R^5$ is Hydrogen, and $R^3$ is Methyl

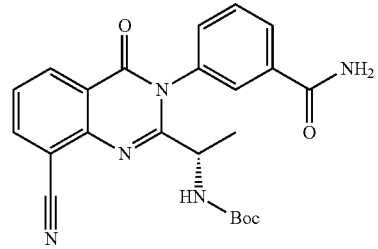 [SMILES: C[C@H](NC(=O)OC(C)(C)C)c1nc2c(C#N)cccc2c(=O)n1-c1cccc(C(N)=O)c1]

(S)-tert-butyl(1-(3-(3-carbamoylphenyl)-8-iodo-4-oxo-3,4-dihydroquinazolin-2-yl)ethyl)carbamate (0.42 g, 0.79 mmol) was combined with zinc cyanide (111 mg, 0.94 mmol) and tetrakis (PPh₃) Pd(0) (91 mg, 0.08 mmol) in NMP (3 mL). The mixture was heated to 80° C. with stirring for 18 hours. After cooling, the mixture was poured into EtOAc, washed 2× with aq. NaHCO3, and adsorbed onto isolute. Purification on silica (40 g column, 0-100% EtOAc/hexane) provided (S)-tert-butyl(1-(3-(3-carbamoylphenyl)-8-cyano-4-oxo-3,4-dihydroquinazolin-2-yl)ethyl)carbamate. ES/MS 456.1 (M+Na).

E. Preparation of a Compound of Formula (2b) where $W^2$ is CH, n is 1, $R^1$ is Allyl, m is 0, $R^5$ is Hydrogen, $R^6$ is Ethyl, and $R^3$ is Methyl

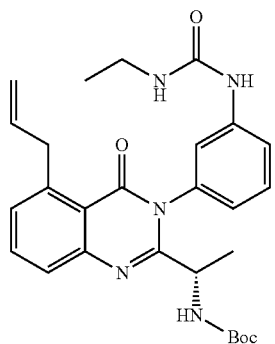 [SMILES: C=CCc1cccc2nc([C@H](C)NC(=O)OC(C)(C)C)n(-c3cccc(NC(=O)NCC)c3)c(=O)c12]

A solution of(S)-tert-butyl(1-(5-bromo-3-(3-(3-ethylureido)phenyl)-4-oxo-3,4-dihydroquinazolin-2-yl)ethyl)carbamate (1.0 g, 1.89 mmol), pinacol allylboronate (0.60 mL, 3.21 mmol) and cesium fluoride (574 mg, 3.78 mmol) in dioxane (19 mL) was degassed with argon for 10 minutes. Tetrakis(triphenylphosphine)palladium(O) (218 mg, 0.19 mmol) was added and the reaction was stirred at 100° C. for 16 hours. Water was then added and the mixture was extracted twice with ethyl acetate. The combined organic layers were dried over MgSO₄, filtered and concentrated in vacuuo to afford material which was purified by column chromatography on SiO₂ eluting with EtOAc in hexanes (20-100%) to afford (S)-tert-butyl (1-(5-allyl-3-(3-(3-ethylureido)phenyl)-4-oxo-3,4-dihydroquinazolin-2-yl)ethyl) carbamate.

ES/MS m/z=491.1 (M+H+).

Example 3. Preparation of a Compound of Formula (3)

A. Preparation of a compound of formula (3) in which $W^2$ is CH, n is 1, $R^1$ is chloro, m is 0, $R^5$ is hydrogen, and $R^3$ is methyl

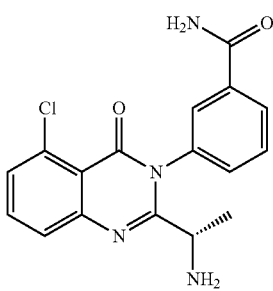 [SMILES: C[C@H](N)c1nc2cccc(Cl)c2c(=O)n1-c1cccc(C(N)=O)c1]

A solution of (S)-tert-butyl(1-(3-(3-carbamoylphenyl)-5-chloro-4-oxo-3,4-dihydroquinazolin-2-yl)ethyl)carbamate (approximately 1 mmol) in dichloromethane (5 mL) was treated with trifluoroacetic acid (1.75 mL). After overnight at room temperature, the mixture was concentrated under reduced pressure to give (S)-1-(3-(3-carbamoylphenyl)-5-chloro-4-oxo-3,4-dihydroquinazolin-2-yl)ethanaminium 2,2,2-trifluoroacetate. ES/MS 343.1 (M+H+).

b. Preparation of the below compounds of formula (3) using the procedures described in Example 3A and Reaction Scheme I:

(S)-3-(2-(1-aminoethyl)-5,8-dichloro-4-oxoquinazolin-3(4H)-yl)benzamide;
(S)-3-(2-(1-aminoethyl)-5-chloro-4-oxoquinazolin-3(4H)-yl)-2-methylbenzamide;
(S)-3-(2-(1-aminopropyl)-5-chloro-4-oxoquinazolin-3(4H)-yl)benzamide;
(S)-3-(2-(amino(cyclopropyl)methyl)-5-chloro-4-oxoquinazolin-3(4H)-yl)benzamide;
(S)-3-(2-(amino(cyclopropyl)methyl)-5,8-dichloro-4-oxoquinazolin-3(4H)-yl)benzamide;
(S)-3-(2-(amino(cyclopropyl)methyl)-5-chloro-8-fluoro-4-oxoquinazolin-3(4H)-yl)benzamide;
(S)-3-(5,8-dichloro-4-oxo-2-(pyrrolidin-2-yl)quinazolin-3(4H)-yl)benzamide;
(S)-3-(2-(1-aminopropyl)-5,8-dichloro-4-oxoquinazolin-3(4H)-yl)benzamide;
(S)-3-(2-(1-aminobutyl)-5,8-dichloro-4-oxoquinazolin-3(4H)-yl)benzamide;
(S)-3-(2-(1-aminobutyl)-5-chloro-4-oxoquinazolin-3(4H)-yl)benzamide;
(S)-3-(2-(1-aminoethyl)-8-chloro-6-fluoro-4-oxoquinazolin-3(4H)-yl)benzamide;
(S)-3-(2-(1-aminoethyl)-8-cyano-6-fluoro-4-oxoquinazolin-3(4H)-yl)benzamide;
(S)-3-(2-(1-aminopropyl)-5-(difluoromethyl)-4-oxoquinazolin-3(4H)-yl)benzamide;
(S)-3-(2-(amino(cyclopropyl)methyl)-5-(difluoromethyl)-4-oxoquinazolin-3(4H)-yl)benzamide;
(S)-3-(2-(amino(cyclopropyl)methyl)-8-chloro-6-fluoro-4-oxoquinazolin-3(4H)-yl)benzamide;
(S)-3-(2-(amino(cyclopropyl)methyl)-8-cyano-6-fluoro-4-oxoquinazolin-3(4H)-yl)benzamide;
(S)-3-(2-(1-aminoethyl)-8-cyano-4-oxoquinazolin-3(4H)-yl)benzamide;
(S)-3-(2-(1-aminobutyl)-5,8-dichloro-4-oxoquinazolin-3(4H)-yl)benzamide;
(S)-3-(2-(1-aminopropyl)-5,8-dichloro-4-oxoquinazolin-3(4H)-yl)benzamide;
(R)-1-(3-(2-(1-aminoethyl)-5-chloro-4-oxoquinazolin-3(4H)-yl)phenyl)-3-ethylurea; 1-(3-(2-((1S,2S)-1-amino-2-methylbutyl)-5-chloro-4-oxoquinazolin-3(4H)-yl)phenyl)-3-ethylurea;
(S)-1-(3-(2-(1-aminoethyl)-5,8-dichloro-4-oxoquinazolin-3(4H)-yl)phenyl)-3-ethylurea;
(S)-1-(3-(2-(1-aminoethyl)-5-bromo-4-oxoquinazolin-3(4H)-yl)phenyl)-3-ethylurea;
(S)-1-(3-(2-(1-aminoethyl)-5-fluoro-4-oxoquinazolin-3(4H)-yl)phenyl)-3-ethylurea;
(S)-1-(3-(5-allyl-2-(1-aminoethyl)-4-oxoquinazolin-3(4H)-yl)phenyl)-3-ethylurea;
(S)-1-(3-(2-(1-aminoethyl)-4-oxo-5-(trifluoromethyl)quinazolin-3(4H)-yl)phenyl)-3-ethylurea;
(S)-1-(3-(2-(1-aminoethyl)-4-oxoquinazolin-3(4H)-yl)phenyl)-3-ethylurea;
(S)-1-(3-(2-(1-aminoethyl)-5,8-difluoro-4-oxoquinazolin-3(4H)-yl)phenyl)-3-ethylurea;
(S)-1-(3-(2-(1-aminoethyl)-8-fluoro-4-oxoquinazolin-3(4H)-yl)phenyl)-3-ethylurea;
(S)-1-(3-(2-(1-aminoethyl)-5-methoxy-4-oxoquinazolin-3(4H)-yl)phenyl)-3-ethylurea;
(S)-1-(3-(2-(1-aminoethyl)-5-methyl-4-oxoquinazolin-3(4H)-yl)phenyl)-3-ethylurea;
(S)-1-(3-(2-(1-aminoethyl)-6-fluoro-4-oxoquinazolin-3(4H)-yl)phenyl)-3-ethylurea;
(S)-1-(3-(2-(1-aminoethyl)-7-fluoro-4-oxoquinazolin-3(4H)-yl)phenyl)-3-ethylurea;
(S)-1-(3-(2-(1-aminoethyl)-5-chloro-4-oxoquinazolin-3(4H)-yl)-4-chlorophenyl)-3-ethylurea;
(S)-1(-(2-(1-aminoethyl)-5-chloro-4-oxoquinazolin-3(4H)-yl)-4-methylphenyl)-3-ethylurea;
(S)-1-(3-(5-chloro-2-(1-(methylamino)ethyl)-4-oxoquinazolin-3(4H)-yl)phenyl)-3-ethylurea;
(S)-1-(3-(2-(1-aminoethyl)-5-chloro-8-fluoro-4-oxoquinazolin-3(4H)-yl)phenyl)-3-ethylurea;
(S)-1-(3-(2-(1-aminoethyl)-5,8-dichloro-4-oxoquinazolin-3(4H)-yl)phenyl)-3-(3-hydroxypropyl)urea;
(S)-1-(3-(2-(1-aminoethyl)-5,8-difluoro-4-oxoquinazolin-3(4H)-yl)phenyl)-3-(3-hydroxypropyl)urea;
(S)-1-(3-(2-(1-aminoethyl)-5-chloro-8-fluoro-4-oxoquinazolin-3(4H)-yl)phenyl)-3-(3-hydroxypropyl)urea;
(S)-1-(3-(2-(1-aminoethyl)-8-chloro-4-oxoquinazolin-3(4H)-yl)phenyl)-3-(3-hydroxypropyl)urea;
(S)-1-(3-(2-(1-aminoethyl)-8-fluoro-4-oxoquinazolin-3(4H)-yl)phenyl)-3-(3-hydroxypropyl)urea;
(S)-1-(3-(2-(1-aminoethyl)-5-chloro-4-oxoquinazolin-3(4H)-yl)phenyl)-3-(1-(trifluoromethyl)cyclopropyl)urea;
(S)-1-(3-(2-(1-aminoethyl)-5-chloro-4-oxoquinazolin-3(4H)-yl)phenyl)-3-(2,2,2-trifluoroethyl)urea;
(S)-1-(3-(2-(1-aminoethyl)-5-chloro-4-oxoquinazolin-3(4H)-yl)phenyl)-3-(5-(tert-butyl)isoxazol-3-yl)urea;
1-(3-(5-chloro-2-((2S,4S)-4-fluoropyrrolidin-2-yl)-4-oxoquinazolin-3(4H)-yl)phenyl)-3-ethylurea;
(S)—N-((3-(2-(1-aminoethyl)-5-chloro-4-oxoquinazolin-3(4H)-yl)phenyl)carbamoyl)cyclopentanesulfonamide;
(S)—N-((3-(2-(1-aminoethyl)-5-chloro-4-oxoquinazolin-3(4H)-yl)phenyl)carbamoyl)cyclopropanesulfonamide;
(S)-1-(5-(2-(1-aminoethyl)-5-chloro-4-oxoquinazolin-3(4H)-yl)-2-fluorophenyl)-3-ethylurea;
(S)-1-(5-(2-(1-aminoethyl)-5-chloro-4-oxoquinazolin-3(4H)-yl)-2-fluorophenyl)-3-isopropylurea;
(S)-1-((1,3-dioxolan-2-yl)methyl)-3-(3-(5-chloro-4-oxo-2-(pyrrolidin-2-yl)quinazolin-3(4H)-yl)phenyl)urea;

(S)-1-(3-(5-chloro-4-oxo-2-(pyrrolidin-2-yl)quinazolin-3(4H)-yl)phenyl)-3-(2-methoxyethyl)urea;
(S)-1-(3-(5-chloro-4-oxo-2-(pyrrolidin-2-yl)quinazolin-3(4H)-yl)phenyl)-3-(pyridin-2-yl)urea;
(S)-1-(3-(5-chloro-4-oxo-2-(pyrrolidin-2-yl)quinazolin-3(4H)-yl)phenyl)-3-ethylurea;
(S)-1-(3-(2-(1-aminoethyl)-5-chloro-4-oxoquinazolin-3(4H)-yl)phenyl)-3-methylurea;
(S)-1-(3-(2-(1-aminoethyl)-5-chloro-4-oxoquinazolin-3(4H)-yl)phenyl)urea;
(S)-2-(3-(3-(2-(1-aminoethyl)-5-chloro-4-oxoquinazolin-3(4H)-yl)phenyl)ureido)benzoic acid;
(S)-1-(3-(2-(1-aminoethyl)-5-chloro-4-oxoquinazolin-3(4H)-yl)-2-chlorophenyl)-3-ethylurea;
(S)-1-(3-(2-(1-aminoethyl)-5-chloro-4-oxoquinazolin-3(4H)-yl)phenyl)-3-ethylurea;
(S)-2-(2-(3-(3-(2-(1-aminoethyl)-5-chloro-4-oxoquinazolin-3(4H)-yl)phenyl)ureido)phenoxy)acetic acid;
(S)-2-(3-(3-(2-(1-aminoethyl)-5-chloro-4-oxoquinazolin-3(4H)-yl)phenyl)ureido)benzenesulfonic acid;
(S)-1-(3-(2-(1-aminoethyl)-5-chloro-4-oxoquinazolin-3(4H)-yl)phenyl)-3-(2-chlorophenyl)urea;
(S)-1-(3-(2-(1-aminoethyl)-5-chloro-4-oxoquinazolin-3(4H)-yl)phenyl)-3-(4-chloro-3-(trifluoromethyl)phenyl)urea;
(S)-1-(3-(2-(1-aminoethyl)-5-chloro-4-oxoquinazolin-3(4H)-yl)phenyl)-3-(2,4-difluorophenyl)urea;
(S)-1-(3-(2-(1-aminoethyl)-5-chloro-4-oxoquinazolin-3(4H)-yl)phenyl)-3-(2,6-dichlorophenyl)urea;
(S)-1-(3-(2-(1-aminoethyl)-5-chloro-4-oxoquinazolin-3(4H)-yl)phenyl)-3-(2-(trifluoromethyl)phenyl)urea;
(S)-1-(3-(2-(1-aminoethyl)-5-chloro-4-oxoquinazolin-3(4H)-yl)phenyl)-3-(2-cyanophenyl)urea; (S)-1-(3-(2-(1-aminoethyl)-5-chloro-4-oxoquinazolin-3(4H)-yl)phenyl)-3-(2-methoxyphenyl)urea;
(S)-1-(3-(2-(1-aminoethyl)-5-chloro-4-oxoquinazolin-3(4H)-yl)phenyl)-3-(o-tolyl)urea;
(S)-1-(3-(2-(1-aminoethyl)-5-fluoro-4-oxoquinazolin-3(4H)-yl)phenyl)-3-(2-(trifluoromethyl)phenyl)urea;
(S)-1-(3-(2-(1-aminoethyl)-5-fluoro-4-oxoquinazolin-3(4H)-yl)phenyl)-3-(2-chlorophenyl)urea;
(S)-1-(3-(2-(1-aminoethyl)-5-chloro-4-oxoquinazolin-3(4H)-yl)phenyl)-3-(3-chloropyridin-4-yl)urea;
(S)-1-(3-(2-(1-aminoethyl)-5-chloro-4-oxoquinazolin-3(4H)-yl)phenyl)-3-methoxyurea;
(S)-1-(3-(2-(1-aminoethyl)-5-chloro-4-oxoquinazolin-3(4H)-yl)phenyl)-3-(2-(dimethylamino)ethyl)urea;
(S)-1-(3-(2-(1-aminoethyl)-5-chloro-4-oxoquinazolin-3(4H)-yl)phenyl)-3-(2-hydroxyethyl)urea;
(S)-1-(3-(2-(1-aminoethyl)-5-chloro-4-oxoquinazolin-3(4H)-yl)phenyl)-3-(pyridin-3-yl)urea;
(S)-1-(3-(2-(1-aminoethyl)-5-chloro-4-oxoquinazolin-3(4H)-yl)phenyl)-3-phenylurea;
(S)-1-(3-(2-(1-aminoethyl)-5-chloro-4-oxoquinazolin-3(4H)-yl)phenyl)-3-cyclobutylurea;
(S)-1-(3-(2-(1-aminoethyl)-5-chloro-4-oxoquinazolin-3(4H)-yl)phenyl)-3-cyclohexylurea;
(S)-1-(3-(2-(1-aminoethyl)-5-chloro-4-oxoquinazolin-3(4H)-yl)phenyl)-3-cyclopentylurea;
(S)-1-(3-(2-(1-aminoethyl)-5-chloro-4-oxoquinazolin-3(4H)-yl)phenyl)-3-isopropylurea;
(S)-1-(3-(2-(1-aminoethyl)-5-chloro-4-oxoquinazolin-3(4H)-yl)phenyl)-3-(2-fluoroethyl)urea;
(S)-1-(3-(2-(1-aminoethyl)-5-chloro-4-oxoquinazolin-3(4H)-yl)phenyl)-3-(tert-butyl)urea;
(S)-1-(3-(2-(1-aminoethyl)-5-chloro-4-oxoquinazolin-3(4H)-yl)phenyl)-3-cyclopropylurea;
(S)-1-(3-(2-(1-aminoethyl)-5-chloro-4-oxoquinazolin-3(4H)-yl)phenyl)-3-propylurea;
(R)-1-(3-(2-(1-amino-2-(benzyloxy)ethyl)-5-chlor 4-oxoquinazolin-3(4H)-yl)phenyl)-3-(3-hydroxypropyl)urea;
(S)-1-(3-(2-(1-aminoethyl)-5-chloro-4-oxoquinazolin-3(4H)-yl)phenyl)-3-(3-hydroxypropyl)urea;
1-(3-(2-((S)-1-aminoethyl)-5-chloro-4-oxoquinazolin-3(4H)-yl)phenyl)-3-(2-hydroxypropyl)urea;
(S)-3-(3-(3-(2-(1-aminoethyl)-5-chloro-4-oxoquinazolin-3(4H)-yl)phenyl)ureido)propanoic acid;
(R)-1-(3-(2-(1-amino-2-(benzyloxy)ethyl)-5-chloro-4-oxoquinazolin-3(4H)-yl)phenyl)-3-ethylurea;
(S)-1-(3-(2-(1-aminoethyl)-5-chloro-4-oxoquinazolin-3(4H)-yl)phenyl)-3-(3-methoxypropyl)urea;
(S)-2-(3-(3-(2-(1-aminoethyl)-5-chloro-4-oxoquinazolin-3(4H)-yl)phenyl)ureido)-2-methylpropanoic acid;
(S)-1-(3-(2-(1-aminoethyl)-5-chloro-4-oxoquinazolin-3(4H)-yl)phenyl)-3-(1-hydroxy-2-methylpropan-2-yl)urea;
(S)-1-(3-(2-(1-aminoethyl)-5-chloro-4-oxoquinazolin-3(4H)-yl)phenyl)-3-(3-hydroxy-2,2-dimethylpropyl)urea;
(S)-1-(3-(2-(1-aminoethyl)-5-chloro-4-oxoquinazolin-3(4H)-yl)phenyl)-3-(4-hydroxy-2-methylbutan-2-yl)urea;
(S)-1-(3-(2-(1-aminoethyl)-5-chloro-4-oxoquinazolin-3(4H)-yl)phenyl)-3-(2-(2-hydroxyethoxy)phenyl)urea;
(S)-1-(3-(2-(1-aminoethyl)-5-chloro-4-oxoquinazolin-3(4H)-yl)phenyl)-3-(2-(methylsulfonyl)phenyl)urea;
(S)-1-(3-(2-(1-aminoethyl)-5-chloro-4-oxoquinazolin-3(4H)-yl)phenyl)-3-(3-hydroxy-3-methylbutyl)urea;
(S)-3-(2-(amino(cyclopropyl)methyl)-5-chloro-4-oxoquinazolin-3(4H)-yl)-5-fluorobenzamide;
(S)-5-(2-(amino(cyclopropyl)methyl)-5-chloro-4-oxoquinazolin-3(4H)-yl)nicotinamide; and
(S)-1-(3-(5-chloro-4-oxo-2-(pyrrolidin-2-yl)quinazolin-3(4H)-yl)phenyl)-3-(2,2,2-trifluoroethyl)urea.

Example 4. Preparation of a Compound of Formula (4)

A. Preparation of a compound of formula (4) in which $R^{4a}$ is CN and X is Cl (2,4-diamino-6-chloropyrimidine-5-carbonitrile)

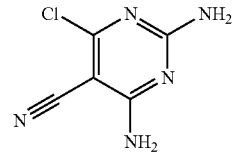 [SMILES: N#Cc1c(N)nc(N)nc1Cl]

Ammonium hydroxide (20 mL) was added to a solution of 2,4,6-trichloropyrimidine-5-carbonitrile (5.0 g, 24 mmol) in dioxane (20 mL) at room temperature. The solution was heated to 50° C. and stirred for 3 hrs. The reaction mixture was cooled to 10° C. and added to water (50 mL). The resulting solid was filtered, washed with water, and dried under high vacuum to afford the title compound. 13H NMR (100 MHz, DMSO) 164.8, 162.6, 161.9, 115.8, 77.6. ES/MS m/z=169.9 (M+H+).

B. preparation of the below compounds of formula (4) using the procedures described in Example 4A and Reaction Scheme I:
5-chloro-6-fluoropyrimidine-2,4-diamine;
6-chloro-5-(methylsulfonyl)pyrimidine-2,4-diamine;

2-amino-4-chloro-6-(difluoromethyl)pyrimidine-5-carbonitrile;
6-chloro-5-(trifluoromethyl)pyrimidine-2,4-diamine; and
2,4-diamino-6-chloropyrimidine-5-carboxamide.

Example 5. Preparation of a Compound of Formula (J), (I), (II), or (III)

A. Preparation of a compound of formula (I) where $W^2$ is CH, n is 1, $R^1$ is chloro, m is 0, $R^3$ is methyl, $R^4$ is 2,6-diamino-5-chloropyrimidin-4-yl, and $R^5$ is hydrogen (Compound 1)

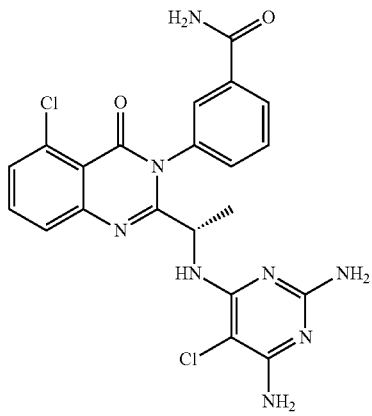 [SMILES: C[C@H](Nc1nc(N)nc(N)c1Cl)c1nc2cccc(Cl)c2c(=O)n1-c1cccc(C(N)=O)c1]

A suspension of (S)-1-(3-(3-carbamoylphenyl)-5-chloro-4-oxo-3,4-dihydroquinazolin-2-yl)ethanaminium 2,2,2-trifluoroacetate (0.77 mmol) in isopropanol (6 mL) was treated with 2,6-diamino-5-chloro-4-fluoropyrimidine (1.1 eq) and diisopropylethylamine (10 eq). The mixture was stirred overnight at 115° C. when it was concentrated under reduced pressure. The residue was purified by HPLC, eluting with 5% acetonitrile/95% water (0.1% TFA modifier in both solvents) to 70% acetonitrile over 28 to 30 minutes. Fractions were concentrated and lyophilized to furnish (S)-3-(5-chloro-2-(1-((2,6-diamino-5-chloropyrimidin-4-yl)amino)ethyl)-4-oxoquinazolin-3(4H)-yl)benzamide (Compound 1). 1H NMR (400 MHz, DMSO-d6) δ 8.29 (s, 1H), 8.05 (m, 1H), 8.01 (m, 2H), 7.96 (m, 0.5H), 7.82-7.59 (m, 5.5H), 7.53 (br, 2H), 7.47 (br, 2H), 4.77 (m, 1H), 1.36 (m, 3H). ES/MS 485.1 (M+H+).

B. Preparation of the below compound of formula (I), (II), or (III), using the procedure described in Example 5A, Reaction Scheme I, or Reaction Scheme II:

(S)-3-(5-chloro-2-(1-((2,6-diamino-5-cyanopyrimidin-4-yl)amino)ethyl)-4-oxoquinazolin-3(4H)-yl)benzamide (Compound 2). 1H NMR (400 MHz, DMSO-d6) δ 8.29 (s, 1H), 8.18-7.95 (m, 3H), 7.84-7.76 (m, 3H), 7.21-7.54 (m, 5H), 4.80 (m, 1H), 1.34 (m, 3H). ES/MS 476.1 (M+H+);

(S)-3-(5,8-dichloro-2-(1-((2,6-diamino-5-cyanopyrimidin-4-yl)amino)ethyl)-4-oxoquinazolin-3(4H)-yl)benzamide (Compound 3). 1H NMR (400 MHz, DMSO-d6) δ 8.24 (s, 1H), 8.06-7.95 (m, 5H), 7.79 (m, 1H), 7.68 (m, 3H), 7.63-7.54 (m, 3H), 4.86 (m, 1H), 1.33 (m, 3H). ES/MS 510.1 (M+H+);

(S)-3-(5,8-dichloro-2-(1-((2,6-diamino-5-chloropyrimidin-4-yl)amino)ethyl)-4-oxoquinazolin-3(4H)-yl)benzamide (Compound 4). 1H NMR (400 MHz, DMSO-d6) δ 8.22 (s, 1H), 8.05-8.00 (m, 2H), 7.99-7.94 (m, 1H), 7.79 (m, 1H), 7.75 (br, 1H), 7.70-7.57 (m, 3H), 7.55-7.44 (br, 4H), 4.84 (m, 1H), 1.37 (m, 3H). ES/MS 519.0 (M+H+);

(S)-3-(5-chloro-2-(1-((2,6-diamino-5-cyanopyrimidin-4-yl)amino)ethyl)-4-oxoquinazolin-3(4H)-yl)-2-methylbenzamide (Compound 5). 1H NMR (400 MHz, DMSO-d6) δ 7.88 (s, 1H), 7.84 (t, J=8.0 Hz, 1H), 7.71 (dd, J=8.4, 1.2 Hz, 1H), 7.64 (dd, J=8.0, 1.2 Hz, 1H), 7.43 (m, 1H), 7.30 (t, J=7.6 Hz, 1H), 4.83 (m, 1H), 2.09 (s, 3H), 1.32 (d, J=6.8 Hz, 3H). ES/MS 490.1 (M+H+);

(S)-3-(5-chloro-2-(1-((2,6-diamino-5-cyanopyrimidin-4-yl)amino)ethyl)-4-oxoquinazolin-3(4H)-yl)-2-methylbenzamide (Compound 6). 1H NMR (400 MHz, DMSO-d6) δ 8.03 (s, 1H), 7.83 (t, J=8.0 Hz, 1H), 7.72 (dd, J=8.4, 1.2 Hz, 1H), 7.66 (br, 1H), 7.62 (m, 2H), 7.46 (m, 2H), 5.08 (m, 1H), 2.07 (s, 3H), 1.35 (d, J=6.8 Hz, 3H). ES/MS 490.1 (M+H+);

(S)-3-(5-chloro-2-(1-((2,6-diamino-5-chloropyrimidin-4-yl)amino)propyl)-4-oxoquinazolin-3(4H)-yl)benzamide (Compound 7). 1H NMR (400 MHz, DMSO-d6) δ 8.38 (s, 1H), 8.14-8.01 (m, 2H), 7.87-7.67 (m, 4H), 7.66-7.60 (m, 2H), 7.60-7.38 (br, 4H), 4.68 (m, 0.3H), 4.55 (m, 0.7H), 1.87 (m, 2H), 0.73 (t, J=7.2 Hz, 0.7H), 0.67 (t, J=7.6 Hz, 2.3H). ES/MS 499.3 (M+H+);

(S)-3-(5-chloro-2-(1-((2,6-diamino-5-cyanopyrimidin-4-yl)amino)propyl)-4-oxoquinazolin-3(4H)-yl)benzamide (Compound 8). 1H NMR (400 MHz, DMSO-d6) δ 8.37 (s, 1H), 8.11 (m, 2H), 8.04 (m, 1H), 7.87-7.80 (m, 4H), 7.78-7.69 (m, 2H), 7.68-7.60 (m, 2H), 7.60-7.50 (br, 4H), 4.69 (m, 0.4H), 4.58 (m, 0.6H), 1.85 (m, 2H), 0.73 (t, J=7.6 Hz, 0.7H), 0.67 (t, J=7.2 Hz, 2.3H). ES/MS 490.4 (M+H+);

(S)-3-(5-chloro-2-(cyclopropyl((2,6-diamino-5-cyanopyrimidin-4-yl)amino)methyl)-4-oxoquinazolin-3(4H)-yl)benzamide (Compound 9). 1H NMR (400 MHz, DMSO-d6) δ 8.17 (s, 1H), 8.04-7.97 (m, 3H), 7.86 (m, 2H), 7.82 (m, 1H), 7.81-7.63 (m, 4H), 7.61 (br, 1H), 7.55 (br, 1H), 4.59 (t, J=7.6 Hz, 0.3H), 4.52 (t, J=8.0 Hz, 0.7H), 1.43 (m, 0.8H), 1.30 (m, 0.2H), 0.49 (m, 2H), 0.33 (m, 1H), 0.04 (m, 1H). ES/MS 502.4 (M+H+);

(S)-3-(5-chloro-2-(cyclopropyl((2,6-diamino-5-chloropyrimidin-4-yl)amino)methyl)-4-oxoquinazolin-3(4H)-yl)benzamide (Compound 10). 1H NMR (400 MHz, DMSO-d6) δ 8.14 (s, 1H), 8.01 (m, 1H), 7.96 (m, 1H), 7.83 (m, 1H), 7.78-7.70 (m, 2H), 7.70-7.63 (m, 2H), 7.59-7.30 (br, 4H), 4.52 (t, J=7.6 Hz, 0.3H), 4.48 (t, J=8.4 Hz, 0.7H), 1.45 (m, 1H), 0.47 (m, 2H), 0.34 (m, 1H), 0.05 (m, 1H). ES/MS 511.3 (M+H+);

(S)-3-(5,8-dichloro-2-(cyclopropyl((2,6-diamino-5-chloropyrimidin-4-yl)amino)methyl)-4-oxoquinazolin-3(4H)-yl)benzamide (Compound 11). 1H NMR (400 MHz, DMSO-d6) δ 8.14 (s, 1H), 8.08-7.98 (m, 4H), 7.95 (s, 1H), 7.76 (m, 1H), 7.67 (m, 1H), 7.65 (m, 1H), 7.59-7.30 (br, 4H), 4.71 (t, J=7.6 Hz, 0.4H), 4.64 (t, J=8.4 Hz, 0.6H), 1.44 (m, 1H), 0.50 (m, 2H), 0.37 (m, 1H), 0.12 (m, 1H). ES/MS 545.6 (M+H+);

(S)-3-(5,8-dichloro-2-(cyclopropyl((2,6-diamnino-5-cyanopyrimidin-4-yl)amino)methyl)-4-oxoquinazolin-3(4H)-yl)benzamide (Compound 12). 1H NMR (400 MHz, DMSO-d6) δ 8.20-8.09 (m, 1H), 8.08-7.98 (m, 3H), 7.76 (m, 1H), 7.73-7.60 (m, 3H), 7.59-7.53 (m, 1H), 7.45-7.18 (br, 3H), 4.76 (t, J=7.2 Hz, 0.4H), 4.67 (t, J=7.2 Hz, 0.6H), 1.41 (m, 1H), 0.50 (m, 2H), 0.35 (m, 1H), 0.13 (m, 1H). ES/MS 536.5 (M+H+);

(S)-3-(2-(((2-amino-5-cyano-6-methylpyrimidin-4-yl)amino)(cyclopropyl)methyl)-5,8-dichloro-4-oxoquinazolin-3(4H)-yl)benzamide (Compound 13). 1H NMR (400 MHz, DMSO-d6) δ 8.20 (bs, 1H), 8.08 (m, 1H), 8.04-8.00 (m, 1H), 7.95-7.89 (m, 1H), 7.86 (s, 1H), 7.76 (m, 1H), 7.64 (m, 2H), 7.60 (m, 1H), 7.53 (m, 1H), 7.42 (bs, 1H), 4.76 (t, J=8.0 Hz, 0.3H), 4.66 (t, J=8.0 Hz, 0.7H), 2.36 (s, 1H), 2.33 (s, 2H), 1.59-1.45 (m, 1H), 0.61 (m, 1H), 0.53-0.42 (m, 2H), 0.23 (m, 0.8H), 0.10 (m, 0.2H).

ES/MS 535.6 (M+H+);

(S)-3-(2-(((2-amino-5-cyano-6-methylpyrimidin-4-yl) amino)(cyclopropyl)methyl)-5-chloro-8-fluoro-4-oxoquinazolin-3(4H)-yl)benzamide (Compound 14). 1H NMR (400 MHz, DMSO-d6) δ 8.24 (bs, 1H), 8.09 (s, 0.5H), 8.00 (m, 0.5H), 7.96-7.79 (m, 3H), 7.74 (m, 1H), 7.67 (m, 2H), 7.60 (m, 1H), 7.51 (m, 1H), 7.38 (bs, 1H), 4.62 (t, J=8.0 Hz, 0.3H), 4.56 (t, J=8.0 Hz, 0.7H), 2.35 (s, 1H), 2.33 (s, 2H), 1.57 (m, 0.7H), 1.47 (m, 0.3H), 0.61 (m, 1H), 0.50-0.41 (m, 2H), 0.18 (m, 0.8H), 0.06 (m, 0.2H).

ES/MS 519.4 (M+H+);

(S)-3-(5-chloro-2-(cyclopropyl((2,6-diamino-5-cyanopyrimidin-4-yl)amino)methyl)-8-fluoro-4-oxoquinazolin-3(4H)-yl)benzamide (Compound 15). 1H NMR (400 MHz, DMSO-d6) δ 8.09 (s, 0.5H), 8.04-7.95 (m, 3H), 7.85-7.73 (m, 3H), 7.72-7.60 (m, 5H), 7.54 (m, 1.5H), 4.62 (t, J=7.6 Hz, 0.3H), 4.53 (t, J=8.0 Hz, 0.7H), 1.43 (m, 1H), 0.50 (m, 2H), 0.33 (m, 1H), 0.05 (m, 1H). ES/MS 520.4 (M+H+);

(S)-3-(5-chloro-2-(cyclopropyl((2,6-diamino-5-chloropyrimidin-4-yl)amino)methyl)-8-fluoro-4-oxoquinazolin-3(4H)-yl)benzamide (Compound 16). 1H NMR (400 MHz, DMSO-d6) δ 8.09 (s, 1H), 8.02-7.91 (m, 2H), 7.85-7.73 (m, 2H), 7.69-7.63 (m, 2H), 7.54 (br, 2H), 7.46 (m, 3H), 7.22 (b, 1H), 4.58 (t, J=7.6 Hz, 0.3H), 4.52 (t, J=8.4 Hz, 0.7H), 1.47 (m, 1H), 0.57-0.48 (m, 2H), 0.36 (m, 1H), 0.07 (m, 1H). ES/MS 529.6 (M+H+);

(S)-3-(5,8-dichloro-2-(1-(2,6-diamino-5-cyanopyrimidin-4-yl)pyrrolidin-2-yl)-4-oxoquinazolin-3(4H)-yl)benzamide (Compound 17). 1H NMR (400 MHz, DMSO-d6) δ 8.34 (s, 1H), 8.17 (s, 1H), 8.10 (m, 1H), 8.03 (m, 1H), 7.94 (m, 1H), 7.81-7.69 (m, 3H), 7.59-7.52 (m, 2H), 7.39 (br, 1H), 7.11 (br, 1H), 4.77 (d, J=7.2 Hz, 0.7H), 4.69 (m, 0.3H), 4.24 (m, 0.6H), 4.17 (m, 0.4H), 3.92 (m, 1H), 2.26 (m, 1H), 2.07 (m, 2H), 1.78 (m, 1H). ES/MS 536.1 (M+H+);

(S)-3-(5,8-dichloro-2-(1-((2,6-diamino-5-cyanopyrimidin-4-yl)amino)propyl)-4-oxoquinazolin-3(4H)-yl)benzamide (Compound 18). 1H NMR (400 MHz, DMSO-d6) δ 8.30 (s, 1H), 8.14-7.88 (m, 3H), 7.81-7.47 (m, 5H), 6.67-6.61 (m, 2H), 6.56 (d, J=6.5 Hz, 1H), 6.23 (d, J=9.0 Hz, 1H), 4.59-4.50 (m, 1H), 1.69-1.61 (m, 1H), 0.64 (m, 3H). ES/MS 524.1 (M+H+);

(S)-3-(5,8-dichloro-2-(1-((2,6-diamino-5-chloropyrimidin-4-yl)amino)propyl)-4-oxoquinazolin-3(4H)-yl)benzamide (Compound 19). 1H NMR (400 MHz, DMSO-d6) δ 8.31 (s, 1H), 8.17-7.87 (m, 4H), 7.80-7.62 (m, 3H), 7.51 (m, 1H), 6.27-6.08 (m, 1H), 6.02 (m, 1H), 5.78 (d, J=9.6 Hz, 1H), 4.45 (td, J=9.7, 2.9 Hz, 1H), 1.76-1.65 (m, 1H), 1.55 (dt, J=14.3, 7.2 Hz, 1H), 0.69-0.59 (m, 3H). ES/MS 535.1 (M+H+);

(S)-3-(5,8-dichloro-2-(1-((2,6-diamino-5-cyanopyrimidin-4-yl)amino)butyl)-4-oxoquinazolin-3(4H)-yl)benzamide (Compound 20). 1H NMR (400 MHz, DMSO-d6) δ 8.35 (s, 1H), 8.23-7.84 (m, 3H), 7.77-7.26 (m, 3H), 6.71 (s, 3H), 6.27 (s, 1H), 4.93-4.51 (m, 1H), 1.89-1.47 (m, 2H), 1.24 (td, J=14.0, 13.0, 8.4 Hz, 1H), 0.94 (dt, J=14.8, 7.5 Hz, 1H), 0.48 (dt, J=27.0, 7.3 Hz, 3H). ES/MS 538.1 (M+H+);

(S)-3-(5,8-dichloro-2-(1-((2,6-diamino-5-chloropyrimidin-4-yl)amino)butyl)-4-oxoquinazolin-3(4H)-yl)benzamide (Compound 21). 1H NMR (400 MHz, DMSO-d6) δ 8.50-8.21 (m, 1H), 8.19-7.97 (m, 2H), 8.02-7.63 (m, 3H), 7.63-7.24 (m, 1H), 6.34-5.92 (m, 2H), 5.79 (d, J=9.7 Hz, 1H), 4.69 (td, J=9.2, 4.4 Hz, 1H), 1.60 (s, 2H), 1.50-0.77 (m, 2H), 0.70-0.31 (m, 3H). ES/MS 547.1 (M+H+);

(S)-3-(5-chloro-2-(1-((2,6-diamino-5-cyanopyrimidin-4-yl)amino)butyl)-4-oxoquinazolin-3(4H)-yl)benzamide (Compound 22). 1H NMR (400 MHz, DMSO-d6) δ 8.48-8.18 (m, 2H), 8.18-7.91 (m, 2H), 7.90-7.43 (m, 5H), 6.66 (m, 4H), 4.67 (m, 1H), 1.91-1.41 (m, 2H), 1.34-0.74 (m, 2H), 0.63-0.27 (m, 3H). ES/MS 504.1 (M+H+);

(S)-3-(5-chloro-2-(1-((2,6-diamino-5-chloropyrimidin-4-yl)amino)butyl)-4-oxoquinazolin-3(4H)-yl)benzamide (Compound 23). 1H NMR (400 MHz, DMSO-d6) δ 8.45-8.19 (m, 2H), 8.19-7.93 (m, 2H), 7.91-7.66 (m, 3H), 7.63-7.36 (m, 2H), 6.26 (m, 1H), 6.11-5.79 (m, 3H), 4.76-4.48 (m, 1H), 1.83-1.49 (m, 2H), 1.38-0.75 (m, 2H), 0.44 (t, J=7.4 Hz, 3H). ES/MS 513.1 (M+H+);

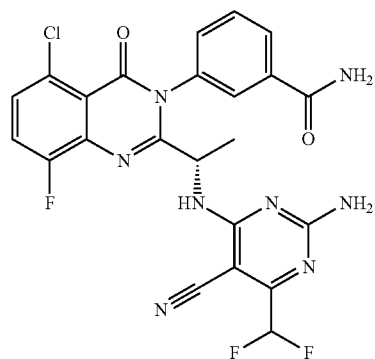

(24)

(S)-3-(2-(1-((2-amino-5-cyano-6-(difluoromethyl)pyrimidin-4-yl)amino)ethyl)-5-chloro-8-fluoro-4-oxoquinazolin-3(4H)-yl)benzamide (Compound 24): 1H NMR (400 MHz, DMSO) δ 8.22 (s, 1H), 8.10-7.98 (m, 2H), 7.93-7.65 (m, 5H), 7.65-7.43 (m, 3H), 6.81-6.50 (m, 1H), 4.88-4.78 (m, 1H), 1.40-1.34 (m, 3H). ES/MS 529.1 (M+H+);

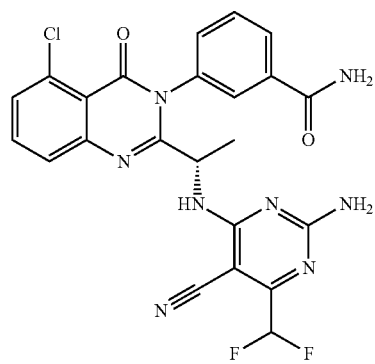

(25)

(S)-3-(2-(1-((2-amino-5-cyano-6-(difluoromethyl)pyrimidin-4-yl)amino)ethyl)-5-chloro-4-oxoquinazolin-3(4H)-yl)benzamide (Compound 25): 1H NMR (400 MHz, DMSO) δ 8.24 (s, 1H), 8.10-7.97 (m, 2H), 7.95-7.88 (m, 1H), 7.85-7.46 (m, 8H), 6.81-6.51 (m, 1H), 4.86-4.75 (m, 1H), 1.38-1.33 (m, 3H). ES/MS 511.1 (M+H+);

(26)

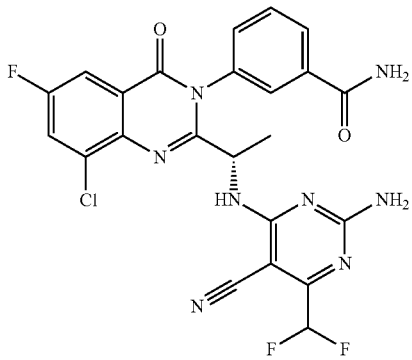

(S)-3-(2-(1-((2-amino-5-cyano-6-(difluoromethyl)pyrimidin-4-yl)amino)ethyl)-8-chloro-6-fluoro-4-oxoquinazolin-3(4H)-yl)benzamide (Compound 26): $^1$H NMR (400 MHz, DMSO) δ 8.20-8.11 (m, 2H), 8.07-7.98 (m, 2H), 7.94-7.75 (m, 2H), 7.74-7.58 (m, 3H), 7.56-7.41 (m, 2H), 6.82-6.49 (m, 1H), 5.00-4.89 (m, 1H), 1.43-1.35 (m, 3H). ES/MS 529.1 (M+H$^+$);

(27)

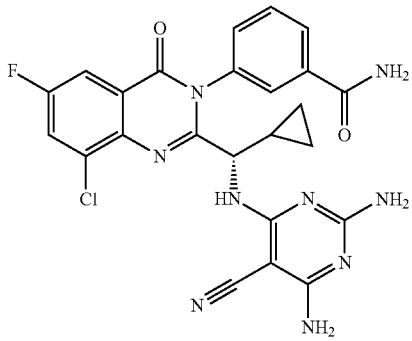

(S)-3-(8-chloro-2-(cyclopropyl((2,6-diamino-5-cyanopyrimidin-4-yl)amino)methyl)-6-fluoro-4-oxoquinazolin-3(4H)-yl)benzamide (Compound 27). $^1$H NMR (400 MHz, DMSO-d$_6$) δ 8.30 (s, 1H), 8.21-8.09 (m, 1H), 8.06-7.97 (m, 1H), 7.85-7.70 (m, 1H), 7.66-7.53 (m, 0H), 6.72 (s, 4H), 6.62 (s, 1H), 6.48 (d, J=7.7 Hz, 1H), 5.97 (d, J=9.0 Hz, 1H), 4.82-4.71 (m, 1H), 4.03 (q, J=7.1 Hz, 1H), 1.99 (d, J=0.6 Hz, 1H), 1.28-1.10 (m, 4H). ES/MS 520.1 (M+H$^+$).

(28)

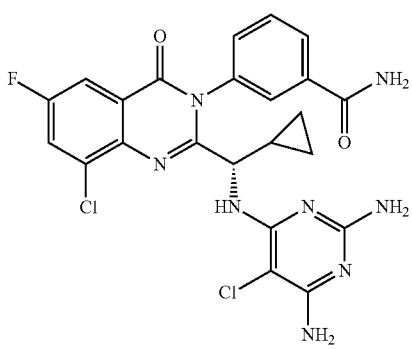

(S)-3-(8-chloro-2-(cyclopropyl((2,6-diamino-5-chloropyrimidin-4-yl)amino)methyl)-6-fluoro-4-oxoquinazolin-3

(4H)-yl)benzamide (Compound 28). $^1$H NMR (400 MHz, DMSO-d$_6$) δ 8.30 (s, 1H), 8.22 (s, J=2.9 Hz, 1H), 8.15-7.90 (m, 1H), 7.82-7.52 (m, 1H), 6.14-5.97 (m, 1H), 5.72-5.66 (m, 1H), 5.50 (s, 1H), 4.77-4.63 (m, 4H), 4.04-3.97 (m, 1H), 2.07-2.04 (m, 1H), 1.97 (dd, J=2.6, 1.7 Hz, 1H), 1.25-1.03 (m, 4H). ES/MS 529.0 (M+H$^+$).

(29)

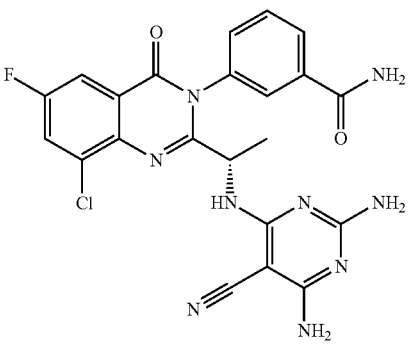

(S)-3-(8-chloro-2-(1-((2,6-diamino-5-cyanopyrimidin-4-yl)amino-4-yl)amino)ethyl)-6-fluoro 4-oxoquinazolin-3(4H)-yl)benzamide (Compound 29). $^1$H NMR (400 MHz, DMSO-d$_6$) δ 8.30 (s, 2H), 8.18-8.09 (m, 1H), 8.02-7.98 (m, 1H), 7.86-7.68 (m, 1H), 7.63-7.57 (m, 0H), 6.65 (s, 1H), 6.57 (s, 1H), 6.51 (d, J=8.5 Hz, 1H), 4.87-4.74 (m, 4H), 1.32 (d, J=6.6 Hz, 1H), 1.27 (d, J=6.9 Hz, 3H). ES/MS 594.1 (M+H$^+$).

(30)

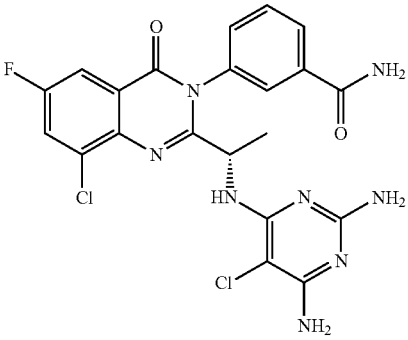

(S)-3-(8-chloro-2-(1-((2,6-diamino-5-chloropyrimidin-4-yl)amino)ethyl)-6-fluoro-4-oxoquinazolin-3(4H)-yl)benzamide (Compound 30). $^1$H NMR (400 MHz, DMSO-d$_6$) δ 8.32 (s, 2H), 8.22-8.00 (m, 2H), 7.84-7.52 (m, 0H), 7.65 (t, J=7.8 Hz, 1H), 6.37 (d, J=7.7 Hz, 1H), 6.05 (d, J=31.9 Hz, 1H), 5.55 (s, 1H), 4.70 (dp, J=9.3, 6.8 Hz, 4H), 1.29 (m, J=6.7 Hz, 1H), 1.26 (d, J=6.9 Hz, 3H). ES/MS 503.1 (M+H$^+$).

(31)

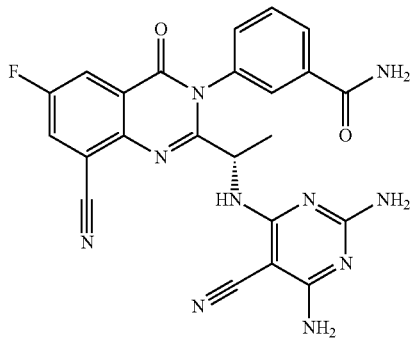

(S)-3-(8-cyano-2-(1-((2,6-diamino-5-cyanopyrimidin-4-yl)amino)ethyl)-6-fluoro-4-oxoquinazolin-3(4H)-yl)benzamide (Compound 31). ¹H NMR (400 MHz, DMSO-d₆) δ 8.49 (ddd, J=13.3, 8.3, 3.0 Hz, 2H), 8.29 (s, 2H), 8.19-8.10 (m, 0H), 7.99-7.93 (m, 2H), 7.67-7.63 (m, 0H), 7.55-7.50 (m, 2H), 6.76 (d, J=7.1 Hz, 0H), 6.63 (s, 4H), 6.54 (s, 0H), 6.45 (d, J=8.3 Hz, 0H), 4.87-4.74 (m, 1H), 1.37 (m, J=6.6 Hz, 1H), 1.31 (d, J=6.9 Hz, 3H). ES/MS 485.1 (M+H⁺).

(32)

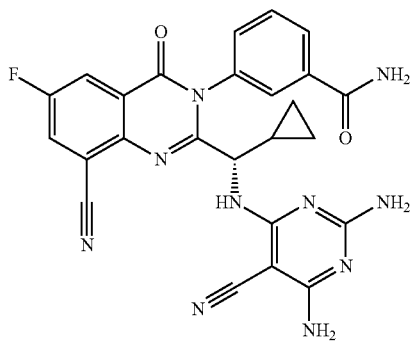

(S)-3-(8-cyano-2-(cyclopropyl((2,6-diamino-5-cyanopyrimidin-4-yl)amino)methyl)-6-fluoro-4-oxoquinazolin-3(4H)-yl)benzamide (Compound 32). ¹H NMR (400 MHz, DMSO-d₆) δ 8.50 (ddd, J=13.0, 8.3, 3.0 Hz, 1H), 8.27 (s, 2H), 8.20 (q, J=1.4 Hz, 0H), 8.18-8.09 (m, 1H), 8.00 (s, 0H), 7.96-7.91 (m, 0H), 7.77-7.70 (m, 1H), 7.58-7.43 (m, 1H), 6.69 (s, 1H), 6.58 (s, 1H), 4.68 (s, J=8.8, 7.5 Hz, 4H), 1.29-1.15 (m, 1H), 0.55-0.40 (m, 5H). ES/MS 511.1 (M+H⁺).

(33)

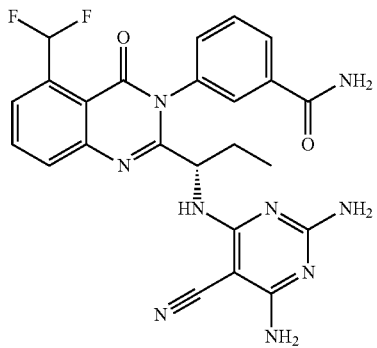

(S)-3-(2-(1-((2,6-diamino-5-cyanopyrimidin-4-yl)amino)propyl)-5-(difluoromethyl)-4-oxoquinazolin-3(4H)-yl)benzamide (Compound 33). ¹H NMR (400 MHz, DMSO-d₆) δ 8.37 (s, 2H), 8.18-7.94 (m, 2H), 7.91-7.62 (m, 2H), 6.73-6.57 (m, 3H), 4.53-4.43 (m, 4H), 1.88-1.65 (m, 1H), 1.28-1.23 (m, 2H), 0.68-0.59 (m, 3H). ES/MS 506.1 (M+H⁺).

(34)

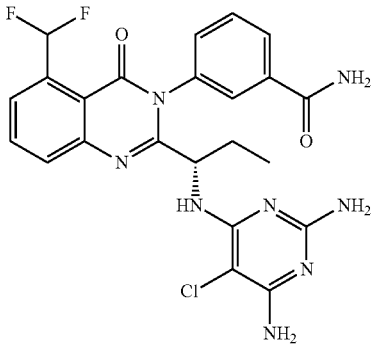

(S)-3-(2-(1-((2,6-diamino-5-chloropyrimidin-4-yl)amino)propyl)-5-(difluoromethyl)-4-oxoquinazolin-3(4H)-yl)benzamide (Compound 34). ¹H NMR (400 MHz, DMSO-d₆) δ 8.36 (s, 2H), 8.22-7.93 (m, 4H), 7.90-7.63 (m, 2H), 6.03 (d, J=22.7 Hz, 1H), 4.42 (td, J=8.7, 4.3 Hz, 1H), 2.71 (d, J=6.9 Hz, 1H), 1.71 (dt, J=14.6, 7.9 Hz, 2H), 0.64 (td, J=7.2, 4.6 Hz, 3H). ES/MS 515.1 (M+H⁺).

(35)

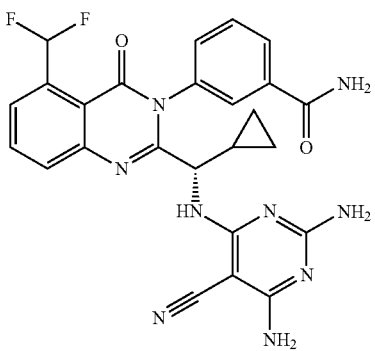

(S)-3-(2-(cyclopropyl((2,6-diamino-5-cyanopyrimidin-4-yl)amino)methyl)-5-(difluoromethyl)-4-oxoquinazolin-3(4H)-yl)benzamide (Compound 35). ¹H NMR (400 MHz, DMSO-d₆) δ 8.36 (s, 2H), 8.20 (t, J=1.9 Hz, 1H), 8.18-8.12 (m, 1H), 8.01-7.93 (m, 1H), 7.90-7.69 (m, 1H), 6.03 (d, J=22.7 Hz, 3H), 4.42 (td, J=8.7, 4.3 Hz, 1H), 2.71 (d, J=6.9 Hz, 1H), 1.71 (dt, J=14.6, 7.9 Hz, 1H), 0.64 (td, J=7.2, 4.6 Hz, 4H). ES/MS 518.2 (M+H⁺).

(36)

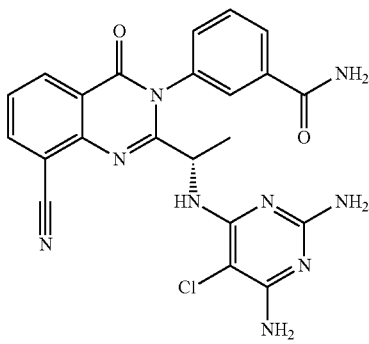

(S)-3-(8-cyano-2-(1-((2,6-diamino-5-chloropyrimidin-4-yl)amino)ethyl)-4-oxoquinazolin-3(4H)-yl)benzamide (Compound 36). ¹H NMR (400 MHz, DMSO-d₆) δ 8.49-8.29 (m, 2H), 8.25-7.87 (m, 3H), 7.83-7.16 (m, 8H), 4.95-4.80 (m, 1H), 1.44-1.30 (m, 3H). ES/MS 476.1 (M+H⁺).

(37)

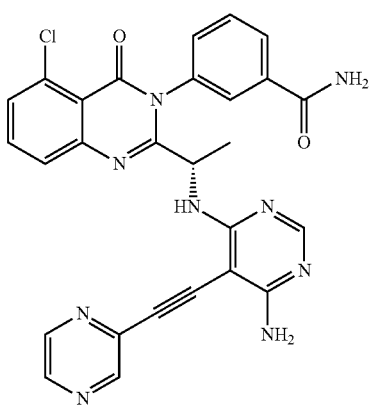

(S)-3-(2-(1-((6-amino-5-(pyrazin-2-ylethynyl)pyrimidin-4-yl)amino)ethyl)-5-chloro-4-oxoquinazolin-3(4H)-yl)benzamide (Compound 37). ¹H NMR (400 MHz, DMSO-d₆) δ 9.03 (dd, J=4.8, 1.6 Hz, 1H), 8.77 (td, J=2.5, 1.6 Hz, 1H), 8.63 (d, J=2.6 Hz, 1H), 8.24-7.94 (m, 4H), 7.92-7.71 (m, 3H), 7.70-7.41 (m, 5H), 4.78 (dt, J=32.1, 6.7 Hz, 1H), 1.36 (dd, J=6.7, 5.0 Hz, 3H). ES/MS 538.1 (M+H⁺).

(38)

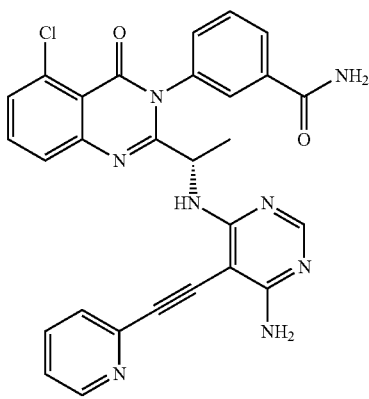

(S)-3-(2-(1-((6-amino-5-(pyridin-2-ylethynyl)pyrimidin-4-yl)amino)ethyl)-5-chloro-4-oxoquinazolin-3(4H)-yl)benzamide (Compound 38). ¹H NMR (400 MHz, DMSO-d₆) δ 8.74 (dd, J=5.0, 1.5 Hz, 1H), 8.19-7.94 (m, 5H), 7.86 (m, 3H), 7.79-7.64 (m, 3H), 7.65-7.40 (m, 4H), 4.85 (q, J=6.6 Hz, 0.5H), 4.75 (t, J=6.6 Hz, 0.5H), 1.38 (ddd, J=6.6, 3.6, 1.2 Hz, 3H). ES/MS 537.1 (M+H⁺).

(39)

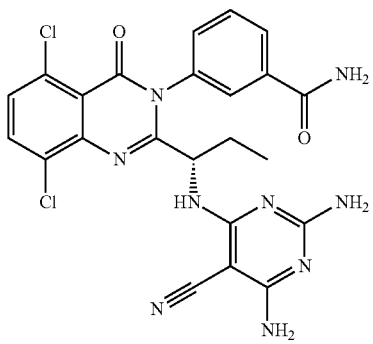

(S)-3-(5,8-dichloro-2-(1-((2,6-diamino-5-cyanopyrimidin-4-yl)amino)propyl)-4-oxoquinazolin-3(4H)-yl)benzamide (Compound 39). ¹H NMR (400 MHz, DMSO-d₆) δ 8.30 (s, 1H), 8.15-8.04 (m, 2H), 8.01-7.86 (m, 2H), 7.82-7.57 (m, 4H), 7.53 (dd, J=13.3, 8.5 Hz, 2H), 6.23 (d, J=9.0 Hz, 1H), 4.80-4.41 (m, 1H), 1.83-1.47 (m, 2H), 0.64 (dt, J=19.9, 7.3 Hz, 3H). ES/MS 525.1 (M+H⁺).

(40)

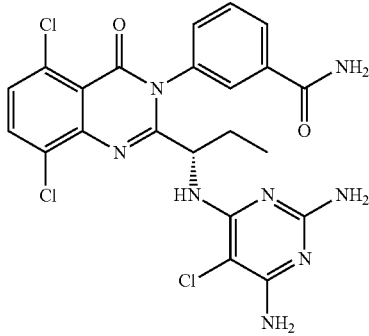

(S)-3-(5,8-dichloro-2-(1-((2,6-diamino-5-chloropyrimidin-4-yl)amino)propyl)-4-oxoquinazolin-3(4H)-yl)benzamide (Compound 40). ¹H NMR (400 MHz, DMSO-d₆) δ 8.31 (s, 1H), 8.24-7.85 (m, 3H), 7.85-7.61 (m, 3H), 7.51 (dd, J=12.2, 8.5 Hz, 1H), 6.05 (t, J=23.8 Hz, 5H), 4.69-4.23 (m, 1H), 1.88-1.40 (m, 2H), 0.77-0.54 (m, 3H). ES/MS 534.1 (M+H⁺).

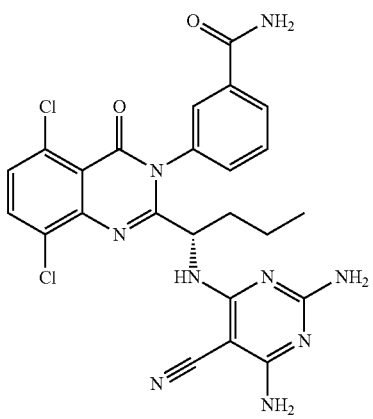

(41)

(S)-3-(5,8-dichloro-2-(1-((2,6-diamino-5-cyanopyrimidin-4-yl)amino)butyl)-4-oxoquinazolin-3(4H)-yl)benzamide (Compound 41). $^1$H NMR (400 MHz, DMSO-d$_6$) δ 8.35 (s, 1H), 8.23-7.84 (m, 3H), 7.77-7.26 (m, 3H), 6.71 (s, 3H), 6.27 (s, 1H), 4.93-4.51 (m, 1H), 1.89-1.47 (m, 2H), 1.24 (td, J=14.0, 13.0, 8.4 Hz, 1H), 0.94 (dt, J=14.8, 7.5 Hz, 1H), 0.48 (dt, J=27.0, 7.3 Hz, 3H). ES/MS 539.1 (M+H$^+$).

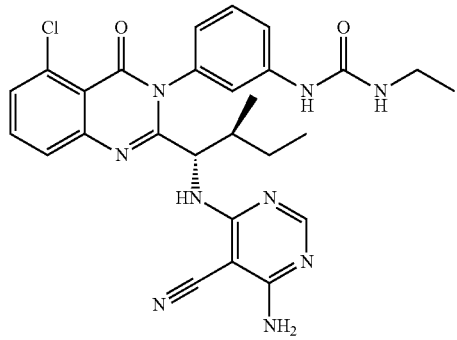

(42)

1-(3-(2-((1S,2S)-1-((6-amino-5-cyanopyrimidin-4-yl)amino)-2-methylbutyl)-5-chloro-4-oxoquinazolin-3(4H)-yl)phenyl)-3-ethylurea (Compound 42): $^1$H NMR (400 MHz, DMSO-d$_6$) δ 8.58 (d, J=63.1 Hz, 1H), 7.87-7.74 (m, 2H), 7.70-7.48 (m, 2H), 7.47-7.17 (m, 4H), 7.00-6.76 (m, 1H), 6.76-6.59 (m, 1H), 6.24-6.07 (m, 1H), 4.96 (dt, J=33.2, 8.2 Hz, 1H), 3.19-2.99 (m, 2H), 2.17-2.01 (m, 1H), 1.58-1.39 (m, 1H), 1.30-1.18 (m, 1H), 1.05 (td, J=7.2, 4.5 Hz, 3H), 0.96-0.86 (m, 1H), 0.82-0.68 (m, 6H). ES/MS 546.1 (M+H$^+$).

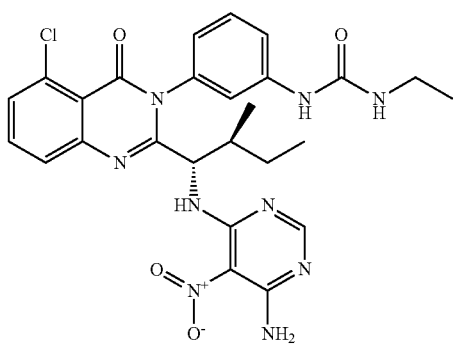

(43)

1-(3-(2-((1S,2S)-1-((6-amino-5-nitropyrimidin-4-yl)amino)-2-methylbutyl)-5-chloro-4-oxoquinazolin-3(4H)-yl)phenyl)-3-ethylurea (Compound 43): $^1$H NMR (400 MHz, DMSO-d$_6$) δ 9.55 (dd, J=32.6, 8.6 Hz, 1H), 8.71-8.55 (m, 3H), 7.86-7.81 (m, 1H), 7.77 (tdd, J=8.1, 5.5, 1.0 Hz, 1H), 7.68-7.54 (m, 3H), 7.51-7.30 (m, 2H), 7.06-6.85 (m, 1H), 6.26-6.12 (m, 1H), 5.26-4.98 (m, 1H), 3.18-2.97 (m, 2H), 2.08-1.94 (m, 1H), 1.77-1.50 (m, 1H), 1.10-0.90 (m, 4H), 0.76 (ddd, J=18.9, 14.5, 7.0 Hz, 6H).). ES/MS 566.1 (M+H$^+$)

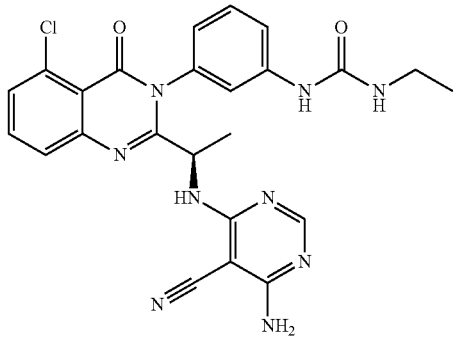

(44)

(R)-1-(3-(2-(1-((6-amino-5-cyanopyrimidin-4-yl)amino)ethyl)-5-chloro-4-oxoquinazolin-3(4H)-yl)phenyl)-3-ethylurea (Compound 44): $^1$H NMR (400 MHz, DMSO-d$_6$) δ 8.68-8.56 (m, 1H), 7.99 (dd, J=47.0, 0.9 Hz, 1H), 7.82-7.70 (m, 2H), 7.67-7.50 (m, 3H), 7.45-7.22 (m, 5H), 7.07-6.95 (m, 1H), 6.20 (d, J=11.5 Hz, 1H), 4.87-4.62 (m, 1H), 3.10 (t, J=6.6 Hz, 2H), 1.42-1.32 (m, 2H), 1.05 (tt, J=7.1, 1.3 Hz, 3H). ES/MS 504.1 (M+H$^+$).

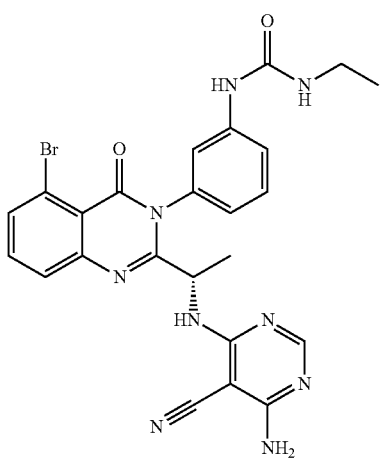

(45)

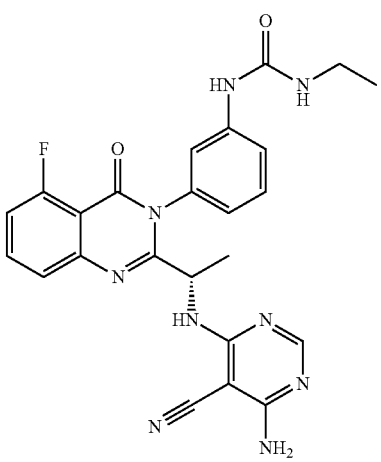

(47)

(S)-1-(3-(2-(1-(((6-amino-5-cyanopyrimidin-4-yl)amino)ethyl)-5-bromo-4-oxoquinazolin-3(4H)-yl)phenyl)-3-ethylurea (Compound 45): $^1$H NMR (400 MHz, DMSO) δ 8.62 (s, 0.5H), 8.58 (s, 0.5H), 8.01 (s, 0.5H), 7.89 (s, 0.5H), 7.81-7.71 (m, 1H), 7.67-7.49 (m, 3H), 7.41-7.17 (m, 4H), 7.03-6.95 (m, 1H), 6.21-6.13 (m, 1H), 4.82-4.60 (m, 1H), 3.14-3.02 (m, 2H), 1.38-1.32 (m, 3H), 1.06-0.99 (m, 3H). ES/MS 548.1 (M+H$^+$);

(S)-1-(3-(2-(1-(((6-amino-5-cyanopyrimidin-4-yl)amino)ethyl)-5-fluoro-4-oxoquinazolin-3(4H)-yl)phenyl)-3-ethylurea (Compound 47): $^1$H NMR (400 MHz, DMSO) δ 8.63 (s, 0.5H), 8.60 (s, 0.5H), 8.03 (s, 0.5H), 7.91 (s, 0.5H), 7.85-7.75 (m, 2H), 7.68-7.23 (m, 5H), 7.03-6.95 (m, 1H), 6.24-6.15 (m, 1H), 4.84-4.66 (m, 1H), 3.13-3.03 (m, 2H), 1.38-1.33 (m, 3H), 1.05-1.00 (m, 3H). ES/MS 488.2 (M+H$^+$);

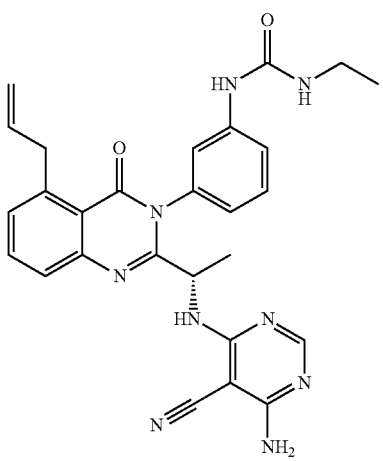

(46)

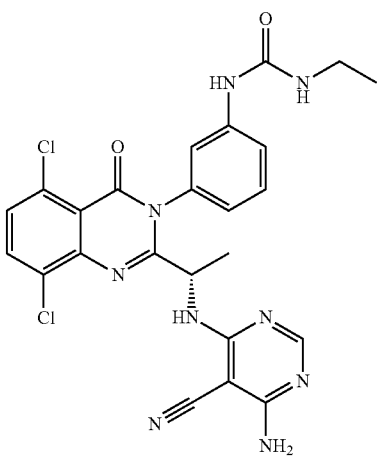

(48)

(S)-1-(3-(5-allyl-2-(1-(((6-amino-5-cyanopyrimidin-4-yl)amino)ethyl)-4-oxoquinazolin-3(4H)-yl)phenyl)-3-ethylurea (Compound 46): $^1$H NMR (400 MHz, DMSO) δ 8.64 (s, 0.5H), 8.61 (s, 0.5H), 8.04 (s, 0.5H), 7.92 (s, 0.5H), 7.83-7.65 (m, 3H), 7.56-7.49 (m, 1H), 7.47-7.23 (m, 3H), 7.01-6.94 (m, 1H), 6.22-6.11 (m, 1H), 6.05-5.91 (m, 1H), 5.02-4.91 (m, 2H), 4.85-4.65 (m, 1H), 3.97-3.91 (m, 2H), 3.13-3.03 (m, 2H), 1.40-1.33 (m, 3H), 1.06-1.00 (m, 3H). ES/MS 510.2 (M+H$^+$);

(S)-1-(3-(2-(1-(((6-amino-5-cyanopyrimidin-4-yl)amino)ethyl)-5,8-dichloro-4-oxoquinazolin-3(4H)-yl)phenyl)-3-ethylurea (Compound 48): $^1$H NMR (400 MHz, DMSO) δ 8.65 (s, 0.5H), 8.60 (s, 0.5H), 8.02-7.89 (m, 2H), 7.71-7.51 (m, 4H), 7.52-7.23 (m, 3H), 7.05-6.91 (m, 1H), 6.25-6.13 (m, 1H), 4.96-4.77 (m, 1H), 3.14-3.06 (m, 2H), 1.38-1.33 (m, 3H), 1.07-1.00 (m, 3H). ES/MS 538.1 (M+H$^+$);

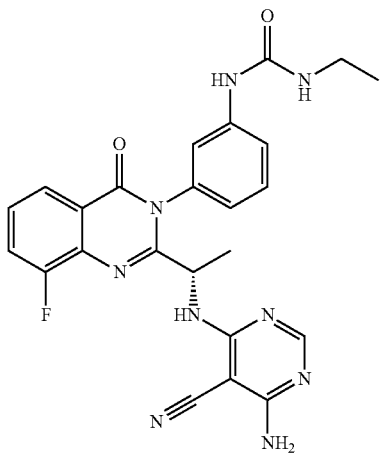

(49)

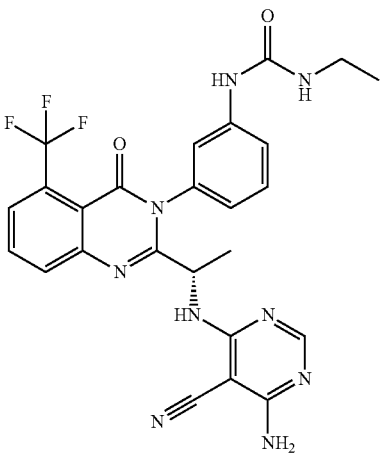

(51)

(S)-1-(3-(2-(1-(((6-amino-5-cyanopyrimidin-4-yl)amino)ethyl)-8-fluoro-4-oxoquinazolin-3(4H)-yl)phenyl)-3-ethylurea (Compound 49): $^1$H NMR (400 MHz, DMSO) δ 8.66 (s, 0.5H), 8.63 (s, 0.5H), 8.04 (s, 0.5H), 7.97-7.92 (m, 1H), 7.91 (s, 0.5H), 7.89-7.66 (m, 2H), 7.61-7.49 (m, 2H), 7.46-7.26 (m, 3H), 7.06-6.97 (m, 1H), 6.25-6.15 (m, 1H), 4.92-4.72 (m, 1H), 3.15-3.05 (m, 2H), 1.43-1.37 (m, 3H), 1.07-1.02 (m, 3H). ES/MS 488.2 (M+H$^+$);

(S)-1-(3-(2-(1-(((6-amino-5-cyanopyrimidin-4-yl)amino)ethyl)-4-oxo-5-(trifluoromethyl)quinazolin-3(4H)-yl)phenyl)-3-ethylurea (Compound 51): $^1$H NMR (400 MHz, DMSO) δ 8.67 (s, 0.5H), 8.64 (s, 0.5H), 8.05 (s, 0.5H), 8.01-7.93 (m, 3H), 7.91-7.82 (m, 1H), 7.72 (br s, 1H), 7.63-7.59 (m, 0.5H), 7.50-7.26 (m, 2H), 7.07-6.97 (m, 1H), 6.26-6.17 (m, 1H), 4.91-4.68 (m, 1H), 3.15-3.05 (m, 2H), 1.44-1.38 (m, 3H), 1.07-1.02 (m, 3H). ES/MS 538.2 (M+H$^+$);

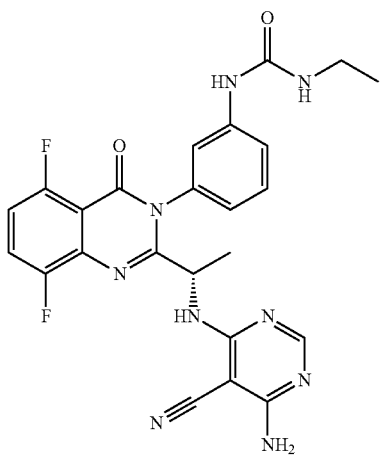

(50)

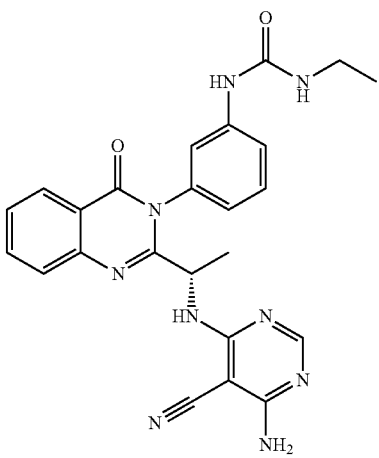

(52)

(S)-1-(3-(2-(1-(((6-amino-5-cyanopyrimidin-4-yl)amino)ethyl)-5,8-difluoro-4-oxoquinazolin-3(4H)-yl)phenyl)-3-ethylurea (Compound 50): $^1$H NMR (400 MHz, DMSO) δ 8.66 (s, 0.5H), 8.63 (s, 0.5H), 8.05 (s, 0.5H), 7.93 (s, 0.5H), 7.86-7.57 (m, 3H), 7.45-7.25 (m, 4H), 7.05-6.97 (m, 1H), 6.26-6.15 (m, 1H), 4.89-4.66 (m, 1H), 3.15-3.06 (m, 2H), 1.42-1.38 (m, 3H), 1.08-1.03 (m, 3H). ES/MS 506.2 (M+H$^+$);

(S)-1-(3-(2-(1-(((6-amino-5-cyanopyrimidin-4-yl)amino)ethyl)-4-oxoquinazolin-3(4H)-yl)phenyl)-3-ethylurea (Compound 52): $^1$H NMR (400 MHz, DMSO) δ 8.67 (s, 0.5H), 8.64 (s, 0.5H), 8.15-8.11 (m, 1H), 8.07 (s, 0.5H), 7.95 (s, 0.5H), 7.90-7.66 (m, 3H), 7.62-7.26 (m, 5H), 7.06-6.98 (m, 1H), 6.28-6.16 (m, 1H), 4.93-4.73 (m, 1H), 3.16-3.05 (m, 2H), 1.43-1.37 (m, 3H), 1.08-1.02 (m, 3H). ES/MS 470.2 (M+H$^+$);

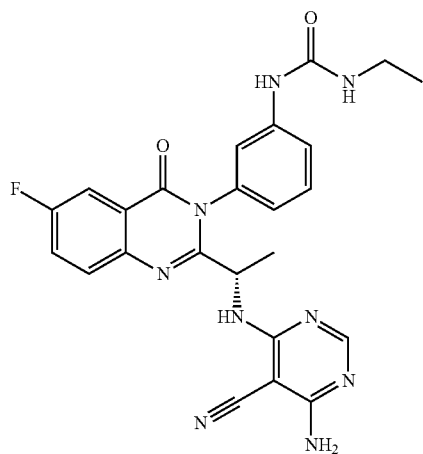

(53)

(S)-1-(3-(2-(1-(((6-amino-5-cyanopyrimidin-4-yl)amino)ethyl)-6-fluoro-4-oxoquinazolin-3(4H)-yl)phenyl)-3-ethylurea (Compound 53): $^1$H NMR (400 MHz, DMSO) δ 8.65 (s, 0.5H), 8.62 (s, 0.5H), 8.04 (s, 0.5H), 7.92 (s, 0.5H), 7.85-7.56 (m, 5H), 7.45-7.25 (m, 3H), 7.06-6.96 (m, 1H), 6.25-6.16 (m, 1H), 4.91-4.72 (m, 1H), 3.15-3.05 (m, 2H), 1.42-1.37 (m, 3H), 1.08-1.01 (m, 3H). ES/MS 488.2 (M+H$^+$);

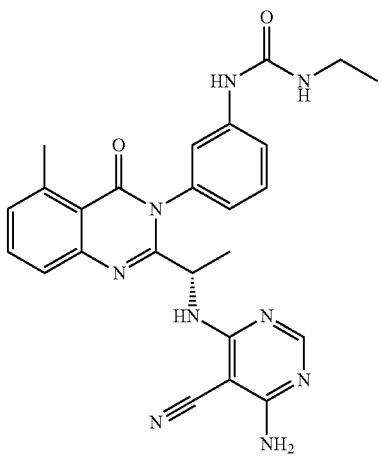

(55)

(S)-1-(3-(2-(1-(((6-amino-5-cyanopyrimidin-4-yl)amino)ethyl)-5-methyl-4-oxoquinazolin-3(4H)-yl)phenyl)-3-ethylurea (Compound 55): $^1$H NMR (400 MHz, DMSO) δ 8.66 (s, 0.5H), 8.63 (s, 0.5H), 8.07 (s, 0.5H), 7.96 (s, 0.5H), 7.93-7.65 (m, 2H), 7.60-7.26 (m, 6H), 7.03-6.97 (m, 1H), 6.26-6.15 (m, 1H), 4.88-4.68 (m, 1H), 3.14-3.04 (m, 2H), 2.72 (s, 3H), 1.40-1.36 (m, 3H), 1.08-1.02 (m, 3H). ES/MS 484.2 (M+H$^+$);

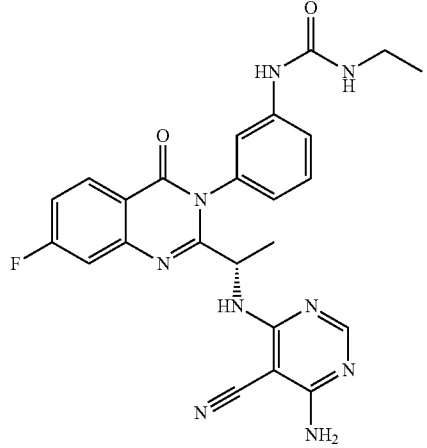

(54)

(S)-1-(3-(2-(1-(((6-amino-5-cyanopyrimidin-4-yl)amino)ethyl)-7-fluoro-4-oxoquinazolin-3(4H)-yl)phenyl)-3-ethylurea (Compound 54): $^1$H NMR (400 MHz, DMSO) δ 8.65 (s, 0.5H), 8.62 (s, 0.5H), 8.22-8.15 (m, 1H), 8.06-7.56 (m, 3H), 7.50-7.25 (m, 5H), 7.05-6.98 (m, 1H), 6.25-6.16 (m, 1H), 4.89-4.66 (m, 1H), 3.17-3.04 (m, 3H), 1.42-1.37 (m, 3H), 1.08-1.01 (m, 3H). ES/MS 488.2 (M+H$^+$);

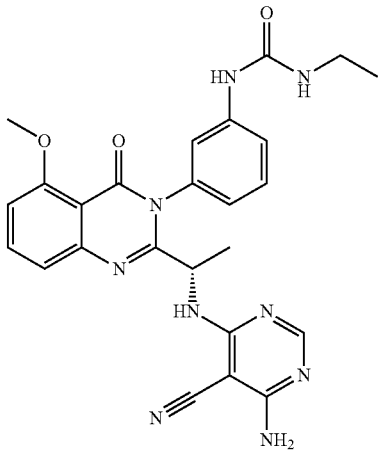

(56)

(S)-1-(3-(2-(1-(((6-amino-5-cyanopyrimidin-4-yl)amino)ethyl)-5-methoxy-4-oxoquinazolin-3(4H)-yl)phenyl)-3-ethylurea (Compound 56): $^1$H NMR (400 MHz, DMSO) δ 8.63 (s, 0.5H), 8.60 (s, 0.5H), 8.07 (s, 0.5H), 7.95 (s, 0.5H), 7.76-7.68 (m, 2H), 7.54-7.26 (m, 5H), 7.21-7.15 (m, 1H), 7.08-7.01 (m, 1H), 6.98-6.93 (m, 1H), 6.27-6.16 (m, 1H), 4.85-4.64 (m, 1H), 3.83 (s, 3H), 3.17-3.05 (m, 2H), 1.38-1.33 (m, 3H), 1.08-1.02 (m, 3H). ES/MS 500.2 (M+H$^+$);

(57)

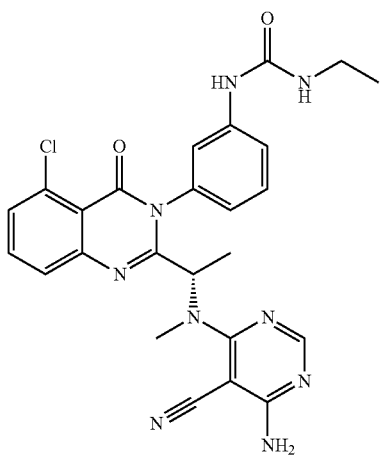

(S)-1-(3-(2-(1-(((6-amino-5-cyanopyrimidin-4-yl)(methyl)amino)ethyl)-5-chloro-4-oxoquinazolin-3(4H)-yl)phenyl)-3-ethylurea (Compound 57): $^1$H NMR (400 MHz, DMSO) δ 8.51 (s, 0.5H), 8.37 (s, 0.5H), 7.83-7.47 (m, 5H), 7.27-6.72 (m, 4H), 6.18-6.03 (m, 1H), 5.81-5.57 (m, 1H), 3.16-3.01 (m, 5H), 1.43-1.37 (m, 3H), 1.06-1.00 (m, 3H). ES/MS 518.1 (M+H$^+$);

(58)

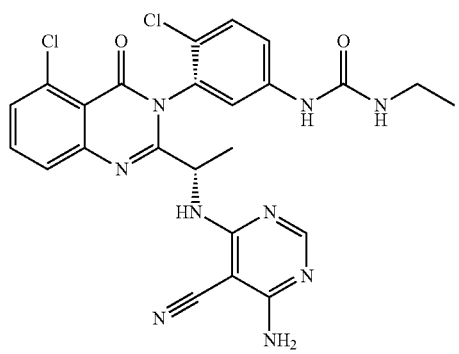

(S)-1-(3-(2-(1-(((6-amino-5-cyanopyrimidin-4-yl)amino)ethyl)-5-chloro-4-oxoquinazolin-3(4H)-yl)-4-chlorophenyl)-3-ethylurea (Compound 58): $^1$H NMR (400 MHz, DMSO) δ 8.67 (s, 1H), 7.96 (s, 1H), 7.94 (d, J=2.6 Hz, 1H), 7.82 (s, 1H), 7.81-7.75 (m, 1H), 7.64 (dd, J=8.2, 1.2 Hz, 1H), 7.59 (dd, J=7.8, 1.2 Hz, 1H), 7.50 (d, J=8.9 Hz, 1H), 7.38 (dd, J=8.9, 2.6 Hz, 1H), 7.32 (br s, 2H), 6.21-6.16 (m, 1H), 4.84-4.75 (m, 1H), 3.07 (p, J=7.1 Hz, 2H), 1.36 (d, J=6.8 Hz, 3H), 1.02 (t, J=7.2 Hz, 3H). ES/MS 552.1 (M+H$^+$);

(59)

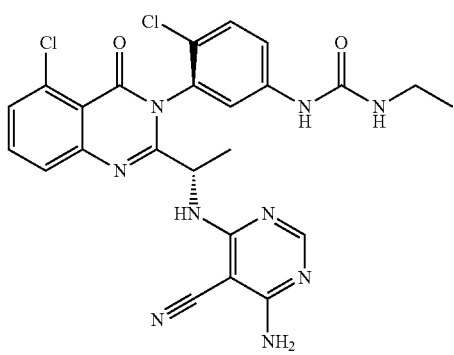

(S)-1-(3-(2-(1-(((6-amino-5-cyanopyrimidin-4-yl)amino)ethyl)-5-chloro-4-oxoquinazolin-3(4H)-yl)-4-chlorophenyl)-3-ethylurea (Compound 59): $^1$H NMR (400 MHz, DMSO) δ 8.75 (s, 1H), 7.84-7.78 (m, 1H), 7.76 (d, J=0.5 Hz, 1H), 7.73 (d, J=2.5 Hz, 1H), 7.71 (s, 1H), 7.69 (dd, J=8.2, 1.2 Hz, 1H), 7.61 (dd, J=7.8, 1.2 Hz, 1H), 7.42 (br s, 2H), 7.34 (dd, J=8.8, 2.5 Hz, 1H), 7.27 (d, J=8.8 Hz, 1H), 6.28 (br s, 1H), 5.18-5.09 (m, 1H), 3.14-3.05 (m, 2H), 1.41 (d, J=6.6 Hz, 3H), 1.04 (t, J=7.2 Hz, 3H). ES/MS 552.1 (M+H$^+$);

(60)

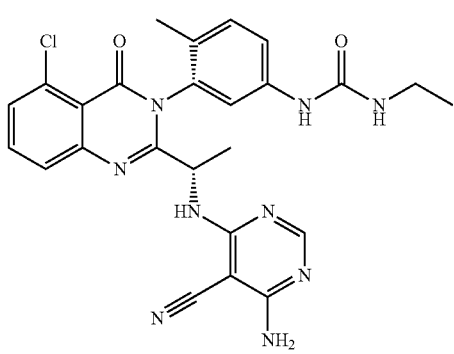

(S)-1-(3-(2-(1-(((6-amino-5-cyanopyrimidin-4-yl)amino)ethyl)-5-chloro-4-oxoquinazolin-3(4H)-yl)-4-methylphenyl)-3-ethylurea (Compound 60): $^1$H NMR (400 MHz, DMSO) δ 8.49 (s, 1H), 7.80-7.74 (m, 2H), 7.65 (dd, J=8.2, 1.2 Hz, 1H), 7.57 (dd, J=7.8, 1.2 Hz, 1H), 7.48 (d, J=2.2 Hz, 1H), 7.38 (br s, 2H), 7.19 (dd, J=8.3, 2.2 Hz, 1H), 7.07 (dd, J=8.4, 0.9 Hz, 1H), 6.15 (br s, 1H), 5.04-4.95 (m, 1H), 3.12-3.02 (m, 2H), 1.96 (s, 3H), 1.41 (d, J=6.8 Hz, 3H), 1.02 (t, J=7.2 Hz, 3H). ES/MS 518.1 (M+H$^+$);

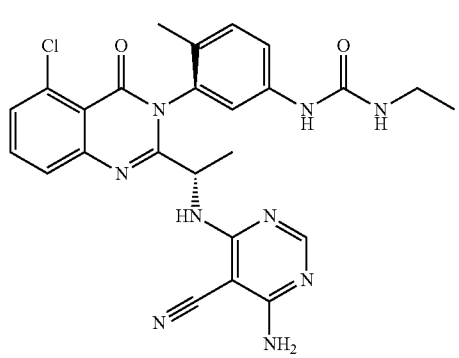

(61)

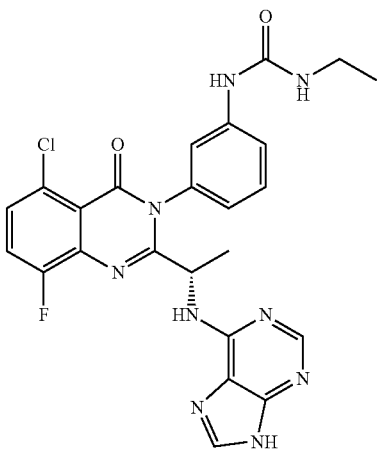

(63)

(S)-1-(3-(2-(1-(((6-amino-5-cyanopyrimidin-4-yl)amino)ethyl)-5-chloro-4-oxoquinazolin-3(4H)-yl)-4-methylphenyl)-3-ethylurea (Compound 61): $^1$H NMR (400 MHz, DMSO) δ 8.41 (s, 1H), 7.98 (d, J=1.1 Hz, 1H), 7.80-7.72 (m, 2H), 7.70-7.68 (m, 1H), 7.62 (dt, J=8.2, 1.3 Hz, 1H), 7.57 (dt, J=7.8, 1.3 Hz, 1H), 7.39 (br s, 2H), 7.30 (dt, J=8.3, 1.5 Hz, 1H), 7.23 (d, J=8.4 Hz, 1H), 6.13-6.05 (m, 1H), 4.89-4.77 (m, 1H), 3.10-3.00 (m, 3H), 1.94 (s, 3H), 1.26 (d, J=6.8, 3H), 1.04-0.98 (m, 3H). ES/MS 518.1 (M+H$^+$);

(S)-1-(3-(2-(1-(((9H-purin-6-yl)amino)ethyl)-5-chloro-8-fluoro-4-oxoquinazolin-3(4H)-yl)phenyl)-3-ethylurea (Compound 63): $^1$H NMR (400 MHz, DMSO) δ 8.72-8.60 (m, 1H), 8.47-8.33 (m, 2H), 7.95 (s, 0.5H), 7.73-7.65 (m, 1.5H), 7.60-7.52 (m, 1H), 7.44-7.25 (m, 2H), 7.15-7.05 (m, 1H), 6.28-6.15 (m, 1H), 4.95-4.84 (m, 1H), 3.16-3.04 (m, 2H), 1.54-1.50 (m, 3H), 1.08-1.02 (m, 3H). ES/MS 522.1 (M+H$^+$);

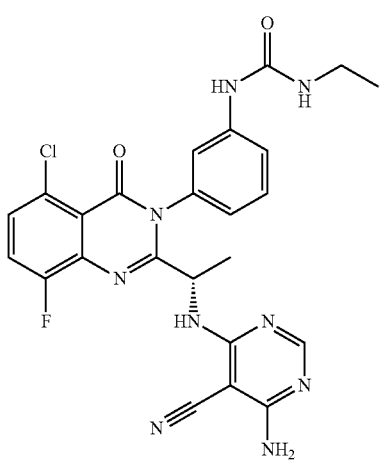

(62)

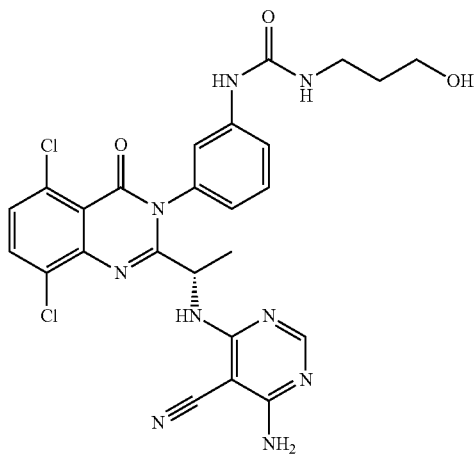

(64)

(S)-1-(3-(2-(1-(((6-amino-5-cyanopyrimidin-4-yl)amino)ethyl)-5-chloro-8-fluoro-4-oxoquinazolin-3(4H)-yl)phenyl)-3-ethylurea (Compound 62): $^1$H NMR (400 MHz, DMSO) δ 8.59 (s, 0.5H), 8.56 (s, 0.5H), 7.98 (s, 0.5H), 7.86 (s, 0.5H), 7.78-7.73 (m, 1), 7.69-7.45 (m, 3H), 7.40-7.18 (m, 4H), 6.99-6.90 (m, 1H), 6.19-6.09 (m, 1H), 4.83-4.57 (m, 1H), 3.10-2.96 (m, 2H), 1.35-1.29 (m, 3H), 1.02-0.96 (m, 3H). ES/MS 522.1 (M+H$^+$);

(S)-1-(3-(2-(1-(((6-amino-5-cyanopyrimidin-4-yl)amino)ethyl)-5,8-dichloro-4-oxoquinazolin-3(4H)-yl)phenyl)-3-(3-hydroxypropyl)urea (Compound 64): $^1$H NMR (400 MHz, DMSO) δ 8.77 (s, 1H), 8.07 (s, 0.5H), 7.99-7.92 (m, 1.5H), 7.77-7.52 (m, 2H), 7.45-7.23 (m, 2H), 7.06-6.91 (m, 1H), 6.29 (br s, 1H), 4.97-4.80 (m, 1H), 3.51-3.40 (m, 2H), 3.17-3.09 (m, 2H), 1.69-1.50 (m, 2H), 1.41-1.35 (m, 3H). ES/MS 568.1 (M+H$^+$);

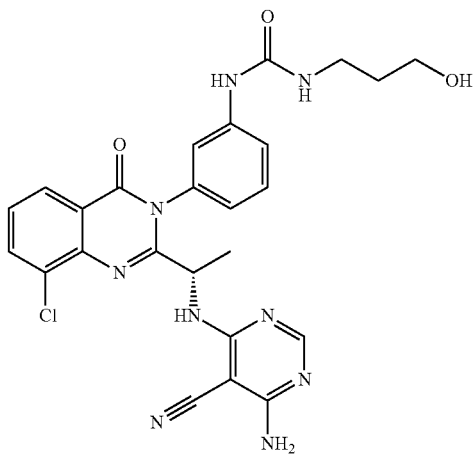

(65)

(S)-1-(3-(2-(1-((6-amino-5-cyanopyrimidin-4-yl)amino)ethyl)-8-chloro-4-oxoquinazolin-3(4H)-yl)phenyl)-3-(3-hydroxypropyl)urea (Compound 65): $^1$H NMR (400 MHz, DMSO) δ 8.78 (s, 1H), 8.12-7.93 (m, 3H), 7.84 (br s, 1H), 7.73-7.48 (m, 3H), 7.45-7.23 (m, 2H), 7.06-6.92 (m, 1H), 6.29 (br s, 1H), 5.02-4.85 (m, 1H), 3.51-3.39 (m, 2H), 3.17-3.08 (m, 2H), 1.70-1.50 (m, 2H), 1.43-1.38 (m, 3H). ES/MS 534.1 (M+H$^+$);

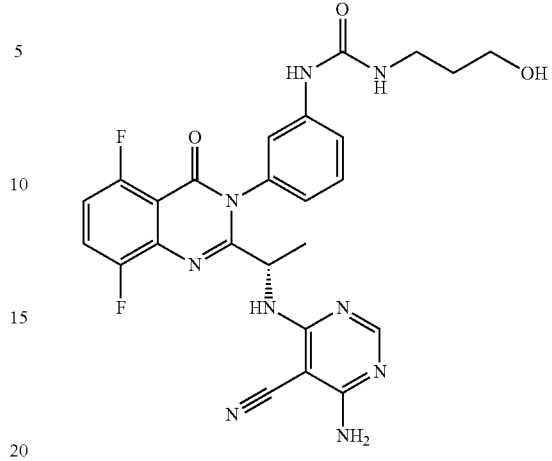

(67)

(S)-1-(3-(2-(1-((6-amino-5-cyanopyrimidin-4-yl)amino)ethyl)-5,8-difluoro-4-oxoquinazolin-3(4H)-yl)phenyl)-3-(3-hydroxypropyl)urea (Compound 67): $^1$H NMR (400 MHz, DMSO) δ 8.78 (br s, 0.5H), 8.41 (s, 0.5H), 8.17-8.08 (m, 1.5H), 7.98 (hr s, 0.5H), 7.80-7.72 (m, 2H), 7.68-7.47 (m, 2H), 7.42-7.25 (m, 3H), 7.06-6.96 (m, 1H), 6.30 (br s, 1H), 4.90-4.70 (m, 1H), 3.52-3.40 (m, 2H), 3.17-3.11 (m, 2H), 1.71-1.53 (m, 2H), 1.42-1.36 (m, 3H). ES/MS 536.1 (M+H$^+$);

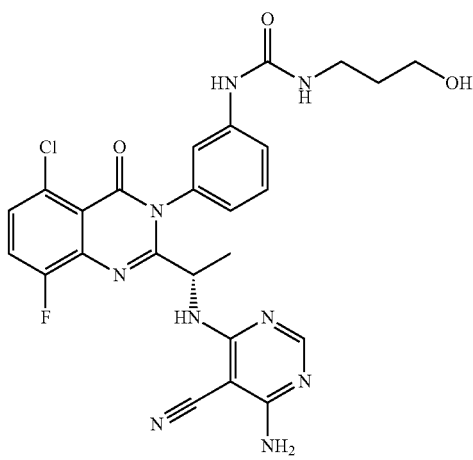

(66)

(S)-1-(3-(2-(1-((6-amino-5-cyanopyrimidin-4-yl)amino)ethyl)-5-chloro-8-fluoro-4-oxoquinazolin-3(4H)-yl)phenyl)-3-(3-hydroxypropyl)urea (Compound 66): $^1$H NMR (400 MHz, DMSO) δ 8.74 (s, 0.5H), 8.08 (s, 0.5H), 7.95 (d, J=1.3 Hz, 0.5H), 7.80 (s, 0.5H), 7.74-7.69 (m, 1H), 7.62-7.40 (m, 3H), 7.40-7.25 (m, 2H), 7.06-6.96 (m, 1H), 4.89-4.67 (m, 1H), 3.53-3.42 (m, 2H), 3.18-3.11 (m, 2H), 1.70-1.54 (m, 2H), 1.42-1.36 (m, 3H). ES/MS 552.1 (M+H$^+$);

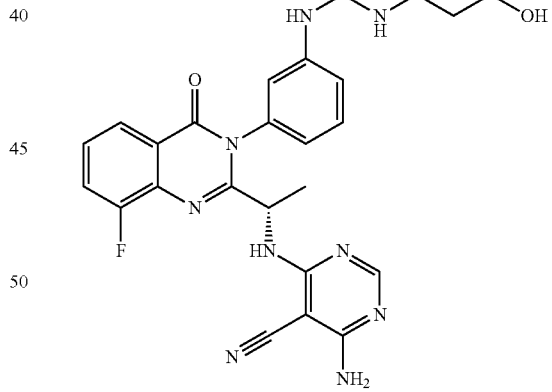

(68)

(S)-1-(3-(2-(1-((6-amino-5-cyanopyrimidin-4-yl)amino)ethyl)-8-fluoro-4-oxoquinazolin-3(4H)-yl)phenyl)-3-(3-hydroxypropyl)urea (Compound 68): $^1$H NMR (400 MHz, DMSO) δ 8.79 (s, 0.5H), 8.41 (s, 0.5H), 8.14 (br s, 1H), 8.01-7.90 (m, 1H), 7.82-7.47 (m, 3H), 7.42-7.25 (m, 2H), 7.06-6.96 (m, 1H), 6.31 (br s, 1H), 4.95-4.75 (m, 1H), 3.50-3.42 (m, 2H), 3.17-3.11 (m, 2H), 1.71-1.52 (m, 2H), 1.46-1.38 (m, 3H). ES/MS 518.1 (M+H$^+$);

(71)

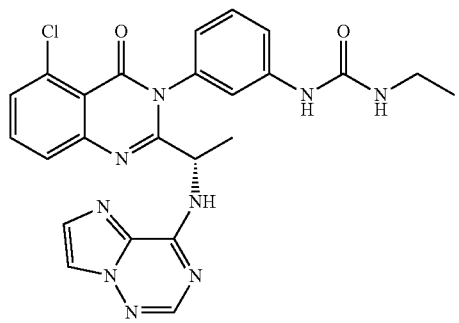

(S)-1-(3-(5-chloro-2-(1-(imidazo[2,1-f][1,2,4]triazin-4-ylamino)ethyl)-4-oxoquinazolin-3(4H)-yl)phenyl)-3-ethylurea (Compound 71). $^1$H NMR (400 MHz, DMSO) δ 9.09 (d, J=6.4 Hz, 1H), 8.97 (d, J=8 Hz, 1H), 8.63 (s, 1H), 8.51 (s, 1H), 8.10 (s, 1H), 8.05-8.01 (m, 3H), 7.87 (t, J=2.0, 2.0 Hz, 1H), 7.72 (td, J=8.0, 8.0, 6.6 Hz, 2H), 7.60 (m, 3H), 7.59-7.50 (m, 3H), 7.40-7.30 (m, 3H), 7.17 (t, J=8.0, 8.0 Hz, 1H), 7.03 (m, 1H), 6.20 (s, 1H), 6.13 (s, 1H), 4.91 (q, J=6.7 Hz, 2H), 4.81 (q, J=6.7 Hz, 2H), 3.08 (m, 2H), 1.48 (m, 6H), 1.04 (m, 6H). ES/MS 504.2 (M+H$^+$).

(73)

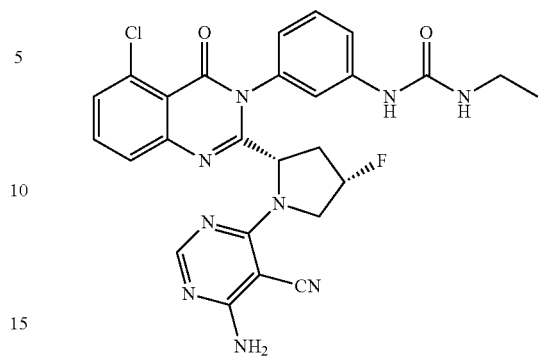

1-(3-(2-((2S,4S)-1-(6-amino-5-cyanopyrimidin-4-yl)-4-fluoropyrrolidin-2-yl)-5-chloro-4-oxoquinazolin-3(4H)-yl)phenyl)-3-ethylurea (Compound 73). $^1$H NMR (400 MHz, DMSO-d$_6$) δ 8.66 (d, J=5.4 Hz, 2H), 8.02 (d, J=11.2 Hz, 1H), 7.86 (s, 1H), 7.67 (t, J=8.0 Hz, 1H), 7.50 (ddd, J=12.1, 10.0, 7.9 Hz, 3H), 7.39 (dt, J=13.9, 7.3 Hz, 2H), 7.17-6.99 (m, 1H), 6.21 (m, 2H), 5.58-5.20 (m, 1H), 4.92 (m, J=37.4 Hz, 1H), 4.50-3.93 (m, 2H), 3.09 (dd, J=11.1, 5.7 Hz, 2H), 2.42-2.13 (m, 2H), 1.03 (q, J=7.2 Hz, 3H). ES/MS 548.2 (M+H$^+$).

(72)

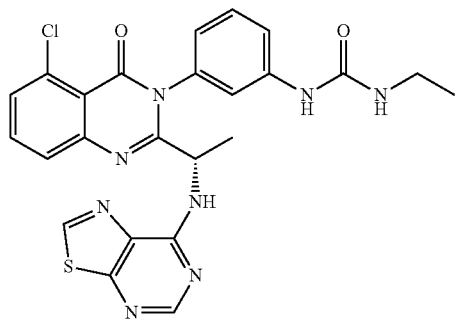

(S)-1-(3-(5-chloro-4-oxo-2-(1-(thiazolo[5,4-d]pyrimidin-7-ylamino)ethyl)quinazolin-3(4H)-yl)phenyl)-3-ethylurea (Compound 72). $^1$H NMR (400 MHz, DMSO) δ 9.28 (s, 1H), 9.25 (s, 1H), 8.63 (s, 1H), 8.53 (d, J=6.7 Hz, 1H), 8.43 (s, 1H), 8.37 (s, 1H), 8.32 (s, 1H), 7.81 (s, 1H), 7.74-7.67 (m, 2H), 7.62-7.59 (m, 1H), 7.57 (d, J=1.1 Hz, 1H), 7.56-7.50 (m, 3H), 7.36-7.26 (m, 3H), 7.17 (t, J=8.0, 8.0 Hz, 1H), 7.03 (t, J=9.0, 9.0 Hz, 1H), 6.20 (s, 1H), 6.08 (s, 1H), 4.90 (m, 4H), 3.06 (m, 4H), 1.48 (m, 6H), 1.04 (m, 6H). ES/MS 521.2 (M+H$^+$).

(74)

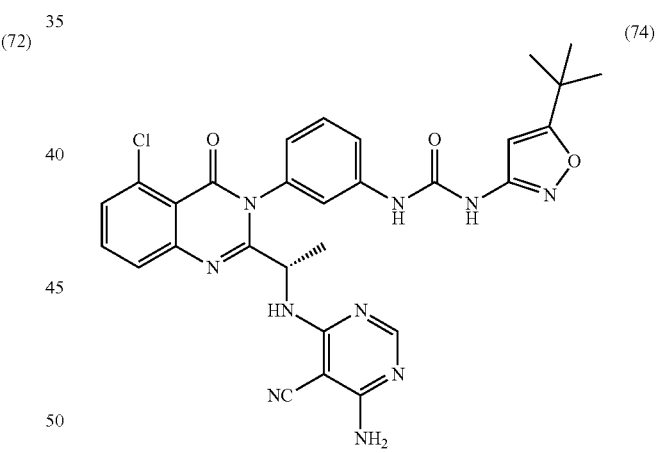

(S)-1-(3-(2-(1-((6-amino-5-cyanopyrimidin-4-yl)amino)ethyl)-5-chloro-4-oxoquinazolin-3(4H)-yl)phenyl)-3-(5-(tert-butyl)isoxazol-3-yl)urea (Compound 74). $^1$H NMR (400 MHz, DMSO-d$_6$) δ 9.59 (d, J=5.5 Hz, 1H), 8.95 (d, J=35.9 Hz, 1H), 7.94 (d, J=19.9 Hz, 1H), 7.80-7.69 (m, 2H), 7.69-7.59 (m, 2H), 7.56 (ddd, J=7.9, 3.2, 1.2 Hz, 1H), 7.53-7.47 (m, 1H), 7.47-7.39 (m, 1H), 7.40-7.28 (m, 2H), 7.13 (ddt, J=16.8, 7.9, 1.3 Hz, 1H), 6.48 (d, J=2.5 Hz, 1H), 4.80 (dq, J=35.7, 6.8 Hz, 1H), 1.37 (dd, J=6.7, 2.8 Hz, 3H), 1.27 (d, J=1.2 Hz, 9H). ES/MS 599.2 (M+H$^+$).

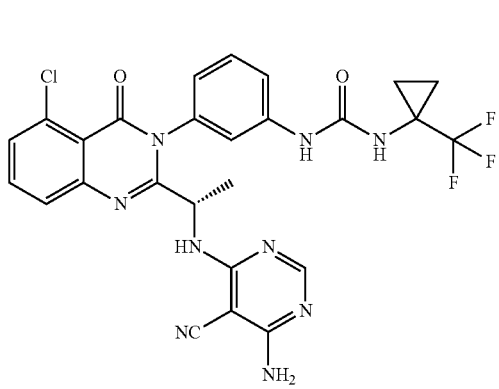

(75)

(S)-1-(3-(2-(1-(((6-amino-5-cyanopyrimidin-4-yl)amino)ethyl)-5-chloro-4-oxoquinazolin-3(4H)-yl)phenyl)-3-(1-(trifluoromethyl)cyclopropyl)urea (Compound 75). $^1$H NMR (400 MHz, DMSO-d$_6$) δ 8.65 (d, J=9.2 Hz, 1H), 7.96 (d, J=36.0 Hz, 1H), 7.86 (t, J=2.1 Hz, 1H), 7.83-7.65 (m, 2H), 7.66-7.48 (m, 2H), 7.49-7.23 (m, 4H), 7.15 (d, J=12.2 Hz, 1H), 7.05 (ddt, J=12.5, 7.4, 1.5 Hz, 1H), 4.73 (dq, J=57.5, 6.8 Hz, 1H), 1.36 (dd, J=6.8, 4.2 Hz, 3H), 1.27-1.17 (m, 2H), 1.13 (d, J=5.6 Hz, 2H). ES/MS 584.2 (M+H$^+$).

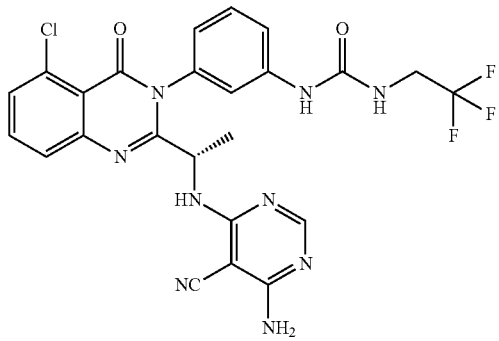

(76)

(S)-1-(3-(2-(1-(((6-amino-5-cyanopyrimidin-4-yl)amino)ethyl)-5-chloro-4-oxoquinazolin-3(4H)-yl)phenyl)-3-(2,2,2-trifluoroethyl)urea (Compound 76). $^1$H NMR (400 MHz, DMSO-d$_6$) δ 8.93 (d, J=18.4 Hz, 1H), 7.95 (d, J=32.1 Hz, 1H), 7.85-7.67 (m, 2H), 7.69-7.48 (m, 3H), 7.49-7.20 (m, 3H), 7.13-6.99 (m, 1H), 6.83 (dt, J=13.7, 6.5 Hz, 1H), 4.74 (dt, J=53.3, 6.7 Hz, 1H), 4.02-3.77 (m, 2H), 1.36 (dd, J=6.8, 4.5 Hz, 3H). ES/MS 558.2 (M+H$^+$).

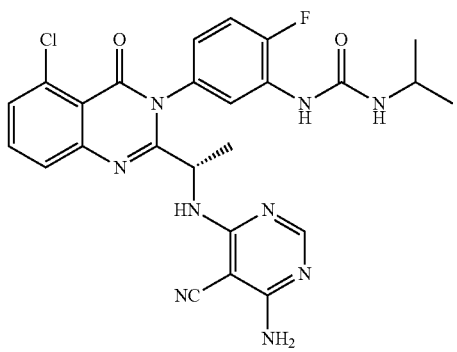

(77)

(S)-1-(5-(2-(1-(((6-amino-5-cyanopyrimidin-4-yl)amino)ethyl)-5-chloro-4-oxoquinazolin-3(4H)-yl)-2-fluorophenyl)-3-isopropylurea (compound 77). $^1$H NMR (400 MHz, Methanol-d$_4$) δ 8.36-7.97 (m, 2H), 7.71 (td, J=8.0, 3.0 Hz, 1H), 7.65 (ddd, J=8.2, 3.8, 1.3 Hz, 1H), 7.52 (ddd, J=7.7, 2.4, 1.4 Hz, 1H), 7.31 (ddd, J=13.1, 10.7, 8.6 Hz, 1H), 7.16 (dddd, J=24.1, 8.6, 4.2, 2.6 Hz, 1H), 5.11-4.89 (m, 2H), 1.54 (dd, J=9.7, 6.8 Hz, 3H), 1.42-1.22 (m, 6H). ES/MS 537.2 (M+H$^+$).

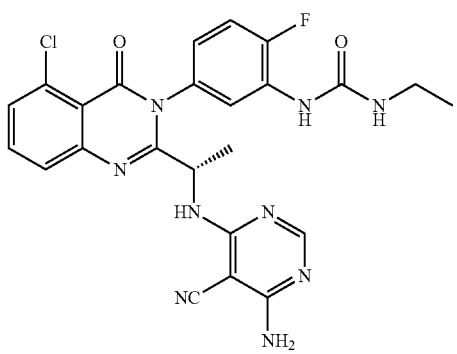

(78)

(S)-1-(5-(2-(1-(((6-amino-5-cyanopyrimidin-4-yl)amino)ethyl)-5-chloro-4-oxoquinazolin-3(4H)-yl)-2-fluorophenyl)-3-ethylurea (Compound 78). $^1$H NMR (400 MHz, Methanol-d$_4$) δ 8.48-8.07 (m, 2H), 7.73-7.64 (m, 2H) 7.58-7.47 (m, 1H), 7.29 (td, J=10.9, 8.5 Hz, 1H), 7.17-6.95 (m, 1H), 5.05 (m, 1H), 3.24-3.19 (m, 2H), 1.55 (dd, J=11.9, 6.8 Hz, 3H), 1.14 (td, J=7.3, 3.6 Hz, 3H). ES/MS 522.2 (M+H$^+$).

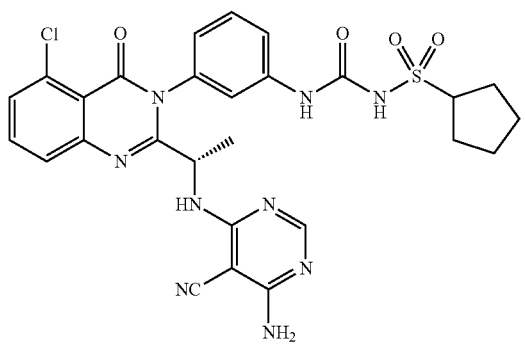

(79)

(S)—N-((3-(2-(1-(((6-amino-5-cyanopyrimidin-4-yl)amino)ethyl)-5-chloro-4-oxoquinazolin-3(4H)-yl)phenyl)carbamoyl)cyclopentanesulfonamide (Compound 79). ¹H NMR (400 MHz, Methanol-d₄) δ 8.13 (d, J=27.9 Hz, 1H), 8.08-7.91 (m, 1H), 7.77-7.63 (m, 1H), 7.59-7.50 (m, 1H), 7.50-7.37 (m, 1H), 7.21-7.03 (m, 1H), 5.15-4.91 (m, 1H), 4.22-3.87 (m, 1H), 2.12-1.96 (m, 3H), 1.83-1.61 (m, 2H), 1.56-1.44 (m, 3H), 1.28 (d, J=6.2 Hz, 3H). ES/MS 608.2 (M+H⁺).

(80)

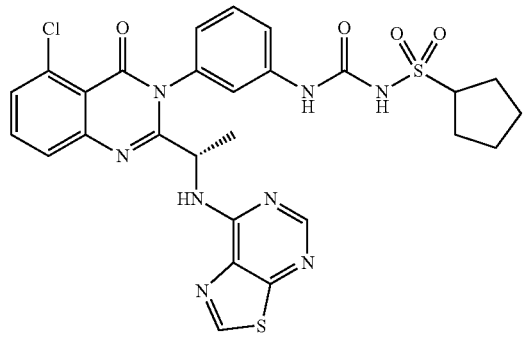

(S)—N-((3-(5-chloro-4-oxo-2-(1-(thiazolo[5,4-d]pyrimidin-7-ylamino)ethyl)quinazolin-3(4H)-yl)phenyl)carbamoyl)cyclopentanesulfonamide (Compound 80). ¹H NMR (400 MHz, Methanol-d₄) δ 9.10 (d, J=5.4 Hz, 1H), 8.42 (d, J=2.2 Hz, 1H), 8.38-8.28 (m, 1H), 7.94 (s, 1H), 7.74-7.59 (m, 3H), 7.56-7.46 (m, 2H), 7.40 (q, J=8.4 Hz, 1H), 7.36-7.27 (m, 1H), 7.26-7.14 (m, 1H), 5.30-5.07 (m, 1H), 4.20-3.96 (m, 1H), 2.07-1.99 (m, 4H), 1.78 (dt, J=12.1, 6.1 Hz, 1H), 1.67-1.56 (m, 6H). ES/MS 625.2 (M+H⁺).

(81)

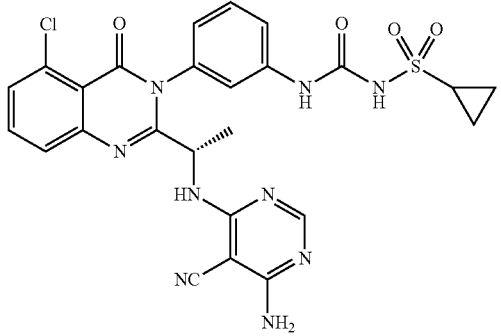

(S)—N-((3-(2-(1-((6-amino-5-cyanopyrimidin-4-yl)amino)ethyl)-5-chloro-4-oxoquinazolin-3(4H)-yl)phenyl)carbamoyl)cyclopropanesulfonamide (Compound 81). ¹H NMR (400 MHz, Methanol-d₄) δ 8.08-7.85 (m, 1H), 7.73-7.51 (m, 3H), 7.51-7.28 (m, 3H), 7.21-7.04 (m, 1H), 4.97 (m, 1H), 3.06-2.91 (m, 1H), 1.52-1.37 (m, 3H), 1.34-1.14 (m, 2H), 1.13-1.04 (m, 2H). ES/MS 580.1 (M+H⁺).

(82)

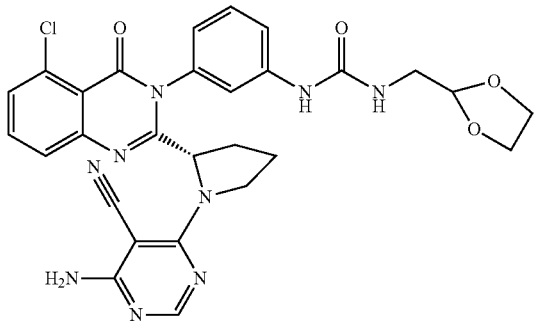

(S)-1-((1,3-dioxolan-2-yl)methyl)-3-(3-(2-(1-(6-amino-5-cyanopyrimidin-4-yl)pyrrolidin-2-yl)-5-chloro-4-oxoquinazolin-3(4H)-yl)phenyl)urea (Compound 82). ¹H NMR (400 MHz, DMSO-d6) δ 8.76 (S, 1H, minor rotamer), 8.73 (S, 1H, major rotamer), 7.97 (s, 1H, major rotamer), 7.92 (s, 1H, minor rotamer), 7.83 (s, 1H, major rotamer), 7.68-7.61 (m, 1H), 7.54-7.45 (m, 3H), 7.42-7.35 (m, 2H), 7.00-6.96 (m, 1H), 6.27 (q, J=6 Hz, 1H), 4.84 (q, J=4 Hz, 1H), 3.91-3.75 (m, 2H), 3.80-3.75 (m, 2H), 3.26-3.19 (m, 2H), 2.31-2.14 (m, 1H), 2.09-2.00 (m, 1H), 1.96-1.85 (m, 2H). ES/MS 588.1 (M+H⁺).

(83)

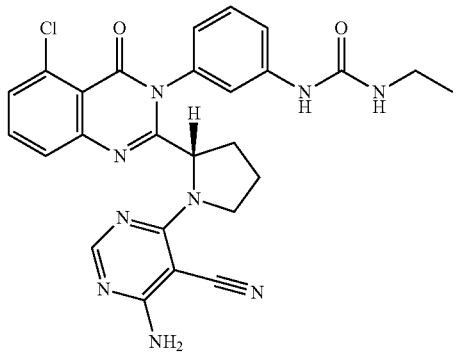

(S)-1-(3-(2-(1-(6-amino-5-cyanopyrimidin-4-yl)pyrrolidin-2-yl)-5-chloro-4-oxoquinazolin-3(4H)-yl)phenyl)-3-ethylurea (Compound 83). ¹H NMR (400 MHz, DMSO-d6) δ 8.61 (s, 1H), 7.98 (s, 1H, major rotamer), 7.90 (s, 1H, minor rotamer), 7.87 (s, 1H, major rotamer), 7.67-7.62 (m, 1H), 7.55-7.44 (m, 2H), 7.41-7.33 (m, 2H), 7.25-7.05 (m, 2H), 6.96-6.94 (m, 1H, minor rotamer), 6.19-6.14 (m, 1H), 4.68-4.58 (m, 1H), 4.02-3.95 (m, 1H), 3.92-3.81 (m, 1H), 3.12-3.03 (m, 2H), 2.30 (s, 1H), 2.10-1.85 (m, 3H), 1.08-0.99 (m, 3H). ES/MS 530.1 (M+H⁺).

(84)

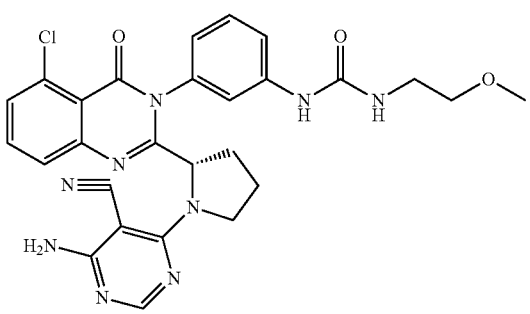

(S)-3-(5-chloro-2-(1-((2,6-diamino-5-chloropyrimidin-4-yl)amino)ethyl)-4-oxoquinazolin-3(4H)-yl)benzamide (Compound 84). ¹H NMR (400 MHz, DMSO-d6) δ 8.01 (s, 1H, major rotamer), 7.98 (s, 1H, minor rotamer), 7.68-7.63 (m, 1H), 7.56-7.45 (m, 2H), 7.45-7.31 (m, 2H), 7.12 (t, J=8 Hz, 1H), 6.98 (d, J=8 Hz, 1H, minor rotamer), 6.72 (d, J=8 Hz, 1H, major rotamer), 6.32-6.25 (m, 1H), 4.70-4.60 (m, 1H), 4.10-3.95 (m, 1H), 3.94-3.83 (m, 1H), 3.37-3.32 (m, 1h), 3.24 (s, 3H, minor rotamer), 3.23 (s, 3H, major rotamer), 2.30-16 (m, 1H), 2.10-2.02 (m, 1H), 1.97-1.85 (m, 2H). ES/MS 560.2 (M+H⁺).

(85)

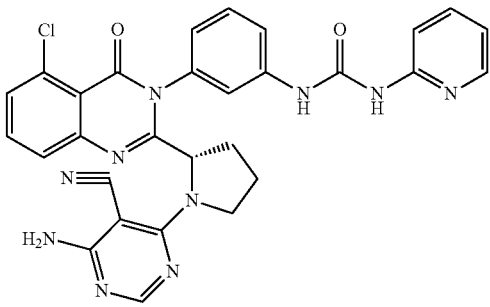

(S)-1-(3-(2-(1-(6-amino-5-cyanopyrimidin-4-yl)pyrrolidin-2-yl)-5-chloro-4-oxoquinazolin-3(4H)-yl)phenyl)-3-(2-methoxyethyl)urea (Compound 84). ¹H NMR (400 MHz, DMSO-d6) δ 8.01 (s, 1H, major rotamer), 7.98 (s, 1H, minor rotamer), 7.68-7.63 (m, 1H), 7.56-7.45 (m, 2H), 7.45-7.31 (m, 2H), 7.12 (t, J=8 Hz, 1H), 6.98 (d, J=8 Hz, 1H, minor rotamer), 6.72 (d, J=8 Hz, 1H, major rotamer), 6.32-6.25 (m, 1H), 4.70-4.60 (m, 1H), 4.10-3.95 (m, 1H), 3.94-3.83 (m, 1H), 3.37-3.32 (m, 1h), 3.24 (s, 3H, minor rotamer), 3.23 (s, 3H, major rotamer), 2.30-2.16 (m, 1H), 2.10-2.02 (m, 1H), 1.97-1.85 (m, 2H). ES/MS 560.2 (M+H⁺).

(86)

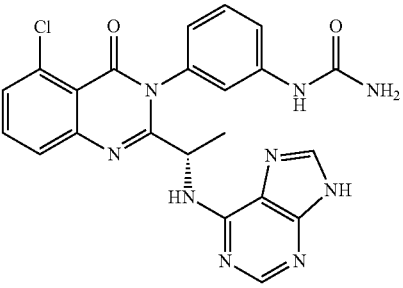

(S)-1-(3-(2-(1-((9H-purin-6-yl)amino)ethyl)-5-chloro-4-oxoquinazolin-3(4H)-yl)phenyl)urea (Compound 86). ¹H NMR (400 MHz, DMSO-d₆) δ 8.75 (br, 1H), 8.72 (m, 1H), 8.47 (m, 2H), 8.01 (s, 1H), 7.78 (m, 1H), 7.67-7.56 (m, 2H), 7.44 (m, 1H), 7.33 (m, 1H), 7.14 (t, J=7.3 Hz, 1H), 5.98 (br, 2H), 4.88 (m, 1H), 1.55 (d, J=6.7 Hz, 3H). ES/MS 476.1 (M+H⁺).

(87)

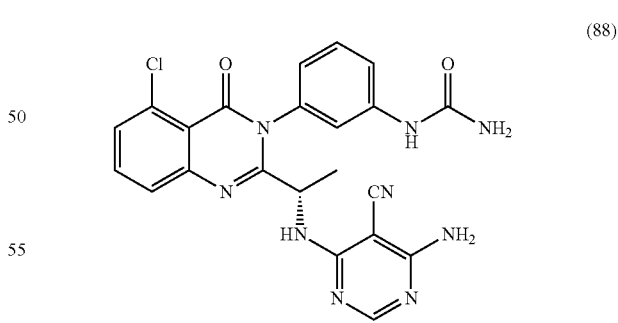

(S)-1-(3-(2-(1-((9H-purin-6-yl)amino)ethyl)-5-chloro-4-oxoquinazolin-3(4H)-yl)phenyl)-3-methylurea (Compound 87). ¹H NMR (400 MHz, DMSO-4) δ 9.10 (br, 1H), 8.78 (m, 1H), 8.52 (s, 2H), 7.91 (s, 1H), 7.79 (m, 1H), 7.73-7.54 (m, 2H), 7.44 (m, 1H), 7.32 (d, J=8.3 Hz, 1H), 7.12 (m, 1H), 6.18 (m, 18), 5.00 (m, 1H), 2.71-2.62 (d, J=16 Hz, 3H), 1.56 (d, J=6.7 Hz, 3H). ES/MS 490.2 (M+H⁺).

(88)

(S)-1-(3-(2-(1-((6-amino-5-cyanopyrimidin-4-yl)amino)ethyl)-5-chloro-4-oxoquinazolin-3(4H)-yl)phenyl)urea (Compound 88). ¹H NMR (400 MHz, DMSO-d₆) δ 8.74 (d, J=7.4 Hz, 1H), 8.05 (s, 0.5H), 7.94 (s, 0.5H), 7.84 (m, 0.5H), 7.67 (d, J=6.7 Hz, 0.5H), 7.63 (dd, J=8.2, 1.2 Hz, 0.5H), 7.61-7.59 (m, 0.75H), 7.58 (dd, J=3.3, 1.2 Hz, 1H), 7.56 (dd, J=1.2, 0.6 Hz, 0.5H), 7.54 (d, J=1.2 Hz, 0.25H), 7.42-7.38 (m, 2H), 7.38-7.35 (m, 1H), 7.31 (d, J=7.6 Hz, 1H), 7.05-

6.99 (m, 1H), 5.95 (br, 3H), 4.83 (p, J=6.7 Hz, 0.5H), 4.70 (p, J=6.8 Hz, 0.5H), 1.38 (dd, J=6.8, 4.0 Hz, 3H). ES/MS 476.1 (M+H+).

(89)

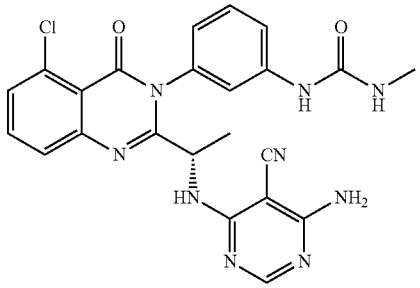

(S)-1-(3-(2-(1-(((6-amino-5-cyanopyrimidin-4-yl)amino) ethyl)-5-chloro-4-oxoquinazolin-3(4H)-yl)phenyl)-3-methylurea (Compound 89). ¹H NMR (400 MHz, DMSO-d₆) δ 8.77 (s, 0.5H), 8.72 (s, 0.5H), 8.10 (s, 0.5H), 7.99 (s, 0.5H), 7.89 (br, 0.5H), 7.83-7.80 (m, 1H), 7.80-7.77 (m, 0.5H), 7.77-7.72 (b, 0.5H), 7.68 (d, J=1.2 Hz, 0.25H), 7.65 (m, 0.5H), 7.64-7.61 (m, 1H), 7.60 (dd, J=2.1, 1.2 Hz, 0.5H), 7.58 (d, J=1.2 Hz, 0.25H), 7.55-7.44 (br, 2.5H), 7.44-7.41 (m, 0.5H), 7.41-7.36 (m, 0.5H), 7.33 (dd, J=8.2, 7.6 Hz, 0.5H), 7.08-7.02 (m, 1H), 6.15 (bs, 1H), 4.87 (m, 0.5H), 4.76 (m, 0.5H), 2.68 (s, 3H), 1.42 (dd, J=6.8, 4.1 Hz, 3H). ES/MS 490.2 (M+H+).

(90)

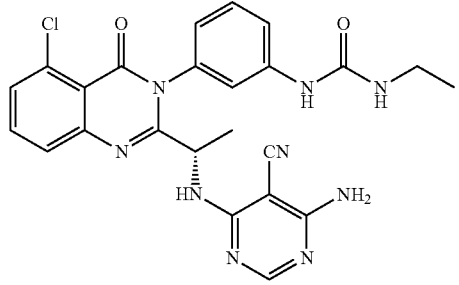

(S)-1-(3-(2-(1-(((6-amino-5-cyanopyrimidin-4-yl)amino) ethyl)-5-chloro-4-oxoquinazolin-3(4H)-yl)phenyl)-3-ethylurea (Compound 90). ¹H NMR (400 MHz, DMSO-d₆) δ 8.70 (d, J=8.8 Hz, 1H), 8.14 (s, 0.5H), 8.10 (d, J=6.5 Hz, 0.5H), 8.03 (s, 0.5H), 7.92 (d, J=6.7 Hz, 0.5H), 7.86-7.76 (m, 1.5H), 7.67 (dd, J=8.6, 1.2 Hz, 1H), 7.64-7.57 (m, 2H), 7.46-7.36 (m, 1.5H), 7.33 (t, J=7.9 Hz, 0.5H), 7.11-7.00 (m, 1H), 6.27 (bs, 1H), 5.36 (bs, 1H), 4.89 (m, 0.5H), 4.78 (m, 0.5H), 3.14 (m, 2H), 1.44 (d, J=6.8 Hz, 1.5H), 1.43 (d, J=6.8 Hz, 1.5H), 1.10 (t, J=7.2 Hz, 1.5H), 1.09 (t, J=7.2 Hz, 1.5H). ES/MS 504.1 (M+H+).

(91)

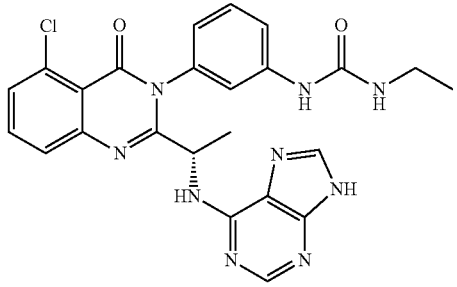

(S)-1-(3-(2-(1-(((9H-purin-6-yl)amino)ethyl)-5-chloro-4-oxoquinazolin-3(4H)-yl)phenyl)-3-ethylurea (Compound 91). ¹H NMR (400 MHz, DMSO-d₆) δ 8.97 (m, 1H), 8.73 (m, 1H), 8.57-8.41 (m, 2H), 7.94 (s, 1H), 7.79 (t, J=7.9 Hz, 1H), 7.73-7.56 (m, 2H), 7.44 (t, J=8.1 Hz, 1H), 7.32 (d, J=8.3 Hz, 1H), 7.12 (t, J=7.4 Hz, 1H), 6.30 (m, 1H), 4.93 (m, 1H), 3.07 (m, 2H), 1.56 (d, J=6.7 Hz, 3H), 1.09 (m, 3H). ES/MS 504.2 (M+H+).

(92)

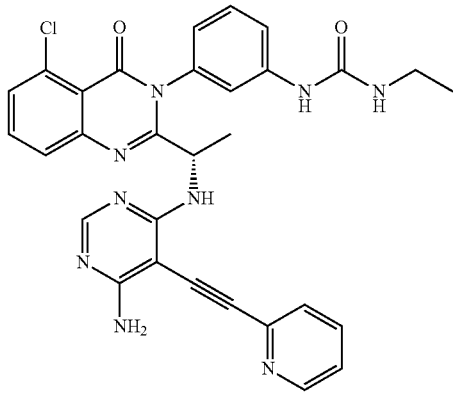

(S)-1-(3-(2-(1-(((6-amino-5-(pyridin-2-yl)ethynyl)pyrimidin-4-yl)amino)ethyl)-5-chloro-4-oxoquinazolin-3(4H)-yl) phenyl)-3-ethylurea (Compound 92). ¹H NMR (400 MHz, DMSO-d₆) δ 8.79 (tdd, J=5.1, 1.7, 1.0 Hz, 1H), 8.79 (bs, 1H), 8.75 (d, J=8.2 Hz, 1H), 8.23 (s, 0.5H), 8.18 (s, 0.5H), 8.00 (tdd, J=7.6, 3.6, 1.8 Hz, 1H), 7.95-7.90 (m, 1H), 7.90-7.86 (m, 1H), 7.85 (d, J=1.3 Hz, 0.5H), 7.84 (s, 0.5H), 7.81 (m, 1H), 7.80-7.70 (m, 1H), 7.68 (t, J=2.0 Hz, 1H), 7.65-7.61 (m, 1H), 7.53 (dddd, J=7.4, 4.9, 2.3, 1.4 Hz, 1H), 7.47-7.39 (m, 2H), 7.13-7.08 (m, 1H), 6.29 (m, 1H), 4.95-4.82 (m, 1H), 3.15 (m, 2H), 1.45 (d, J=6.6 Hz, 3H), 1.09 (m, 3H). ES/MS 580.2 (M+H+).

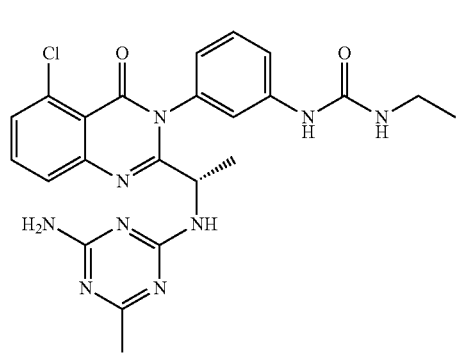

(93)

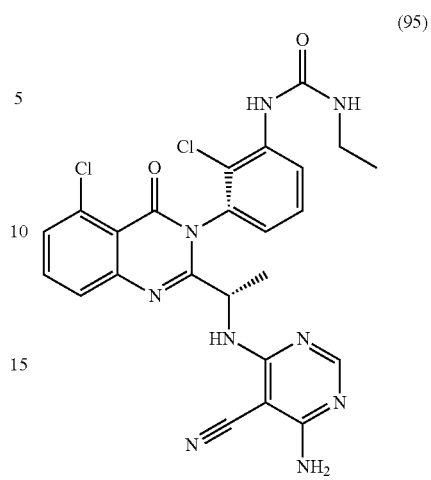

(95)

(S)-1-(3-(2-(1-((4-amino-6-methyl-1,3,5-triazin-2-yl)amino)ethyl)-5-chloro-4-oxoquinazolin-3(4H)-yl)phenyl)-3-ethylurea (Compound 93). $^1$H NMR (400 MHz, DMSO-$d_6$) δ 9.23 (br, 1H), 8.99 (s, 1H), 8.79-8.72 (m, 1H), 8.20 (br, 1H), 8.16 (t, J=2.1 Hz, 1H), 7.81 (m, 1H), 7.64 (m, 2H), 7.44 (m, 1H), 7.14 (m, 2H), 6.53 (m, 1H), 4.75 (m, 1H), 3.14 (m, 2H), 2.35-2.22 (m, 3H), 1.38 (d, J=6.8 Hz, 3H), 1.09 (td, J=7.2, 0.8 Hz, 3H). ES/MS 494.1 (M+H$^+$).

(S)-1-(3-(2-(1-(((6-amino-5-cyanopyrimidin-4-yl)amino)ethyl)-5-chloro-4-oxoquinazolin-3(4H)-yl)-2-chlorophenyl)-3-ethylurea, second diastereomer to elute on reverse-phase HPLC, (Compound 95). $^1$H NMR (400 MHz, DMSO-$d_6$) δ 8.22 (dd, J=8.4, 1.6 Hz, 1H), 8.19 (s, 1H), 7.90-7.89 (m, 1H), 7.86 (d, J=8.0 Hz, 1H), 7.85 (m, 1H), 7.75 (dd, J=8.4, 1.2 Hz, 1H), 7.67 (dd, J=7.8, 1.2 Hz, 1H), 7.60-7.39 (br, 2H), 7.27 (m, 1H), 7.17 (dd, J=7.9, 1.6 Hz, 1H), 7.07 (m, 1H), 4.92 (m, 1H), 3.25-3.13 (m, 2H), 1.42 (d, J=6.7 Hz, 3H), 1.12 (t, J=7.2 Hz, 3H). ES/MS 538.1 (M+H$^+$).

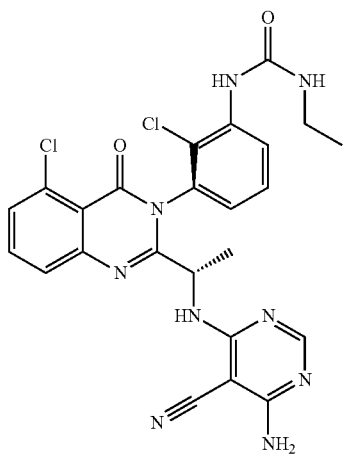

(94)

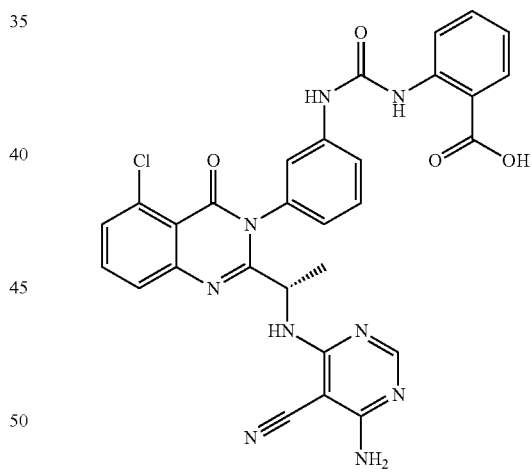

(96)

(S)-1-(3-(2-(1-(((6-amino-5-cyanopyrimidin-4-yl)amino)ethyl)-5-chloro-4-oxoquinazolin-3(4H)-yl)-2-chlorophenyl)-3-ethylurea, first diastereomer to elute on reverse-phase HPLC, (Compound 94). $^1$H NMR (400 MHz, DMSO-$d_6$) δ 8.30 (dd, J=8.5, 1.6 Hz, 1H), 8.03 (s, 1H), 7.91-7.86 (m, 1H), 7.85 (s, 1H), 7.80-7.76 (br, 1H), 7.76 (dd, J=8.2, 1.2 Hz, 1H), 7.67 (dd, J=7.8, 1.2 Hz, 1H), 7.52 (bs, 2H), 7.46-7.40 (m, 1H), 7.35 (dd, J=7.8, 1.6 Hz, 1H), 7.09 (t, J=5.3 Hz, 1H), 5.11 (m, 1H), 3.17 (m, 2H), 1.45 (d, J=6.7 Hz, 3H), 1.12 (t, J=7.2 Hz, 3H). ES/MS 538.1 (M+H$^+$).

(S)-2-(3-(3-(2-(1-(((6-amino-5-cyanopyrimidin-4-yl)amino)ethyl)-5-chloro-4-oxoquinazolin-3(4H)-yl)phenyl)ureido)benzoic acid (Compound 96). $^1$H NMR (400 MHz, DMSO-$d_6$) δ 10.46 (d, J=10.1 Hz, 1H), 10.09 (d, J=15.6 Hz, 1H), 8.39 (dddd, J=8.5, 5.4, 1.2, 0.4 Hz, 1H), 8.09 (s, 0.5H), 8.02-7.97 (m, 2H), 7.94 (bd, J=6.5 Hz, 0.5H), 7.85-7.77 (m, 1.5H), 7.73 (dd, J=2.1 Hz, 0.5H), 7.67 (m, 0.5H), 7.61 (ddd, J=7.8, 5.0, 1.2 Hz, 1H), 7.58-7.54 (m, 1H), 7.54-7.50 (m, 1H), 7.50-7.44 (m, 4H), 7.41 (dd, J=8.0 Hz, 0.5H), 7.17 (dddd, J=10.9, 7.8, 2.0, 1.2 Hz, 1H), 7.09 (m, 0.5H), 4.89 (m, 0.5H), 4.79 (m, 0.5H), 1.44 (d, J=6.8 Hz, 1.5H), 1.43 (d, J=6.8 Hz, 1.5H). ES/MS 596.1 (M+H$^+$).

(97)

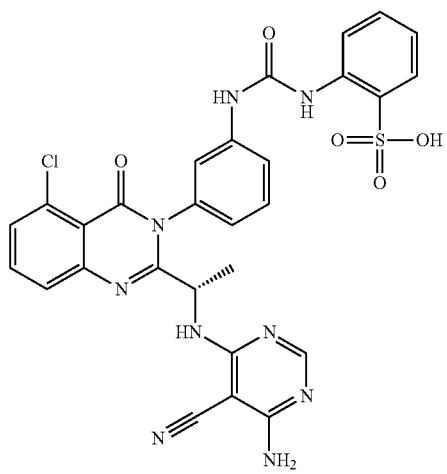

(S)-2-(3-(3-(2-(1-((6-amino-5-cyanopyrimidin-4-yl)amino)ethyl)-5-chloro-4-oxoquinazolin-3(4H)-yl)phenyl)ureido)benzenesulfonic acid (Compound 97). $^1$H NMR (400 MHz, DMSO-d$_6$) δ 9.91 (d, J=10.7 Hz, 1H), 9.42 (s, 0.5H), 9.35 (s, 0.5H), 8.77 (s, 0.5H), 8.44 (d, J=6.6 Hz, 0.5H), 8.18 (d, J=2.2 Hz, 1H), 8.11 (bs, 1H), 8.05-7.92 (m, 1H), 7.89 (bs, 0.5H), 7.82 (td, J=8.0, 1.2 Hz 1H), 7.74-7.67 (m, 2H), 7.63 (ddd, J=7.8, 1.2, 0.8 Hz, 1H), 7.54 (ddd, J=8.3, 2.1, 1.0 Hz, 0.5H), 7.53 (br, 2H), 7.45 (t, J=8.0 Hz, 0.5H), 7.38 (t, J=8.0 Hz, 0.5H), 7.31 (dddd, J=8.3, 7.3, 4.2, 1.7 Hz, 1H), 7.22-7.16 (m, 0.5H), 7.13 (ddd, J=7.7, 2.1, 1.1 Hz, 0.5H), 7.07 (ddd, J=7.8, 2.0, 1.0 Hz, 0.5H), 7.02 (ddd, J=14.8, 2.8, 1.2 Hz, 0.5H), 7.00 (m, 0.5H), 6.82-6.76 (m, 0.5H), 4.97 (m, 1H), 1.48 (d, J=6.6 Hz, 3H).

ES/MS 632.1 (M+H$^+$).

(99)

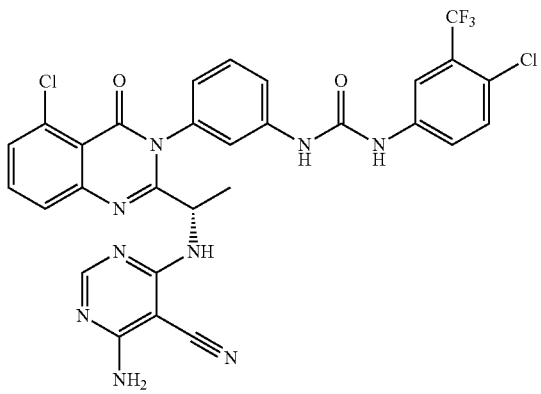

(S)-1-(3-(2-(1-((6-amino-5-cyanopyrimidin-4-yl)amino)ethyl)-5-chloro-4-oxoquinazolin-3(4H)-yl)phenyl)-3-(4-chloro-3-(trifluoromethyl)phenyl)urea (Compound 99). $^1$H NMR (400 MHz, DMSO-d6) δ 9.29 (d, J=13.8 Hz, 1H), 9.09 (d, J=12.2 Hz, 1H), 8.06 (dd, J=8.9, 2.3 Hz, 1H), 7.95 (s, 0.5H), 7.91 (s, 0.5H), 7.82-7.74 (m, 1H), 7.70 (td, J=8.0, 3.6 Hz, 1H), 7.66-7.57 (m, 1H), 7.57-7.53 (m, 2H), 7.53-7.48 (m, 1H), 7.45 (br, 3H), 7.41-7.34 (m, 1.5H), 7.30 (t, J=8.0 Hz, 0.5H), 7.08 (dt, J=6.5, 2.1 Hz, 0.5H), 7.04 (ddd, J=7.8, 2.0, 1.1 Hz, 0.5H), 4.80 (m, 0.5H), 4.73 (m, 0.5H), 1.34 (d, J=6.7 Hz, 1.5H), 1.32 (d, J=6.8 Hz, 1.5H). ES/MS 654.1 (M+H$^+$).

(98)

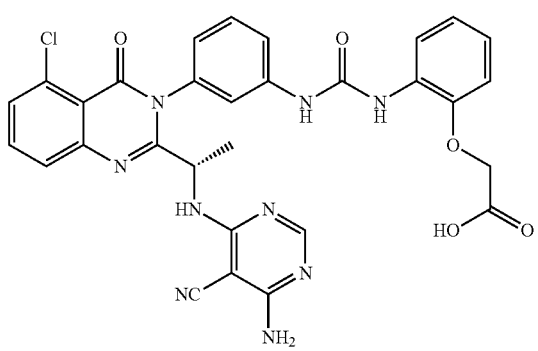

(S)-2-(2-(3-(3-(2-(1-((6-amino-5-cyanopyrimidin-4-yl)amino)ethyl)-5-chloro-4-oxoquinazolin-3(4H)-yl)phenyl)ureido)phenoxy)acetic acid (Compound 98). $^1$H NMR (400 MHz, DMSO-d$_6$) δ 9.65 (s, 0.5H), 9.61 (s, 0.5H), 8.37 (s, 0.5H), 8.34 (s, 0.5H), 8.15 (m, 1H), 8.11 (s, 0.5H), 8.01 (s, 0.5H), 8.00-7.96 (br, 0.5H), 7.95 (t, J=2.1 Hz, 0.5H), 7.81 (m, 1.5H), 7.72 (t, J=2.0 Hz, 0.5H), 7.67 (m, 1H), 7.62 (dd, J=4.3, 1.2 Hz, 0.5H), 7.60 (dd, J=4.3, 1.2 Hz, 0.5H), 7.53 (bs, 2H), 7.49 (m, 1H), 7.45-7.37 (m, 2H), 7.16 (dt, J=7.8, 1.5 Hz, 0.5H), 7.12 (dt, J=7.0, 1.9 Hz, 0.5H), 6.95 (m, 3H), 4.92 (m, 0.5H), 4.86 (s, 2H), 4.81 (m, 0.5H), 1.44 (d, J=6.5 Hz, 1.5H). 1.43 (d, J=6.5 Hz, 1.5H). ES/MS 626.1 (M+H$^+$).

(100)

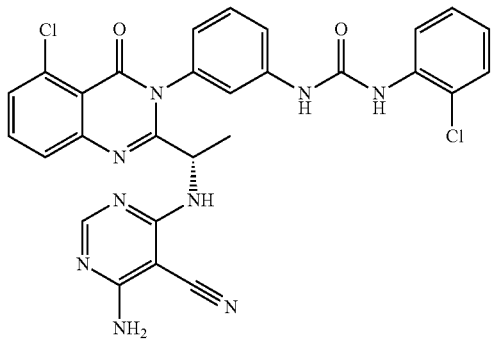

(S)-1-(3-(2-(1-((6-amino-5-cyanopyrimidin-4-yl)amino)ethyl)-5-chloro-4-oxoquinazolin-3(4H)-yl)phenyl)-3-(2-chlorophenyl)urea (Compound 100). $^1$H NMR (400 MHz, DMSO-d$_6$) δ 9.64 (d, J=11.3 Hz, 1H), 8.43 (d, J=17.5 Hz, 1H), 8.17 (dt, J=8.3, 1.3 Hz, 1H), 8.07 (d, J=1.0 Hz, 0.5H), 8.01 (d, J=1.0 Hz, 0.5H), 7.98 (d, J=6.8 Hz, 0.5H), 7.95 (s, 0.5H), 7.87-7.77 (m, 1.5H), 7.71 (m, 0.5H), 7.67 (m, 1H), 7.61 (ddt, J=7.9, 3.6, 1.2 Hz, 1H), 7.57-7.45 (m, 3H), 7.33 (dd, J=8.6, 7.0 Hz, 1H), 7.17 (m, 1H), 7.08 (m, 1H), 4.91 (m, 0.5H), 4.83 (m, 0.5H), 4.09 (bs, 2H), 1.45 (d, J=6.7 Hz, 1.5H), 1.44 (d, J=6.7 Hz, 1.5H). ES/MS 586.1 (M+H$^+$).

(101)

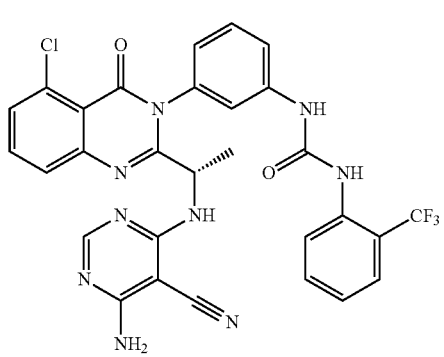

(103)

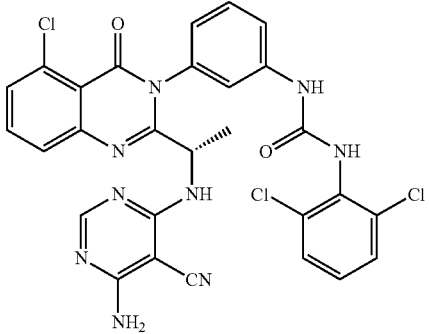

(S)-1-(3-(2-(1-(((6-amino-5-cyanopyrimidin-4-yl)amino)ethyl)-5-chloro-4-oxoquinazolin-3(4H)-yl)phenyl)-3-(2-(trifluoromethyl)phenyl)urea (Compound 101). $^1$H NMR (400 MHz, DMSO-$d_6$) δ 9.59 (d, J=15.2 Hz, 1H), 8.21 (d, J=16.8 Hz, 1H), 8.00 (m, 1H), 7.96-7.91 (m, 1H), 7.86 (d, J=6.5 Hz, 0.5H), 7.84-7.78 (m, 1H), 7.78-7.70 (m, 2.5H), 7.68 (m, 2H), 7.61 (ddd, J=7.8, 4.5, 1.2 Hz, 1H), 7.57-7.47 (m, 2H), 7.46-7.38 (m, 2H), 7.34 (m, 1H), 7.19 (ddd, J=7.7, 2.0, 1.1 Hz, 0.5H), 7.16 (m, 0.5H), 4.90 (m, 0.5H), 4.82 (m, 0.5H), 1.44 (d, J=6.8 Hz, 1.5H), 1.43 (d, J=6.8 Hz, 1.5H). ES/MS 621.1 (M+H$^+$).

(S)-1-(3-(2-(1-(((6-amino-5-cyanopyrimidin-4-yl)amino)ethyl)-5-chloro-4-oxoquinazolin-3(4H)-yl)phenyl)-3-(2,6-dichlorophenyl)urea (Compound 103). $^1$H NMR (400 MHz, DMSO-$d_6$) δ 9.25 (s, 1H), 8.39 (d, J=8.0 Hz, 1H), 8.06 (d, J=0.5 Hz, 0.5H), 8.00 (d, J=0.5 Hz, 0.5H), 7.94 (m, 0.5H), 7.87 (d, J=6.4 Hz, 0.5H), 7.80 (m, 0.5H), 7.77 (m, 0.5H), 7.69-7.63 (m, 1H), 7.63-7.59 (m, 1H), 7.58 (m, 1H), 7.56 (d, J=1.7 Hz, 1H), 7.53-7.48 (m, 1H), 7.47 (br, 2H), 7.42-7.33 (m, 2H), 7.17 (dt, J=6.6, 2.0 Hz, 0.5H), 7.13 (ddd, J=7.8, 2.0, 1.0 Hz, 0.5H), 4.88 (m, 0.5H), 4.72 (m, 0.5H), 1.43 (d, J=6.8 Hz, 3H). ES/MS 620.1 (M+H$^+$).

(102)

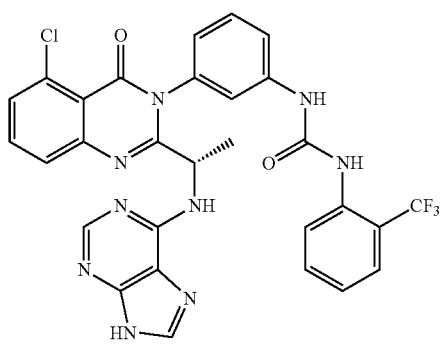

(104)

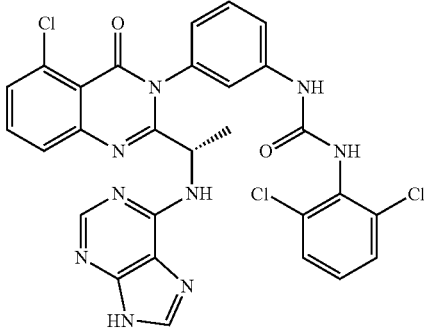

(S)-1-(3-(2-(1-((9H-purin-6-yl)amino)ethyl)-5-chloro-4-oxoquinazolin-3(4H)-yl)phenyl)-3-(2-(trifluoromethyl)phenyl)urea (Compound 102). $^1$H NMR (400 MHz, DMSO-$d_6$) δ 9.66 (s, 0.5H), 9.53 (s, 0.5H), 8.79 (br, 1H), 8.42 (m, 2H), 8.26 (s, 0.5H), 8.15 (s, 0.5H), 8.00 (s, 0.5H), 7.97 (d, J=8.3 Hz, 0.5H), 7.89 (d, J=8.3 Hz, 0.5H), 7.83-7.71 (m, 2H), 7.71-7.56 (m, 4H), 7.52 (m, 1H), 7.45-7.30 (m, 2H), 7.25 (m, 1H), 5.00 (m, 1H), 1.57 (d, J=6.8 Hz, 1.5H), 1.56 (d, J=6.8 Hz, 1.5H). ES/MS 620.1 (M+H$^+$).

(S)-1-(3-(2-(1-((9H-purin-6-yl)amino)ethyl)-5-chloro-4-oxoquinazolin-3(4H)-yl)phenyl)-3-(2,6-dichlorophenyl)urea (Compound 104). $^1$H NMR (400 MHz, DMSO-$d_6$) δ 9.31 (m, 1H), 9.10-8.90 (br, 1H), 8.58-8.36 (m, 2H), 8.31 (m, 1H), 8.04 (m, 1H), 7.86 (td, J=8.0, 1.4 Hz, 0.5H), 7.82-7.72 (m, 1H), 7.70 (dt, J=8.1, 1.1 Hz, 0.5H), 7.67-7.50 (m, 3H), 7.50-7.43 (m, 0.5H), 7.43-7.33 (m, 1.5H), 7.26 (m, 2H), 7.16-7.00 (m, 1H), 4.95 (m, 1H), 1.56 (d, J=6.8 Hz, 3H). ES/MS 620.1 (M+H$^+$).

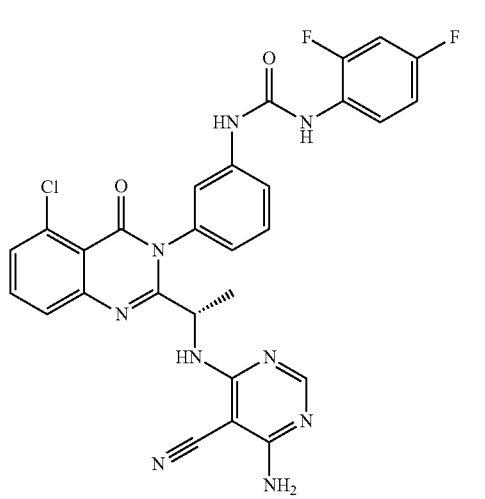

(105)

(S)-1-(3-(2-(1-((6-amino-5-cyanopyrimidin-4-yl)amino)ethyl)-5-chloro-4-oxoquinazolin-3(4H)-yl)phenyl)-3-(2,4-difluorophenyl)urea (Compound 105). ¹H NMR (400 MHz, DMSO-d₆) δ 9.42 (d, J=13.5 Hz, 1H), 8.71 (m, 1H), 8.14-8.01 (m, 2.5H), 7.86 (m, 1H), 7.81 (m, 1H), 7.70-7.64 (m, 1.5H), 7.61 (ddd, J=7.8, 4.3, 1.2 Hz, 1H), 7.55 (br, 2H), 7.49 (m, 1H), 7.46 (dd, J=2.1, 1.2 Hz, 0.5H), 7.41 (d, J=7.9 Hz, 0.5H), 7.36 (m, 1H), 7.18 (ddd, J=4.8, 4.1, 2.0 Hz, 0.5H), 7.14 (ddd, J=7.7, 2.0, 1.2 Hz, 0.5H), 7.08 (m, 1H), 4.90 (m, 0.5H), 4.81 (m, 0.5H), 1.44 (d, J=6.8 Hz, 1.5H), 1.43 (d, J=6.8 Hz, 1.5H). ES/MS 588.1 (M+H⁺).

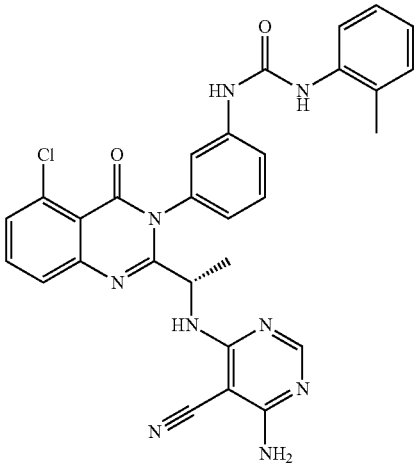

(107)

(S)-1-(3-(2-(1-(((6-amino-5-cyanopyrimidin-4-yl)amino)ethyl)-5-chloro-4-oxoquinazolin-3(4H)-yl)phenyl)-3-(o-tolyl)urea (Compound 107). ¹H NMR (400 MHz, DMSO-d₆) δ 9.27 (d, J=6.0 Hz, 1H), 8.09 (s, 0.5H), 8.08 (s, 0.5H), 8.05 (s, 0.5H), 8.02 (s, 0.5H), 7.96 (t, J=2.1 Hz, 0.5H), 7.89-7.76 (m, 2H), 7.72 (t, J=2.0 Hz, 0.5H), 7.67 (m, 1H), 7.61 (dddd, J=7.9, 4.6, 1.2, 0.5 Hz, 1H), 7.53 (br, 2H), 7.51-7.36 (m, 2H), 7.24-7.18 (m, 1H), 7.18-7.10 (m, 2H), 6.99 (td, J=7.4, 1.3 Hz, 1H), 5.55 (br, 1H), 4.92 (m, 0.5H), 4.82 (m, 0.5H), 2.29 (s, 1.5H), 2.28 (s, 1.5H), 1.45 (d, J=6.8 Hz, 1.5H), 1.44 (d, J=6.8 Hz, 1.5H). ES/MS 566.2 (M+H⁺).

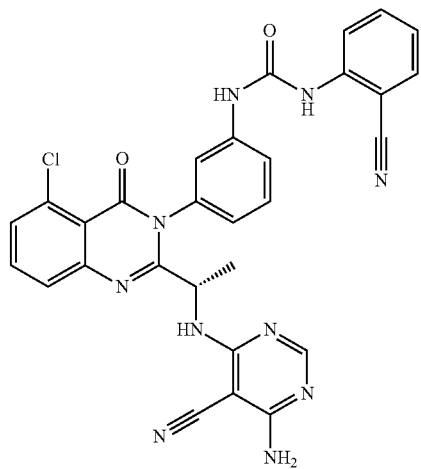

(106)

(S)-1-(3-(2-(1-(((6-amino-5-cyanopyrimidin-4-yl)amino)ethyl)-5-chloro-4-oxoquinazolin-3(4H)-yl)phenyl)-3-(2-cyanophenyl)urea (Compound 106). ¹H NMR (400 MHz, DMSO-d₆) δ 12.63 (s, 0.5H), 12.57 (s, 0.5H), 10.75 (br, 0.5H), 10.40 (br, 0.5H), 9.01 (s, 0.5H), 8.93 (s, 0.5H), 8.83 (s, 0.5H), 8.58-8.49 (m, 0.5H), 8.43-8.35 (m, 0.5H), 8.14-8.01 (m, 1H), 8.01-7.90 (m, 2H), 7.89-7.81 (m, 2H), 7.81-7.74 (m, 2H), 7.67-7.56 (m, 2H), 7.54-7.40 (m, 2H), 7.40-7.25 (m, 1.5H), 4.87 (m, 0.5H), 4.81 (m, 0.5H), 1.48 (d, J=6.9 Hz, 1.5H), 1.41 (d, J=6.8 Hz, 1.5H). ES/MS 577.1 (M+H⁺).

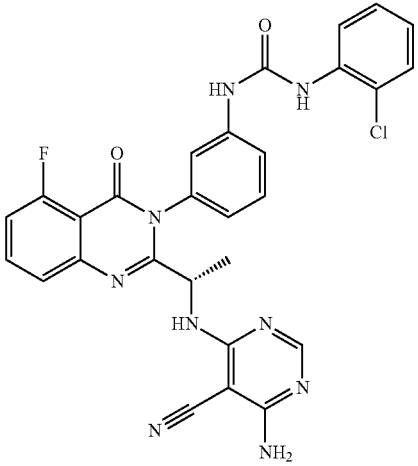

(108)

(S)-1-(3-(2-(1-(((6-amino-5-cyanopyrimidin-4-yl)amino)ethyl)-5-fluoro-4-oxoquinazolin-3(4H)-yl)phenyl)-3-(2-chlorophenyl)urea (Compound 108). ¹H NMR (400 MHz, DMSO-d₆) δ 9.65 (d, J=9.3 Hz, 1H), 8.46 (s, 0.5H), 8.41 (s, 0.5H), 8.18 (dd, J=8.3, 1.5 Hz, 1H), 8.09 (s, 1H), 8.03 (s, 0.5H), 7.97-7.91 (m, 1H), 7.88 (dtd, J=8.4, 5.2, 2.8 Hz, 1H), 7.72 (t, J=2.0 Hz, 0.5H), 7.59 (bs, 2H), 7.58-7.46 (m, 2H), 7.46-7.39 (m, 1H), 7.35 (m, 2H), 7.17 (m, 1H), 7.08 (m, 1H), 4.94 (m, 0.5H), 4.86 (m, 0.5H), 1.45 (d, J=6.8 Hz, 1.5H), 1.44 (d, J=6.8 Hz, 1.5H). ES/MS 570.2 (M+H⁺).

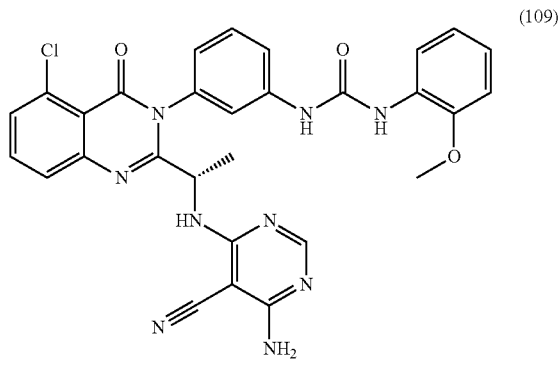 [SMILES: COc1ccccc1NC(=O)Nc1cccc(-n2c([C@H](C)Nc3ncnc(N)c3C#N)nc3cccc(Cl)c3c2=O)c1]

(109)

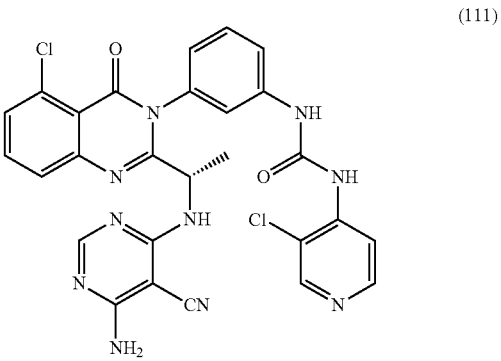

(111)

(S)-1-(3-(2-(1-(((6-amino-5-cyanopyrimidin-4-yl)amino)ethyl)-5-chloro-4-oxoquinazolin-3(4H)-yl)phenyl)-3-(2-methoxyphenyl)urea (Compound 109). $^1$H NMR (400 MHz, DMSO-$d_6$) δ 9.56 (d, J=10.8 Hz, 1H), 8.34 (d, J=13.6 Hz, 1H), 8.15 (ddd, J=8.0, 5.2, 1.7 Hz, 1H), 8.12 (s, 0.5H), 8.01 (m, 1H), 7.96 (t, J=2.0 Hz, 1H), 7.88-7.81 (m, 1H), 7.81-7.78 (m, 0.5H), 7.72 (m, 0.5H), 7.67 (td, J=8.2, 1.2 Hz, 1H), 7.61 (ddd, J=7.8, 4.7, 1.2 Hz, 1H), 7.54 (bs, 2H), 7.49 (t, J=8.0 Hz, 0.5H), 7.45-7.37 (m, 1H), 7.16 (m, 0.5H), 7.12 (dt, J=6.6, 2.1 Hz, 0.5H), 7.06 (dt, J=8.1, 1.6 Hz, 1H), 6.99 (td, J=7.7, 1.7 Hz, 1H), 6.92 (tt, J=7.6, 1.7 Hz, 1H), 4.91 (m, 0.5H), 4.80 (m, 0.5H), 3.92 (s, 1.5H), 3.92 (s, 1.5H), 1.44 (d, J=6.4 Hz, 1.5H), 1.43 (d, J=6.4 Hz, 1.5H). ES/MS 582.2 (M+H$^+$).

(S)-1-(3-(2-(1-(((6-amino-5-cyanopyrimidin-4-yl)amino)ethyl)-5-chloro-4-oxoquinazolin-3(4H)-yl)phenyl)-3-(3-chloropyridin-4-yl)urea, trifluoroacetic acid salt (Compound 111). $^1$H NMR (400 MHz, DMSO-$d_6$) δ 10.10 (d, J=15.3 Hz, 1H), 9.17 (d, J=18.7 Hz, 1H), 8.81 (m, 1H), 8.52 (m, 2H), 7.99 (d, J=4.7 Hz, 1H), 7.93 (t, J=2.0 Hz, 0.5H), 7.91-7.88 (m, 0.5H), 7.86-7.79 (m, 1H), 7.79-7.75 (m, 0.5H), 7.73 (t, J=2.0 Hz, 0.5H), 7.71-7.67 (m, 1H), 7.64-7.60 (m, 1H), 7.56-7.47 (m, 2H), 7.46-7.39 (m, 1H), 7.26 (ddd, J=7.8, 2.0, 1.0 Hz, 0.5H), 7.22 (ddd, J=7.5, 2.0, 1.3 Hz, 0.5H), 6.00 (br, 1H), 4.98-4.81 (m, 1H), 1.44 (d, J=6.8 Hz, 1.5H), 1.43 (d, J=6.8 Hz, 1.5H). ES/MS 587.1 (M+H$^+$).

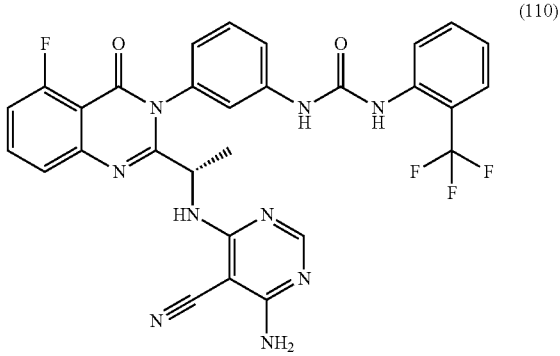 [SMILES: C[C@H](Nc1ncnc(N)c1C#N)c1nc2cccc(F)c2c(=O)n1-c1cccc(NC(=O)Nc2ccccc2C(F)(F)F)c1]

(110)

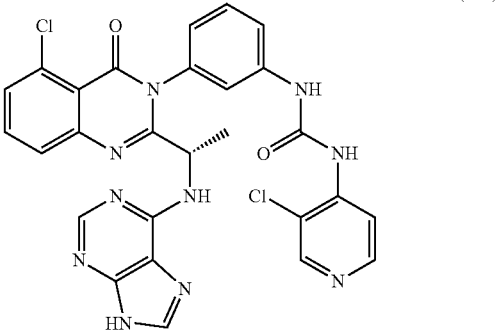

(112)

(S)-1-(3-(2-(1-(((6-amino-5-cyanopyrimidin-4-yl)amino)ethyl)-5-fluoro-4-oxoquinazolin-3(4H)-yl)phenyl)-3-(2-(trifluoromethyl)phenyl)urea (Compound 110). $^1$H NMR (400 MHz, DMSO-$d_6$) δ 9.59 (d, J=12.4 Hz, 1H), 8.21 (d, J=17.0 Hz, 1H), 8.02 (d, J=13.8 Hz, 1H), 7.99-7.91 (m, 2H), 7.87 (m, 1.5H), 7.75-7.70 (m, 1.5H), 7.67 (t, J=7.8 Hz, 1H), 7.60-7.46 (m, 3H), 7.46-7.41 (m, 1H), 7.41-7.30 (m, 2H), 7.19 (ddd, J=7.7, 2.0, 1.1 Hz, 0.5H), 7.15 (ddd, J=7.4, 2.0, 1.3 Hz, 0.5H), 4.92 (m, 0.5H), 4.84 (m, 0.5H), 1.44 (d, J=6.8 Hz, 1.5H), 1.43 (d, J=6.8 Hz, 1.5H). ES/MS 604.2 (M+H$^+$).

(S)-1-(3-(2-(1-(((9H-purin-6-yl)amino)ethyl)-5-chloro-4-oxoquinazolin-3(4H)-yl)phenyl)-3-(3-chloropyridin-4-yl)urea (Compound 112). $^1$H NMR (400 MHz, DMSO-$d_6$) δ 10.09 (s, 0.5H), 9.90 (s, 0.5H), 9.08 (s, 0.5H), 8.91 (s, 1H), 8.90-8.75 (br, 1H), 8.80 (s, 0.5H), 8.72 (d, J=4.3 Hz, 1H), 8.48 (dd, J=6.0, 2.0 Hz, 1H), 8.44 (m, 0.5H), 8.40 (s, 1H), 8.31 (d, J=6.0 Hz, 0.5H), 7.95 (s, 0.5H), 7.81 (m, 1.5H), 7.72-7.66 (m, 1H), 7.66-7.59 (m, 1H), 7.59-7.38 (m, 1H), 7.33 (m, 2H), 5.03 (m, 1H), 1.57 (d, J=6.8 Hz, 3H). ES/MS 587.0 (M+H$^+$).

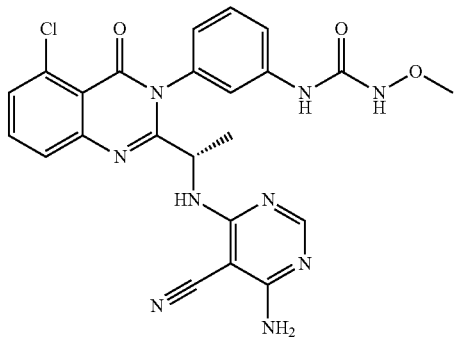

(115)

(S)-1-(3-(2-(1-(((6-amino-5-cyanopyrimidin-4-yl)amino) ethyl)-5-chloro-4-oxoquinazolin-3(4H)-yl)phenyl)-3-methoxyurea (Compound 115). $^1$H NMR (400 MHz, DMSO-d$_6$) δ 9.69 (d, J=8.5 Hz, 1H), 9.17 (s, 1H), 9.10 (s, 0.5H), 8.07 (s, 0.5H), 8.05 (t, J=2.1 Hz, 0.5H), 7.99 (s, 0.5H), 7.95-7.89 (m, 0.5H), 7.84-7.74 (m, 2H), 7.74-7.56 (m, 3.5H), 7.49 (br, 2H), 7.48 (t, J=8.0 Hz, 0.5H), 7.39 (t, J=8.1 Hz, 0.5H), 7.17 (m, 1H), 4.86 (m, 0.5H), 4.73 (m, 0.5H), 3.67 (s, 1.5H), 3.65 (s, 1.5H), 1.43 (d, J=6.8 Hz, 1.5H), 1.42 (d, J=6.8 Hz, 1.5H). ES/MS 506.1 (M+H$^+$).

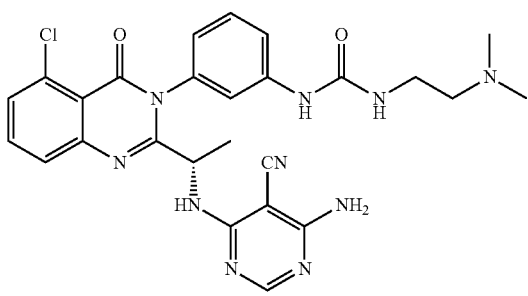

(116)

(S)-1-(3-(2-(1-(((6-amino-5-cyanopyrimidin-4-yl)amino) ethyl)-5-chloro-4-oxoquinazolin-3(4H)-yl)phenyl)-3-(2-(dimethylamino)ethyl)urea, trifluoroacetic acid salt (Compound 116). $^1$H NMR (400 MHz, DMSO-d$_6$) δ 9.32 (bs, 1H), 9.17 (d, J=5.1 Hz, 1H), 8.08 (d, J=1.2 Hz, 0.5H), 7.96 (d, J=1.2 Hz, 0.5H), 7.91 (m, 0.5H), 7.85-7.76 (m, 1.5H), 7.71-7.57 (m, 3H), 7.45 (m, 1H), 7.43-7.33 (m, 3H), 7.10 (m, 1H), 6.69 (q, J=5.7 Hz, 1H), 4.86 (m, 0.5H), 4.69 (m, 0.5H), 3.49 (m, 2H), 3.20 (m, 2H), 2.86 (s, 6H), 1.42 (d, J=6.6 Hz, 3H). ES/MS 547.2 (M+H$^+$).

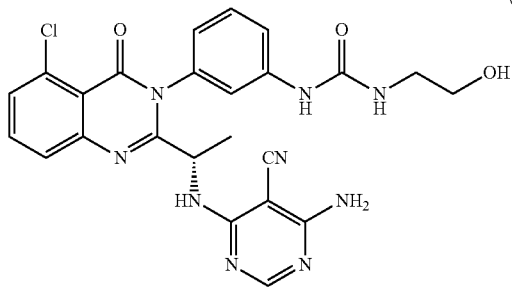

(117)

(S)-1-(3-(2-(1-(((6-amino-5-cyanopyrimidin-4-yl)amino) ethyl)-5-chloro-4-oxoquinazolin-3(4H)-yl)phenyl)-3-(2-hydroxyethyl)urea (Compound 117). $^1$H NMR (400 MHz, DMSO-d$_6$) δ 8.83 (d, J=12.2 Hz, 1H), 8.21 (d, J=6.6 Hz, 0.5H), 8.14 (s, 0.5H), 8.04 (s, 0.5H), 8.01 (d, J=6.6 Hz, 0.5H), 7.84-7.77 (m, 2H), 7.74 (bs, 1H), 7.68 (d, J=1.2 Hz, 0.5H), 7.66 (d, J=1.2 Hz, 0.5H), 7.65-7.58 (m, 1.5H), 7.45-7.31 (m, 1.5H), 7.11-6.99 (m, 1H), 6.35 (bs, 1H), 5.98 (br, 2H), 4.89 (m, 0.5H), 4.79 (m, 0.5H), 3.49 (td, J=5.8, 1.0 Hz, 2H), 3.20 (m, 2H), 1.44 (d, J=6.8 Hz, 1.5H), 1.43 (d, J=6.8 Hz, 1.5H). ES/MS 520.1 (M+H$^+$).

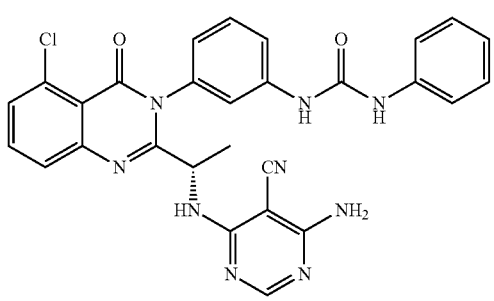

(118)

(S)-1-(3-(2-(1-(((6-amino-5-cyanopyrimidin-4-yl)amino) ethyl)-5-chloro-4-oxoquinazolin-3(4H)-yl)phenyl)-3-phenylurea (Compound 118). $^1$H NMR (400 MHz, DMSO-d$_6$) δ 8.97 (m, 1H), 8.87 (s, 0.5H), 8.85 (s, 0.5H), 8.13 (s, 0.5H), 8.02 (s, 0.5H), 7.90 (m, 1H), 7.86-7.76 (m, 1H), 7.71-7.66 (m, 1H), 7.66-7.59 (m, 1H), 7.56 (bs, 2H), 7.52-7.37 (m, 4H), 7.32 (m, 2H), 7.16 (m, 0.5H), 7.12 (m, 0.5H), 7.01 (m, 1H), 4.91 (m, 0.5H), 4.80 (m, 0.5H), 4.30 (br, 1H), 1.45 (m, 3H). ES/MS 552.1 (M+H$^+$).

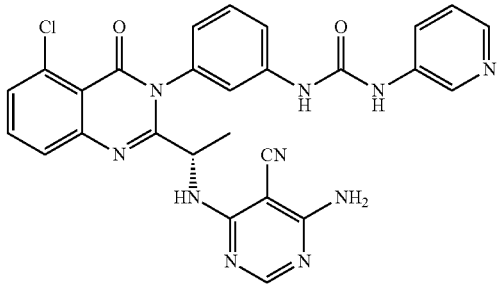

(119)

(S)-1-(3-(2-(1-(((6-amino-5-cyanopyrimidin-4-yl)amino) ethyl)-5-chloro-4-oxoquinazolin-3(4H)-yl)phenyl)-3-(pyridin-3-yl)urea, trifluoroacetic acid salt (Compound 119). $^1$H NMR (400 MHz, DMSO-d$_6$) δ 10.10 (m, 1H), 9.77 (m, 1H), 9.09 (m, 1H), 8.50 (d, J=5.4 Hz, 1H), 8.34 (m, 1H), 8.05 (s, 0.5H), 7.99 (s, 0.5H), 7.89 (m, 2H), 7.85-7.75 (m, 1H), 7.73 (t, J=2.1 Hz, 0.5H), 7.67 (m, 1H), 7.61 (m, 1H), 7.57 (m, 0.5H), 7.55-7.50 (m, 1H), 7.45 (m, 2H), 7.20 (m, 1H), 5.75 (br, 1H), 4.90 (m, 0.5H), 4.80 (m, 0.5H) 1.44 (m, 3H). ES/MS 553.1 (M+H$^+$).

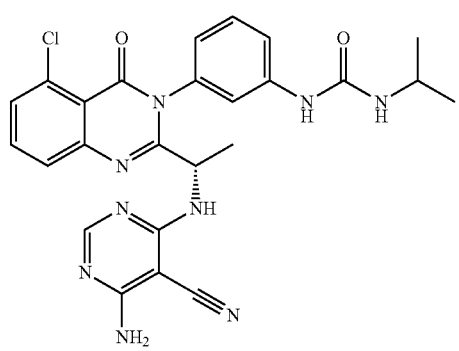

(120)

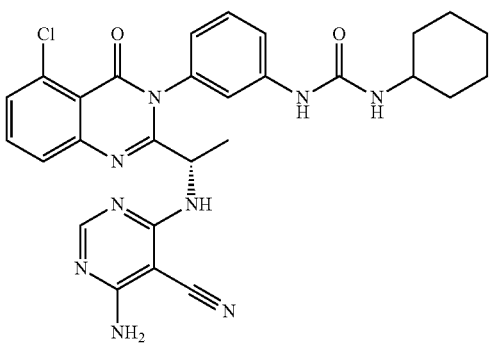

(122)

(S)-1-(3-(2-(1-(((6-amino-5-cyanopyrimidin-4-yl)amino)ethyl)-5-chloro-4-oxoquinazolin-3(4H)-yl)phenyl)-3-isopropylurea (Compound 120). $^1$H NMR (400 MHz, DMSO-$d_6$) δ 8.56 (d, J=5.8 Hz, 1H), 8.12 (s, 1H), 7.99 (m, 1H), 7.89-7.82 (m, 1H), 7.82-7.77 (m, 1H), 7.65 (m, 1H), 7.62-7.58 (m, 1H), 7.55 (br, 2H), 7.45-7.29 (m, 2H), 7.05 (m, 1H), 6.17 (dd, J=13.6, 7.4 Hz, 1H), 4.87 (m, 0.5H), 4.74 (m, 0.5H), 3.78 (m, 1H), 1.43 (dd, J=6.8, 4.3 Hz, 3H), 1.13 (dd, J=6.5, 0.9 Hz, 6H). ES/MS 518.2 (M+H$^+$).

(S)-1-(3-(2-(1-(((6-amino-5-cyanopyrimidin-4-yl)amino)ethyl)-5-chloro-4-oxoquinazolin-3(4H)-yl)phenyl)-3-cyclohexylurea (Compound 122). $^1$H NMR (400 MHz, DMSO-$d_6$) δ 8.56 (d, J=7.1 Hz, 1H), 8.10 (s, 0.5H), 7.99 (s, 0.5H), 7.95 (d, J=6.5 Hz, 0.5H), 7.86-7.76 (m, 2H), 7.70-7.57 (m, 2H), 7.57-7.47 (br, 2H), 7.46-7.29 (m, 2H), 7.05 (m, 1H), 6.22 (m, 1H), 4.87 (m, 0.5H), 4.73 (m, 0.5H), 3.48 (m, 1H), 1.84 (m, 2H), 1.69 (m, 2H), 1.57 (m, 1H), 1.42 (m, 3H), 1.37-1.10 (m, 6H). ES/MS 558.2 (M+H$^+$).

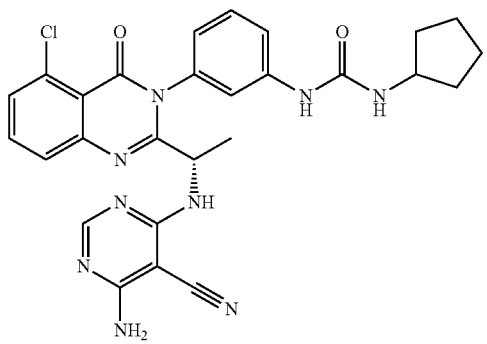

(121)

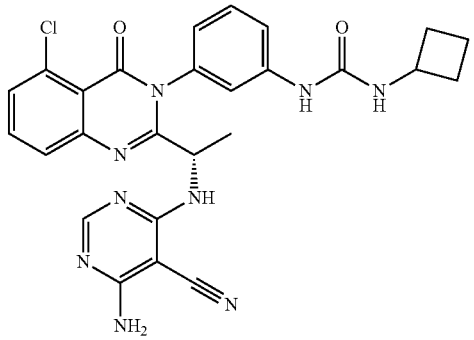

(123)

(S)-1-(3-(2-(1-(((6-amino-5-cyanopyrimidin-4-yl)amino)ethyl)-5-chloro-4-oxoquinazolin-3(4H)-yl)phenyl)-3-cyclopentylurea (Compound 121). $^1$H NMR (400 MHz, DMSO-$d_6$) δ 8.53 (s, 1H), 8.13 (s, 1H), 8.09-7.96 (m, 1H), 7.86 (m, 1H), 7.80 (m, 1H), 7.72-7.57 (m, 2H), 7.56 (bs, 2H), 7.50-7.27 (m, 2H), 7.05 (m, 1H), 6.32 (dd, J=13.0, 7.0 Hz, 1H), 4.87 (m, 0.5H), 4.74 (m, 0.5H), 3.96 (p, J=5.7 Hz, 1H), 1.94-1.82 (m, 2H), 1.76-1.50 (m, 4H), 1.37 (m, 5H). ES/MS 544.2 (M+H$^+$).

(S)-1-(3-(2-(1-(((6-amino-5-cyanopyrimidin-4-yl)amino)ethyl)-5-chloro-4-oxoquinazolin-3(4H)-yl)phenyl)-3-cyclobutylurea (Compound 123). 1H NMR (400 MHz, DMSO-$d_6$) δ 8.57 (d, J=8.0 Hz, 1H), 8.09 (s, 0.5H), 7.98 (s, 0.5H), 7.90 (d, J=6.4 Hz, 0.5H), 7.85-7.74 (m, 2H), 7.69-7.61 (m, 1H), 7.59 (m, 1H), 7.46 (br, 2H), 7.41 (m, 1H), 7.37-7.30 (m, 1H), 7.06 (m, 1H), 6.56 (dd, J=13.5, 7.9 Hz, 1H), 4.86 (m, 0.5H), 4.73 (m, 0.5H), 4.15 (m, 1H), 2.22 (m, 2H), 1.89 (m, 2H), 1.64 (m, 2H), 1.43 (d, J=6.8 Hz, 1.5H), 1.41 (d, J=6.8 Hz, 1.5H). ES/MS 530.2 (M+H$^+$).

(124)

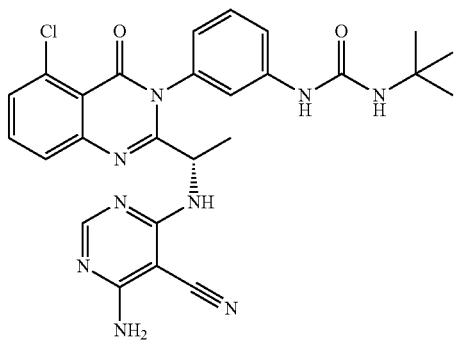

(126)

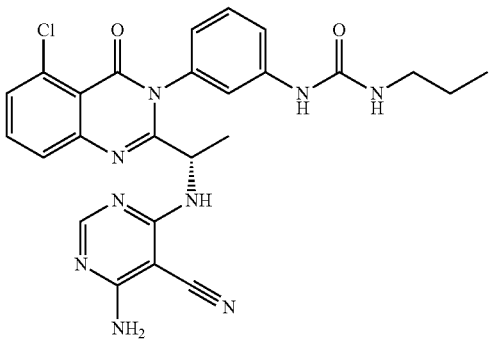

(S)-1-(3-(2-(1-((6-amino-5-cyanopyrimidin-4-yl)amino)ethyl)-5-chloro-4-oxoquinazolin-3(4H)-yl)phenyl)-3-(tert-butyl)urea (Compound 124). $^1$H NMR (400 MHz, DMSO-d$_6$) δ 8.50 (s, 1H), 8.13 (s, 0.5H), 7.98 (m, 1H), 7.91 (d, J=6.4 Hz, 0.5H), 7.80 (m, 1.5H), 7.69-7.57 (m, 2H), 7.48 (bs, 2H), 7.41 (t, J=8.0 Hz, 1H), 7.37-7.22 (m, 1.5H), 7.12-6.96 (m, 1H), 6.13 (d, J=13.9 Hz, 1H), 4.88 (m, 0.5H), 4.72 (m, 0.5H), 1.43 (d, J=6.8 Hz, 1.5H), 1.42 (d, J=6.8 Hz, 1.5H), 1.32 (s, 9H). ES/MS 532.2 (M+H$^+$).

(S)-1-(3-(2-(1-((6-amino-5-cyanopyrimidin-4-yl)amino)ethyl)-5-chloro-4-oxoquinazolin-3(4H)-yl)phenyl)-3-propylurea (Compound 126). $^1$H NMR (400 MHz, DMSO-d$_6$) δ 8.66 (d. J=11.5 Hz, 1H), 8.09 (s, 0.5H), 7.98 (s, 0.5H), 7.89 (d, J=6.5 Hz, 0.5H), 7.85 (m, 0.5H), 7.80 (m, 1H), 7.75 (d, J=6.4 Hz, 0.5H), 7.68-7.58 (m, 2H), 7.46 (br, 2H), 7.44-7.37 (m, 1H), 7.33 (t, J=7.9 Hz, 0.5H), 7.05 (m, 1H), 6.29 (m, 1H), 4.87 (m, 0.5H), 4.73 (m, 0.5H), 3.08 (m, 2H), 1.49 (m, 2H), 1.42 (d, J=6.8, Hz, 1.5H), 1.41 (d, J=6.8, Hz, 1.5H), 0.91 (td, J=7.4, 2.3 Hz, 3H). ES/MS 518.2 (M+H$^+$).

(125)

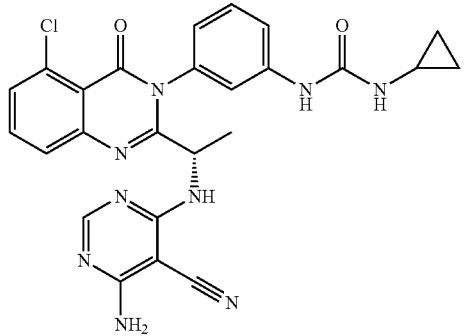

(127)

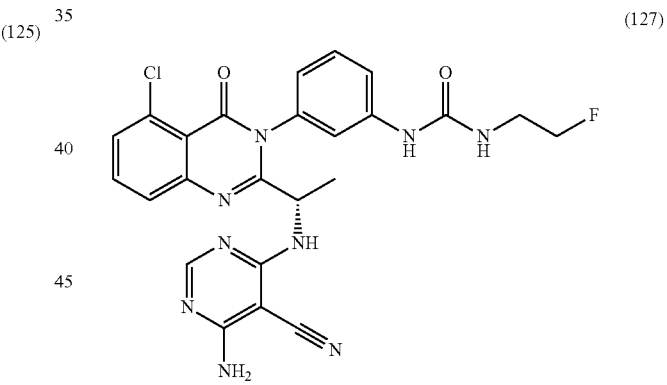

(S)-1-(3-(2-(1-((6-amino-5-cyanopyrimidin-4-yl)amino)ethyl)-5-chloro-4-oxoquinazolin-3(4H)-yl)phenyl)-3-cyclopropylurea (Compound 125). $^1$H NMR (400 MHz, DMSO-d$_6$) δ 8.57 (s, 0.5H), 8.53 (s, 0.5H), 8.10 (s, 0.5H), 7.99 (s, 0.5H), 7.93 (d, J=6.5 Hz, 0.5H), 7.86-7.76 (m, 2H), 7.70-7.57 (m, 2.5H), 7.56-7.47 (br, 2H), 7.46-7.38 (m, 1.5H), 7.34 (t, J=8.0 Hz, 0.5H), 7.06 (m, 1H), 6.55 (d, J=10.2 Hz, 1H), 4.87 (m, 0.5H), 4.74 (m, 0.5H), 2.58 (m, 1H), 1.43 (d, J=6.8 Hz, 1.5H), 1.41 (d, J=6.8 Hz, 1.5H), 0.67 (m, 2H), 0.45 (m, 2H). ES/MS 516.2 (M+H$^+$).

(S)-1-(3-(2-(1-((6-amino-5-cyanopyrimidin-4-yl)amino)ethyl)-5-chloro-4-oxoquinazolin-3(4H)-yl)phenyl)-3-(2-fluoroethyl)urea (Compound 127). $^1$H NMR (400 MHz, DMSO-d$_6$) δ 8.82 (d, J=16.3 Hz, 1H), 8.09 (s, 0.5H), 8.00 (s, 0.5H), 7.97 (d, J=1.2 Hz, 0.5H), 7.84-7.76 (m, 2H), 7.66 (dd, J=8.6, 1.2 Hz, 1H), 7.63-7.58 (m, 1H), 7.53 (br, 1.5H), 7.45-7.41 (m, 1H), 7.40 (ddd, J=8.2, 2.0, 1.2 Hz, 0.5H), 7.35 (m, 0.5H), 7.07 (m, 1H), 6.53 (dt, J=12.0, 5.8 Hz, 1H), 5.25 (br, 1H), 4.88 (m, 0.5H), 4.76 (m, 0.5H), 4.56 (td, J=5.1, 1.0 Hz, 1H), 4.44 (td, J=5.0, 1.0 Hz, 1H), 3.43 (m, 2H), 1.43 (d, J=6.8 Hz, 1.5H), 1.41 (d, J=6.8 Hz, 1.5H). ES/MS 522.1 (M+H$^+$).

(128)

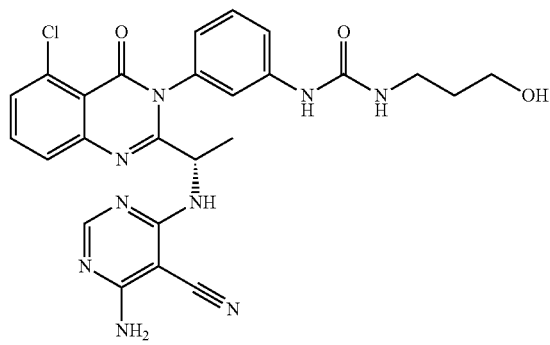

(S)-1-(3-(2-(1-(((6-amino-5-cyanopyrimidin-4-yl)amino)ethyl)-5-chloro-4-oxoquinazolin-3(4H)-yl)phenyl)-3-(3-hydroxypropyl)urea (Compound 128). ¹H NMR (400 MHz, DMSO-d₆) δ 8.73 (d, J=12.4 Hz, 1H), 8.14-8.07 (m, 0.5H), 8.02-7.96 (m, 1), 7.85-7.81 (m, 1H), 7.81-7.77 (m, 1H), 7.65 (ddd, J=9.8, 8.2, 1.2 Hz, 1H), 7.63-7.58 (m, 1.5H), 7.55 (br, 2H), 7.45-7.38 (m, 1H), 7.38-7.29 (m, 1H), 7.05 (m, 1H), 6.29 (m, 1H), 4.87 (m, 0.5H), 4.75 (m, 0.5H), 3.49 (td, J=6.3, 1.1 Hz, 2H), 3.18 (bs, 2H), 1.63 (m, 2H), 1.43 (d, J=6.8 Hz, 1.5H), 1.42 (d, J=6.8 Hz, 1.5H). ES/MS 534.2 (M+H⁺).

(130)

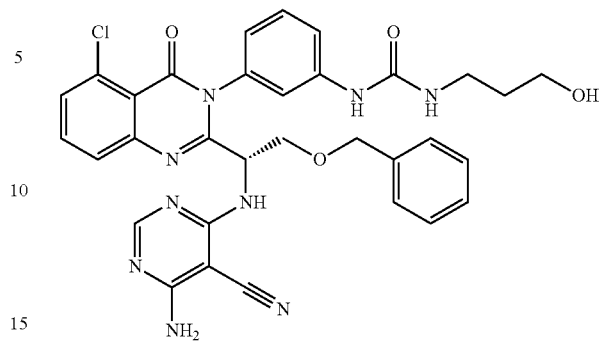

(R)-1-(3-(2-(1-((6-amino-5-cyanopyrimidin-4-yl)amino)-2-(benzyloxy)ethyl)-5-chloro-4-oxoquinazolin-3(4H)-yl)phenyl)-3-(3-hydroxypropyl)urea (Compound 130). ¹H NMR (400 MHz, DMSO-d₆) δ 8.74 (s, 0.5H), 8.67 (s, 0.5H), 8.04 (s, 0.5H), 7.93 (s, 0.5H), 7.87-7.77 (m, 1.5H), 7.74 (d, J=6.8 Hz, 0.5H), 7.70-7.56 (m, 3H), 7.51-7.33 (m, 4H), 7.33-7.25 (m, 3H), 7.21 (m, 2H), 6.99 (ddd, J=7.7, 2.0, 1.1 Hz, 0.5H), 6.91 (dt, J=7.4, 1.7 Hz, 0.5H), 6.27 (m, 1H), 5.18 (m, 0.5H), 5.04 (m, 0.5H), 4.85 (br, 1H), 4.38 (m, 2H), 3.97 (dd, J=10.1, 5.6 Hz, 0.5H), 3.86 (m, 1H), 3.78 (m, 0.5H), 3.49 (m, 2H), 3.19 (m, 2H), 1.74-1.52 (m, 2H). ES/MS 640.2 (M+H⁺).

(129)

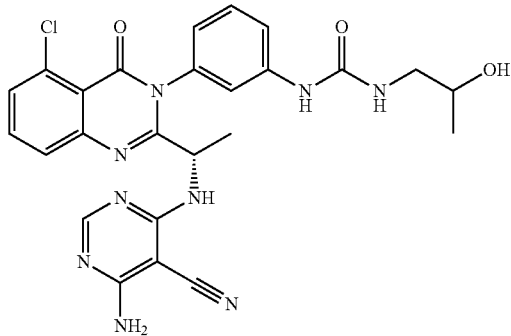

1-(3-(2-((S)-1-((6-amino-5-cyanopyrimidin-4-yl)amino)ethyl)-5-chloro-4-oxoquinazolin-3(4H)-yl)phenyl)-3-(2-hydroxypropyl)urea (Compound 129). ¹H NMR (400 MHz, DMSO-d₆) δ 8.81 (d, J=15.7 Hz, 1H), 8.10 (s, 0.5H), 7.99 (s, 0.5H), 7.95 (d, J=6.4 Hz, 0.5H), 7.80 (m, 2H), 7.63 (m, 2.5H), 7.51 (hr, 2H), 7.42 (m, 1H), 7.40-7.30 (m, 1H), 7.05 (m, 1H), 6.31 (m, 1H), 4.87 (m, 0.5H), 4.74 (m, 0.5H), 3.71 (m, 1H), 3.16 (m, 1H), 2.98 (m, 1H), 1.43 (d, J=6.8 Hz, 1.5H), 1.42 (d, J=6.8 Hz, 1.5H), 1.08 (m, 3H). ES/MS 534.2 (M+H⁺).

(131)

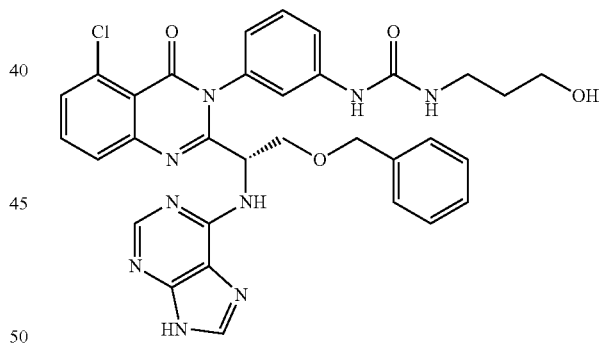

(R)-1-(3-(2-(1-((9H-purin-6-yl)amino)-2-(benzyloxy)ethyl)-5-chloro-4-oxoquinazolin-3(4H)-yl)phenyl)-3-(3-hydroxypropyl)urea (Compound 131). ¹H NMR (400 MHz, DMSO-d₆) δ 8.79 (s, 0.5H), 8.66 (s, 0.5H), 8.36 (m, 2H), 7.88 (bs, 0.5H), 7.81 (dd, J=8.0, 2.9 Hz, 0.5H), 7.79 (dd, J=8.0, 2.8 Hz, 0.5H), 7.74 (bs, 0.5H), 7.68-7.58 (m, 2H), 7.40 (m, 2H), 7.33-7.22 (m, 3H), 7.19 (m, 2H), 7.08 (d, J=7.7 Hz, 0.5H), 6.98 (d, J=7.5 Hz, 0.5H), 6.33 (m, 0.5H), 6.25 (m, 0.5H), 5.25 (m, 1H), 4.52-4.34 (m, 2H), 4.03 (m, 1H), 3.88 (m, 1H), 3.50 (t, J=6.2 Hz, 2H), 3.18 (m, 2H), 1.62 (m, 2H). ES/MS 640.2 (M+H⁺).

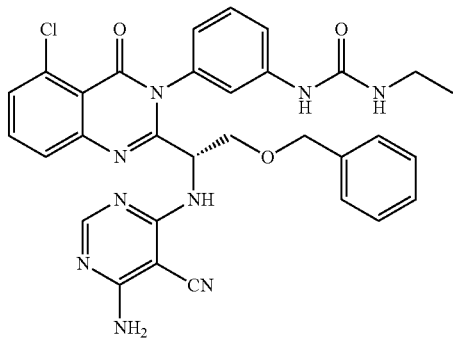

(132)

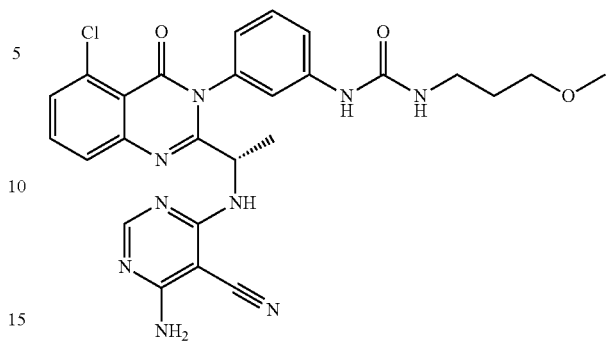

(134)

(R)-1-(3-(2-(1-((6-amino-5-cyanopyrimidin-4-yl)amino)-2-(benzyloxy)ethyl)-5-chloro-4-oxoquinazolin-3(4H)-yl)phenyl)-3-ethylurea (Compound 132). $^1$H NMR (400 MHz, DMSO-d$_6$) δ 8.69 (s, 0.5H), 8.63 (s, 0.5H), 8.04 (s, 0.5H), 7.98 (d, J=6.8 Hz, 0.5H), 7.93 (s, 0.5H), 7.81-7.75 (m, 21), 7.67-7.55 (m, 2H), 7.58 (br, 1H), 7.52 (br, 1H), 7.38-7.32 (m, 1.5H), 7.31-7.21 (m, 3H), 7.17 (m, 2H), 6.96 (m, 0.5H), 6.90 (m, 0.5H), 6.21 (m, 1H), 5.15 (m, 0.5H), 5.02 (m, 0.5H), 4.51-4.24 (m, 2H), 4.00-3.70 (m, 2H), 3.18-3.05 (m, 2H), 1.05 (td, J=7.2, 1.1 Hz, 3H). ES/MS 610.2 (M+H$^+$).

(S)-1-(3-(2-(1-((6-amino-5-cyanopyrimidin-4-yl)amino)ethyl)-5-chloro-4-oxoquinazolin-3(4H)-yl)phenyl)-3-(3-methoxypropyl)urea (Compound 134). $^1$H NMR (400 MHz, DMSO-d$_6$) δ 8.73 (s, 0.5H), 8.69 (s, 0.5H), 8.10 (s, 0.5H), 7.99 (s, 0.5H), 7.92 (d, J=6.4 Hz, 0.5H), 7.84 (m, 0.5H), 7.83-7.76 (m, 1.5H), 7.68-7.62 (m, 1H), 7.62-7.57 (m, 1H), 7.47 (br, 2H), 7.41 (m, 1.5H), 7.37-7.30 (m, 1H), 7.05 (m, 1H), 6.29 (m, 1H), 4.87 (m, 0.5H), 4.74 (m, 0.5H), 3.40 (td, J=6.3, 1.9 Hz, 2H), 3.27 (s, 1.5H), 3.27 (s, 1.5H), 3.18 (m, 2H), 1.70 (pd, J=6.2, 1.6 Hz, 2H), 1.43 (d, J=6.8 Hz, 1.5H), 1.42 (d, J=6.8 Hz, 1.5H).

ES/MS 548.2 (M+H$^+$).

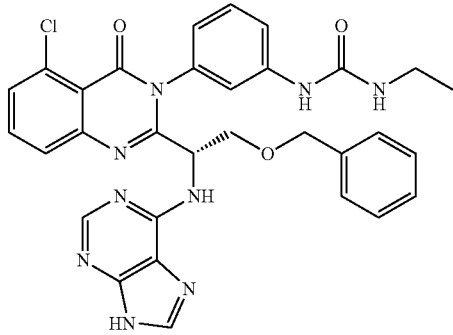

(133)

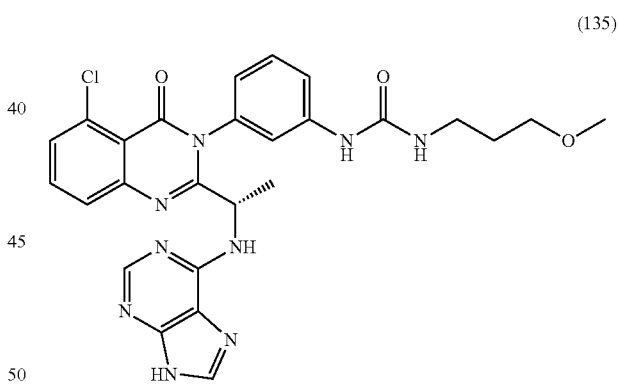

(135)

(R)-1-(3-(2-(1-((9H-purin-6-yl)amino)-2-(benzyloxy)ethyl)-5-chloro-4-oxoquinazolin-3(4H)-yl)phenyl)-3-ethylurea (Compound 133). $^1$H NMR (400 MHz, DMSO-d$_6$) δ 8.74 (s, 0.5H), 8.62 (s, 0.5H), 8.37 (m, 2H), 7.89 (s, 0.5H), 7.81 (dd, J=8.0, 2.3 Hz, 0.5H), 7.79 (dd, J=8.0, 2.3 Hz, 0.5H), 7.74 (br, 0.5H), 7.63 (m, 2H), 7.39 (m, 2H), 7.33-7.22 (m, 3H), 7.19 (dt, J=8.2, 3.4 Hz, 2H), 7.08 (d, J=7.7 Hz, 0.5H), 6.99 (d, J=7.6 Hz, 0.5H), 6.29 (m, 0.5H), 6.19 (m, 0.5H), 5.26 (m, 1H), 4.49-4.36 (m, 2H), 4.04 (m, 1H), 3.88 (m 1H), 3.14 (m, 2H), 1.09 (m, 3H). ES/MS 610.2 (M+H$^+$).

(S)-1-(3-(2-(1-((9H-purin-6-yl)amino)ethyl)-5-chloro-4-oxoquinazolin-3(4H)-yl)phenyl)-3-(3-methoxypropyl)urea (Compound 135). $^1$H NMR (400 MHz, DMSO-d$_6$) δ 8.98 (br, 1H), 8.81 (s, 0.5H), 8.70 (s, 0.5H), 8.52-8.44 (m, 2H), 7.95 (s, 0.5H), 7.78 (t, J=8.0 Hz, 1H), 7.69 (s, 0.5H), 7.64 (d, J=8.2 Hz, 1H), 7.60 (d, J=7.9 Hz, 1H), 7.44 (t, J=8.4 Hz, 1H), 7.32 (d, J=8.4 Hz, 1H), 7.13 (t, J=8.3 Hz, 1H), 6.37 (s, 0.5H), 6.29 (s, 0.5H), 4.96 (m, 1H), 3.40 (td, J=6.3, 3.6 Hz, 2H), 3.28 (s, 1.5H), 3.27 (s, 1.5H), 3.17 (m, 2H), 1.70 (m, 2H), 1.55 (d, J=6.8 Hz, 3H). ES/MS 548.2 (M+H$^+$).

139

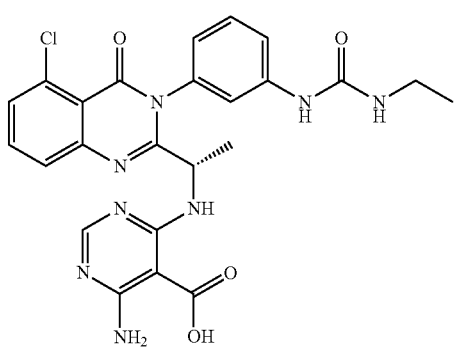
(136)

(S)-4-amino-6-((1-(5-chloro-3-(3-(3-ethylureido)phenyl)-4-oxo-3,4-dihydroquinazolin-2-yl)ethyl)amino)pyrimidine-5-carboxylic acid (Compound 136). $^1$H NMR (400 MHz, DMSO-$d_6$) δ 10.15 (br, 0.5H), 9.94 (br, 0.5H), 8.78 (d, =11.2 Hz, 1H), 8.22 (br, 1H), 8.21 (d, J=6.7 Hz, 1H), 7.83 (m, 1H), 7.78 (m, 0.5H), 7.69 (m, 0.5H), 7.66 (d, J=1.2 Hz, 0.5H), 7.65-7.60 (m, 1.5H), 7.52-7.41 (m, 2H), 7.13-7.09 (m, 0.5H), 7.07 (ddd, J=7.4, 2.1, 1.3 Hz, 0.5H), 6.30 (m, 1H), 4.97 (m, 0.5H), 4.90 (m, 0.5H), 3.15 (m, 2H), 1.43 (d, J=6.6 Hz, 1.5H), 1.42 (d, J=6.6 Hz, 1.5H), 1.09 (td, J=7.2, 2.7 Hz, 3H). ES/MS 523.1 (M+H$^+$).

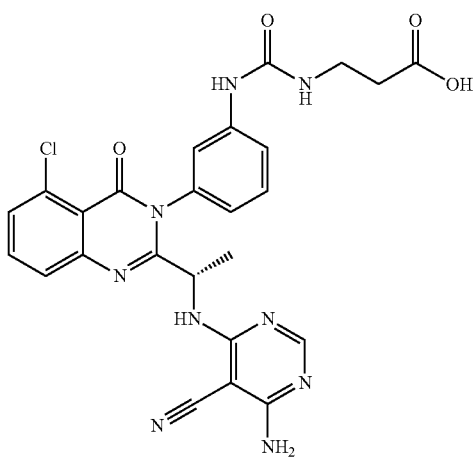
(137)

(S)-3-(3-(3-(2-(1-((6-amino-5-cyanopyrimidin-4-yl)amino)ethyl)-5-chloro-4-oxoquinazolin-3(4H)-yl)phenyl)ureido)propanoic acid (Compound 137). $^1$H NMR (400 MHz, DMSO-$d_6$) δ 8.83 (d, J=14.6 Hz, 1H), 8.11 (s, 0.5H), 7.99 (s, 0.5H), 7.98 (d, J=6.4 Hz, 0.5H), 7.84-7.77 (m, 2H), 7.65 (ddd, J=9.6, 8.2, 1.2 Hz, 1H), 7.63-7.58 (m, 2H), 7.53 (br, 2H), 7.45-7.37 (m, 1H), 7.37-7.31 (m, 1H), 7.09-7.02 (m, 1H), 6.37 (m, 1H), 4.87 (m, 0.5H), 4.75 (m, 0.5H), 3.33 (m, 2H), 2.46 (m, 2H), 1.42 (d, J=6.8 Hz, 1.5H), 1.41 (d, J=6.8 Hz, 1.5H). ES/MS 548.1 (M+H$^+$).

140

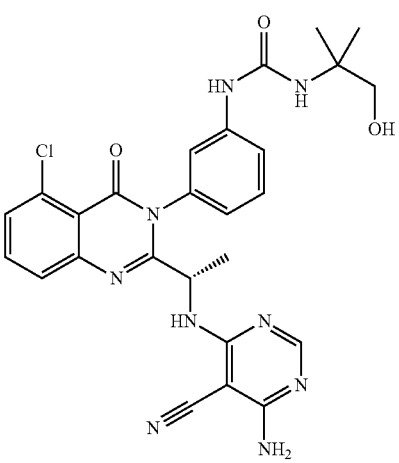
(138)

(S)-1-(3-(2-(1-(((6-amino-5-cyanopyrimidin-4-yl)amino)ethyl)-5-chloro-4-oxoquinazolin-3(4H)-yl)phenyl)-3-(1-hydroxy-2-methylpropan-2-yl)urea (Compound 138). $^1$H NMR (400 MHz, DMSO-$d_6$) δ 8.96 (s, 0.5H), 8.88 (s, 0.5H), 8.43 (br, 0.5H), 8.26 (s, 0.5H), 8.19 (d, J=6.6, 0.5H), 8.09 (s, 0.5H), 7.91 (t, J=2.1 Hz, 1H), 7.85 (br, 2H), 7.81 (m, 1H), 7.69-7.58 (m, 2H), 7.40 (t, J=8.0 Hz, 0.5H), 7.35-7.26 (m, 1.5H), 7.05 (ddd, J=7.7, 2.0, 1.0 Hz, 0.5H), 7.00 (dt, J=7.1, 1.9 Hz, 0.5H), 6.17 (bs, 1H), 4.92 (m, 0.5H), 4.83 (bs, 1H), 4.79 (m, 0.5H), 3.41 (m, 2H), 1.44 (d, J=6.7 Hz, 1.5H), 1.43 (d, J=6.7 Hz, 1.5H), 1.26 (s, 6H). ES/MS 548.2 (M+H$^+$).

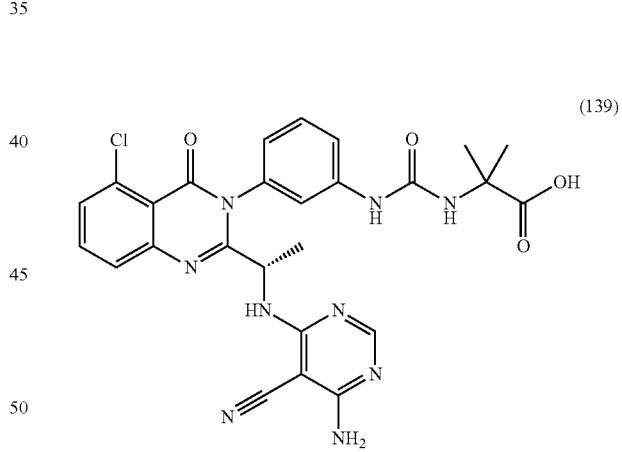
(139)

(S)-2-(3-(3-(2-(1-((6-amino-5-cyanopyrimidin-4-yl)amino)ethyl)-5-chloro-4-oxoquinazolin-3(4H)-yl)phenyl)ureido)-2-methylpropanoic acid (Compound 139). $^1$H NMR (400 MHz, DMSO-$d_6$) δ 9.11 (s, 0.5H), 8.95 (s, 0.5H), 8.46 (br, 0.5H), 8.29 (s, 0.5H), 8.28 (br, 0.5H), 8.10 (s, 0.5H), 7.89 (bs, 2H), 7.81 (m, 2H), 7.73-7.51 (m, 3H), 7.45-7.37 (m, 1H), 7.33 (d, J=4.7 Hz, 1H), 7.08 (m, 0.5H), 7.03 (m, 0.5H), 6.78 (m, 1H), 4.92 (m, 0.5H), 4.79 (m, 0.5H), 1.46 (m, 9H). ES/MS 562.2 (M+H$^+$).

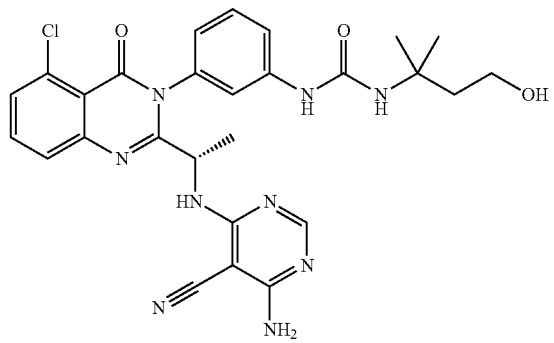

(140)

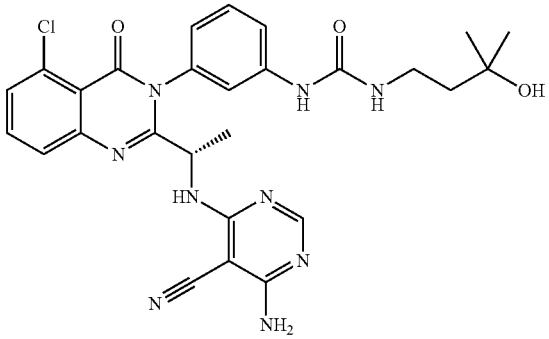

(142)

(S)-1-(3-(2-(1-(((6-amino-5-cyanopyrimidin-4-yl)amino)ethyl)-5-chloro-4-oxoquinazolin-3(4H)-yl)phenyl)-3-(4-hydroxy-2-methylbutan-2-yl)urea (Compound 140). $^1$H NMR (400 MHz, DMSO-d$_6$) δ 9.07 (s, 0.5H), 8.89 (s, 0.5H), 8.68 (br, 0.5H), 8.43 (br, 0.5H), 8.38 (s, 0.5H), 8.14 (s, 0.5H), 8.04 (br, 2H), 7.89-7.82 (m, 1H), 7.82-7.77 (m, 1H), 7.72-7.57 (m, 2H), 7.46-7.33 (m, 1H), 7.33-7.29 (m, 1H), 7.04 (ddd, J=7.5, 2.0, 1.3 Hz, 0.5H), 6.99 (m, 0.5H), 6.37 (bs, 1H), 5.00-4.76 (m, 1H), 3.54 (m, 2H), 1.85 (m, 2H), 1.45 (d, J=6.6 Hz, 1.5H), 1.44 (d, J=6.6 Hz, 1.5H), 1.34-1.27 (m, 6H). ES/MS 562.2 (M+H$^+$).

(S)-1-(3-(2-(1-(((6-amino-5-cyanopyrimidin-4-yl)amino)ethyl)-5-chloro-4-oxoquinazolin-3(4H)-yl)phenyl)-3-(3-hydroxy-3-methylbutyl)urea (Compound 142). $^1$H NMR (400 MHz, DMSO-d$_6$) δ 9.01 (s, 0.5H), 8.93 (s, 0.5H), 8.38 (s, 0.5H), 8.27 (s, 0.5H), 8.15 (d, J=6.6 Hz, 0.5H), 8.07 (s, 0.5H), 7.93-7.72 (m, 3H), 7.69-7.58 (m, 2H), 7.48-7.29 (m, 2H), 7.05 (ddd, J=7.4, 2.0, 1.3 Hz, 0.5H), 7.02 (ddd, J=7.6, 2.1, 1.3 Hz, 0.5H), 6.34 (br, 1H), 4.91 (m, 0.5H), 4.79 (m, 0.5H), 4.50 (br, 2H), 3.21 (td, J=7.2, 2.4 Hz, 2H), 1.58 (m, 2H), 1.44 (d, J=6.8 Hz, 1.5H), 1.43 (d, J=6.8 Hz, 1.5H), 1.15 (s, 6H). ES/MS 562.2 (M+H$^+$).

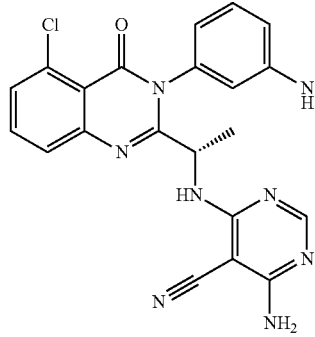

(141)

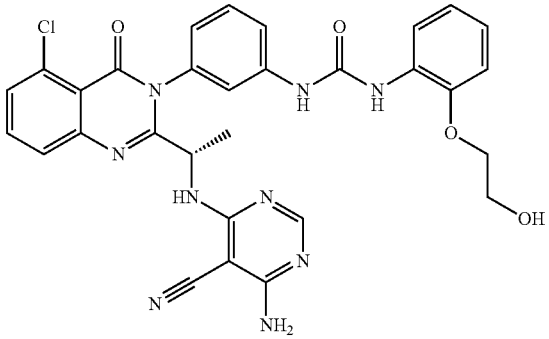

(143)

(S)-1-(3-(2-(1-(((6-amino-5-cyanopyrimidin-4-yl)amino)ethyl)-5-chloro-4-oxoquinazolin-3(4H)-yl)phenyl)-3-(3-hydroxy-2,2-dimethylpropyl)urea (Compound 141). $^1$H NMR (400 MHz, DMSO-d$_6$) δ 9.14 (s, 0.5H), 9.01 (s, 0.5H), 8.50 (br, 0.5H), 8.30 (s, 0.5H), 8.23 (d, J=6.6 Hz, 0.5H), 8.09 (s, 0.5H), 7.90 (br, 2H), 7.83-7.77 (m, 1H), 7.66 (ddd, J=10.5, 8.2, 1.2 Hz, 1H), 7.63-7.58 (m, 2H), 7.42 (m, 1H), 7.36 (m, 1H), 7.10-7.04 (m, 0.5H), 7.02 (dt, J=7.5, 1.8 Hz, 0.5H), 6.49 (m, 1H), 4.91 (m, 0.5H), 4.80 (m, 0.5H), 4.70 (br, 1H), 3.16 (d, J=1.8 Hz, 2H), 3.00 (m, 2H), 1.45 (d, J=6.8 Hz, 1.5H), 1.44 (d, J=6.8 Hz, 1.5H), 0.83 (s, 6H). ES/MS 562.2 (M+H$^+$).

(S)-1-(3-(2-(1-(((6-amino-5-cyanopyrimidin-4-yl)amino)ethyl)-5-chloro-4-oxoquinazolin-3(4H)-yl)phenyl)-3-(2-(2-hydroxyethoxy)phenyl)urea (Compound 143). $^1$H NMR (400 MHz, DMSO-d$_6$) δ 10.44 (s, 0.5H), 10.24 (s, 0.5H), 8.79 (d, J=6.3 Hz, 0.5H), 8.69 (s, 0.5H), 8.62 (s, 0.5H), 8.48 (s, 0.5H), 8.45 (d, J=7.1 Hz, 0.5H), 8.20 (dd, J=12.0, 2.0 Hz, 0.5H), 8.18 (dd, J=12.4, 2.0 Hz, 0.5H), 8.15 (s, 0.5H), 8.13-7.95 (br, 2H), 7.87 (t, J=2.0 Hz, 0.5H), 7.82 (m, 1H), 7.74 (t, J=2.0 Hz, 0.5H), 7.69 (dd, J=8.2, 1.2 Hz, 0.5H), 7.67-7.65 (m, 0.5H), 7.66 (dd, J=8.2, 1.2 Hz, 0.5H), 7.64-7.59 (m, 1H), 7.50 (m, 0.5H), 7.49 (t, J=8.0 Hz, 0.5H), 7.40 (t, J=8.0 Hz, 0.5H), 7.15 (ddd, J=7.8, 2.0, 1.0 Hz, 0.5H), 7.09 (ddd, J=7.8, 2.1, 1.1 Hz, 0.5H), 7.04-6.96 (m, 1H), 6.96-6.87 (m, 2H), 4.98 (m, 0.5H), 4.84 (m, 0.5H), 4.22 (br, 1H), 4.07 (t, J=4.2 Hz, 1H), 4.04 (t, J=4.2 Hz, 1H), 3.83 (t, J=4.4 Hz, 2H), 1.48 (d, J=6.7 Hz, 1.5H), 1.47 (d, J=6.7 Hz, 1.5H). ES/MS 612.2 (M+H$^+$).

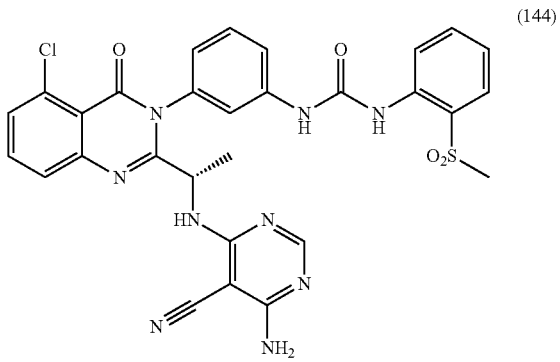 [SMILES: C[C@H](Nc1ncnc(N)c1C#N)c1nc2cccc(Cl)c2c(=O)n1-c1cccc(NC(=O)Nc2ccccc2S(C)(=O)=O)c1]

(144)

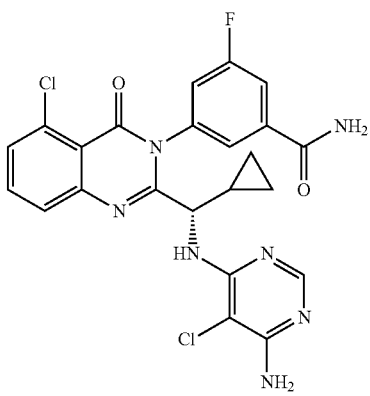

(160)

(S)-1-(3-(2-(1-((6-amino-5-cyanopyrimidin-4-yl)amino)ethyl)-5-chloro-4-oxoquinazolin-3(4H)-yl)phenyl)-3-(2-(methylsulfonyl)phenyl)urea (Compound 144). $^1$H NMR (400 MHz, DMSO-d$_6$) δ 10.15 (s, 0.5H), 10.10 (s, 0.5H), 8.71 (s, 0.5H), 8.64 (s, 0.5H), 8.17 (dd, J=13.4, 1.1 Hz, 0.5H), 8.14 (dd, J=13.4, 1.1 Hz, 0.5H), 8.04 (s, 0.5H), 8.01 (s, 0.5H), 8.00-7.95 (m, 0.5H), 7.95-7.92 (m, 0.5H), 7.90 (t, J=1.8 Hz, 0.5H), 7.88 (t, J=1.8 Hz, 0.5H), 7.84-7.78 (m, 1H), 7.75-7.70 (m, 1H), 7.70-7.65 (m, 1H), 7.62 (dd, J=3.0, 1.2 Hz, 0.5H), 7.60 (dd, J=3.0, 1.2 Hz, 0.5H), 7.55-7.39 (m, 4H), 7.33 (ddt, J=8.2, 7.4, 1.0 Hz, 1H), 7.18 (m, 1H), 4.88 (m, 1H), 3.32 (s, 1.5H), 3.29 (s, 1.5H), 1.45 (d, J=6.7, 1.5H), 1.44 (d, J=6.7, 1.5H). ES/MS 630.2 (M+H$^+$).

(S)-3-(2-(((6-amino-5-chloropyrimidin-4-yl)amino)(cyclopropyl)methyl)-5-chloro-4-oxoquinazolin-3(4H)-yl)-5-fluorobenzamide (Compound 160). $^1$H NMR (400 MHz, DMSO-d6) δ 8.03 (d, J=45.4 Hz, 1H), 7.85 (s, 1H), 7.83 (s, 1H), 7.76-7.70 (m, 3H), 7.70-7.66 (m, 1H), 7.63 (dd, J=7.8, 1.2 Hz, 1H), 7.51 (s, 1H), 7.36 (dt, J=9.0, 2.2 Hz, 1H), 7.31 (s, 1H), 7.18 (d, J=7.8 Hz, 2H), 4.50 (dt, J=14.9, 8.1 Hz, 1H), 1.53 (dddt, J=14.0, 8.0, 5.5, 3.0 Hz, 1H), 0.62-0.49 (m, 1H), 0.44 (dtt, J=8.7, 5.5, 2.8 Hz, 1H), 0.39-0.28 (m, 1H), 0.18 (ddt, J=20.5, 9.7, 5.0 Hz, 1H).

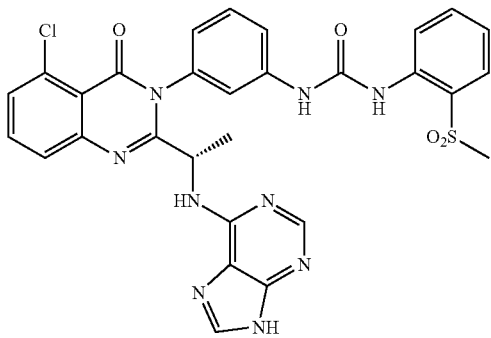

(145)

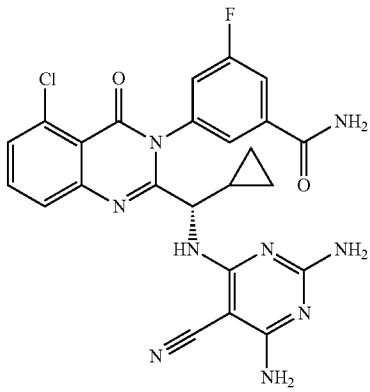

(161)

(S)-1-(3-(2-(1-((9H-purin-6-yl)amino)ethyl)-5-chloro-4-oxoquinazolin-3(4H)-yl)phenyl)-3-(2-(methylsulfonyl)phenyl)urea (Compound 145). $^1$H NMR (400 MHz, DMSO-d$_6$) δ 10.18 (s, 0.5H), 10.02 (s, 0.5H), 9.02 (br, 0.5H), 8.84 (br, 0.5H), 8.73 (s, 0.5H), 8.60 (s, 0.5H), 8.46 (m, 2H), 8.17 (dd, J=8.4, 1.1 Hz, 0.5H), 8.05 (d, J=8.5 Hz, 0.5H), 7.96 (s, 0.5H), 7.90 (dd, J=7.6, 1.2 Hz, 0.5H), 7.90 (dd, J=8.0, 1.2 Hz, 0.5H), 7.86-7.76 (m, 1.5H), 7.72 (m, 1H), 7.70-7.58 (m, 2H), 7.53 (t, J=7.7 Hz, 1H), 7.42 (d, J=8.4 Hz, 1H), 7.36 (dd, J=2.5, 1.2 Hz, 0.5H), 7.34 (m, 1H), 7.32 (dd, J=2.5, 1.2 Hz, 0.5H), 7.26 (m, 1H), 5.03 (m, 1H), 3.33 (s, 1.5H), 3.31 (s, 1.5H), 1.58 (d, J=6.8 Hz, 1.5-1), 1.57 (d, J=6.8 Hz, 1.5H). ES/MS 630.1 (M+H$^+$).

(S)-3-(5-chloro-2-(cyclopropyl((2,6-diamino-5-cyanopyrimidin-4-yl)amino)methyl)-4-oxoquinazolin-3(4H)-yl)-5-fluorobenzamide (Compound 161). $^1$H NMR (400 MHz, DMSO-d$_6$) δ 8.27 (s, 1H), 8.11-8.00 (m, 1H), 7.97 (dt, J=9.4, 2.0 Hz, 1H), 7.87-7.73 (m, 3H), 7.71-7.57 (m, 2H), 6.74-6.48 (m, 3H), 6.21 (d, J=8.5 Hz, 1H), 4.56 (dt, J=12.0, 7.8 Hz, 1H), 1.26-1.20 (m, 1H), 0.52-0.35 (m, 2H), 0.28 (dd, J=9.7, 4.8 Hz, 1H), 0.08-0.00 (m, 1H), −0.01-0.07 (m, 1H).

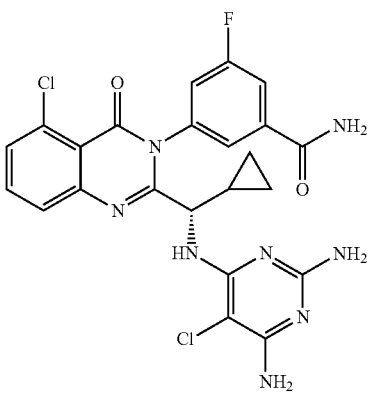

(162)

(S)-3-(5-chloro-2-(cyclopropyl((2,6-diamino-5-chloropyrimidin-4-yl)amino)methyl)-4-oxoquinazolin-3(4H)-yl)-5-fluorobenzamide (Compound 162). 1H NMR (400 MHz, DMSO-$d_6$) δ 8.31 (s, 1H), 8.11 (t, J=1.7 Hz, 1H), 8.00 (ddd, J=9.5, 2.4, 1.4 Hz, 1H), 7.89-7.74 (m, 3H), 7.71-7.53 (m, 2H), 7.00 (s, 2H), 6.53 (s, 2H), 6.14-5.90 (m, 4H), 5.80-5.33 (m, 1H), 4.60-4.45 (m, 1H), 1.41-1.09 (m, 4H), 1.07-0.85 (m, 1H), 0.51-0.21 (m, 3H).

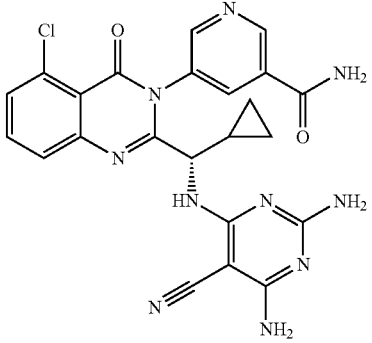

(164)

(S)-5-(5-chloro-2-(cyclopropyl((2,6-diamino-5-cyanopyrimidin-4-yl)amino)methyl)-4-oxoquinazolin-3(4H)-yl)nicotinamide (Compound 164). $^1$H NMR (400 MHz, DMSO-$d_6$) δ 9.07 (d, J=1.9 Hz, 1H), 8.98 (d, J=2.0 Hz, 1H), 8.90 (d, J=2.3 Hz, 1H), 8.57 (d, J=2.3 Hz, 1H), 8.41 (t, J=2.2 Hz, 1H), 8.23 (d, J=17.8 Hz, 2H), 8.13 (s, 1H), 7.89-7.81 (m, 2H), 7.77-7.69 (m, 2H), 7.65 (dq, J=7.9, 1.0 Hz, 1H), 4.41 (dt, J=13.9, 8.2 Hz, 1H), 1.50 (d, J=9.5 Hz, 1H), 0.54 (d, J=12.2 Hz, 1H), 0.44 (ddt, J=14.7, 10.6, 5.3 Hz, 1H), 0.40-0.29 (m, 1H), 0.19-0.02 (m, 1H).

C. Preparation of a compound of formula (II) where $W^2$ is CH, n is 1, $R^1$ is cyano, m is 0, $R^3$ is methyl, $R^4$ is 6-amino-5-cyanopyrimidin-4-yl, $R^6$ is ethyl, $R^7$ is H, and $R^5$ is hydrogen (Compound 69)

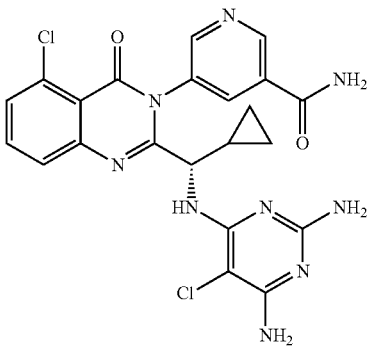

(163)

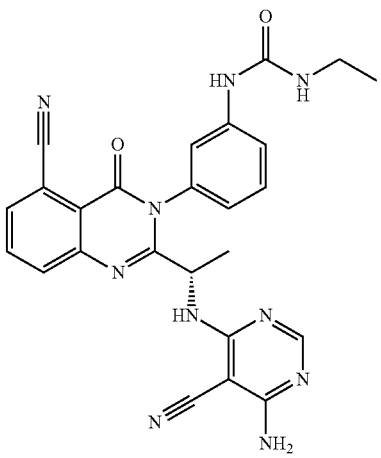

(69)

(S)-5-(5-chloro-2-(cyclopropyl((2,6-diamino-5-chloropyrimidin-4-yl)amino)methyl)-4-oxoquinazolin-3(4H)-yl)nicotinamide (Compound 163). $^1$H NMR (400 MHz, DMSO-$d_6$) δ 10.12 (d, J=8.0 Hz, 1H), 9.31-9.03 (m, 5H), 8.96-8.81 (m, 2H), 8.48-8.34 (m, 1H), 8.18 (t, J=2.2 Hz, 1H), 7.92-7.73 (m, 3H), 7.70 (ddd, J=8.2, 2.4, 1.2 Hz, 1H), 7.63 (dq, J=7.6, 1.6 Hz, 1H), 4.08 (dd, J=9.0, 7.9 Hz, 1H), 1.60-1.41 (m, 1H), 0.59-0.41 (m, 3H), 0.41-0.20 (m, 1H).

(S)-1-(3-(2-(1-((6-amino-5-cyanopyrimidin-4-yl)amino)ethyl)-5-bromo-4-oxoquinazolin-3(4H)-yl)phenyl)-3-ethylurea (42 mg, 0.091 mmol), zinc cyanide (13 mg, 0.110 mmol), and tetrakis(triphenylphosphine)palladium(0) (10.5 mg, 0.009 mmol) were combined in DMF. The resulting solution was heated to 120° C. for 20 hours. Upon cooling, the DMF solution was filtered and purified by HPLC eluting with 5%-95% water/acetonitrile (0.1% v/v trifluoroacetic acid). The appropriate fractions were pooled and lyophilized to afford (S)-1-(3-(2-(1-((6-amino-5-cyanopyrimidin-4-yl)amino)ethyl)-5-cyano-4-oxoquinazolin-3(4H)-yl)phenyl)-3-ethylurea 2,2,2-trifluoroacetic acid salt (Compound 69).

$^1$H NMR (400 MHz, DMSO) δ 8.67 (s, 0.5H), 8.64 (s, 0.5H), 8.08-7.61 (m, 6H), 7.43-7.27 (m, 4H), 7.08-7.01 (m, 1H), 6.25-6.17 (m, 1H), 4.89-4.68 (m, 1H), 3.15-3.07 (m, 2H), 1.42-1.37 (m, 3H), 1.08-1.02 (m, 3H). ES/MS 495.1 (M+H$^+$);

D. Preparation of a compound of formula (III) where $W^2$ is CH, n is 1, $R^1$ is chloro, m is 0, $R^3$ is methyl, $R^4$ is 6-amino-5-cyanopyrimidin-4-yl, $R^6$ is ethyl, and $R^7$ is H, (Compound 70)

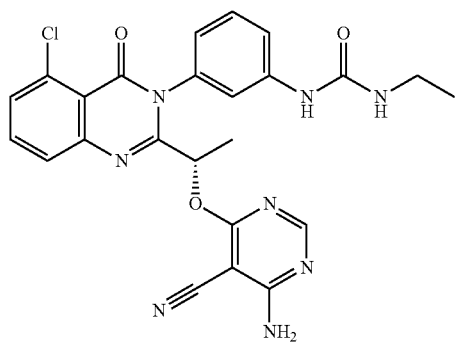

(70)

To (S)-1-(3-(5-chloro-2-(1-hydroxyethyl)-4-oxoquinazolin-3(4H)-yl)phenyl)-3-ethylurea in THF was added NaHMDS (0.65 mL as a 1M solution in THF, 2.5 eq). 4-Amino-6-chloropyrimidine-5-carbonitrile (80 mg, 2 eq) was immediately added as a solution in 1 mL THF. The reaction mixture was heated overnight at 65° C. MeOH (10 mL) and ethyl acetate (10 mL) were added and concentrated to dryness. The residue was brought up in 4 mL DMSO and purified by preparative HPLC. The fractions containing desired material were pooled and concentrated to give (S)-1-(3-(2-(1-((6-amino-5-cyanopyrimidin-4-yl)oxy)ethyl)-5-chloro-4-oxoquinazolin-3(4H)-yl)phenyl)-3-ethylurea (Compound 70). $^1$H NMR (400 MHz, DMSO-d$_6$) δ 8.64 (d, J=13.9 Hz, 1H), 8.20 (s, 0.5H), 8.13 (s, 0.5H), 7.90 (t, J=2.0 Hz, 0.5H), 7.75 (td, J=8.0, 3.9 Hz, 1H), 7.69-7.54 (m, 2.5H), 7.43-7.24 (m, 2H), 7.02 (dddd, J=17.0, 7.6, 2.0, 1.1 Hz, 1H), 6.22 (s, 0.5H), 6.17 (d, J=6.0 Hz, 0.5H), 5.49 (q, J=6.4 Hz, 0.5H), 5.34 (q, J=6.5 Hz, 0.5H), 3.10 (dt, J=7.5, 5.2 Hz, 2H), 1.55 (dd, J=9.3, 6.5 Hz, 3H), 1.05 (td, J=7.2, 3.3 Hz, 3H).

E. Preparation of the below compounds of formula (III) using the procedure described above:

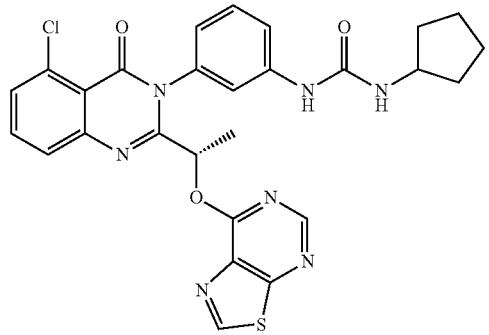

(146)

(S)-1-(3-(5-chloro-4-oxo-2-(1-(thiazolo[5,4-d]pyrimidin-7-yloxy)ethyl)quinazolin-3(4H)-yl)phenyl)-3-cyclopentylurea (Compound 146). $^1$H NMR (400 MHz, CD$_3$OD-d6) δ 9.28 (s, 1H, minor rotamer), 9.26 (s, 1H, major rotamer), 8.56 (s, 1H, major rotamer), 8.54 (s, 1H, major rotamer), 7.78-7.58 (m, 3H), 7.54-7.51 (m, 1H), 7.36 (t, J=8 Hz, 1H), 6.03 (dd, J=13, 6 Hz, 1H, major rotamer), 5.96 (dd, J=13, 6 Hz, 1H, minor rotamer), 4.03 (pentet, J=6 Hz, 1H, minor rotamer), 3.94 (pentet, J=6 Hz, 1H, major isomer), 1.95-1.80 (m, 2H), 1.80 (d, J=6 Hz, 3H, minor rotamer), 1.76 (d, J=6 Hz, 3H, major rotamer), 1.73-1.65 (m, 2H), 1.65-1.55 (m, 2H), 1.50-1.38 (m, 2H). ES/MS 562.0 (M+H$^+$).

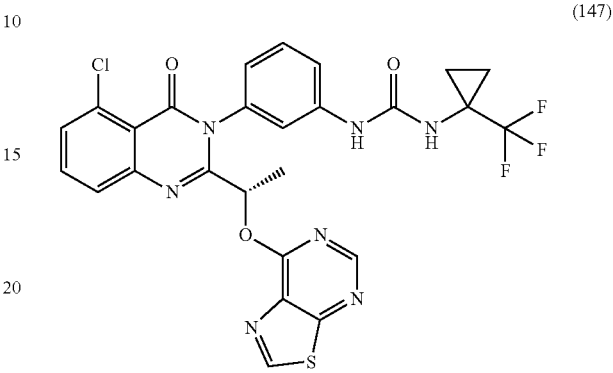

(147)

(S)-1-(3-(5-chloro-4-oxo-2-(1-(thiazolo[5,4-d]pyrimidin-7-yloxy)ethyl)quinazolin-3(4H)-yl)phenyl)-3-(1-(trifluoromethyl)cyclopropyl)urea (Compound 147). $^1$H NMR (400 MHz, MeOH-d4) δ 9.40 (s, 1H, minor rotamer), 9.31 (s, 1H, major rotamer), 8.99 (s, 1H, major rotamer), 8.94 (s, 1H, minor rotamer), 7.70-7.54 (m, 3H), 7.33-7.09 (m, 2H), 6.99-6.91 (m, 1H), 5.31 (q, J=6 Hz, 1H, major rotamer), 5.27 (q, J=6 Hz, 1H, minor rotamer), 1.64 (d, J=6 Hz, 3H, minor rotamer), 1.60 (d, J=6 Hz, 3H, major rotamer), 0.51-0.42 (m, 2H), 0.28-0.19 (m, 2H). ES/MS 602.0 (M+H$^+$).

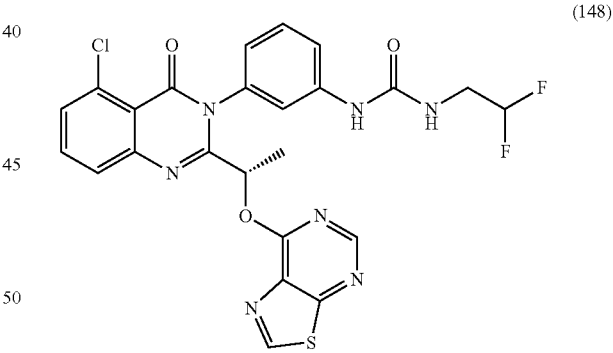

(148)

(S)-1-(3-(5-chloro-4-oxo-2-(1-(thiazolo[5,4-d]pyrimidin-7-yloxy)ethyl)quinazolin-3(4H)-yl)phenyl)-3-(2,2-difluoroethyl)urea (Compound 148). $^1$H NMR (400 MHz, DMSO-d6) δ 9.44 (s, 1H, minor rotamer), 9.39 (s, 1H, major rotamer), 8.86 (s, 1H, major rotamer), 8.62 (s, 1H, minor rotamer), 8.58 (s, 1H, major rotamer), 8.55 (s, 1H, minor rotamer), 7.75-7.53 (m, 5H), 7.33 (t, J=8 Hz, 1H), 7.12 (dt, J=7, 1 Hz, 1H, minor rotamer), 7.17-7.01 (m, 2H), 6.56 (t, J=6 Hz, 1H, minor rotamer), 6.36 (t, J=6 Hz, 1H, major rotamer), 6.03 (tt, J=56, 4 Hz, minor rotamer), 5.99 (tt, J=56, 4 Hz, major rotamer), 5.80 (dd, J=6 Hz, 1H, major rotamer), 5.72 (dd, J=6 Hz, 1H, minor rotamer), 3.52-3.39 (m, 2H), 1.68-1.64 (m, 3H). ES/MS 558.0 (M+H$^+$).

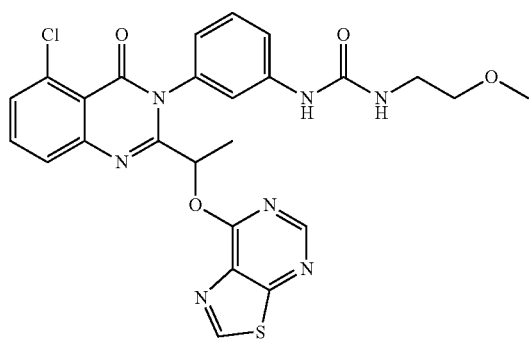

(149)

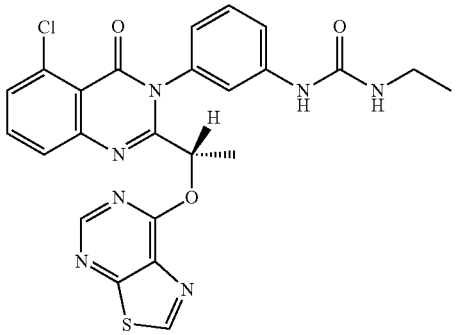

(151)

1-(3-(5-chloro-4-oxo-2-(1-(thiazolo[5,4-d]pyrimidin-7-yloxy)ethyl)quinazolin-3(4H)-yl)phenyl)-3-(2-methoxyethyl)urea (Compound 149). ¹H NMR (400 MHz, DMSO-d6) δ9.44 (S, 1H, minor rotamer), 9.39 (s, 1H, major rotamer), 8.71 (s, 1H, minor rotamer), 8.62 (s, 1H, minor rotamer), 8.60 (s, 1H, major rotamer), 8.42 (s, 1H, major rotamer), 7.74-7.67 (m, 2H), 7.62-7.52 (m, 3H), 7.31 (t, J=8 Hz, 1H), 7.23 (d, J=8 Hz, 1H, minor rotamer), 7.12 (d, J=8 Hz, 1H, major rotamer), 7.13-6.96 (m, 1H), 6.28 (t, J=6 Hz, 1H, minor rotamer), 6.08 (t, J=6 Hz, 1H, minor rotamer), 5.78 (dd, J=6 Hz, 1H, major rotamer), 5.72 (dd, J=7 Hz, 1H, minor rotamer), 3.37-3.32 (m, 2H), 3.24 (s, 3H), 3.23-3.15 (m, 2H), 1.66 (app t, J=6 Hz, 3H). ES/MS 552.0 (M+H⁺).

(S)-1-(3-(5-chloro-4-oxo-2-(1-(thiazolo[5,4-d]pyrimidin-7-yloxy)ethyl)quinazolin-3(4H)-yl)phenyl)-3-ethylurea (Compound 151). ¹H NMR (400 MHz, DMSO-d6) δ 9.41 (s, 1H, minor rotamer), 9.37, (s, 1H, major rotamer), 8.58 (s, 1H, minor rotamer), 8.57 (s, 1H, major rotamer), 8.40 (s, 1H, minor rotamer), 8.28 (s, 1H, major rotamer), 7.71-6.64 (m, 2H), 7.60-7.49 (m, 2H), 7.32 (m, 1H), 7.12-6.95 (m, 2H), 6.15 (bs, 1H, minor rotamer), 5.95 (bs, 1H, major rotamer), 5.74 (q, J=6 Hz, 1H, major rotamer), 5.68 (q, J=6 Hz, 1H, minor rotamer), 3.05-2.96 (m, 2H), 1.63 (t, J=6 Hz, 3H), 1.01-0.95 (m, 3H). ES/MS 522.0 (M+H⁺).

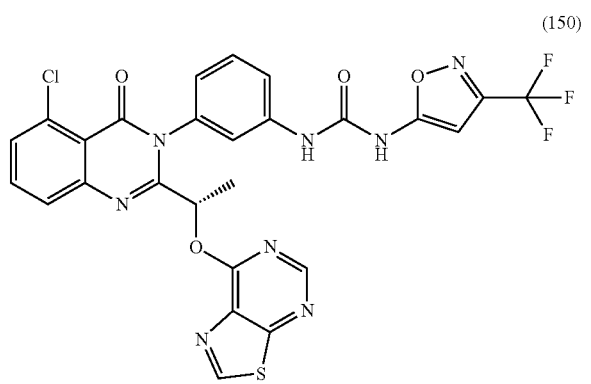 [SMILES: C[C@H](Oc1ncnc2scnc12)c1nc2cccc(Cl)c2c(=O)n1-c1cccc(NC(=O)Nc2cc(C(F)(F)F)no2)c1]

(150)

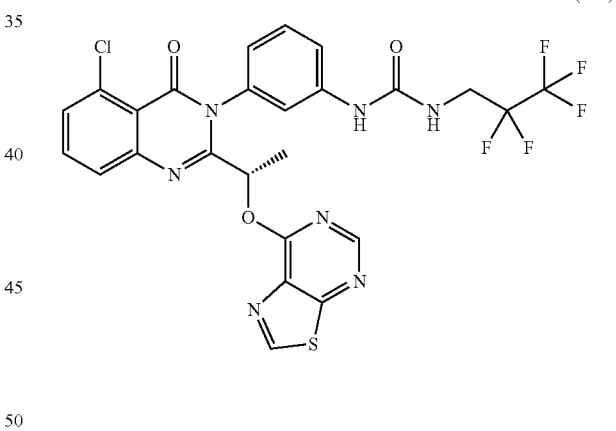

(152)

(S)-1-(3-(5-chloro-4-oxo-2-(1-(thiazolo[5,4-d]pyrimidin-7-yloxy)ethyl)quinazolin-3(4H)-yl)phenyl)-3-(3-(trifluoromethyl)isoxazol-5-yl)urea (Compound 150). ¹H NMR (400 MHz, DMSO-d6) 9.40 (s, 1H, minor rotamer), 9.33 (s, 1H, major rotamer) 9.18 (s, 1H, minor rotamer), 8.77 (s, 1H, minor rotamer), 8.59 (s, 1H, minor rotamer), 8.52 (s, 1H, major), 7.75-7.50 (m, 4H), 7.39-7.34 (m, 1H), 7.24 (t, J=7 Hz, 1H), 7.15-7.05 (m, 1H), 6.43 (s, 1H, minor rotamer), 6.35 (s, 1H, major rotamer), 5.84 (q, J=6 Hz, 1H, major rotamer), 5.72 (q, J=6 Hz, 1H, minor rotamer), 1.68-1.60 (m, 3H). ES/MS 629.0 (M+H⁺).

(S)-1-(3-(5-chloro-4-oxo-2-(1-(thiazolo[5,4-d]pyrimidin-7-yloxy)ethyl)quinazolin-3(4H)-yl)phenyl)-3-(2,2,3,3,3-pentafluoropropyl)urea (Compound 152). ¹H NMR (400 MHz, DMSO-d6) δ 9.41 (s, 1H, minor rotamer), 9.36 (s, 1H, major rotamer), 8.94 (s, 1H, minor rotamer), 8.65 (s, 1H, major rotamer), 8.58 (s, 1H, minor rotamer), 8.54 (s, 1H, major rotamer), 7.71-7.49 (m, 4H), 7.31 (t, J=8 Hz, 1H), 7.14 (ddd, J=8, 2, 1 Hz, 1H), 7.09 (ddd, J=8, 2, 1 Hz, 1H), 7.05-7.01 (m, 1H), 6.77 (t, J=6 Hz, 1H, minor rotamer), 6.58 (t, J=6 Hz, 1H, major rotamer), 5.75 (q, J=6 Hz, 1H, major rotamer), 5.68 (q, J=6 Hz, 1H, minor rotamer), 3.96 (td, J=16, 6 Hz, 2H, minor rotamer), 3.89 (td, J=16, 6 Hz, 2H, major isomer), 1.66-1.61 (m, 3H). ES/MS 626.0 (M+H⁺).

(153)

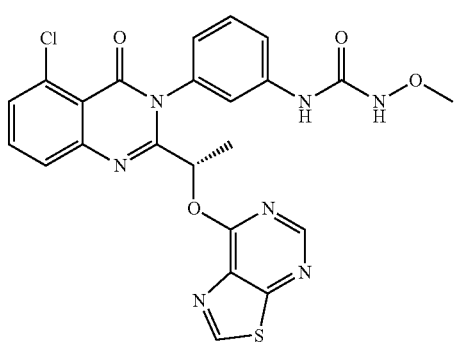

(S)-1-(3-(5-chloro-4-oxo-2-(1-(thiazolo[5,4-d]pyrimidin-7-yloxy)ethyl)quinazolin-3(4H)-yl)phenyl)-3-methoxyurea (Compound 153). $^1$H NMR (400 MHz, DMSO-d6) δ 9.77 (s, 1H, minor rotamer), 9.62 (s, 1H, minor rotamer), 9.52 (s, 1H, minor rotamer), 9.48 (s, 1H, major rotamer), 9.09 (s, 1H, minor rotamer), 8.79 (s, 1H, major rotamer), 8.63 (s, 1H, minor rotamer), 8.62 (s, 1H, major rotamer), 7.98-7.96 (m, 1H, major), 7.78-7.76 (m, 1H, minor rotamer), 7.74 (7.67, m, 1H), 7.61-7.49 (m, 3H), 7.37 (t, J=8 Hz, 1H), 7.17 (d, J=8 Hz, 1H, major rotamer), 7.13-7.09 (m, 1H), 5.75-5.68 (m, 1H, major rotamer), 3.53 (s, 3H), 1.66 (d, J=6 Hz, 3H), 1.68 (d, J=6 Hz, 3H). ES/MS 523.9 (M+H$^+$).

(156)

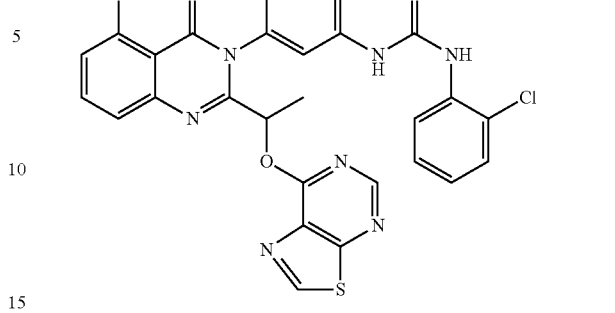

1-(3-(5-chloro-4-oxo-2-(1-(thiazolo[5,4-d]pyrimidin-7-yloxy)ethyl)quinazolin-3(4H)-yl)phenyl)-3-(2-chlorophenyl)urea (Compound 156). $^1$H NMR (400 MHz, DMSO-d6) δ 9.45 (s, 1H, minor rotamer), 9.36 (s, 1H, major rotamer), 9.21 (s, 1H, major rotamer), 8.57 (s, 1H, major rotamer), 8.53 (s, 1H, minor rotamer), 8.38 (s, 1H, minor rotamer), 8.15-8.11 (m, 1H), 8.03 (dd, J=8, 2 Hz, 1H, minor rotamer), 7.03 (t, J=8 Hz, 1H), 7.80-7.65 (m, 2H), 7.63-7.43 (m, 2H), 7.39 (t, J=8 Hz, 1H), 7.33-7.25 (m, 1H), 7.20-7.10 (m, 2H), 5.97-5.85 (m, 1H), 1.72-1.66 (m, 3H). ES/MS 603.9 (M+H$^+$).

(154)

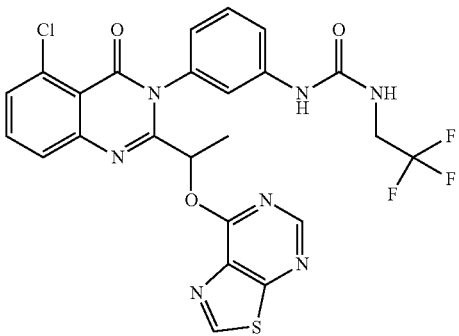

1-(3-(5-chloro-4-oxo-2-(1-(thiazolo[5,4-d]pyrimidin-7-yloxy)ethyl)quinazolin-3(4H)-yl)phenyl)-3-(2,2,2-trifluoroethyl)urea (Compound 154). $^1$H NMR (400 MHz, DMSO-d6) δ 9.44 (s, 1H, minor rotamer), 9.39 (s, 1H, major rotamer), 8.93 (s, 1H, minor rotamer), 8.63 (s, 1H, major rotamer, 8.61 (s, 1H, minor rotamer), 8.58 (s, 1H, major rotamer), 7.74 (m, 2H), 7.64-7.52 (m, 3H), 7.34 (t, J=8 Hz, 1H), 7.20-7.05 (m, 2H), 6.82 (t, J=6 Hz, 1H, minor rotamer), 6.63 (t, J=6 Hz, 1H, major rotamer), 5.78 (q, J=6 Hz, 1H, major rotamer), 5.72 (q, J=6 Hz, 1H, minor rotamer), 3.96-3.79 (m, 2H), 1.67 (d, J=6 Hz, 3H, minor rotamer), 1.65 (d, 6 Hz, 3H, major rotamer). ES/MS 576.0 (M+H$^+$).

(157)

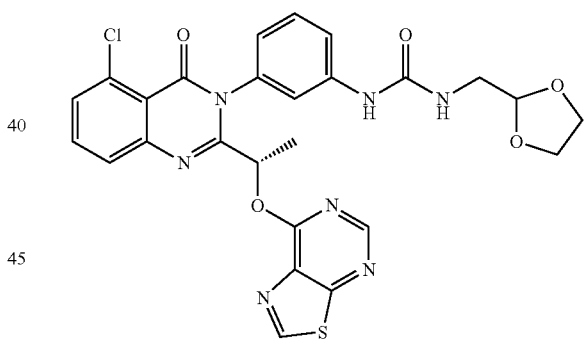

(S)-1-((1,3-dioxolan-2-yl)methyl)-3-(3-(5-chloro-4-oxo-2-(1-(thiazolo[5,4-d]pyrimidin-7-yloxy)ethyl)quinazolin-3(4H)-yl)phenyl)urea (Compound 157). $^1$H NMR (400 MHz, DMSO-d6) δ 9.44 (s, 1H, minor rotamer), 9.39 (s, 1H, major rotamer), 8.76 (s, 1H, minor rotamer), 8.61 (s, 1H, minor rotamer), 8.59 (s, 1H, major rotamer), 8.44 (s, 1H, major rotamer), 7.74-7.67 (m, 2H), 7.63-7.52 (m, 3H), 7.31 (t, J=8 Hz, 1H, major rotamer), 7.25-7.21 (s, 1H, minor rotamer), 7.12-6.97 (m, 2H), 6.28 (t, J=6 Hz, 1H, minor), 6.10 (t, J=6 Hz, 1H), 5.79 (J=6 Hz, 1H, major rotamer), 5.72 (q, J=6 Hz, 1H, major rotamer), 4.86 (t, J=4 Hz, 1H, major rotamer), 4.83 (t, J=4 Hz, 2H), 1.67 (d, J=5 Hz, 3H, minor rotamer), 1.65 (d, J=5 Hz, 3H, major rotamer). ES/MS 580.0 (M+H$^+$).

(158)

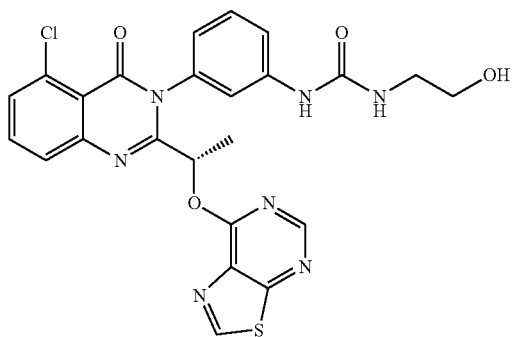

(S)-1-(3-(5-chloro-4-oxo-2-(1-(thiazolo[5,4-d]pyrimidin-7-yloxy)ethyl)quinazolin-3(4H)-yl)phenyl)-3-(2-hydroxyethyl)urea (Compound 158). $^1$H NMR (400 MHz, DMSO-d6) δ 9.43 (s, 1H, minor rotamer), 9.40 (s, 1H, major rotamer), 8.76 (s, 1H, minor rotamer), 8.63 (s, 1H, minor rotamer), 8.62 (s, 1H, major rotamer), 8.47 (s, 1H, major rotamer), 7.75-7.68 (m, 2H), 7.64-7.53 (m, 3H), 7.32 (t, J=8 Hz, 1H, major rotamer), 7.24 (d, J=8 Hz, 1H, minor rotamer), 7.15 (d, J=8 Hz, 1H, major rotamer), 7.08-6.99 (m, 2H), 6.28 (t, J=6 Hz, 1H, minor rotamer), 6.09 (t, J=6 Hz, 1H, major rotamer), 5.79 (q, J=6 Hz, 1H, major rotamer), 5.73 (q, J=6 Hz, 1H, minor rotamer), 4.75-4.71 (m, 1H), 3.46-3.39 (m, 2H), 3.17-3.00 (m, 2H), 1.68 (d, J=6 Hz, 3H, minor rotamer), 1.66 (d, J=6 Hz, 3H, major rotamer). ES/MS 538.1 (M+H$^+$).

(159)

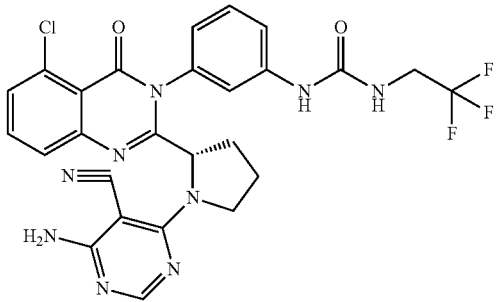

(S)-1-(3-(2-(1-(6-amino-5-cyanopyrimidin-4-yl)pyrrolidin-2-yl)-5-chloro-4-oxoquinazolin-3(4H)-yl)phenyl)-3-(2,2,2-trifluoroethyl)urea (Compound 159). $^1$H NMR (400 MHz, DMSO-d6) δ 9.44 (S, 1H, minor rotamer), 9.39 (S, 1H, major rotamer), 8.93 (S, 1H, minor rotamer), 8.63 (S, 1H, major rotamer), 8.61 (S, 1H, minor rotamer), 8.58 (S, 1H, major rotamer), 7.74 (m, 2H), 7.64-7.52 (m, 3H), 7.34 (t, J=8 Hz, 1H), 7.20-7.05 (m, 2H), 6.82 (t, J=6 Hz, 1H, minor rotamer) 6.63 (t, J=Hz, 1H major rotamer), 5.78 (q, J=6 Hz, major rotamer), 5.72 (S, 1H, minor rotamer), 3.96-3.79 (m, 2H), 1.67 (d, J=6 Hz, 3H, minor rotamer), 1.65 (d, J=6 Hz, 3H, major rotamer). ES/MS 584.2 (M+H$^+$).

F. Preparation of a compound of formula (I) where W$^2$ is CH, n is 1, R$^1$ is chloro, m is 0, R$^3$ is methyl, R$^4$ is 6-amino-5-cyanopyrimidin-4-yl, R$^6$ is 2-trifluoromethylphenyl, and R$^7$ is H, (Compound 113)

(113)

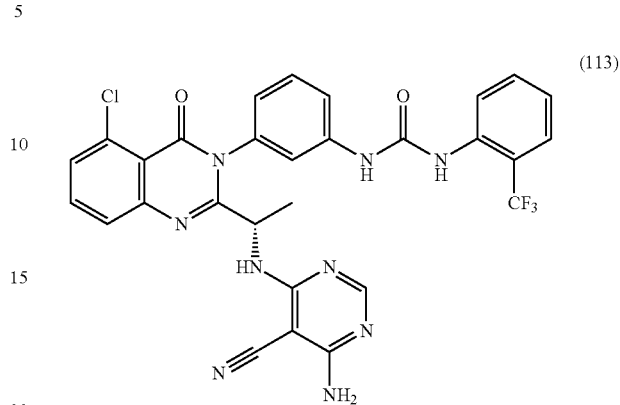

A mixture of (S)-4-amino-6-((1-(5-chloro-3-(3-nitrophenyl)-4-oxo-3,4-dihydroquinazolin-2-yl)ethyl)amino)pyrimidine-5-carbonitrile (0.88 g, 1.9 nmol), which was prepared in a manner as described above from (S)-tert-butyl(1-(5-chloro-3-(3-nitrophenyl)-4-oxo-3,4-dihydroquinazolin-2-yl)ethyl)carbamate, in acetic acid/water (15 mL/10 mL) was treated with iron powder (0.53 g, 9.5 mmol). The mixture was heated to reflux for 20 minutes and then allowed to cool to room temperature. The mixture was then added dropwise to saturated aqueous sodium hydrogen carbonate solution (~200 mL). Most of the insoluble material was removed via filtration. The filtrate was extracted once with ethyl acetate, filtered through a pad of Celite diatomaceous earth, and extracted three more times with ethyl acetate. The combined organics were washed once with saturated aqueous sodium chloride solution, dried over anhydrous magnesium sulfate, filtered, and concentrated under reduced pressure to provide (S)-4-amino-6-((1-(3-(3-aminophenyl)-5-chloro-4-oxo-3,4-dihydroquinazolin-2-yl)ethyl)amino)pyrimidine-5-carbonitrile. ES/MS 433.2 (M+H$^+$). A solution of 3-amino-2-trifluoromethylpyridine (0.50 g, 3.1 mmol) in acetonitrile (5 mL) was treated dropwise with phenyl chloroformate (0.24 g, 1.5 mmol). The mixture was stirred overnight at room temperature. The mixture was partitioned between ethyl acetate and saturated aqueous sodium chloride solution. The aqueous phase was extracted thrice with ethyl acetate. The combined extracts were washed once with saturated aqueous sodium chloride solution, dried over anhydrous magnesium sulfate, filtered, and concentrated to dryness under reduced pressure. The residue was purified by column chromatography on SiO$_2$, eluting with ethyl acetate in hexanes to provide phenyl(2-(trifluoromethyl)pyridin-3-yl)carbamate. ES/MS m/z=283.1 (M+H$^+$). The phenyl(2-(trifluoromethyl)pyridin-3-yl)carbamate (0.16 g, 0.56 mmol) was added to a solution of (S)-4-amino-6-((1-(3-(3-aminophenyl)-5-chloro-4-oxo-3,4-dihydroquinazolin-2-yl)ethyl)amino)pyrimidine-5-carbonitrile (0.22 g, 0.51 mmol) in DMF (3 mL) and DIEA (0.13 g, 1.0 mmol), and DMAP (0.060 g, 0.51 mmol). The mixture was stirred at 45° C. for 30 minutes. The mixture was purified by reverse-phase HPLC (acetonitrile/water/0.1% TFA) to provide (S)-1-(3-(2-(1-((6-amino-5-cyanopyrimidin-4-yl)amino)ethyl)-5-chloro-4-oxoquinazolin-3(4H)-yl)phenyl)-3-(2-(trifluoromethyl)pyridin-3-yl) urea (Compound 113). $^1$H NMR (400 MHz, DMSO-d$_6$) δ 9.69 (s, 0.5H), 9.66 (s, 0.5H), 8.49-8.40 (m, 3H), 8.01 (d, J=2.9 Hz, 1H), 7.96 (d, J=6.6 Hz, 0.5H), 7.91 (t, J=2.0 Hz, 0.5H), 7.85-7.78 (m, 1.5H), 7.76-7.70 (m, 1.5H), 7.68 (ddd, J=8.2, 3.4, 1.2 Hz, 1H), 7.61 (ddd, J=7.8, 3.0, 1.2 Hz, 1H), 7.52-7.45 (m, 1H), 7.51 (br, 2H), 7.45-7.39 (m, 1H), 7.20 (ddd, J=7.8, 2.0, 1.0 Hz, 0.5H), 7.17 (ddd, J=7.5, 2.0, 1.4 Hz, 0.5H), 4.92 (m, 0.5H), 4.85 (m, 0.5H), 4.29 (bs, 1H), 1.44 (d, J=6.7 Hz, 1.5H), 1.43 (d, J=6.7 Hz, 1.5H). ES/MS 621.1 (M+H+).

G. Preparation of the below compound of formula (II) using the procedures described above:

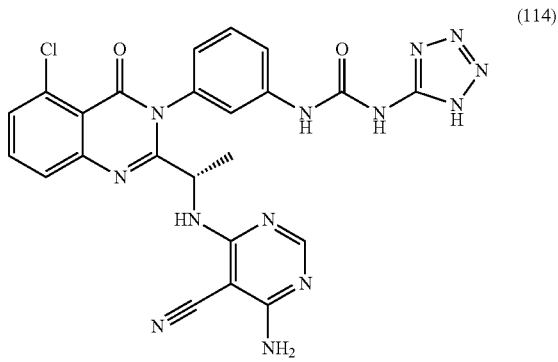 [SMILES: C[C@H](Nc1ncnc(N)c1C#N)c1nc2cccc(Cl)c2c(=O)n1-c1cccc(NC(=O)Nc2nnn[nH]2)c1]

(114)

(S)-1-(3-(2-(1-((6-amino-5-cyanopyrimidin-4-yl)amino) ethyl)-5-chloro-4-oxoquinazolin-3(4H)-yl)phenyl)-3-(1H-tetrazol-5-yl)urea (Compound 114). $^1$H NMR (400 MHz, DMSO-$d_6$) δ 10.74 (s, 1H), 9.33 (s, 0.5H), 9.27 (s, 0.5H), 8.09 (s, 0.5H), 8.00 (s, 0.5H), 7.97 (d, J=6.8 Hz, 0.5H), 7.86 (d, J=6.7 Hz, 0.5H), 7.84-7.80 (m, 1H), 7.80-7.78 (m, 1H), 7.68 (td, J=8.1, 1.2 Hz, 1H), 7.65-7.58 (m, 2H), 7.53 (t, J=8.0 Hz, 0.5H), 7.52 (bs, 2H), 7.44 (t, J=8.0 Hz, 0.5H), 7.27 (ddd, J=7.8, 2.0, 1.0 Hz, 0.5H), 7.21 (ddd, J=7.9, 2.0, 1.0 Hz, 0.5H), 4.93 (m, 0.5H), 4.80 (m, 0.5H), 1.44 (d, J=6.8 Hz, 3H). ES/MS 544.2 (M+H+).

Example 6. Preparation of a Compound of Formula (2b)

A. Preparation of a compound of formula (2b) where $W^2$ is CH, n is 2, each $R^1$ is chloro, m is 0, $R^3$ is methyl, $R^6$ is hydroxypropyl, $R^7$ is H, and $R^5$ is hydrogen

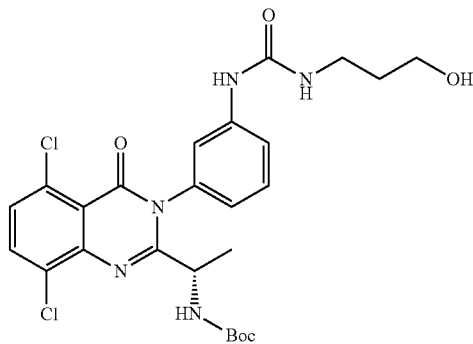 [SMILES: C[C@H](NC(=O)OC(C)(C)C)c1nc2c(Cl)ccc(Cl)c2c(=O)n1-c1cccc(NC(=O)NCCCO)c1]

A solution of (S)-tert-butyl(1-(3-(3-aminophenyl)-5,8-dichloro-4-oxo-3,4-dihydroquinazolin-2-yl)ethyl)carbamate (60 mg, 0.134 mmol) in THF (1 mL) was treated with phenyl chloroformate (0.034 mL, 0.268 mmol). The mixture was stirred at room temperature for 2 hours then concentrated under reduced pressure. DMF (0.4 mL), 3-aminopropanol (0.020 mL, 0.268 mmol) and DMAP (16 mg, 0.134 mmol) were then added. The mixture was stirred at room temperature for 20 hours followed by concentration under reduce pressure. The crude material was purified by column chromatography on SiO$_2$ eluting with EtOAc in hexanes (0-30%) to afford (S)-tert-butyl(1-(5,8-dichloro-3-(3-(3-(3-hydroxypropyl)ureido)phenyl)-4-oxo-3,4-dihydroquinazolin-2-yl) ethyl)carbamate. ES/MS m/z=550.1 (M+H+).

B. The below compounds of formula (2b) were prepared using the procedures described above:

(S)-tert-butyl(1-(5,8-dichloro-3-(3-(3-(3-hydroxypropyl) ureido)phenyl)-4-oxo-3,4-dihydroquinazolin-2-yl)ethyl) carbamate;

(S)-tert-butyl(1-(5-chloro-8-fluoro-3-(3-(3-(3-hydroxypropyl)ureido)phenyl)-4-oxo-3,4-dihydroquinazolin-2-yl) ethyl)carbamate;

(S)-tert-butyl(1-(8-chloro-3-(3-(3-(3-hydroxypropyl)ureido) phenyl)-4-oxo-3,4-dihydroquinazolin-2-yl)ethyl)carbamate;

(S)-tert-butyl(1-(8-fluoro-3-(3-(3-(3-hydroxypropyl)ureido) phenyl)-4-oxo-3,4-dihydroquinazolin-2-yl)ethyl)carbamate;

(S)-tert-butyl(1-(3-(3-(3-(5-(tert-butyl)isoxazol-3-yl)ureido) phenyl)-5-chloro-4-oxo-3,4-dihydroquinazolin-2-yl) ethyl)carbamate;

(S)-tert-butyl(1-(5-chloro-4-oxo-3-(3-(3-(1-(trifluoromethyl)cyclopropyl)ureido)phenyl)-3,4-dihydroquinazolin-2-yl)ethyl)carbamate;

(S)-tert-butyl(1-(5-chloro-4-oxo-3-(3-(3-(2,2,2-trifluoroethyl)ureido)phenyl)-3,4-dihydroquinazolin-2-yl)ethyl) carbamate;

(S)-tert-butyl(1-(5-chloro-3-(3-(3-ethylureido)-4-fluorophenyl)-4-oxo-3,4-dihydroquinazolin-2-yl)ethyl)carbamate;

(S)-tert-butyl(1-(5-chloro-3-(4-fluoro-3-(3-isopropylureido) phenyl)-4-oxo-3,4-dihydroquinazolin-2-yl)ethyl)carbamate;

(S)-tert-butyl(1-(5-chloro-3-(3-(3-(cyclopentylsulfonyl) ureido)phenyl)-4-oxo-3,4-dihydroquinazolin-2-yl)ethyl) carbamate;

(S)-tert-butyl(1-(5-chloro-3-(3-(3-(cyclopropylsulfonyl) ureido)phenyl)-4-oxo-3,4-dihydroquinazolin-2-yl)ethyl) carbamate;

(S)-tert-butyl 2-(3-(3-(3-((1,3-dioxolan-2-yl)methyl)ureido) phenyl)-5-chloro-4-oxo-3,4-dihydroquinazolin-2-yl)pyrrolidine-1-carboxylate;

(S)-tert-butyl 2-(5-chloro-3-(3-(3-(2-methoxyethyl)ureido) phenyl)-4-oxo-3,4-dihydroquinazolin-2-yl)pyrrolidine-1-carboxylate;

(S)-tert-butyl 2-(5-chloro-4-oxo-3-(3-(3-(pyridin-2-yl) ureido)phenyl)-3,4-dihydroquinazolin-2-yl)pyrrolidine-1-carboxylate;

(S)-tert-butyl 2-(5-chloro-3-(3-(3-ethylureido)phenyl)-4-oxo-3,4-dihydroquinazolin-2-yl)pyrrolidine-1-carboxylate;

(S)-tert-butyl 2-(5-chloro-4-oxo-3-(3-(3-(pyridin-2-yl) ureido)phenyl)-3,4-dihydroquinazolin-2-yl)pyrrolidine-1-carboxylate;

(S)-tert-butyl(1-(5-chloro-3-(3-(3-(2-(dimethylamino)ethyl) ureido)phenyl)-4-oxo-3,4-dihydroquinazolin-2-yl)ethyl) carbamate;

(S)-tert-butyl(1-(5-chloro-3-(3-(3-(2-hydroxyethyl)ureido) phenyl)-4-oxo-3,4-dihydroquinazolin-2-yl)ethyl)carbamate;

(S)-tert-butyl(1-(5-chloro-4-oxo-3-(3-(3-(pyridin-3-yl) ureido)phenyl)-3,4-dihydroquinazolin-2-yl)ethyl)carbamate;

(S)-tert-butyl(1-(5-chloro-4-oxo-3-(3-(3-phenylureido)phenyl)-3,4-dihydroquinazolin-2-yl)ethyl)carbamate;

(S)-tert-butyl(1-(5-chloro-3-(3-(3-cyclobutylureido)phenyl)-4-oxo-3,4-dihydroquinazolin-2-yl)ethyl)carbamate;
(S)-tert-butyl(1-(5-chloro-3-(3-(3-cyclohexylureido)phenyl)-4-oxo-3,4-dihydroquinazolin-2-yl)ethyl)carbamate;
(S)-tert-butyl(1-(5-chloro-3-(3-(3-cyclopentylureido)phenyl)-4-oxo-3,4-dihydroquinazolin-2-yl)ethyl)carbamate;
(S)-tert-butyl(1-(5-chloro-3-(3-(3-isopropylureido)phenyl)-4-oxo-3,4-dihydroquinazolin-2-yl)ethyl)carbamate; (S)-tert-butyl(1-(3-(3-(3-(tert-butyl)ureido)phenyl)-5-chloro-4-oxo-3,4-dihydroquinazolin-2-yl)ethyl)carbamate;
(S)-tert-butyl(1-(5-chloro-3-(3-(3-(2-fluoroethyl)ureido)phenyl)-4-oxo-3,4-dihydroquinazolin-2-yl)ethyl)carbamate;
(S)-tert-butyl(1-(5-chloro-3-(3-(3-cyclopropylureido)phenyl)-4-oxo-3,4-dihydroquinazolin-2-yl)ethyl)carbamate;
(S)-tert-butyl(1-(5-chloro-4-oxo-3-(3-(3-propylureido)phenyl)-3,4-dihydroquinazolin-2-yl)ethyl)carbamate;
(R)-tert-butyl(2-(benzyloxy)-1-(5-chloro-3-(3-(3-(3-hydroxypropyl)ureido)phenyl)-4-oxo-3,4-dihydroquinazolin-2-yl)ethyl)carbamate;
(S)-tert-butyl(1-(5-chloro-3-(3-(3-(3-hydroxypropyl)ureido)phenyl)-4-oxo-3,4-dihydroquinazolin-2-yl)ethyl)carbamate;
tert-butyl((1S)-1-(5-chloro-3-(3-(3-(2-hydroxypropyl)ureido)phenyl)-4-oxo-3,4-dihydroquinazolin-2-yl)ethyl)carbamate;
(S)-tert-butyl 3-(3-(3-(2-(1-((tert-butoxycarbonyl)amino)ethyl)-5-chloro-4-oxoquinazolin-3(4H)-yl)phenyl)ureido)propanoate;
(R)-tert-butyl(2-(benzyloxy)-1-(5-chloro-3-(3-(3-ethylureido)phenyl)-4-oxo-3,4-dihydroquinazolin-2-yl)ethyl)carbamate;
(S)-tert-butyl(1-(5-chloro-3-(3-(3-(3-methoxypropyl)ureido)phenyl)-4-oxo-3,4-dihydroquinazolin-2-yl)ethyl)carbamate;
(S)-tert-butyl 2-(3-(3-(2-(1-((tert-butoxycarbonyl)amino)ethyl)-5-chloro-4-oxoquinazolin-3(4H)-yl)phenyl)ureido)-2-methylpropanoate;
(S)-tert-butyl(1-(5-chloro-3-(3-(3-(1-hydroxy-2-methylpropan-2-yl)ureido)phenyl)-4-oxo-3,4-dihydroquinazolin-2-yl)ethyl)carbamate;
(S)-tert-butyl(1-(5-chloro-3-(3-(3-(3-hydroxy-2,2-dimethylpropyl)ureido)phenyl)-4-oxo-3,4-dihydroquinazolin-2-yl)ethyl)carbamate;
(S)-tert-butyl(1-(5-chloro-3-(3-(3-(4-hydroxy-2-methylbutan-2-yl)ureido)phenyl)-4-oxo-3,4-dihydroquinazolin-2-yl)ethyl)carbamate;
(S)-tert-butyl(1-(5-chloro-3-(3-(3-(2-(2-hydroxyethoxy)phenyl)ureido)phenyl)-4-oxo-3,4-dihydroquinazolin-2-yl)ethyl)carbamate;
(S)-tert-butyl(1-(5-chloro-3-(3-(3-(2-(methylsulfonyl)phenyl)ureido)phenyl)-4-oxo-3,4-dihydroquinazolin-2-yl)ethyl)carbamate;
(S)-tert-butyl(1-(5-chloro-3-(3-(3-(3-hydroxy-3-methylbutyl)ureido)phenyl)-4-oxo-3,4-dihydroquinazolin-2-yl)ethyl)carbamate;
(S)-1-(3-(2-(1-(((triisopropylsilyl)oxy)ethyl)-5-chloro-4-oxoquinazolin-3(4H)-yl)phenyl)-3-(1-(trifluoromethyl)cyclopropyl)urea;
(S)-1-(3-(2-(1-(((triisopropylsilyl)oxy)ethyl)-5-chloro-4-oxoquinazolin-3(4H)-yl)phenyl)-3-(2,2-difluoroethyl)urea;
(S)-1-(3-(2-(1-(((triisopropylsilyl)oxy)ethyl)-5-chloro-4-oxoquinazolin-3(4H)-yl)phenyl)-3-cyclopentylurea;
(S)-1-(3-(2-(1-(((triisopropylsilyl)oxy)ethyl)-5-chloro-4-oxoquinazolin-3(4H)-yl)phenyl)-3-(2,2,3,3,3-pentafluoropropyl)urea;
(S)-1-(3-(2-(1-(((triisopropylsilyl)oxy)ethyl)-5-chloro-4-oxoquinazolin-3(4H)-yl)phenyl)-3-(3-(trifluoromethyl)isoxazol-5-yl)urea;
(S)-1-(3-(2-(1-(((triisopropylsilyl)oxy)ethyl)-5-chloro-4-oxoquinazolin-3(4H)-yl)phenyl)-3-ethylurea;
1-(3-(2-(1-(((triisopropylsilyl)oxy)ethyl)-5-chloro-4-oxoquinazolin-3(4H)-yl)phenyl)-3-(2-methoxyethyl)urea;
(S)-1-(3-(2-(1-(((triisopropylsilyl)oxy)ethyl)-5-chloro-4-oxoquinazolin-3(4H)-yl)phenyl)-3-methoxyurea;
1-(3-(2-(1-(((triisopropylsilyl)oxy)ethyl)-5-chloro-4-oxoquinazolin-3(4H)-yl)phenyl)-3-(2,2,2-trifluoroethyl)urea;
1-(3-(2-(1-(((triisopropylsilyl)oxy)ethyl)-5-chloro-4-oxoquinazolin-3(4H)-yl)phenyl)-3-(2-chlorophenyl)urea;
(S)-1-((1,3-dioxolan-2-yl)methyl)-3-(3-(2-(1-(((triisopropylsilyl)oxy)ethyl)-5-chloro-4-oxoquinazolin-3(4H)-yl)phenyl)urea;
(S)-1-(3-(2-(1-(((triisopropylsilyl)oxy)ethyl)-5-chloro-4-oxoquinazolin-3(4H)-yl)phenyl)-3-(2-hydroxyethyl)urea; and
(S)-tert-butyl 2-(5-chloro-4-oxo-3-(3-(3-(2,2,2-trifluoroethyl)ureido)phenyl)-3,4-dihydroquinazolin-2-yl)pyrrolidine-1-carboxylate.

C. Preparation of a compound of formula (2b) where $W^2$ is CH, n is 1, $R^1$ is chloro, m is 0, $R^3$ is methyl, $R^6$ is 3-trifluoromethyl-4-methylphenyl, $R^7$ is H, and $R^5$ is hydrogen

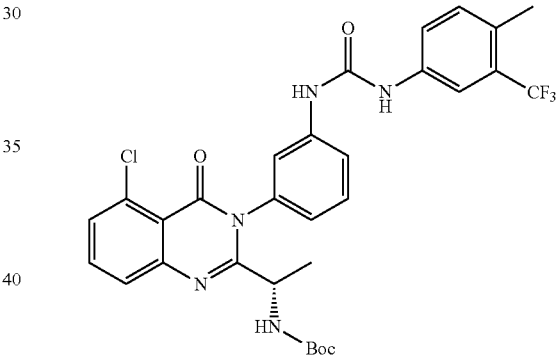

A solution of 4-chloro-3-trifluoromethylaniline (0.27 g, 1.4 mmol) in DMSO (7 mL) was treated with 1,1-carbonyldiimidazole (0.26 g, 1.6 mmol). The mixture was stirred at room temperature for two hours before (S)-tert-butyl(1-(3-(3-aminophenyl)-5-chloro-4-oxo-3,4-dihydroquinazolin-2-yl)ethyl)carbamate (0.54 g, 1.3 mmol) was added in a single portion. The mixture was partitioned between ethyl acetate and water. The aqueous phase was extracted three times with ethyl acetate. The combined extracts were washed three times with water and once with saturated aqueous sodium chloride solution. The organics were dried over anhydrous magnesium sulfate, filtered, and concentrated. The residue was purified by flash chromatography (silica gel, ethyl acetate/hexanes) to provide (S)-tert-butyl(1-(5-chloro-3-(3-(3-(4-chloro-3-(trifluoromethyl)phenyl)ureido)phenyl)-4-oxo-3,4-dihydroquinazolin-2-yl)ethyl)carbamate. ES/MS m/z=636.1 (M+H$^+$).

D. Preparation of the below compounds of formula (2b) using the procedures described above:
(S)-tert-butyl(1-(5-chloro-3-(3-(3-(2-chlorophenyl)ureido)phenyl)-4-oxo-3,4-dihydroquinazolin-2-yl)ethyl)carbamate.

E. Preparation of a compound of formula (2b) where $W^2$ is CH, n is 1, $R^1$ is chloro, m is 0, $R^3$ is methyl, $R^6$ is 2-trifluoromethylphenyl, and $R^5$ is hydrogen

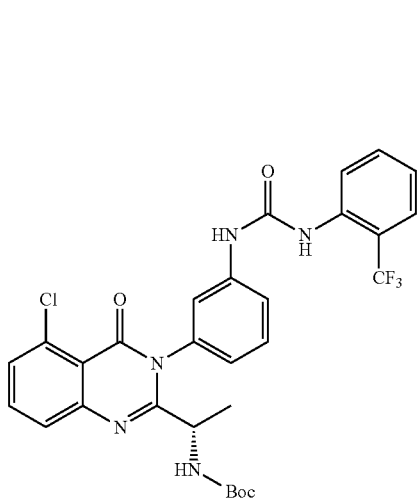 [SMILES: C[C@H](NC(=O)OC(C)(C)C)c1nc2cccc(Cl)c2c(=O)n1-c1cccc(NC(=O)Nc2ccccc2C(F)(F)F)c1]

A solution of (S)-tert-butyl(1-(3-(3-aminophenyl)-5-chloro-4-oxo-3,4-dihydroquinazolin-2-yl)ethyl)carbamate (0.43 g, 1.0 mmol) in dichloromethane (4 mL) was treated with 2-trifluoromethylphenylisocyanate (0.22 g, 0.17 mL, 1.2 mmol). After 1 hour of standing at room temperature, the mixture was treated with MeOH (~1 mL) and then concentrated under reduced pressure to provide (S)-tert-butyl(1-(5-chloro-4-oxo-3-(3-(3-(2-(trifluoromethyl)phenyl)ureido)phenyl)-3,4-dihydroquinazolin-2-yl)ethyl)carbamate. ES/MS m/z=602.1 (M+H⁺).

F. Preparation of the below compounds of formula (2b) using the procedures described above:

(S)-tert-butyl(1-(5-chloro-3-(3-(3-(2,4-difluorophenyl)ureido)phenyl)-4-oxo-3,4-dihydroquinazolin-2-yl)ethyl)carbamate;

(S)-tert-butyl(1-(5-chloro-3-(3-(3-(2,6-dichlorophenyl)ureido)phenyl)-4-oxo-3,4-dihydroquinazolin-2-yl)ethyl)carbamate;

(S)-tert-butyl(1-(5-chloro-3-(3-(3-(2-cyanophenyl)ureido)phenyl)-4-oxo-3,4-dihydroquinazolin-2-yl)ethyl)carbamate;

(S)-tert-butyl(1-(3-(3-(3-(2-chlorophenyl)ureido)phenyl)-5-fluoro-4-oxo-3,4-dihydroquinazolin-2-yl)ethyl)carbamate;

(S)-tert-butyl(1-(5-chloro-3-(3-(3-(2-methoxyphenyl)ureido)phenyl)-4-oxo-3,4-dihydroquinazolin-2-yl)ethyl)carbamate;

(S)-tert-butyl(1-(5-chloro-4-oxo-3-(3-(3-(o-tolyl)ureido)phenyl)-3,4-dihydroquinazolin-2-yl)ethyl)carbamate; and (S)-tert-butyl(1-(5-fluoro-4-oxo-3-(3-(3-(2-(trifluoromethyl)phenyl)ureido)phenyl)-3,4-dihydroquinazolin-2-yl)ethyl)carbamate;

G. Preparation of a compound of formula (2b) where $W^2$ is CH, n is 1, $R^1$ is chloro, m is 0, $R^3$ is methyl, $R^6$ is 3-chloro-4-pyridinyl, and $R^5$ is hydrogen

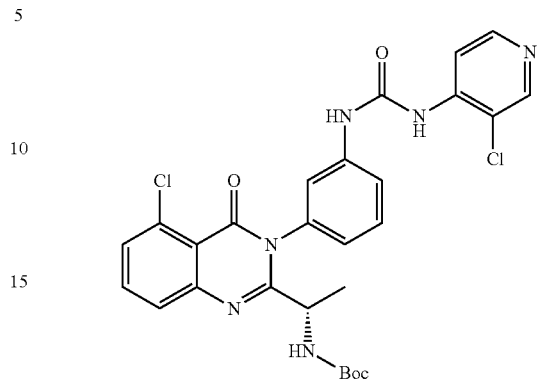

Triethylamine (0.68 mL, 4.9 mmol) was added to a nearly homogeneous mixture of 4-amino-3-chloropyridine (0.21 g, 1.6 mmol) in benzene (16 mL). Triphosgene (0.24 g, 0.80 mmol) was added quickly, dropwise as a solution in benzene (3 mL). The mixture was heated overnight at 100° C. (S)-tert-butyl(1-(3-(3-aminophenyl)-5-chloro-4-oxo-3,4-dihydroquinazolin-2-yl)ethyl)carbamate (0.37 g, 0.89 mmol) was added dropwise as a solution in dichloromethane (3 mL) to the isocyanate mixture at room temperature. The mixture was stirred for 2 hours at room temperature before the addition of ethanolamine (0.20 mL) and concentration under reduced pressure. The residue was partitioned between water and dichloromethane. The aqueous phase was extracted twice with dichloromethane and twice with 10% methanol/dichloromethane. The combined extracts were concentrated to dryness under reduced pressure. The residue was purified by column chromatography on SiO₂, eluting with methanol/ethyl acetate in hexanes to provide (S)-tert-butyl(1-(5-chloro-3-(3-(3-(3-chloropyridin-4-yl)ureido)phenyl)-4-oxo-3,4-dihydroquinazolin-2-yl)ethyl)carbamate. ES/MS m/z=569.1 (M+H⁺).

G. Preparation of a compound of formula (2b) where $W^2$ is CH, n is 1, $R^1$ is chloro, m is 0, $R^3$ is methyl, $R^6$ is methoxy, and $R^5$ is hydrogen

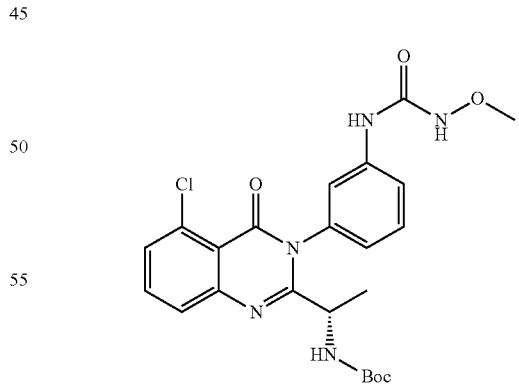

A solution of (S)-tert-butyl(1-(3-(3-aminophenyl)-5-chloro-4-oxo-3,4-dihydroquinazolin-2-yl)ethyl)carbamate and TEA (0.66 g, 6.5 mmol) in DCM (42 mL) was cooled in an ice-water bath and treated with CDI (1.1 g, 6.5 mmol) in a single portion. The mixture was stirred 5 minutes in the bath before removal of bath and overnight stirring at room temperature. The mixture re-cooled in an ice-water bath.

Solid methoxylamine hydrochloride (2.3 g, 28 mmol) was added in a single portion, followed by TEA (2.8 g, 28 mmol). The mixture stirred at room temperature overnight before being washed successively with saturated aqueous sodium hydrogen carbonate solution, water, and saturated aqueous sodium chloride solution. The organic layer was dried over anhydrous magnesium sulfate, filtered, concentrated under reduced pressure to provide (S)-tert-butyl(1-(5-chloro-3-(3-(3-methoxyureido)phenyl)-4-oxo-3,4-dihydroquinazolin-2-yl)ethyl)carbamate. ES/MS m/z=488.1 (M+H$^+$).

Example 7. Preparation of a Compound of Formula (3c)

A. Preparation of a compound of formula (3c) where $W^2$ is CH, n is 1, $R^1$ is chloro, m is 0, $R^3$ is methyl, $R^6$ is ethyl, and $R^7$ is H,

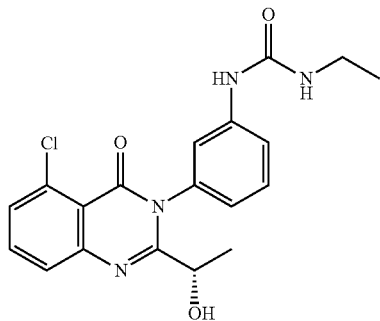 [SMILES: CCNC(=O)Nc1cccc(-n2c([C@H](C)O)nc3cccc(Cl)c3c2=O)c1]

To (S)-1-(3-(2-(1-((tert-butyldiphenylsilyl)oxy)ethyl)-5-chloro-4-oxoquinazolin-3(4H)-yl)phenyl)-3-ethylurea (0.4 g, 0.64 mmol) was added THF (8 mL) followed by HF*Pyr (~1 mL, XS). After 20 min, ethyl acetate (50 mL) and aqueous sodium bicarbonate (50 mL) was added. The organic layer was concentrated and the material dried (Na$_2$SO$_4$). The material was filtered and concentrated by rotary evaporation to give (S)-1-(3-(5-chloro-2-(1-hydroxyethyl)-4-oxoquinazolin-3(4H)-yl)phenyl)-3-ethylurea and used without further purification.

B. Preparation of the below compounds of formula (3c) using the procedures described above:
(S)-1-(3-(5-chloro-2-(1-hydroxyethyl)-4-oxoquinazolin-3(4H)-yl)phenyl)-3-(1-(trifluoromethyl)cyclopropyl)urea;
(S)-1-(3-(5-chloro-2-(1-hydroxyethyl)-4-oxoquinazolin-3(4H)-yl)phenyl)-3-(2,2-difluoroethyl)urea;
(S)-1-(3-(5-chloro-((1-hydroxyethyl)-4-oxoquinazolin-3(4H)-yl)phenyl)-3-cyclopentylurea;
(S)-1-(3-(5-chloro-2-(1-hydroxyethyl)-4-oxoquinazolin-3(4H)-yl)phenyl)-3-(2,2,3,3,3-pentafluoropropyl)urea;
(S)-1-(3-(5-chloro-2-(1-hydroxyethyl)-4-oxoquinazolin-3(4H)-yl)phenyl)-3-(3-(trifluoromethyl)isoxazol-5-yl)urea;
(S)-1-(3-(5-chloro-2-(1-hydroxyethyl)-4-oxoquinazolin-3(4H)-yl)phenyl)-3-ethylurea; 1-(3-(5-chloro-2-(1-hydroxyethyl)-4-oxoquinazolin-3(4H)-yl)phenyl)-3-(2-methoxyethyl)urea;
(S)-1-(3-(5-chloro-2-(1-hydroxyethyl)-4-oxoquinazolin-3(4H)-yl)phenyl)-3-methoxyurea; 1-(3-(5-chloro-2-(1-hydroxyethyl)-4-oxoquinazolin-3(4H)-yl)phenyl)-3-(2,2,2-trifluoroethyl)urea;
1-(3-(5-chloro-2-(1-hydroxyethyl)-4-oxoquinazolin-3(4H)-yl)phenyl)-3-(2-chlorophenyl)urea;
(S)-1-((1,3-dioxolan-2-yl)methyl)-3-(3-(5-chloro-2-(1-hydroxyethyl)-4-oxoquinazolin-3(4H)-yl)phenyl)urea; and
(S)-1-(3-(5-chloro-2-(1-hydroxyethyl)-4-oxoquinazolin-3(4H)-yl)phenyl)-3-(2-hydroxyethyl)urea.

Example 8. Preparation of a Compound of Formula (5c)

A. Preparation of a compound of formula (5c) where $W^2$ is CH, n is 1, $R^1$ is chloro, m is 0, $R^3$ is methyl, and PG is triisopropylsilyl

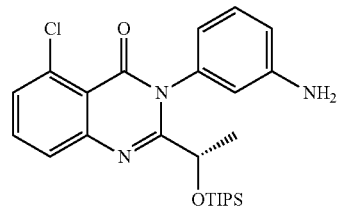

A solution of (S)-5-chloro-3-(3-nitrophenyl)-2-(1-((triisopropylsilyl)oxy)ethyl)quinazolin-4(3H)-one (1.3 g, 2.6 mmol) in 24 mL THF and 18 mL EtOH was treated with tin(II) chloride (4.89 g, 26 mmol) and heated to 65° C. After 30 min stirring, the reaction was cooled to RT and aqueous NaOH (26 mL, 52 mmol, 2N) was added dropwise with vigorous stirring. After 1 h the reaction was filtered and the filtrate partitioned between EtOAc and brine. The organic layer was dried with MgSO$_4$, filtered through celite and concentrated. Purification by silica gel chromatography gave (S)-3-(3-aminophenyl)-5-chloro-2-(1-((triisopropylsilyl)oxy)ethyl)quinazolin-4(3H)-one. [M+H]=471.22.

Biological Examples

The compounds of formula (I) were characterized for their enzymatic activity against the PI3K isoforms. Certain compounds of the present application, including certain compounds of formula (II) and (III) were also characterized for their enzymatic activity against PI3K isoforms. The activities were measured using a time-resolved fluorescence resonance energy transfer (TR-FRET) assay. TR-FRET monitored the formation of 3,4,5-inositol triphosphate molecule that competed with fluorescently labeled PIP3 for binding to the GRP-1 pleckstrin homology domain protein. An increase in phosphatidylinositide 3-phosphate product resulted in a decrease in TR-FRET signal as the labeled fluorophore was displaced from the GRP-1 protein binding site.

Class I PI3K isoforms were expressed and purified as heterodimeric recombinant proteins. All assay reagents and buffers for the TR-FRET assay were purchased from Millipore. PI3K isoforms were assayed under initial rate conditions in the presence of 25 mM Hepes (pH 7.4), and 2×Km ATP (75-500 μM), 2 μM PIP2, 5% glycerol, 5 mM MgCl$_2$, 50 mM NaCl, 0.05% (v/v) Chaps, 1 mM dithiothreitol, and 1% (v/v) DMSO at the following concentrations for each isoform: PI3Kα, PI3Kβ, and PI3Kδ between 25 and 50 pM, and PI3Kγ at 2 nM. The compounds of Table 1 and Compound X ((S)-2,4-diamino-6-((1-(5-chloro-4-oxo-3-phenyl-3,4-dihydroquinazolin-2-yl)ethyl)amino)pyrimidine-5-carbonitrile) were added to the assay solution and incubated for 30 minutes at 25° C. Additionally, Compounds 24-164 were added to the assay solution and incubated for 30 minutes at 250 in a similar manner. The reactions were terminated with a final concentration of 10 mM EDTA, 10 nM labeled-PIP3, and 35 nM Europium labeled GRP-1 detector protein before reading TR-FRET on an Envision plate reader (Ex: 340 nm; Em: 615/665 nm; 100 μs delay and 500 μs read window).

The results were normalized based on positive (1 μM wortmanin) and negative (DMSO) controls, and the $IC_{50}$ values for PI3Kα, β, δ, and γ were calculated from the fit of the dose-response curves to a four-parameter equation. These assays generally produced results within 3-fold of the reported mean.

Table 2 summarizes the $IC_{50}$ (nM) values for PI3K isoforms α, δ, and γ. The results indicate that certain compounds of formula (I), (II), or (III) inhibit both PI3Kδ and PI3Kβ. Also, Compound X exhibited PI3Kδ $IC_{50}$ of 0.2 nM, PI3Kβ $IC_{50}$ of 11 nM, PI3Kγ $IC_{50}$ of 7 nM. The PI3Kγ/PI3Kβ ratio for Compound X is 0.6. The results indicate that certain compounds have greater selectivity for PI3Kβ over PI3Kγ compared to compound X.

TABLE 2

The $IC_{50}$ values (nM) for PI3K isoforms β, δ, and γ.

| Compound | β $IC_{50}$ | δ $IC_{50}$ | γ $IC_{50}$ |
| --- | --- | --- | --- |
| 1 | 14 | 0.7 | 1300 |
| 2 | 6 | 0.5 | 60 |
| 3 | 12 | 0.8 | 460 |
| 4 | 29 | 1 | 4400 |
| 5 | 526 | 2 | 81 |
| 6 | 32 | 4 | 620 |
| 7 | 7 | 1 | 2700 |
| 8 | 2 | 0.4 | 200 |
| 9 | 2 | 0.6 | 220 |
| 10 | 7 | 1 | 2700 |
| 11 | 37 | 3 | 8500 |
| 12 | 6 | 0.3 | 230 |
| 13 | 7 | 0.6 | 510 |
| 14 | 10 | 1 | 360 |
| 15 | 10 | 1 | 330 |
| 16 | 17 | 2 | 3200 |
| 17 | 51 | 2 | 1400 |
| 18 | 8 | 0.5 | 1200 |
| 19 | 28 | 3 | >10000 |
| 20 | 11 | 0.6 | 1400 |
| 21 | 196 | 19 | >10000 |
| 22 | 7 | 0.7 | 300 |
| 23 | 12 | 2 | 3900 |
| 24 | 25 | 1 | 660 |
| 25 | 24 | 1 | 700 |
| 26 | 313 | 12 | 7200 |
| 27 | 5 | 2 | 600 |
| 28 | 267 | 46 | >10000 |
| 29 | 8 | 1 | 440 |
| 30 | 252 | 22 | >10000 |
| 31 | 21 | 2 | 1100 |
| 32 | 25 | 4 | 1800 |
| 33 | 4 | 0.8 | 380 |
| 34 | 22 | 3 | 5000 |
| 35 | 5 | 1 | 200 |
| 36 | 299 | 10 | >10000 |
| 37 | 243 | 7 | >10000 |
| 38 | 52 | 1 | 1500 |
| 39 | 8 | 0.5 | 1200 |
| 40 | 28 | 3 | >10000 |
| 41 | 11 | 0.8 | 1400 |
| 42 | 170 | 130 | >10000 |
| 43 | 18 | 13 | >10000 |
| 44 | 320 | 230 | >10000 |
| 45 | 6 | 2 | 1800 |
| 46 | 35 | 17 | >10000 |
| 47 | 36 | 26 | >10000 |
| 48 | 7 | 3 | >10000 |
| 49 | 230 | 24 | >10000 |
| 50 | 84 | 22 | >10000 |
| 51 | 67 | 17 | 7900 |
| 52 | 340 | 39 | >10000 |

TABLE 2-continued

The $IC_{50}$ values (nM) for PI3K isoforms β, δ, and γ.

| Compound | β $IC_{50}$ | δ $IC_{50}$ | γ $IC_{50}$ |
| --- | --- | --- | --- |
| 53 | 550 | 75 | >10000 |
| 54 | 2600 | 250 | >10000 |
| 55 | 12 | 3 | 1800 |
| 56 | 6600 | 880 | >10000 |
| 57 | 580 | 610 | >10000 |
| 58 | 1300 | 24 | >10000 |
| 59 | 610 | 56 | 2300 |
| 60 | 210 | 4 | 210 |
| 61 | 1130 | 8 | 2500 |
| 62 | 7 | 4 | 3800 |
| 63 | 29 | 29 | 5400 |
| 64 | 7 | 8 | >10000 |
| 65 | 220 | 82 | >10000 |
| 66 | 4 | 9 | 3700 |
| 67 | 38 | 98 | >10000 |
| 68 | 220 | 130 | >10000 |
| 69 | 110 | 8 | 5200 |
| 70 | 12 | 2 | 1500 |
| 71 | 29 | 11 | 2000 |
| 72 | 4 | 5 | 1300 |
| 73 | 38 | 17 | 5600 |
| 74 | 11 | 3 | 4500 |
| 75 | 10 | 9 | >10000 |
| 76 | 5 | 7 | 4400 |
| 77 | 420 | 27 | 9500 |
| 78 | 16 | 32 | 4900 |
| 79 | 71 | 2 | 680 |
| 80 | 120 | 0.9 | 250 |
| 81 | 350 | 2 | 2800 |
| 82 | 29 | 16 | 8600 |
| 83 | 13 | 9 | 3300 |
| 84 | 97 | 38 | 7800 |
| 85 | 420 | 49 | 7400 |
| 86 | 22 | 19 | 4300 |
| 87 | 21 | 33 | 4500 |
| 88 | 4 | 2 | 2700 |
| 89 | 6 | 6 | 4300 |
| 90 | 5 | 7 | 3400 |
| 91 | 32 | 19 | 1400 |
| 92 | 16 | 1 | 1600 |
| 93 | 70 | 110 | 3700 |
| 94 | 5500 | 78 | >10000 |
| 95 | 59 | 5 | 1000 |
| 96 | 230 | 5 | 2600 |
| 97 | 120 | 5 | 6000 |
| 98 | 58 | 29 | 3300 |
| 99 | 8 | 19 | 1600 |
| 100 | 1 | 3 | 1400 |
| 101 | 5 | 13 | 2500 |
| 102 | 7 | 31 | 670 |
| 103 | 2 | 7 | 640 |
| 104 | 8 | 30 | 740 |
| 105 | 3 | 9 | 800 |
| 106 | 4800 | 20 | >10000 |
| 107 | 16 | 6 | 1500 |
| 108 | 3 | 24 | 8500 |
| 109 | 9 | 2 | 2600 |
| 110 | 16 | 57 | >10000 |
| 111 | 4 | 7 | 4300 |
| 112 | 6 | 26 | 1600 |
| 113 | 23 | 11 | 3900 |
| 114 | 37 | 10 | 3800 |
| 115 | 14 | 5 | 3700 |
| 116 | 2 | 4 | >10000 |
| 117 | 4 | 6 | 8300 |
| 118 | 3 | 8 | 1000 |
| 119 | 3 | 5 | 1400 |
| 120 | 9 | 7 | 4800 |
| 121 | 3 | 3 | 1600 |
| 122 | 3 | 4 | 2000 |
| 123 | 7 | 3 | 2200 |
| 124 | 14 | 9 | 3300 |
| 125 | 7 | 7 | 3400 |
| 126 | 8 | 4 | 2900 |
| 127 | 8 | 5 | 5800 |
| 128 | 9 | 4 | 5600 |

TABLE 2-continued

The IC$_{50}$ values (nM) for PI3K isoforms β, δ, and γ.

| Compound | β IC$_{50}$ | δ IC$_{50}$ | γ IC$_{50}$ |
|---|---|---|---|
| 129 | 9 | 4 | 5600 |
| 130 | 24 | 6 | >10000 |
| 131 | 43 | 41 | >10000 |
| 132 | 21 | 10 | 8700 |
| 133 | 50 | 82 | 10000 |
| 134 | 5 | 10 | 6000 |
| 135 | 16 | 35 | 3500 |
| 136 | 1800 | 610 | >10000 |
| 137 | 33 | 12 | 7600 |
| 138 | 4 | 7 | 5200 |
| 139 | 30 | 13 | 8100 |
| 140 | 6 | 5 | 5100 |
| 141 | 6 | 6 | 1600 |
| 142 | 12 | 6 | 7100 |
| 143 | 7 | 5 | 1500 |
| 144 | 17 | 4 | 6500 |
| 145 | 30 | 8 | 2500 |
| 146 | 57 | 6 | 2200 |
| 147 | 16 | 12 | 2300 |
| 148 | 8 | 5 | 1800 |
| 149 | 60 | 11 | 3500 |
| 150 | 47 | 5 | 840 |
| 151 | 20 | 4 | 1300 |
| 152 | 17 | 10 | 2500 |
| 153 | 48 | 4 | 1600 |
| 154 | 4 | 5 | 1400 |
| 156 | 41 | 2 | 930 |
| 157 | 25 | 7 | 3100 |
| 158 | 9 | 4 | 900 |
| 159 | 42 | 33 | 5600 |
| 146 | 57 | 6 | 2200 |
| 147 | 16 | 12 | 2300 |
| 148 | 8 | 5 | 1800 |
| 149 | 60 | 11 | 3500 |
| 150 | 47 | 5 | 840 |
| 151 | 20 | 4 | 1300 |
| 152 | 17 | 10 | 2500 |
| 153 | 48 | 4 | 1600 |
| 154 | 4 | 5 | 1400 |
| 156 | 41 | 2 | 930 |
| 157 | 25 | 7 | 3100 |
| 158 | 9 | 4 | 900 |
| 159 | 42 | 33 | 5600 |
| 160 | 2400 | 66 | >10000 |
| 161 | 2 | 1 | 70 |
| 162 | 21 | 1 | 2600 |
| 163 | 11 | 2 | 8200 |
| 164 | 2 | 1 | 420 |

What is claimed:

1. A compound having the structure of formula (J):

(J)

wherein:
n is 0, 1, or 2;
m is 0 or 1;
q is 0 or 1;
$W^1$ is N;
$W^2$ is CH or N;
$W^3$ is NH;

each $R^1$ is independently halo, cyano, or optionally substituted alkyl;
each $R^2$ is independently halo or optionally substituted alkyl;
$R^3$ is hydrogen, optionally substituted alkyl, or optionally substituted cycloalkyl;
$R^4$ is optionally substituted with one two or three members which are independently halo, cyano, optionally substituted alkyl, or —NH$_2$;
$R^5$ is hydrogen;
$R^6$ is hydrogen, optionally substituted alkyl, optionally substituted heteroalkyl, optionally substituted alkoxy, optionally substituted haloalkyl, optionally substituted sulfonyl, optionally substituted cycloalkyl, optionally substituted heterocycloalkyl, optionally substituted aryl, or optionally substituted heteroaryl; and
$R^7$ is hydrogen,
or a pharmaceutically acceptable salt, stereoisomers, or atropisomers thereof.

2. A compound selected from the group consisting of:
(S)-3-(5-chloro-2-(1-((2,6-diamino-5-chloropyrimidin-4-yl)amino)ethyl)-4-oxoquinazolin-3(4H)-yl)benzamide;
(S)-3-(5-chloro-2-(1-((2,6-diamino-5-cyanopyrimidin-4-yl)amino)ethyl)-4-oxoquinazolin-3(4H)-yl)benzamide;
(S)-3-(5,8-dichloro-2-(1-((2,6-diamino-5-cyanopyrimidin-4-yl)amino)ethyl)-4-oxoquinazolin-3(4H)-yl)benzamide;
(S)-3-(5,8-dichloro-2-(1-((2,6-diamino-5-chloropyrimidin-4-yl)amino)ethyl)-4-oxoquinazolin-3(4H)-yl)benzamide;
(S)-3-(5-chloro-2-(1-((2,6-diamino-5-cyanopyrimidin-4-yl)amino)ethyl)-4-oxoquinazolin-3(4H)-yl)-2-methylbenzamide;
(S)-3-(5-chloro-2-(1-((2,6-diamino-5-chloropyrimidin-4-yl)amino)propyl)-4-oxoquinazolin-3(4H)-yl)benzamide;
(S)-3-(5-chloro-2-(1-((2,6-diamino-5-cyanopyrimidin-4-yl)amino)propyl)-4-oxoquinazolin-3(4H)-yl)benzamide;
(S)-3-(5-chloro-2-(cyclopropyl((2,6-diamino-5-cyanopyrimidin-4-yl)amino)methyl)-4-oxoquinazolin-3(4H)-yl)benzamide;
(S)-3-(5-chloro-2-(cyclopropyl((2,6-diamino-5-chloropyrimidin-4-yl)amino)methyl)-4-oxoquinazolin-3(4H)-yl)benzamide;
(S)-3-(5,8-dichloro-2-(cyclopropyl((2,6-diamino-5-chloropyrimidin-4-yl)amino)methyl)-4-oxoquinazolin-3(4H)-yl)benzamide;
(S)-3-(5,8-dichloro-2-(cyclopropyl((2,6-diamino-5-cyanopyrimidin-4-yl)amino)methyl)-4-oxoquinazolin-3(4H)-yl)benzamide;
(S)-3-(2-(((2-amino-5-cyano-6-methylpyrimidin-4-yl)amino)(cyclopropyl)methyl)-5,8-dichloro-4-oxoquinazolin-3(4H)-yl)benzamide;
(S)-3-(2-(((2-amino-5-cyano-6-methylpyrimidin-4-yl)amino)(cyclopropyl)methyl)-5-chloro-8-fluoro-4-oxoquinazolin-3(4H)-yl)benzamide;

(S)-3-(5-chloro-2-(cyclopropyl((2,6-diamino-5-cyanopyrimidin-4-yl)amino)methyl)-8-fluoro-4-oxoquinazolin-3(4H)-yl)benzamide;

(S)-3-(5-chloro-2-(cyclopropyl((2,6-diamino-5-chloropyrimidin-4-yl)amino)methyl)-8-fluoro-4-oxoquinazolin-3(4H)-yl)benzamide;

(S)-3-(5,8-dichloro-2-(1-(2,6-diamino-5-cyanopyrimidin-4-yl)pyrrolidin-2-yl)-4-oxoquinazolin-3(4H)-yl)benzamide;

(S)-3-(5,8-dichloro-2-(1-((2,6-diamino-5-chloropyrimidin-4-yl)amino)butyl)-4-oxoquinazolin-3(4H)-yl)benzamide;

(S)-3-(5-chloro-2-(1-((2,6-diamino-5-cyanopyrimidin-4-yl)amino)butyl)-4-oxoquinazolin-3(4H)-yl)benzamide;

(S)-3-(5-chloro-2-(1-((2,6-diamino-5-chloropyrimidin-4-yl)amino)butyl)-4-oxoquinazolin-3(4H)-yl)benzamide;

(S)-3-(2-(1-((2-amino-5-cyano-6-(difluoromethyl)pyrimidin-4-yl)amino)ethyl)-5-chloro-8-fluoro-4-oxoquinazolin-3(4H)-yl)benzamide;

(S)-3-(2-(1-((2-amino-5-cyano-6-(difluoromethyl)pyrimidin-4-yl)amino)ethyl)-5-chloro-4-oxoquinazolin-3(4H)-yl)benzamide;

(S)-3-(2-(1-((2-amino-5-cyano-6-(difluoromethyl)pyrimidin-4-yl)amino)ethyl)-8-chloro-6-fluoro-4-oxoquinazolin-3(4H)-yl)benzamide;

(S)-3-(8-chloro-2-(cyclopropyl((2,6-diamino-5-cyanopyrimidin-4-yl)amino)methyl)-6-fluoro-4-oxoquinazolin-3(4H)-yl)benzamide;

(S)-3-(8-chloro-2-(cyclopropyl((2,6-diamino-5-chloropyrimidin-4-yl)amino)methyl)-6-fluoro-4-oxoquinazolin-3(4H)-yl)benzamide;

(S)-3-(8-chloro-2-(1-((2,6-diamino-5-cyanopyrimidin-4-yl)amino)ethyl)-6-fluoro-4-oxoquinazolin-3(4H)-yl)benzamide;

(S)-3-(8-chloro-2-(1-((2,6-diamino-5-chloropyrimidin-4-yl)amino)ethyl)-6-fluoro-4-oxoquinazolin-3(4H)-yl)benzamide;

(S)-3-(8-cyano-2-(1-((2,6-diamino-5-cyanopyrimidin-4-yl)amino)ethyl)-6-fluoro-4-oxoquinazolin-3(4H)-yl)benzamide;

(S)-3-(8-cyano-2-(cyclopropyl((2,6-diamino-5-cyanopyrimidin-4-yl)amino)methyl)-6-fluoro-4-oxoquinazolin-3(4H)-yl)benzamide;

(S)-3-(2-(1-((2,6-diamino-5-cyanopyrimidin-4-yl)amino)propyl)-5-(difluoromethyl)-4-oxoquinazolin-3(4H)-yl)benzamide;

(S)-3-(2-(1-((2,6-diamino-5-chloropyrimidin-4-yl)amino)propyl)-5-(difluoromethyl)-4-oxoquinazolin-3(4H)-yl)benzamide;

(S)-3-(2-(cyclopropyl((2,6-diamino-5-cyanopyrimidin-4-yl)amino)methyl)-5-(difluoromethyl)-4-oxoquinazolin-3(4H)-yl)benzamide;

(S)-3-(8-cyano-2-(1-((2,6-diamino-5-chloropyrimidin-4-yl)amino)ethyl)-4-oxoquinazolin-3(4H)-yl)benzamide;

(S)-3-(5,8-dichloro-2-(1-((2,6-diamino-5-cyanopyrimidin-4-yl)amino)propyl)-4-oxoquinazolin-3(4H)-yl)benzamide;

(S)-3-(5,8-dichloro-2-(1-((2,6-diamino-5-chloropyrimidin-4-yl)amino)propyl)-4-oxoquinazolin-3(4H)-yl)benzamide;

(S)-3-(5,8-dichloro-2-(1-((2,6-diamino-5-cyanopyrimidin-4-yl)amino)butyl)-4-oxoquinazolin-3(4H)-yl)benzamide;

(S)-3-(2-(((6-amino-5-chloropyrimidin-4-yl)amino)(cyclopropyl)methyl)-5-chloro-4-oxoquinazolin-3(4H)-yl)-5-fluorobenzamide;

(S)-3-(5-chloro-2-(cyclopropyl((2,6-diamino-5-cyanopyrimidin-4-yl)amino)methyl)-4-oxoquinazolin-3(4H)-yl)-5-fluorobenzamide;

(S)-3-(5-chloro-2-(cyclopropyl((2,6-diamino-5-chloropyrimidin-4-yl)amino)methyl)-4-oxoquinazolin-3(4H)-yl)-5-fluorobenzamide;

(S)-5-(5-chloro-2-(cyclopropyl((2,6-diamino-5-chloropyrimidin-4-yl)amino)methyl)-4-oxoquinazolin-3(4H)-yl)nicotinamide;

(S)-5-(5-chloro-2-(cyclopropyl((2,6-diamino-5-cyanopyrimidin-4-yl)amino)methyl)-4-oxoquinazolin-3(4H)-yl)nicotinamide;

1-(3-(2-((1S,2S)-1-((6-amino-5-cyanopyrimidin-4-yl)amino)-2-methylbutyl)-5-chloro-4-oxoquinazolin-3(4H)-yl)phenyl)-3-ethylurea;

1-(3-(2-((1S,2S)-1-((6-amino-5-nitropyrimidin-4-yl)amino)-2-methylbutyl)-5-chloro-4-oxoquinazolin-3(4H)-yl)phenyl)-3-ethylurea;

(R)-1-(3-(2-(1-((6-amino-5-cyanopyrimidin-4-yl)amino)ethyl)-5-chloro-4-oxoquinazolin-3(4H)-yl)phenyl)-3-ethylurea;

(S)-1-(3-(2-(1-((6-amino-5-cyanopyrimidin-4-yl)amino)ethyl)-5-bromo-4-oxoquinazolin-3(4H)-yl)phenyl)-3-ethylurea;

(S)-1-(3-(5-allyl-2-(1-((6-amino-5-cyanopyrimidin-4-yl)amino)ethyl)-4-oxoquinazolin-3(4H)-yl)phenyl)-3-ethylurea;

(S)-1-(3-(2-(1-((6-amino-5-cyanopyrimidin-4-yl)amino)ethyl)-5-fluoro-4-oxoquinazolin-3(4H)-yl)phenyl)-3-ethylurea;

(S)-1-(3-(2-(1-((6-amino-5-cyanopyrimidin-4-yl)amino)ethyl)-5,8-dichloro-4-oxoquinazolin-3(4H)-yl)phenyl)-3-ethylurea;

(S)-1-(3-(2-(1-((6-amino-5-cyanopyrimidin-4-yl)amino)ethyl)-8-fluoro-4-oxoquinazolin-3(4H)-yl)phenyl)-3-ethylurea;

(S)-1-(3-(2-(1-((6-amino-5-cyanopyrimidin-4-yl)amino)ethyl)-5,8-difluoro-4-oxoquinazolin-3(4H)-yl)phenyl)-3-ethylurea;

(S)-1-(3-(2-(1-((6-amino-5-cyanopyrimidin-4-yl)amino)ethyl)-4-oxo-5-(trifluoromethyl)quinazolin-3(4H)-yl)phenyl)-3-ethylurea;

(S)-1-(3-(2-(1-((6-amino-5-cyanopyrimidin-4-yl)amino)ethyl)-4-oxoquinazolin-3(4H)-yl)phenyl)-3-ethylurea;

(S)-1-(3-(2-(1-((6-amino-5-cyanopyrimidin-4-yl)amino)ethyl)-6-fluoro-4-oxoquinazolin-3(4H)-yl)phenyl)-3-ethylurea;

(S)-1-(3-(2-(1-((6-amino-5-cyanopyrimidin-4-yl)amino)ethyl)-7-fluoro-4-oxoquinazolin-3(4H)-yl)phenyl)-3-ethylurea;

(S)-1-(3-(2-(1-((6-amino-5-cyanopyrimidin-4-yl)amino)ethyl)-5-methyl-4-oxoquinazolin-3(4H)-yl)phenyl)-3-ethylurea;

(S)-1-(3-(2-(1-((6-amino-5-cyanopyrimidin-4-yl)amino)ethyl)-5-methoxy-4-oxoquinazolin-3(4H)-yl)phenyl)-3-ethylurea;

(S)-1-(3-(2-(1-((6-amino-5-cyanopyrimidin-4-yl)(methyl)amino)ethyl)-5-chloro-4-oxoquinazolin-3(4H)-yl)phenyl)-3-ethylurea;

(S)-1-(3-(2-(1-((6-amino-5-cyanopyrimidin-4-yl)amino)ethyl)-5-chloro-4-oxoquinazolin-3(4H)-yl)-4-chlorophenyl)-3-ethylurea;

(S)-1-(3-(2-(1-((6-amino-5-cyanopyrimidin-4-yl)amino)ethyl)-5-chloro-4-oxoquinazolin-3(4H)-yl)-4-methylphenyl)-3-ethylurea;

(S)-1-(3-(2-(1-((6-amino-5-cyanopyrimidin-4-yl)amino)ethyl)-5-chloro-8-fluoro-4-oxoquinazolin-3(4H)-yl)phenyl)-3-ethylurea;
(S)-1-(3-(2-(1-((6-amino-5-cyanopyrimidin-4-yl)amino)ethyl)-5,8-dichloro-4-oxoquinazolin-3(4H)-yl)phenyl)-3-(3-hydroxypropyl)urea;
(S)-1-(3-(2-(1-((6-amino-5-cyanopyrimidin-4-yl)amino)ethyl)-8-chloro-4-oxoquinazolin-3(4H)-yl)phenyl)-3-(3-hydroxypropyl)urea;
(S)-1-(3-(2-(1-((6-amino-5-cyanopyrimidin-4-yl)amino)ethyl)-5-chloro-8-fluoro-4-oxoquinazolin-3(4H)-yl)phenyl)-3-(3-hydroxypropyl)urea;
(S)-1-(3-(2-(1-((6-amino-5-cyanopyrimidin-4-yl)amino)ethyl)-5,8-difluoro-4-oxoquinazolin-3(4H)-yl)phenyl)-3-(3-hydroxypropyl)urea;
(S)-1-(3-(2-(1-((6-amino-5-cyanopyrimidin-4-yl)amino)ethyl)-8-fluoro-4-oxoquinazolin-3(4H)-yl)phenyl)-3-(3-hydroxypropyl)urea;
(S)-1-(3-(2-(1-((6-amino-5-cyanopyrimidin-4-yl)amino)ethyl)-5-cyano-4-oxoquinazolin-3(4H)-yl)phenyl)-3-ethylurea;
(S)-1-(3-(5-chloro-2-(1-(imidazo[2,1-f][1,2,4]triazin-4-ylamino)ethyl)-4-oxoquinazolin-3(4H)-yl)phenyl)-3-ethylurea;
(S)-1-(3-(5-chloro-4-oxo-2-(1-(thiazolo[5,4-d]pyrimidin-7-ylamino)ethyl)quinazolin-3(4H)-yl)phenyl)-3-ethylurea;
1-(3-(2-((2S,4S)-1-(6-amino-5-cyanopyrimidin-4-yl)-4-fluoropyrrolidin-2-yl)-5-chloro-4-oxoquinazolin-3(4H)-yl)phenyl)-3-ethylurea;
(S)-1-(3-(2-(1-((6-amino-5-cyanopyrimidin-4-yl)amino)ethyl)-5 chloro-4-oxoquinazolin-3(4H)-yl)phenyl)-3-(5-(tert-butyl)isoxazol-3-yl)urea;
(S)-1-(3-(2-(1-((6-amino-5-cyanopyrimidin-4-yl)amino)ethyl)-5-chloro-4-oxoquinazolin-3(4H)-yl)phenyl)-3-(1-(trifluoromethyl)cyclopropyl)urea;
(S)-1-(3-(2-(1-((6-amino-5-cyanopyrimidin-4-yl)amino)ethyl)-5-chloro-4-oxoquinazolin-3(4H)-yl)phenyl)-3-(2,2,2-trifluoroethyl)urea;
(S)-1-(5-(2-(1-((6-amino-5-cyanopyrimidin-4-yl)amino)ethyl)-5-chloro-4-oxoquinazolin-3(4H)-yl)-2-fluorophenyl)-3-isopropylurea;
(S)-1-(5-(2-(1-((6-amino-5-cyanopyrimidin-4-yl)amino)ethyl)-5-chloro-4-oxoquinazolin-3(4H)-yl)-2-fluorophenyl)-3-ethylurea;
(S)—N-((3-(2-(1-((6-amino-5-cyanopyrimidin-4-yl)amino)ethyl)-5-chloro-4-oxoquinazolin-3(4H)-yl)phenyl)carbamoyl)cyclopentanesulfonamide;
(S)—N-((3-(5-chloro-4-oxo-2-(1-(thiazolo[5,4-d]pyrimidin-7-ylamino)ethyl)quinazolin-3(4H)-yl)phenyl)carbamoyl)cyclopentanesulfonamide;
(S)—N-((3-(2-(1-((6-amino-5-cyanopyrimidin-4-yl)amino)ethyl)-5-chloro-4-oxoquinazolin-3(4H)-yl)phenyl)carbamoyl)cyclopropanesulfonamide;
(S)-1-((1,3-dioxolan-2-yl)methyl)-3-(3-(2-(1-(6-amino-5-cyanopyrimidin-4-yl)pyrrolidin-2-yl)-5-chloro-4-oxoquinazolin-3(4H)-yl)phenyl)urea;
(S)-1-(3-(2-(1-(6-amino-5-cyanopyrimidin-4-yl)pyrrolidin-2-yl)-5-chloro-4-oxoquinazolin-3(4H)-yl)phenyl)-3-ethylurea;
(S)-1-(3-(2-(1-(6-amino-5-cyanopyrimidin-4-yl)pyrrolidin-2-yl)-5-chloro-4-oxoquinazolin-3(4H)-yl)phenyl)-3-(2-methoxyethyl)urea;
(S)-1-(3-(2-(1-(6-amino-5-cyanopyrimidin-4-yl)pyrrolidin-2-yl)-5-chloro-4-oxoquinazolin-3(4H)-yl)phenyl)-3-(pyridin-2-yl)urea;
(S)-1-(3-(2-(1-((6-amino-5-cyanopyrimidin-4-yl)amino)ethyl)-5-chloro-4-oxoquinazolin-3(4H)-yl)phenyl)urea;
(S)-1-(3-(2-(1-((6-amino-5-cyanopyrimidin-4-yl)amino)ethyl)-5-chloro-4-oxoquinazolin-3(4H)-yl)phenyl)-3-methylurea;
(S)-1-(3-(2-(1-((6-amino-5-cyanopyrimidin-4-yl)amino)ethyl)-5-chloro-4-oxoquinazolin-3(4H)-yl)phenyl)-3-ethylurea;
(S)-1-(3-(2-(1-((4-amino-6-methyl-1,3,5-triazin-2-yl)amino)ethyl)-5-chloro-4-oxoquinazolin-3(4H)-yl)phenyl)-3-ethylurea;
(S)-1-(3-(2-(1-((6-amino-5-cyanopyrimidin-4-yl)amino)ethyl)-5-chloro-4-oxoquinazolin-3(4H)-yl)-2-chlorophenyl)-3-ethylurea;
(S)-2-(3-(3-(2-(1-((6-amino-5-cyanopyrimidin-4-yl)amino)ethyl)-5-chloro-4-oxoquinazolin-3(4H)-yl)phenyl)ureido)benzoic acid;
(S)-2-(3-(3-(2-(1-((6-amino-5-cyanopyrimidin-4-yl)amino)ethyl)-5-chloro-4-oxoquinazolin-3(4H)-yl)phenyl)ureido)benzenesulfonic acid;
(S)-2-(2-(3-(3-(2-(1-((6-amino-5-cyanopyrimidin-4-yl)amino)ethyl)-5-chloro-4-oxoquinazolin-3(4H)-yl)phenyl)ureido)phenoxy)acetic acid;
(S)-1-(3-(2-(1-((6-amino-5-cyanopyrimidin-4-yl)amino)ethyl)-5-chloro-4-oxoquinazolin-3(4H)-yl)phenyl)-3-(4-chloro-3-(trifluoromethyl)phenyl)urea;
(S)-1-(3-(2-(1-((6-amino-5-cyanopyrimidin-4-yl)amino)ethyl)-5-chloro-4-oxoquinazolin-3(4H)-yl)phenyl)-3-(2-chlorophenyl)urea;
(S)-1-(3-(2-(1-((6-amino-5-cyanopyrimidin-4-yl)amino)ethyl)-5-chloro-4-oxoquinazolin-3(4H)-yl)phenyl)-3-(2-(trifluoromethyl)phenyl)urea;
(S)-1-(3-(2-(1-((6-amino-5-cyanopyrimidin-4-yl)amino)ethyl)-5-chloro-4-oxoquinazolin-3(4H)-yl)phenyl)-3-(2,6-dichlorophenyl)urea;
(S)-1-(3-(2-(1-((6-amino-5-cyanopyrimidin-4-yl)amino)ethyl)-5-chloro-4-oxoquinazolin-3(4H)-yl)phenyl)-3-(2,4-difluorophenyl)urea;
(S)-1-(3-(2-(1-((6-amino-5-cyanopyrimidin-4-yl)amino)ethyl)-5-chloro-4-oxoquinazolin-3(4H)-yl)phenyl)-3-(2-cyanophenyl)urea;
(S)-1-(3-(2-(1-((6-amino-5-cyanopyrimidin-4-yl)amino)ethyl)-5-chloro-4-oxoquinazolin-3(4H)-yl)phenyl)-3-(o-tolyl)urea;
(S)-1-(3-(2-(1-((6-amino-5-cyanopyrimidin-4-yl)amino)ethyl)-5-fluoro-4-oxoquinazolin-3(4H)-yl)phenyl)-3-(2-chlorophenyl)urea;
(S)-1-(3-(2-(1-((6-amino-5-cyanopyrimidin-4-yl)amino)ethyl)-5-chloro-4-oxoquinazolin-3(4H)-yl)phenyl)-3-(2-methoxyphenyl)urea;
(S)-1-(3-(2-(1-((6-amino-5-cyanopyrimidin-4-yl)amino)ethyl)-5-fluoro-4-oxoquinazolin-3(4H)-yl)phenyl)-3-(2-(trifluoromethyl)phenyl)urea;
(S)-1-(3-(2-(1-((6-amino-5-cyanopyrimidin-4-yl)amino)ethyl)-5-chloro-4-oxoquinazolin-3(4H)-yl)phenyl)-3-(3-chloropyridin-4-yl)urea;
(S)-1-(3-(2-(1-((6-amino-5-cyanopyrimidin-4-yl)amino)ethyl)-5-chloro-4-oxoquinazolin-3(4H)-yl)phenyl)-3-(2-(trifluoromethyl)pyridin-3-yl)urea;
(S)-1-(3-(2-(1-((6-amino-5-cyanopyrimidin-4-yl)amino)ethyl)-5-chloro-4-oxoquinazolin-3(4H)-yl)phenyl)-3-(1H-tetrazol-5-yl)urea;
(S)-1-(3-(2-(1-((6-amino-5-cyanopyrimidin-4-yl)amino)ethyl)-5-chloro-4-oxoquinazolin-3(4H)-yl)phenyl)-3-methoxyurea;

(S)-1-(3-(2-(1-((6-amino-5-cyanopyrimidin-4-yl)amino) ethyl)-5-chloro-4-oxoquinazolin-3(4H)-yl)phenyl)-3-(2-(dimethylamino)ethyl)urea;
(S)-1-(3-(2-(1-((6-amino-5-cyanopyrimidin-4-yl)amino) ethyl)-5-chloro-4-oxoquinazolin-3(4H)-yl)phenyl)-3-(2-hydroxyethyl)urea;
(S)-1-(3-(2-(1-((6-amino-5-cyanopyrimidin-4-yl)amino) ethyl)-5-chloro-4-oxoquinazolin-3(4H)-yl)phenyl)-3-phenylurea;
(S)-1-(3-(2-(1-((6-amino-5-cyanopyrimidin-4-yl)amino) ethyl)-5-chloro-4-oxoquinazolin-3(4H)-yl)phenyl)-3-(pyridin-3-yl)urea;
(S)-1-(3-(2-(1-((6-amino-5-cyanopyrimidin-4-yl)amino) ethyl)-5-chloro-4-oxoquinazolin-3(4H)-yl)phenyl)-3-isopropylurea;
(S)-1-(3-(2-(1-((6-amino-5-cyanopyrimidin-4-yl)amino) ethyl)-5-chloro-4-oxoquinazolin-3(4H)-yl)phenyl)-3-cyclopentylurea;
(S)-1-(3-(2-(1-((6-amino-5-cyanopyrimidin-4-yl)amino) ethyl)-5-chloro-4-oxoquinazolin-3(4H)-yl)phenyl)-3-cyclohexylurea;
(S)-1-(3-(2-(1-((6-amino-5-cyanopyrimidin-4-yl)amino) ethyl)-5-chloro-4-oxoquinazolin-3(4H)-yl)phenyl)-3-cyclobutylurea;
(S)-1-(3-(2-(1-((6-amino-5-cyanopyrimidin-4-yl)amino) ethyl)-5-chloro-4-oxoquinazolin-3(4H)-yl)phenyl)-3-(tert-butyl)urea;
(S)-1-(3-(2-(1-((6-amino-5-cyanopyrimidin-4-yl)amino) ethyl)-5-chloro-4-oxoquinazolin-3(4H)-yl)phenyl)-3-cyclopropylurea;
(S)-1-(3-(2-(1-((6-amino-5-cyanopyrimidin-4-yl)amino) ethyl)-5-chloro-4-oxoquinazolin-3(4H)-yl)phenyl)-3-propylurea;
(S)-1-(3-(2-(1-((6-amino-5-cyanopyrimidin-4-yl)amino) ethyl)-5-chloro-4-oxoquinazolin-3(4H)-yl)phenyl)-3-(2-fluoroethyl)urea;
(S)-1-(3-(2-(1-((6-amino-5-cyanopyrimidin-4-yl)amino) ethyl)-5-chloro-4-oxoquinazolin-3(4H)-yl)phenyl)-3-(3-hydroxypropyl)urea;
1-(3-(2-((S)-1-((6-amino-5-cyanopyrimidin-4-yl)amino) ethyl)-5-chloro-4-oxoquinazolin-3(4H)-yl)phenyl)-3-(2-hydroxypropyl)urea;
(R)-1-(3-(2-(1-((6-amino-5-cyanopyrimidin-4-yl)amino)-2-(benzyloxy)ethyl)-5-chloro-4-oxoquinazolin-3(4H)-yl)phenyl)-3-(3-hydroxypropyl)urea;
(R)-1-(3-(2-(1-((6-amino-5-cyanopyrimidin-4-yl)amino)-2-(benzyloxy)ethyl)-5-chloro-4-oxoquinazolin-3(4H)-yl)phenyl)-3-ethylurea;
(S)-1-(3-(2-(1-((6-amino-5-cyanopyrimidin-4-yl)amino) ethyl)-5-chloro-4-oxoquinazolin-3(4H)-yl)phenyl)-3-(3-methoxypropyl)urea;
(S)-4-amino-6-((1-(5-chloro-3-(3-(3-ethylureido)phenyl)-4-oxo-3,4-dihydroquinazolin-2-yl)ethyl)amino) pyrimidine-5-carboxylic acid;
(S)-3-(3-(3-(2-(1-((6-amino-5-cyanopyrimidin-4-yl) amino)ethyl)-5-chloro-4-oxoquinazolin-3(4H)-yl)phenyl)ureido)propanoic acid;
(S)-1-(3-(2-(1-((6-amino-5-cyanopyrimidin-4-yl)amino) ethyl)-5-chloro-4-oxoquinazolin-3(4H)-yl)phenyl)-3-(1-hydroxy-2-methylpropan-2-yl)urea;
(S)-2-(3-(3-(2-(1-((6-amino-5-cyanopyrimidin-4-yl) amino)ethyl)-5-chloro-4-oxoquinazolin-3(4H)-yl)phenyl)ureido)-2-methylpropanoic acid;
(S)-1-(3-(2-(1-((6-amino-5-cyanopyrimidin-4-yl)amino) ethyl)-5-chloro-4-oxoquinazolin-3(4H)-yl)phenyl)-3-(4-hydroxy-2-methylbutan-2-yl)urea;
(S)-1-(3-(2-(1-((6-amino-5-cyanopyrimidin-4-yl)amino) ethyl)-5-chloro-4-oxoquinazolin-3(4H)-yl)phenyl)-3-(3-hydroxy-2,2-dimethylpropyl)urea;
(S)-1-(3-(2-(1-((6-amino-5-cyanopyrimidin-4-yl)amino) ethyl)-5-chloro-4-oxoquinazolin-3(4H)-yl)phenyl)-3-(3-hydroxy-3-methylbutyl)urea;
(S)-1-(3-(2-(1-((6-amino-5-cyanopyrimidin-4-yl)amino) ethyl)-5-chloro-4-oxoquinazolin-3(4H)-yl)phenyl)-3-(2-(2-hydroxyethoxy)phenyl)urea;
(S)-1-(3-(2-(1-((6-amino-5-cyanopyrimidin-4-yl)amino) ethyl)-5-chloro-4-oxoquinazolin-3(4H)-yl)phenyl)-3-(2-(methyl sulfonyl)phenyl)urea;
(S)-1-(3-(2-(1-(6-amino-5-cyanopyrimidin-4-yl)pyrrolidin-2-yl)-5-chloro-4-oxoquinazolin-3(4H)-yl)phenyl)-3-(2,2,2-trifluoroethyl)urea;
(S)-1-(3-(2-(1-((6-amino-5-cyanopyrimidin-4-yl)oxy) ethyl)-5-chloro-4-oxoquinazolin-3(4H)-yl)phenyl)-3-ethylurea;
(S)-1-(3-(5-chloro-4-oxo-2-(1-(thiazolo[5,4-d]pyrimidin-7-yloxy)ethyl)quinazolin-3(4H)-yl)phenyl)-3-cyclopentylurea;
(S)-1-(3-(5-chloro-4-oxo-2-(1-(thiazolo[5,4-d]pyrimidin-7-yloxy)ethyl)quinazolin-3(4H)-yl)phenyl)-3-(1-(trifluoromethyl)cyclopropyl)urea;
(S)-1-(3-(5-chloro-4-oxo-2-(1-(thiazolo[5,4-d]pyrimidin-7-yloxy)ethyl)quinazolin-3(4H)-yl)phenyl)-3-(2,2-difluoroethyl)urea;
1-(3-(5-chloro-4-oxo-2-(1-(thiazolo[5,4-d]pyrimidin-7-yloxy)ethyl)quinazolin-3(4H)-yl)phenyl)-3-(2-methoxyethyl)urea;
(S)-1-(3-(5-chloro-4-oxo-2-(1-(thiazolo[5,4-d]pyrimidin-7-yloxy)ethyl)quinazol-3(4H)-yl)phenyl)-3-(3-(trifluoromethyl)isoxazol-5-yl)urea;
(S)-1-(3-(5-chloro-4-oxo-2-(1-(thiazolo[5,4-d]pyrimidin-7-yloxy)ethyl)quinazolin-3(4H)-yl)phenyl)-3-ethylurea;
(S)-1-(3-(5-chloro-4-oxo-2-(1-(thiazolo[5,4-d]pyrimidin-7-yloxy)ethyl)quinazolin-3(4H)-yl)phenyl)-3-(2,2,3,3,3-pentafluoropropyl)urea;
(S)-1-(3-(5-chloro-4-oxo-2-(1-(thiazolo[5,4-d]pyrimidin-7-yloxy)ethyl)quinazolin-3(4H)-yl)phenyl)-3-methoxyurea;
1-(3-(5-chloro-4-oxo-2-(1-(thiazolo[5,4-d]pyrimidin-7-yloxy)ethyl)quinazolin-3(4H)-yl)phenyl)-3-(2,2,2-trifluoroethyl)urea;
1-(3-(5-chloro-4-oxo-2-(1-(thiazolo[5,4-d]pyrimidin-7-yloxy)ethyl)quinazolin-3(4H)-yl)phenyl)-3-(2-chlorophenyl)urea;
(S)-1-((1,3-dioxolan-2-yl)methyl)-3-(3-(5-chloro-4-oxo-2-(1-(thiazolo[5,4-d]pyrimidin-7-yloxy)ethyl)quinazolin-3(4H)-yl)phenyl)urea; and
(S)-1-(3-(5-chloro-4-oxo-2-(1-(thiazolo[5,4-d]pyrimidin-7-yloxy)ethyl)quinazolin-3(4H)-yl)phenyl)-3-(2-hydroxyethyl)urea,
or a pharmaceutically acceptable salt, stereoisomers, or atropisomers thereof.

3. The compound of claim 1, or a pharmaceutically acceptable salt, stereoisomers, or atropisomers thereof, wherein $W^2$ is N.

4. The compound of claim 1, a pharmaceutically acceptable salt, stereoisomers, or atropisomers thereof, wherein $W^2$ is CH.

5. The compound of claim 1, a pharmaceutically acceptable salt, stereoisomers, or atropisomers thereof, wherein $R^4$ is

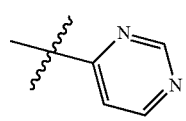

optionally substituted with two or three members which are independently bromo, chloro, fluoro, cyano, methyl, ethyl, propyl, difluoromethyl, trifluoromethyl or —NH$_2$.

6. The compound of claim 1, or a pharmaceutically acceptable salt thereof.

7. The compound of claim 2, or a pharmaceutically acceptable salt thereof.

8. The compound of claim 5, or a pharmaceutically acceptable salt thereof.

9. A compound selected from the group consisting of:

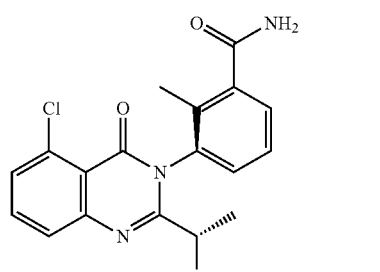

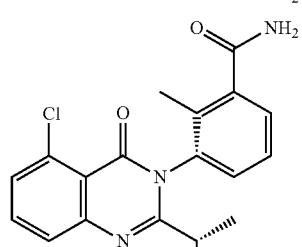

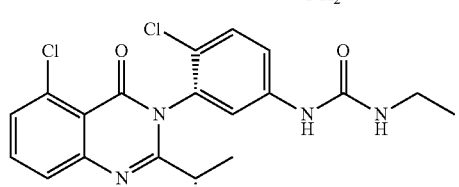

;

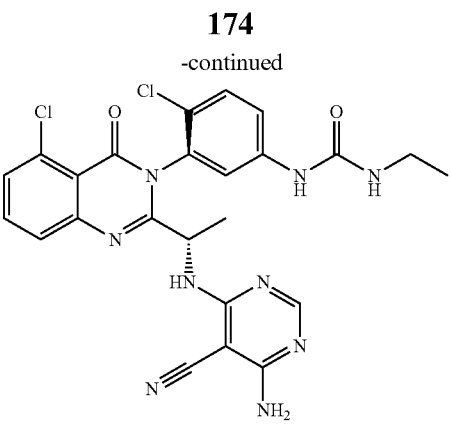

;

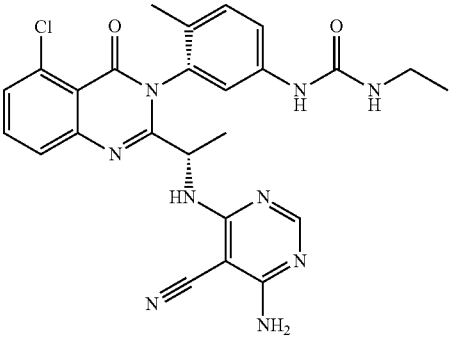

;

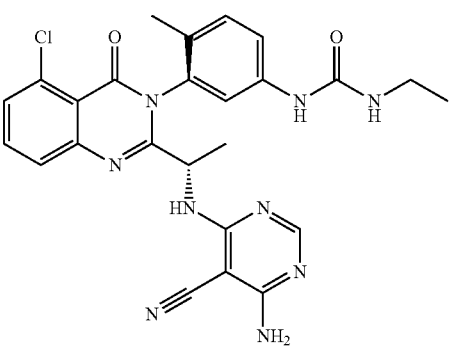

;

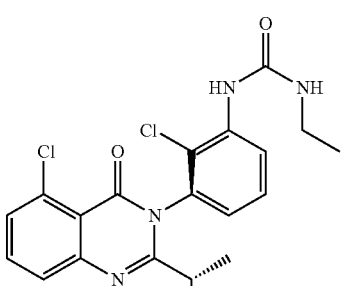

; and

-continued

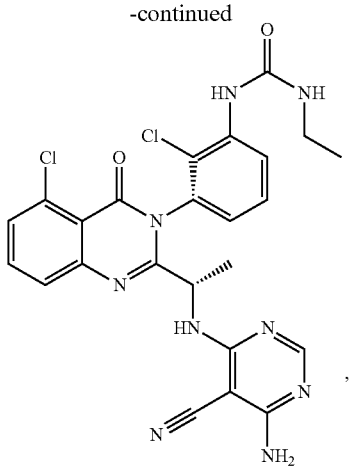

or a pharmaceutically acceptable salt thereof.

10. The compound of claim 1, a pharmaceutically acceptable salt, stereoisomers, or atropisomers thereof, wherein each $R^1$ is independently halo, cyano, $C_{1-4}$haloalkyl, or $C_{1-4}$alkyl.

11. The compound of claim 1, or a pharmaceutically acceptable salt, stereoisomers, or atropisomers thereof, wherein each $R^2$ is independently halo or $C_{1-4}$alkyl.

12. The compound of claim 1, a pharmaceutically acceptable salt, stereoisomers, or atropisomers thereof, wherein $R^3$ is methyl, ethyl, propyl, butyl, cyclopropyl, cyclobutyl, or methyl substituted with phenylmethoxy or methoxy.

13. The compound of claim 1, or a pharmaceutically acceptable salt, stereoisomers, or atropisomers thereof, wherein $R^6$ is hydrogen, methyl, ethyl, propyl, butyl, (1,3-dioxolan-2-yl)methyl, 2-(dimethylamino)ethyl, 2-hydroxyethyl, 2-carboxyethyl, 2-fluoroethyl, 2,2-difluoroethyl, 2-methoxyethyl, 2,2,2-trifluoroethyl, 1-hydroxy-2-methylpropan-2-yl, 2-carboxypropan-2-yl, 2-hydroxypropyl, 3-hydroxypropyl, 3-methoxy propyl, 2,2,3,3,3-pentafluoropropyl, 3-hydroxy-2,2-dimethylpropyl, 3-hydroxy-3-methylbutyl, 4-hydroxy-2-methylbutan-2-yl, methoxy, $SO_2CH_3$, cyclopentylsulfonyl, cyclopropylsulfonyl, 4-fluorophenylsulfonyl, cyclohexyl, cyclopentyl, cyclobutyl, cyclopropyl, 1-(trifluoromethyl)cyclopropyl, pyridin-3-yl, 2-trifluoromethylpyridin-3-yl, tetrazolyl, 3-(trifluoromethyl)isoxazol-5-yl, 5-(trifluoromethyl)isoxazol-3-yl, phenyl, 2-carboxyphenyl, 2-sulfinophenyl, 2-(2-carboxyethoxy)phenyl, 4-chloro-3-(trifluoromethyl)phenyl, 2-trifluoromethylphenyl, 2,6-dichlorophenyl, 2,4-difluorophenyl, 2-cyanophenyl, 2-(2-hydroxyethoxy)phenyl, 2-(methyl sulfonyl) phenyl, 2-methylphenyl, 2-chlorophenyl, or 2-methoxyphenyl.

* * * * *